(12) United States Patent
Cerier et al.

(10) Patent No.: US 8,287,554 B2
(45) Date of Patent: Oct. 16, 2012

(54) METHOD AND DEVICES FOR TISSUE RECONFIGURATION

(75) Inventors: Jeffrey C. Cerier, Franklin, MA (US); Amos G. Cruz, Franklin, MA (US); Jonathan O'Keefe, Scituate, MA (US); Cheryne Ray, Norfolk, MA (US); Joseph M. Gordon, Westborough, MA (US); David Robson, Riverside, RI (US); Daniel Nelsen, Providence, RI (US); Aidan Petrie, Jamestown, RI (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1163 days.

(21) Appl. No.: 10/438,346

(22) Filed: May 15, 2003

(65) Prior Publication Data

US 2004/0010245 A1    Jan. 15, 2004

Related U.S. Application Data

(63) Continuation-in-part of application No. 10/197,574, filed on Jul. 18, 2002, now Pat. No. 6,835,200, and a continuation-in-part of application No. 09/859,579, filed on May 18, 2001, now Pat. No. 6,821,285, which is a continuation-in-part of application No. 09/574,424, filed on May 19, 2000, now Pat. No. 6,494,888, which is a continuation-in-part of application No. 09/520,273, filed on Mar. 7, 2000, now Pat. No. 6,663,639, which is a continuation-in-part of application No. 09/519,945, filed on Mar. 7, 2000, now Pat. No. 6,506,196.

(60) Provisional application No. 60/459,996, filed on Apr. 4, 2003, provisional application No. 60/460,308, filed on Apr. 4, 2003, provisional application No. 60/381,539, filed on May 17, 2002, provisional application No. 60/306,652, filed on Jul. 18, 2001, provisional application No. 60/140,492, filed on Jun. 22, 1999.

(51) Int. Cl.
*A61B 17/10* (2006.01)

(52) U.S. Cl. ........................................ 606/142; 606/205
(58) Field of Classification Search .................. 606/142, 606/205
See application file for complete search history.

(56) References Cited

U.S. PATENT DOCUMENTS 1,343,289 A    6/1920    Suchy
(Continued)

FOREIGN PATENT DOCUMENTS

EP    0 480 428    4/1992
(Continued)

OTHER PUBLICATIONS

Bancewicz et al., "Yield pressure, anatomy of the cardia and gastro-oesophageal reflux", British Journal of Surgery, 1995, vol. 82, No. 7 p. 943-947.

(Continued)

*Primary Examiner* — Gary Jackson
*Assistant Examiner* — Diane Yabut
(74) *Attorney, Agent, or Firm* — Nutter McClennen & Fish LLP

(57) ABSTRACT

An instrument for reconfiguring stomach tissue includes a sealing member that seals a section of a tissue manipulator from contact with bodily fluids. The tissue manipulator includes a first portion that is configured for releasable coupling to an actuating member and a second portion configured to receive an implant to be deployed within the patient. The tissue manipulator also includes a rectangular member and a cavity for receiving a coupler of the actuating member. The tissue manipulator has a first member with tissue penetrating elements and a second member with engaging elements configured to deflect the tissue penetrating elements upon relative movement of the first and second members. The actuating member includes a tissue penetrating element support positioned to limit bending of the tissue manipulator. The instrument includes an actuating mechanism that is configured to move at least one of the first and second members of the tissue manipulator.

10 Claims, 92 Drawing Sheets

U.S. PATENT DOCUMENTS

| | | | |
|---|---|---|---|
| 1,548,250 A | 8/1925 | Bobner | |
| 2,104,885 A | 1/1938 | Robbins | |
| 2,199,025 A | 4/1940 | Conn | |
| 3,216,424 A | 11/1965 | William | |
| 3,399,432 A | 9/1968 | Merser | |
| 3,470,875 A | 10/1969 | Johnson | |
| 3,551,987 A | 1/1971 | Wilkinson | |
| 3,636,594 A | 1/1972 | Faivre et al. | |
| 3,638,653 A | 2/1972 | Berry | |
| 3,734,375 A | 5/1973 | Bone et al. | |
| 3,749,085 A | 7/1973 | Willson et al. | |
| 3,842,840 A | 10/1974 | Schweizer | |
| 3,875,648 A | 4/1975 | Bone | |
| 3,900,925 A | 8/1975 | La Torraca | |
| 3,901,244 A | 8/1975 | Schweizer | |
| 3,933,291 A | 1/1976 | Stephenson | |
| 3,946,740 A | 3/1976 | Bassett | |
| 4,006,747 A | 2/1977 | Kronenthal | |
| 4,014,492 A | 3/1977 | Rothfuss | |
| 4,043,504 A | 8/1977 | Hueil et al. | |
| 4,144,890 A | 3/1979 | Hess | |
| 4,164,225 A | 8/1979 | Johnson | |
| 4,168,703 A | 9/1979 | Kenigsberg | |
| 4,177,818 A | 12/1979 | De Pedro | |
| 4,210,148 A | 7/1980 | Stivala | |
| 4,229,930 A | 10/1980 | Ostermaier | |
| 4,235,238 A | 11/1980 | Ogiu | |
| 4,265,226 A | 5/1981 | Cassimally | |
| 4,375,866 A | 3/1983 | Giersch et al. | |
| 4,399,810 A | 8/1983 | Samuels et al. | |
| 4,407,286 A | 10/1983 | Noiles et al. | |
| 4,448,194 A | 5/1984 | Di Giovanni | |
| 4,471,781 A | 9/1984 | Di Giovanni | |
| 4,500,024 A | 2/1985 | Di Giovanni | |
| 4,506,670 A | 3/1985 | Crossley | |
| 4,573,469 A | 3/1986 | Golden | |
| 4,585,153 A | 4/1986 | Failla | |
| 4,586,502 A | 5/1986 | Bedi | |
| 4,591,085 A | 5/1986 | Di Giovanni | |
| 4,605,004 A | 8/1986 | Di Giovanni | |
| 4,606,345 A | 8/1986 | Dorband | |
| 4,607,638 A | 8/1986 | Crainich | |
| 4,627,437 A | 12/1986 | Bedi | |
| 4,635,637 A | 1/1987 | Schreiber | |
| 4,649,938 A | 3/1987 | McArthur | |
| 4,653,496 A | 3/1987 | Bundy et al. | |
| 4,665,906 A | 5/1987 | Jervis | |
| 4,669,473 A | 6/1987 | Richards et al. | |
| 4,696,300 A | 9/1987 | Anderson | |
| 4,705,040 A | 11/1987 | Mueller | |
| 4,724,840 A | 2/1988 | McVay | |
| 4,736,746 A | 4/1988 | Anderson | |
| 4,741,336 A | 5/1988 | Failla | |
| 4,753,469 A | 6/1988 | Hiscott | |
| 4,809,695 A | 3/1989 | Gwathmey | |
| 4,841,888 A | 6/1989 | Mills et al. | |
| 4,862,359 A | 8/1989 | Trivedi et al. | |
| 4,880,015 A | 11/1989 | Nierman | |
| 4,887,612 A | 12/1989 | Esser | |
| 4,890,615 A | 1/1990 | Caspari | |
| 4,935,027 A | 6/1990 | Yoon | |
| 4,982,727 A * | 1/1991 | Sato | 600/104 |
| 5,015,249 A | 5/1991 | Nakao | |
| 5,037,021 A | 8/1991 | Mills et al. | |
| 5,037,433 A | 8/1991 | Wilk | |
| 5,040,715 A | 8/1991 | Green et al. | |
| 5,067,957 A | 11/1991 | Jervis | |
| 5,076,285 A | 12/1991 | Hess et al. | |
| 5,080,663 A | 1/1992 | Mills et al. | |
| 5,088,979 A | 2/1992 | Filipi | |
| 5,147,373 A | 9/1992 | Ferzli | |
| 5,174,487 A | 12/1992 | Rothfuss et al. | |
| 5,190,546 A | 3/1993 | Jervis | |
| 5,219,359 A | 6/1993 | McQuilkin et al. | |
| 5,222,963 A | 6/1993 | Brinkerhoff | |
| 5,230,344 A | 7/1993 | Ozdamar et al. | |
| 5,254,126 A | 10/1993 | Filipi | |
| 5,289,963 A | 3/1994 | McGarry et al. | |
| 5,290,296 A | 3/1994 | Phillips | |
| 5,309,923 A | 5/1994 | Leuchter et al. | |
| 5,312,391 A * | 5/1994 | Wilk | 606/1 |
| 5,318,589 A | 6/1994 | Lichtman | |
| 5,324,325 A | 6/1994 | Moaddeb | |
| 5,331,969 A | 7/1994 | Silberstein | |
| 5,336,263 A | 8/1994 | Ersek | |
| 5,346,504 A | 9/1994 | Ortiz | |
| 5,350,391 A | 9/1994 | Iacovelli | |
| 5,354,311 A | 10/1994 | Kambin et al. | |
| 5,356,416 A | 10/1994 | Chu | |
| 5,358,508 A | 10/1994 | Cobb | |
| 5,364,408 A | 11/1994 | Gordon | |
| 5,376,095 A | 12/1994 | Ortiz | |
| 5,381,943 A | 1/1995 | Allen et al. | |
| 5,383,260 A | 1/1995 | Deschenes et al. | |
| 5,389,098 A | 2/1995 | Tsuruta et al. | |
| D356,154 S | 3/1995 | Ferragamo | |
| 5,395,030 A | 3/1995 | Kuramoto | |
| 5,395,367 A | 3/1995 | Wilk | |
| 5,403,326 A * | 4/1995 | Harrison et al. | 606/139 |
| 5,405,344 A | 4/1995 | Williamson et al. | |
| 5,433,721 A | 7/1995 | Hooven | |
| 5,437,266 A | 8/1995 | McPherson et al. | |
| 5,441,507 A | 8/1995 | Wilk | |
| 5,447,512 A | 9/1995 | Wilson | |
| 5,451,406 A | 9/1995 | Lawin | |
| 5,464,426 A | 11/1995 | Bonutti | |
| 5,465,894 A | 11/1995 | Clark | |
| 5,470,337 A | 11/1995 | Moss | |
| 5,474,057 A | 12/1995 | Makower et al. | |
| 5,485,952 A | 1/1996 | Fontayne | |
| 5,486,189 A | 1/1996 | Mudry | |
| 5,496,331 A | 3/1996 | Xu | |
| 5,522,820 A | 6/1996 | Caspar | |
| 5,528,334 A | 6/1996 | Lee | |
| 5,538,008 A * | 7/1996 | Crowe | 600/564 |
| 5,549,618 A | 8/1996 | Fleenor | |
| 5,558,665 A | 9/1996 | Kieturakis | |
| 5,571,090 A | 11/1996 | Sherts | |
| 5,571,116 A | 11/1996 | Bolanos | |
| 5,573,496 A | 11/1996 | McPherson | |
| 5,581,943 A | 12/1996 | Deren et al. | |
| 5,588,581 A | 12/1996 | Conlon et al. | |
| 5,597,378 A | 1/1997 | Jervis | |
| 5,613,499 A | 3/1997 | Palmer et al. | |
| 5,624,453 A | 4/1997 | Ahmed | |
| 5,626,613 A | 5/1997 | Schmieding | |
| 5,645,552 A | 7/1997 | Sherts | |
| 5,662,683 A | 9/1997 | Kay | |
| 5,665,096 A | 9/1997 | Yoon | |
| 5,671,507 A | 9/1997 | Deschenes et al. | |
| 5,674,230 A | 10/1997 | Tovey | |
| 5,676,674 A | 10/1997 | Bolanos | |
| 5,697,940 A | 12/1997 | Chu | |
| 5,699,808 A | 12/1997 | John | |
| 5,700,273 A | 12/1997 | Buelna et al. | |
| 5,722,421 A | 3/1998 | Francese | |
| 5,725,524 A | 3/1998 | Mulier | |
| 5,728,109 A | 3/1998 | Schulze | |
| 5,735,861 A | 4/1998 | Peifer | |
| 5,741,280 A | 4/1998 | Fleenor | |
| 5,749,898 A | 5/1998 | Schulze | |
| 5,787,897 A | 8/1998 | Kieturakis | |
| 5,788,138 A | 8/1998 | Deschenes et al. | |
| 5,792,153 A | 8/1998 | Swain | |
| 5,792,478 A | 8/1998 | Lawin | |
| 5,794,948 A | 8/1998 | Schmitt et al. | |
| 5,797,927 A | 8/1998 | Yoon | |
| 5,810,855 A | 9/1998 | Rayburn | |
| 5,810,882 A | 9/1998 | Bolduc | |
| 5,814,054 A | 9/1998 | Kortenbach | |
| 5,820,630 A * | 10/1998 | Lind | 606/208 |
| 5,826,776 A | 10/1998 | Schulze | |
| 5,845,645 A | 12/1998 | Bonutti | |
| 5,846,254 A | 12/1998 | Schulze | |
| 5,853,409 A | 12/1998 | Swanson | |
| 5,855,311 A | 1/1999 | Hamblin | |
| 5,887,594 A | 3/1999 | LoCicero | |

| Patent | Date | Inventor |
|---|---|---|
| 5,893,592 A | 4/1999 | Schulze |
| 5,897,562 A | 4/1999 | Bolanos |
| 5,899,915 A | 5/1999 | Saadat |
| 5,901,895 A | 5/1999 | Heaton |
| 5,947,983 A | 9/1999 | Solar et al. |
| 5,954,731 A | 9/1999 | Yoon |
| 5,958,444 A | 9/1999 | Wallace |
| 5,984,932 A | 11/1999 | Yoon |
| 5,993,466 A | 11/1999 | Yoon |
| 6,009,877 A | 1/2000 | Edwards |
| 6,051,003 A | 4/2000 | Chu |
| 6,059,719 A | 5/2000 | Yamamoto et al. |
| 6,059,798 A | 5/2000 | Tolkoff |
| 6,067,990 A | 5/2000 | Kieturakis |
| 6,083,202 A | 7/2000 | Smith |
| 6,086,600 A | 7/2000 | Kortenbach |
| 6,086,603 A | 7/2000 | Termin et al. |
| 6,098,629 A | 8/2000 | Johnson |
| 6,102,887 A | 8/2000 | Altman |
| 6,113,609 A | 9/2000 | Adams |
| 6,129,761 A | 10/2000 | Hubbell |
| RE36,974 E | 11/2000 | Bonutti |
| 6,152,935 A | 11/2000 | Kammerer |
| 6,159,146 A | 12/2000 | El Gazayerli |
| 6,179,840 B1 | 1/2001 | Bowman |
| 6,221,084 B1 | 4/2001 | Fleenor |
| 6,238,335 B1 | 5/2001 | Silverman et al. |
| 6,254,642 B1 | 7/2001 | Taylor |
| 6,258,064 B1 | 7/2001 | Smith et al. |
| 6,267,285 B1 | 7/2001 | Raymond et al. |
| 6,312,437 B1 | 11/2001 | Kortenbach |
| 6,312,448 B1 | 11/2001 | Bonutti |
| 6,315,184 B1 | 11/2001 | Whitman |
| 6,325,503 B1 | 12/2001 | McCue, Jr. et al. |
| 6,352,503 B1 | 3/2002 | Matsui |
| 6,387,104 B1 | 5/2002 | Pugsley, Jr. |
| 6,443,973 B1 | 9/2002 | Whitman |
| 6,454,778 B2 | 9/2002 | Kortenbach |
| 6,461,366 B1 | 10/2002 | Seguin |
| 6,478,210 B2 | 11/2002 | Adams et al. |
| 6,494,888 B1 | 12/2002 | Laufer et al. |
| 6,506,196 B1 | 1/2003 | Laufer |
| 6,540,789 B1 | 4/2003 | Silverman et al. |
| 6,544,291 B2 | 4/2003 | Taylor |
| 6,544,503 B1 | 4/2003 | Vanderhoff et al. |
| 6,547,776 B1 | 4/2003 | Gaiser et al. |
| 6,548,501 B2 | 4/2003 | Hakkinen |
| 6,548,518 B2 | 4/2003 | Rubin et al. |
| 6,551,315 B2 | 4/2003 | Kortenbach et al. |
| 6,551,328 B2 | 4/2003 | Kortenbach |
| 6,552,045 B2 | 4/2003 | Rubin et al. |
| 6,552,046 B2 | 4/2003 | Druzgala et al. |
| 6,552,047 B2 | 4/2003 | Garvey et al. |
| 6,558,400 B2 | 5/2003 | Deem et al. |
| 6,558,429 B2 | 5/2003 | Taylor |
| 6,559,165 B1 | 5/2003 | Rubin et al. |
| 6,562,034 B2 | 5/2003 | Edwards et al. |
| 6,562,795 B2 | 5/2003 | Ashley et al. |
| 6,569,085 B2 | 5/2003 | Kortenbach et al. |
| 6,569,105 B1 | 5/2003 | Kortenbach et al. |
| 6,572,626 B1 | 6/2003 | Knodel et al. |
| 6,575,971 B2 | 6/2003 | Hauck et al. |
| 6,579,301 B1 | 6/2003 | Bales et al. |
| 6,589,238 B2 | 7/2003 | Edwards et al. |
| 6,591,137 B1 | 7/2003 | Fischell et al. |
| 6,591,838 B2 | 7/2003 | Durgin |
| 6,592,596 B1 | 7/2003 | Geitz |
| 6,592,609 B1 | 7/2003 | Bonutti |
| 6,595,909 B2 | 7/2003 | Silverman et al. |
| 6,595,910 B2 | 7/2003 | Silverman et al. |
| 6,604,004 B1 | 8/2003 | Zelickson et al. |
| 6,604,528 B1 | 8/2003 | Duncan |
| 6,605,078 B2 | 8/2003 | Adams |
| 6,609,140 B1 | 8/2003 | Greene |
| 6,613,047 B2 | 9/2003 | Edwards |
| 6,632,227 B2 | 10/2003 | Adams |
| 6,645,201 B1 | 11/2003 | Utley et al. |
| 6,652,545 B2 | 11/2003 | Shipp et al. |
| 6,660,301 B1 | 12/2003 | Vogel et al. |
| 6,663,639 B1 | 12/2003 | Laufer et al. |
| 6,666,848 B2 | 12/2003 | Stone |
| 6,669,713 B2 | 12/2003 | Adams |
| 6,673,058 B2 | 1/2004 | Snow |
| 6,673,070 B2 | 1/2004 | Edwards et al. |
| 6,692,507 B2 | 2/2004 | Pugsley et al. |
| 6,695,764 B2 | 2/2004 | Silverman et al. |
| 6,695,866 B1 | 2/2004 | Kuehn et al. |
| 6,699,243 B2 | 3/2004 | West et al. |
| 6,712,074 B2 | 3/2004 | Edwards et al. |
| 6,712,814 B2 | 3/2004 | Edwards et al. |
| 6,716,226 B2 | 4/2004 | Sixto, Jr. et al. |
| 6,716,233 B1 | 4/2004 | Whitman |
| 6,725,866 B2 | 4/2004 | Johnson et al. |
| 6,743,240 B2 | 6/2004 | Smith et al. |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,793,652 B1 | 9/2004 | Whitman et al. |
| 6,808,491 B2 | 10/2004 | Kortenbach et al. |
| 6,821,285 B2 | 11/2004 | Laufer et al. |
| 6,824,548 B2 | 11/2004 | Smith et al. |
| 6,835,200 B2 | 12/2004 | Laufer et al. |
| 6,843,403 B2 | 1/2005 | Whitman |
| 6,843,794 B2 | 1/2005 | Sixto, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,916,332 B2 | 7/2005 | Adams |
| 6,926,722 B2 | 8/2005 | Geitz |
| 6,945,979 B2 | 9/2005 | Kortenbach et al. |
| 6,971,395 B2 | 12/2005 | Edwards et al. |
| 6,981,941 B2 | 1/2006 | Whitman et al. |
| 6,986,737 B2 | 1/2006 | Suzuki et al. |
| 7,032,798 B2 | 4/2006 | Whitman et al. |
| 7,033,370 B2 | 4/2006 | Gordon et al. |
| 7,066,944 B2 | 6/2006 | Laufer et al. |
| 7,077,856 B2 | 7/2006 | Whitman |
| 7,087,073 B2 | 8/2006 | Bonutti |
| 7,153,314 B2 | 12/2006 | Laufer et al. |
| 7,758,596 B2 | 7/2010 | Oz et al. |
| 2001/0049537 A1 | 12/2001 | Kortenbach |
| 2001/0056282 A1 | 12/2001 | Sonnenschein |
| 2002/0010418 A1 | 1/2002 | Lary et al. |
| 2002/0022851 A1 | 2/2002 | Kalloo et al. |
| 2002/0063143 A1 | 5/2002 | Adams et al. |
| 2002/0068945 A1 | 6/2002 | Sixto, Jr. et al. |
| 2002/0068946 A1* | 6/2002 | Kortenbach et al. .......... 606/142 |
| 2002/0078967 A1 | 6/2002 | Sixto, Jr. et al. |
| 2002/0082621 A1 | 6/2002 | Schurr et al. |
| 2002/0138086 A1 | 9/2002 | Sixto et al. |
| 2002/0173786 A1 | 11/2002 | Kortenbach et al. |
| 2002/0193816 A1 | 12/2002 | Laufer et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2002/0198549 A1 | 12/2002 | Sixto et al. |
| 2003/0019905 A1 | 1/2003 | Adams et al. |
| 2003/0036679 A1 | 2/2003 | Kortenbach et al. |
| 2003/0065340 A1 | 4/2003 | Geitz |
| 2003/0065359 A1 | 4/2003 | Weller et al. |
| 2003/0068326 A1 | 4/2003 | Gevas et al. |
| 2003/0069280 A1 | 4/2003 | Koch et al. |
| 2003/0069646 A1 | 4/2003 | Stinson |
| 2003/0083241 A1 | 5/2003 | Young |
| 2003/0086968 A1 | 5/2003 | Gray |
| 2003/0092699 A1 | 5/2003 | Uchida et al. |
| 2003/0130560 A1 | 7/2003 | Suzuki et al. |
| 2003/0130561 A1 | 7/2003 | Suzuki et al. |
| 2003/0135206 A1 | 7/2003 | Edwards et al. |
| 2003/0161887 A1 | 8/2003 | Klein |
| 2003/0163029 A1 | 8/2003 | Sonnenschein et al. |
| 2003/0167062 A1 | 9/2003 | Gambale et al. |
| 2003/0171645 A1 | 9/2003 | Silverman et al. |
| 2003/0181929 A1 | 9/2003 | Geitz |

| | | | |
|---|---|---|---|
| 2003/0188755 A1 | 10/2003 | Milbocker | |
| 2003/0191478 A1 | 10/2003 | Kortenbach et al. | |
| 2003/0192558 A1 | 10/2003 | Durgin | |
| 2003/0192559 A1 | 10/2003 | Durgin | |
| 2003/0195387 A1 | 10/2003 | Kortenbach et al. | |
| 2003/0195509 A1 | 10/2003 | Edwards et al. | |
| 2003/0196670 A1 | 10/2003 | Durgin | |
| 2003/0199731 A1 | 10/2003 | Silverman et al. | |
| 2003/0208209 A1 | 11/2003 | Gambale et al. | |
| 2003/0208211 A1 | 11/2003 | Kortenbach | |
| 2003/0216754 A1 | 11/2003 | Kraemer et al. | |
| 2003/0220657 A1 | 11/2003 | Adams | |
| 2003/0220660 A1 | 11/2003 | Kortenbach et al. | |
| 2003/0236535 A1 | 12/2003 | Onuki et al. | |
| 2003/0236536 A1 | 12/2003 | Grigoryants et al. | |
| 2004/0006336 A1 | 1/2004 | Swanson | |
| 2004/0006351 A1 | 1/2004 | Gannoe et al. | |
| 2004/0010245 A1 | 1/2004 | Cerier et al. | |
| 2004/0037887 A1 | 2/2004 | Bourne et al. | |
| 2004/0044364 A1 | 3/2004 | DeVries et al. | |
| 2004/0059349 A1 | 3/2004 | Sixto et al. | |
| 2004/0059350 A1 | 3/2004 | Gordon et al. | |
| 2004/0059354 A1 | 3/2004 | Smith et al. | |
| 2004/0059358 A1 | 3/2004 | Kortenbach et al. | |
| 2004/0082859 A1 | 4/2004 | Schaer | |
| 2004/0082950 A1 | 4/2004 | Edwards et al. | |
| 2004/0082963 A1 | 4/2004 | Gannoe et al. | |
| 2004/0116948 A1 | 6/2004 | Sixto et al. | |
| 2004/0133238 A1 | 7/2004 | Cerier | |
| 2004/0147943 A1 | 7/2004 | Kobayashi | |
| 2004/0153107 A1 | 8/2004 | Kayan et al. | |
| 2004/0162568 A1 | 8/2004 | Saadat et al. | |
| 2004/0176783 A1 | 9/2004 | Edoga et al. | |
| 2004/0193184 A1 | 9/2004 | Laufer et al. | |
| 2004/0193193 A1 | 9/2004 | Laufer et al. | |
| 2004/0193194 A1 | 9/2004 | Laufer et al. | |
| 2004/0194790 A1 | 10/2004 | Laufer et al. | |
| 2005/0033320 A1 | 2/2005 | McGuckin et al. | |
| 2005/0033328 A1 | 2/2005 | Laufer et al. | |
| 2005/0216036 A1 | 9/2005 | Nakao | |
| 2006/0025789 A1 | 2/2006 | Laufer et al. | |
| 2009/0198254 A1 | 8/2009 | Laufer et al. | |

FOREIGN PATENT DOCUMENTS

| | | |
|---|---|---|
| EP | 0 576 265 | 12/1993 |
| EP | 0593920 | 4/1994 |
| EP | 593920 A1 | 4/1994 |
| EP | 0 646 356 | 4/1995 |
| EP | 0 668 058 | 8/1995 |
| EP | 0 743 044 | 4/2003 |
| EP | 0 975 263 | 10/2003 |
| FR | 2 768 324 | 3/1999 |
| GB | 2075829 A | 11/1981 |
| JP | 61122852 A | 6/1986 |
| JP | 1151461 A | 6/1989 |
| JP | 05103241 A | 4/1993 |
| JP | 05323412 A | 12/1993 |
| JP | 08006102 A | 1/1996 |
| JP | 2000254143 A | 9/2000 |
| JP | 2001507972 T | 6/2001 |
| JP | 2003051982 A | 2/2003 |
| JP | 2006311060 A | 11/2006 |
| WO | 8911827 A1 | 12/1989 |
| WO | WO-9529635 A1 | 11/1995 |
| WO | 9627345 A2 | 9/1996 |
| WO | 9803151 | 1/1998 |
| WO | 9900059 | 1/1999 |
| WO | WO 99/22649 | 5/1999 |
| WO | WO 99/60931 | 12/1999 |
| WO | WO 00/35529 | 12/2000 |
| WO | WO 00/78227 | 12/2000 |
| WO | WO 00/78229 | 12/2000 |
| WO | 0185034 | 11/2001 |
| WO | WO 02/24080 | 3/2002 |
| WO | 0228289 | 4/2002 |
| WO | WO 02/40081 | 5/2002 |
| WO | WO 02/45603 | 6/2002 |
| WO | 02076541 | 10/2002 |
| WO | WO 02/076541 | 10/2002 |
| WO | 02094341 A2 | 11/2002 |
| WO | WO 02/094341 | 11/2002 |
| WO | WO 03/000115 | 1/2003 |
| WO | WO 03/004087 | 1/2003 |
| WO | WO 03/007796 | 1/2003 |
| WO | WO 03/015604 | 2/2003 |
| WO | WO 03/030782 | 4/2003 |
| WO | WO 03/035649 | 5/2003 |
| WO | WO 03/037256 | 5/2003 |
| WO | WO 03/053253 | 7/2003 |
| WO | WO 03/072196 | 9/2003 |
| WO | WO 03/082359 | 10/2003 |
| WO | 03096885 A2 | 11/2003 |
| WO | WO 03/090633 | 11/2003 |
| WO | WO 03/092498 | 11/2003 |
| WO | WO 03/092509 | 11/2003 |
| WO | WO 03/094800 | 11/2003 |
| WO | WO 03/096885 | 11/2003 |
| WO | WO03098885 | 11/2003 |
| WO | WO 03/099137 | 12/2003 |
| WO | WO 03/099139 | 12/2003 |
| WO | WO 03/099140 | 12/2003 |
| WO | WO 03/099376 | 12/2003 |
| WO | WO 03/105917 | 12/2003 |
| WO | WO 04/000129 | 12/2003 |
| WO | WO 2004/004542 | 1/2004 |
| WO | WO 2004/004544 | 1/2004 |
| WO | WO 2004/006990 | 1/2004 |
| WO | WO 2004/019787 | 3/2004 |
| WO | WO 2004/019788 | 3/2004 |
| WO | WO 2004/021872 | 3/2004 |
| WO | WO 2004/021873 | 3/2004 |
| WO | WO 2004/021894 | 3/2004 |
| WO | WO 2004/026348 | 4/2004 |
| WO | WO 2004/026349 | 4/2004 |
| WO | WO 2004/026350 | 4/2004 |
| WO | 2005086885 | 9/2005 |

OTHER PUBLICATIONS

Boerema, "Hiatus hernia: repair by right-sided, subhepatic, anterior gastropexy", Surgery, 1969, vol. 65, No. 6, p. 884-893.
Carvalho et al., "Fibrosis of gastric cardia after endoscopic sclerosis", The American Surgeon, vol. 56, p. 163-166, 1990.
Cecconello et al., "Esophagogastric anastomosis with valvuloplasty: an experimental study", International Surgery, 1982, vol. 67, No. 2, p. 121-124.
Collis, "An operation for hiatus hernia with short esophagus", The journal of thoracic surgery, vol. 34, No. 6, p. 769-778.
Collis, "Surgical control of reflux in hiatus hernia", The American journal of surgery, vol. 115, 1968, p. 465-471.
Contractor et al., "Endoscopic esophagitis and gastroesophageal flap valve", J. Clin. Gastroenterol., 1999, vol. 28, No. 3, p. 233-237.
Cuschieri et al., "Multicenter prospective evaluation of laparoscopic antireflux surgery", Surgical endoscopy, vol. 7, No. 6, 1993, p. 505-510.
Demeester et al., "Nissen fundoplication for gastroesophageal reflux disease", Annals of Surgery, 1986, vol. 204, No. 1, p. 9-20.
Donahue et al., "Endoscopic control of gastro-esophageal reflux11:14 AM status report", World Journal of Surgery, 16: 343-346, 1992.
Donahue et al., "Endoscopic sclerosis of the gastric cardia for prevention of experimental gastroesophageal reflux", vol. 36, No. 3, 1990, p. 253-256.
Falk et al., "Laparoscopic fundoplication: a preliminary report of the technique and portoperative care", The Australian and New Zealand journal of surgery, vol. 62, No. 7, 1992, p. 969-972.
Hill et al., "Antireflux surgery", Gastroenterology Clinics of North America, vol. 19, No. 3, 1990, p. 745-775.
Hill et al., "Surgery for peptic esophageal stricture", p. 139-147.
Hill et al., "The esophagus, medical and surgical management", WB Saunders Co., 1988, p. 135-138.
Hill et al., "The gastroesophageal flap valve", J. Clin. Gastroenterol., 1999, vol. 28, No. 3, p. 194-197.
Hill et al., "The gastroesophageal flap valve: in vitro and in vivo observations", Gastrointestinal endoscopy, vol. 44, No. 5, 1996, p. 541-547.

Hill, "An effective operation for hiatal hernia: an eight year appraisal", Annals of Surgery, vol. 166, No. 4, 1967, p. 681-692.

Hill, "Intraoperative measurement of lower esophageal sphincter pressure", The journal of thoracic and cardiovascular surgery, 1978, vol. 75(3), p. 378-382.

Hill, "Myths of the esophagus", The journal of thoracic and cardiovascular surgery, 1989, vol. 98, No. 1, p. 1-10.

Hinder et al., "The surgical option for gastroesophageal reflux disease", Symposium on gastroesophageal reflux disease, Am J. Med., 103: 1445-'485, 1997.

Ismail et al., "Yield pressure, anatomy of the cardia and gastro-oesophageal reflux", Br. J. Surg. 1005, vol. 82, No. 7, p. 943-947.

Ismail et al., "Yield pressure: a new concept in the evaluation of GERD?", AJG, 91: p. 616-617, 1996.

Jamieson et al., "Laparoscopic Nissen fundoplication", Annals of surgery, vol. 220, No. 2, p. 137-145.

Jamieson, "The development of surgery for gastro-oesophageal reflux disease", Surgery of the esophagus, p. 233-245.

Janssen et al., "Prospective randomized comparison of teres cardiopexy and Nissen fundoplication in the surgical therapy of gastro-oesophageal reflux disease", The British journal of surgery, vol. 80, No. 7, 1993, p. 875-877.

Jennings et al., "A novel endoscopic transgastric fundoplication procedure for gastroesophageal reflux: an initial animal evaluation", Journal of laparoendoscopic surgery, vol. 2, No. 5, 1992, p. 207-213.

Kadirkamanathan et al., "An ambulant porcine model of acid reflux used to evaluate endoscopic gastroplasty", Gut, 1999, vol. 44, No. 3, p. 1630166.

Kadirkamanathan et al., "Antireflux operations at flexible endoscopy using endoluminal stitching techniques: an experimental study", Gastrointestinal endoscopy, vol. 44, No. 2, 1996, p. 133-143.

Kahrilas, "Gastroesophageal reflux disease", JAMA, 1996, vol. 276, No. 12, p. 963-968.

Kraemer et al., "Laparoscopic Hill repair", Gastrointestinal endoscopy, vol. 40, No. 2, part 1, 1994, p. 155-159.

Little, "Mechanisms of action of antireflux surgery: theory and fact", World J. Surg., vol. 16, 1992, p. 320-325.

Mason et al., "A new intraluminal antigastroesophageal reflux procedure in baboons", Gastrointestinal endoscopy, vol. 45, No. 3, 1997, p. 283-290.

Mason et al., Nissen fundoplication prevents shortening of the sphincter during gastric distention, Arch. Surg., 1997, vol. 132, p. 719-726.

McGouran et al., "A laser-induced scar at the cardia increases the yield presurre of the lower esophageal sphincter", Gastrointestinal endoscopy, vol. 36, No. 5, 1990, p. 439-443.

McGouran et al., "Does measurement of yield pressure at the cardia during endoscopy provide information on the function of the lower oesophageal sphincter mechanism?", Gut, 1988, vol. 29, 275-278.

McGouran et al., "Is yield pressure at the cardia increased by effective fundoplication?", Gut, 1989, vol. 30, p. 1309-1312.

McKernan, "Laparoscopic repair of gastroesophageal reflux disease", Surgical Endoscopy, vol. 8, 1994, p. 851-856.

Nathanson et al., "Laparoscopic ligamentum teres (round ligamentum) cardiopexy", The British Journal of Surgery, vol. 78, No. 8, 1991, p. 947-951.

Nissen, "Eine einfache operation zur beeinflussung der refluxoesophagitis", Schweizerische Medizinische Wochenschrift, 1956, vol. 86, p. 590-592.

O'Connor et al. "An experimental endoscopic technique for reversing gastroesophageal reflux in dogs by injecting inert material in the distal esophagus", Gastrointestinal Endoscopy, vol. 30, No. 5, 1984, p. 275-280.

O'Connor et al. "Endoscopic placement of collagen at the lower esophageal sphincter to inhibit gastroesophageal reflux: a pilot study of 10 medically intractable patients", Gastrointestinal Endoscopy, vol. 34, No. 2, 1988, p. 106-112.

Pedinelli, "Traitement chirugical de la hernie hiatale par la "technique du collet""., Ann. Chir., vol. 18, p. 1461-1474, No. 23-24.

Polk et al., "Hiatal hernia and esophagitis: a survey of indications for operation and technic and results of fundoplication", presented at the Southern Surgical Association meeting held at Boca Raton, Florida, Dec. 7-9, 1970, p. 775-781.

Rampal et al., "Technique chirurgicale", La presse medicale, vol. 75, No. 12, 1967, p. 2-4.

Rich, "Simple GERD treatment offers new alternative", vol. 35, No. 11, 1999.

Rupp et al., "Endoscopic antireflux techniques", Gastrointestinal endoscopy clinics of North America, vol. 4, No. 2, 1994, p. 353-368.

Shafik, "Intraesophageal polytef injection for the treatment of reflux esophagitis", Surgical Endoscopy, 1996, vol. 10, p. 329-331.

Singh et al., "Evaluation of the Endoscopic Suturing System in the Treatment of the GERD", Conference Abstract for Plenary Session for Digestive Disease Week, p. 314 & A-802, May 16-19, 1999.

Skinner et al., "Surgical Management of Esophageal Reflux and Hiatus Hernia", Journal of Thoracic and Cardiovascular Surgery, vol. 53, No. 1, 1967, p. 33-54.

Slim et al., "Intraoperative esophageal manometry and fundoplications: prospective study", World J. Surg. vol. 20, p. 55-59, 1996.

Starling et al., "Assessment of the angelchik prosthesis for treatment of symptomatic esophageal reflux", World J. Surg., 1987, vol. 11, p. 350-355.

The Americal journal of gastroenterology, vol. 91, No. 3, 1996, p. 616-617.

Thor et al., "Reappraisal of the flap valve mechanism in the gastroesophageal junction", Acta Chir Scand. vol. 153, p. 25-28, 1987.

Tocomal et al., "A mucosol flap valve mechanism to prevent gastroesophageal reflux and esophagitis", Surgery, 1968, vol. 64, No. 2, p. 519-523.

Wang et al., "A new anti-flux procedure: cardaic oblique invagination", Chung Hua Wai Ko Tsa Chih, 33(2) p. 73-75, Feb. 1995 (English abstract).

Watson et al., "Comparison of anterior, posterior and total fundoplication using a viscera model", Disease of the esophagus, 1997, vol. 10, p. 110-114.

Westbrook et al., "Posterior surgical approaches to the rectum", Annals of Surgery, vol. 195, No. 6, 1982, p. 686-691.

European Search Report dated Sep. 2, 2004 in EP 04076389.

** International Search Report dated Oct. 16, 2000.

** International Search Report dated Oct. 22, 2003.

DeMeester, MD et al Nissen Fundoplication for Gastroesophageal Reflux Disease Annals of Surgery 204:9-20 (1986).

Digestive Disease Week, Orange County Convention Center, p. A-802; 314.

Eurpoean Search Report mailed Jul. 10, 2007 in EP Application No. 07075291.

McGouran RC et al., Is yield pressure at the cardia increased by effective fundoplication? Gut Oct. 1989; 30(10): 1309-12.

Donahue, M.D., et al. "Endoscopic Control of Gastro-Esophagel Reflux: Status Report," World Journal of Surgery, 16:343-346 (1992).

Starling et al., "Treatment of Symptomatic Gastroesophageal Reflux Using the Angelchika Prosthesis," Ann. Surg. (1982) 686:690.

Japanese Preliminary Report (Application No. 2004-506665) dated Mar. 31, 2009.

Japanese Office Action for Application No. 2005-122394 dated May 12, 2009.

Japanese Office Action for Application No. 2004-131922 dated Jan. 18, 2010 (English translation).

Feb. 17, 2009, Office Action for U.S. Appl. No. 10/819,996.

Feb. 20, 2009, Office Action for U.S. Appl. No. 10/819,957.

O'Connor KW and Lehman GA, Endoscopic placement of collagen at the lower esophageal sphicter to inhibit gastroesophageal reflux: a pilot study of 10 medically intractable patients. *Gastrointest. Endosc.* Mar.-Apr. 1988 34(2):106-12.

European Office Action dated Apr. 3, 2009 in EP07075291.0.

Moss Tubes advertisement, Annals of Surgery, vol. 220, No. 2, Aug, 1994 (2 pages).

European Office Action dated Feb. 11, 2010 in EP03 728 882.6.

European Office Action dated Sep. 11, 2009 in EP05 077 998.2.

Dodds WJ et al. 1982, N Engl J Med 307:1547-52.

Hetzel DJ et al. 1988, Gastroenterology 95:903-12.
Klinkenberg-Knol EC and Meuwissen SG 1988, Aliment Pharmacol Ther 2:221-7.
Lambert R et al. 1993, Gastroenterology 104:1554-7.
Poynter D et al. 1985, Gut 26:1284-95.

Solcia E et al. 1993, Aliment Pharmacol Ther 7(supp. 1):25-8.
Spechler SJ 1992, N Engl J Med 326:786-92.
Klinkenberg-Knol EC and Meuwissen SG 1989, Digestion 1:47-53.

* cited by examiner

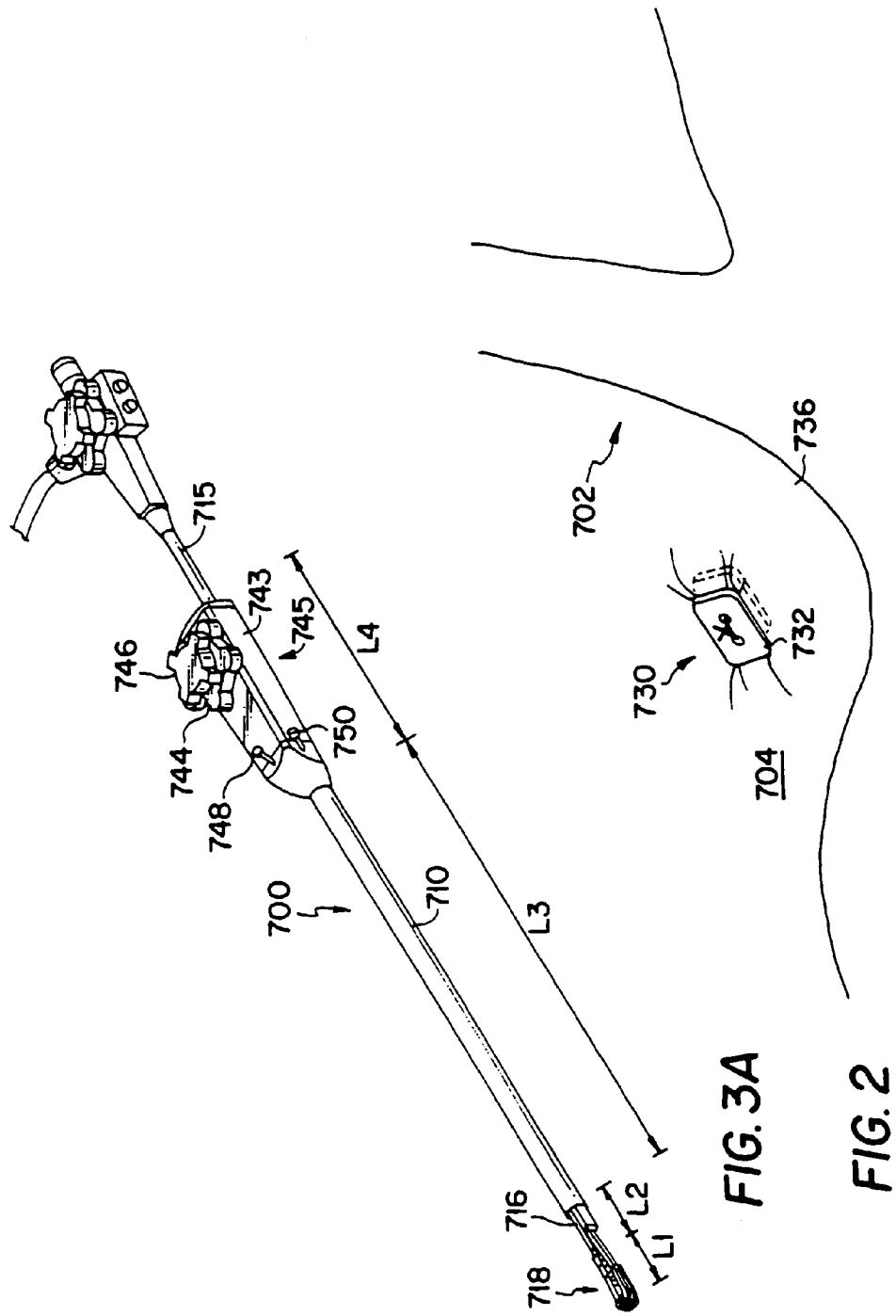

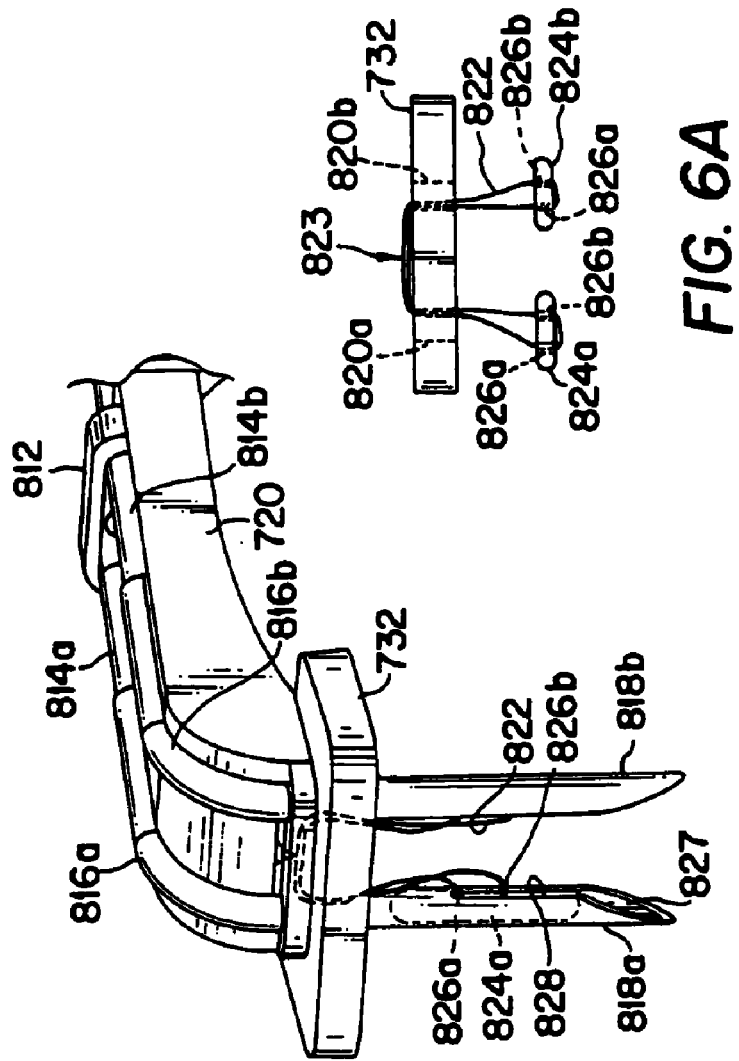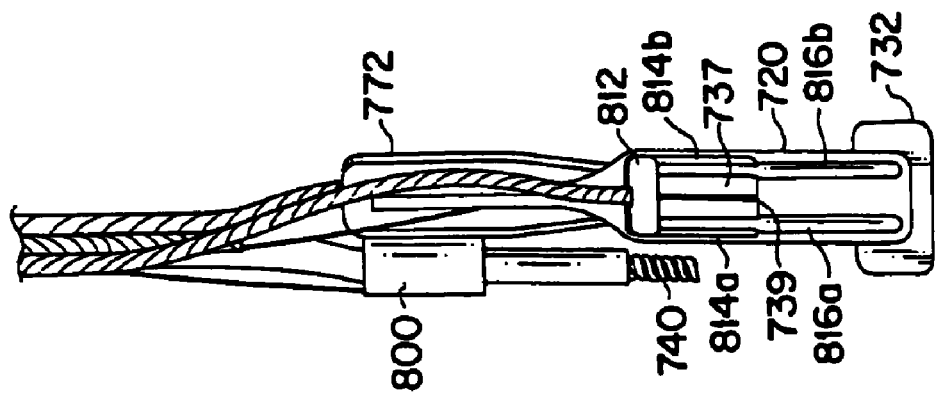

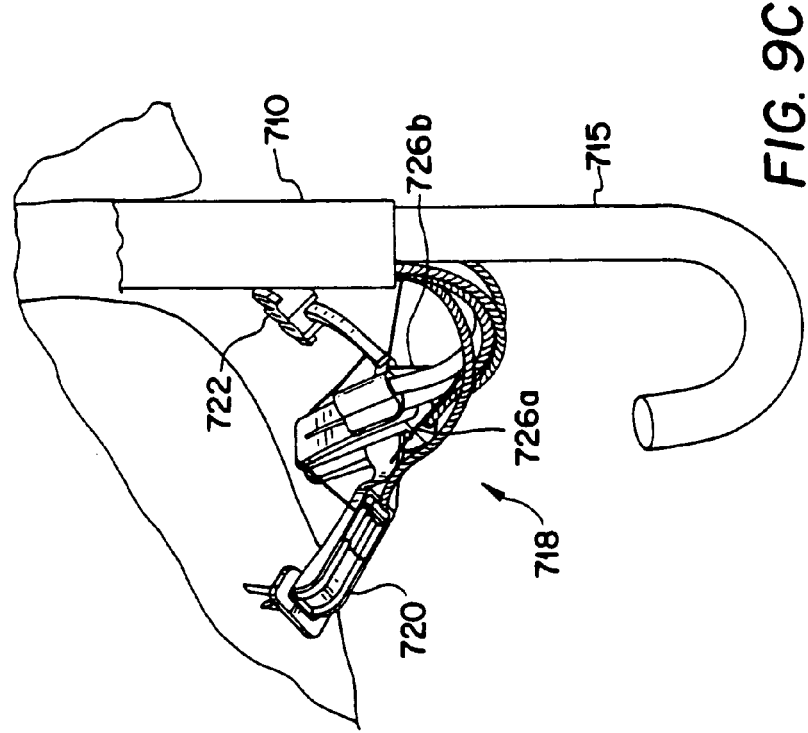
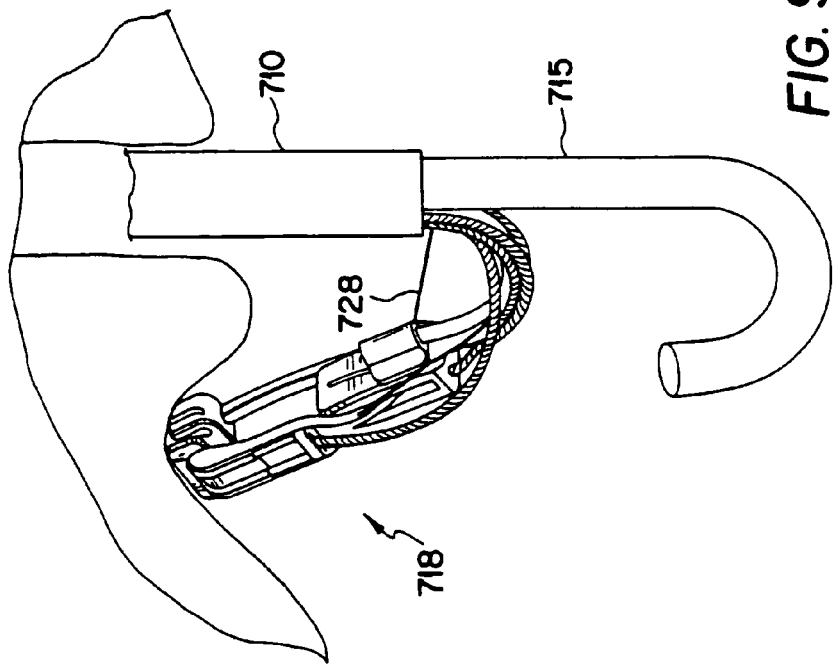

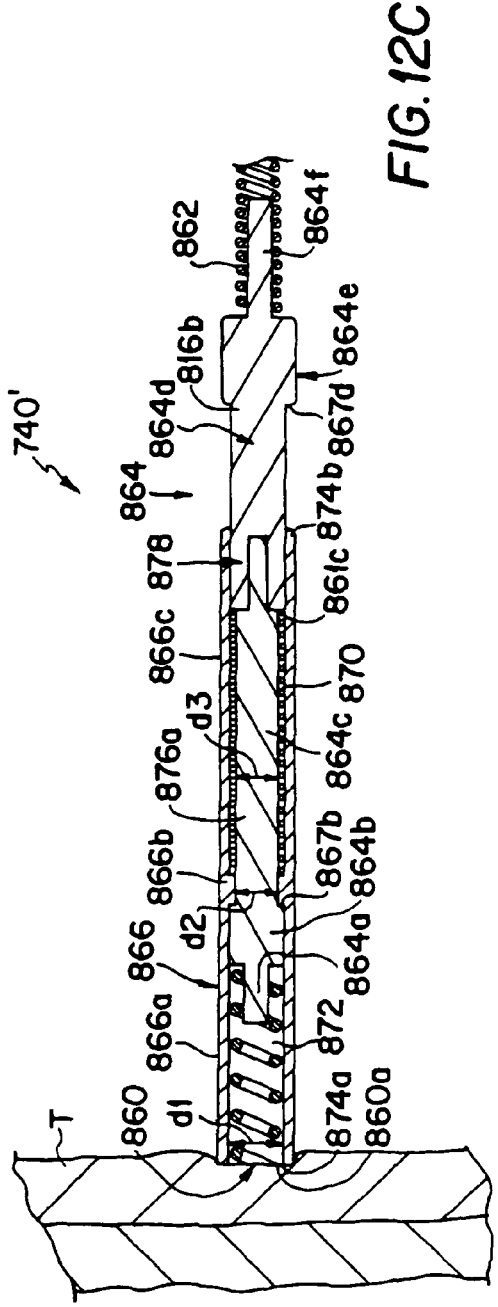
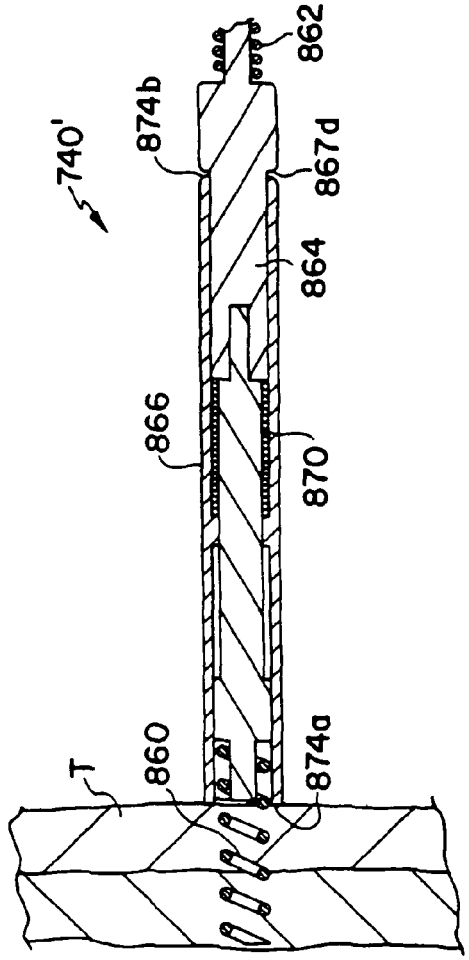
FIG.12C
FIG.12D

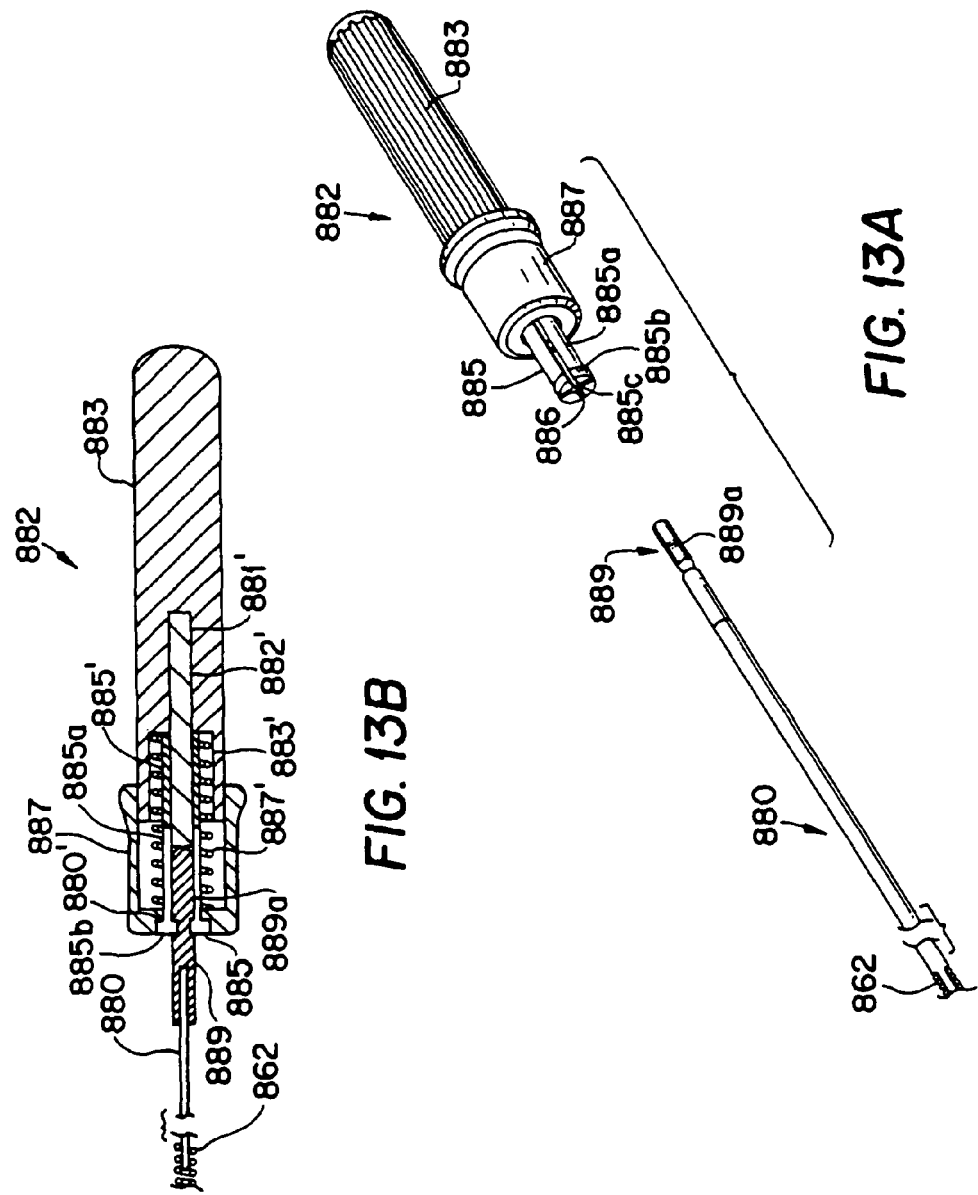

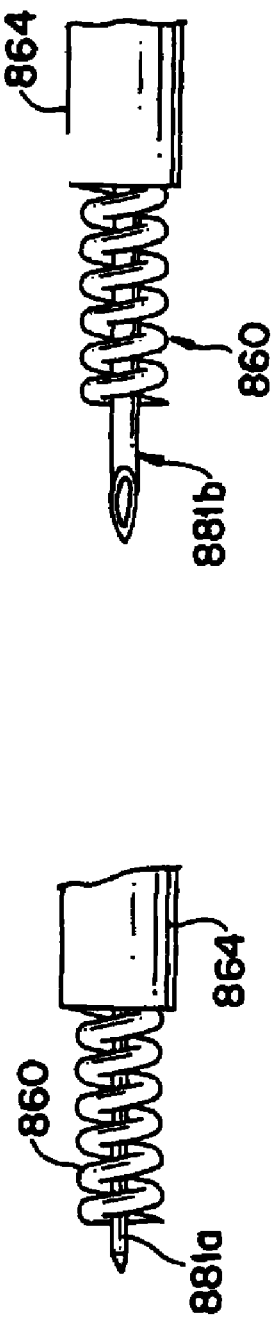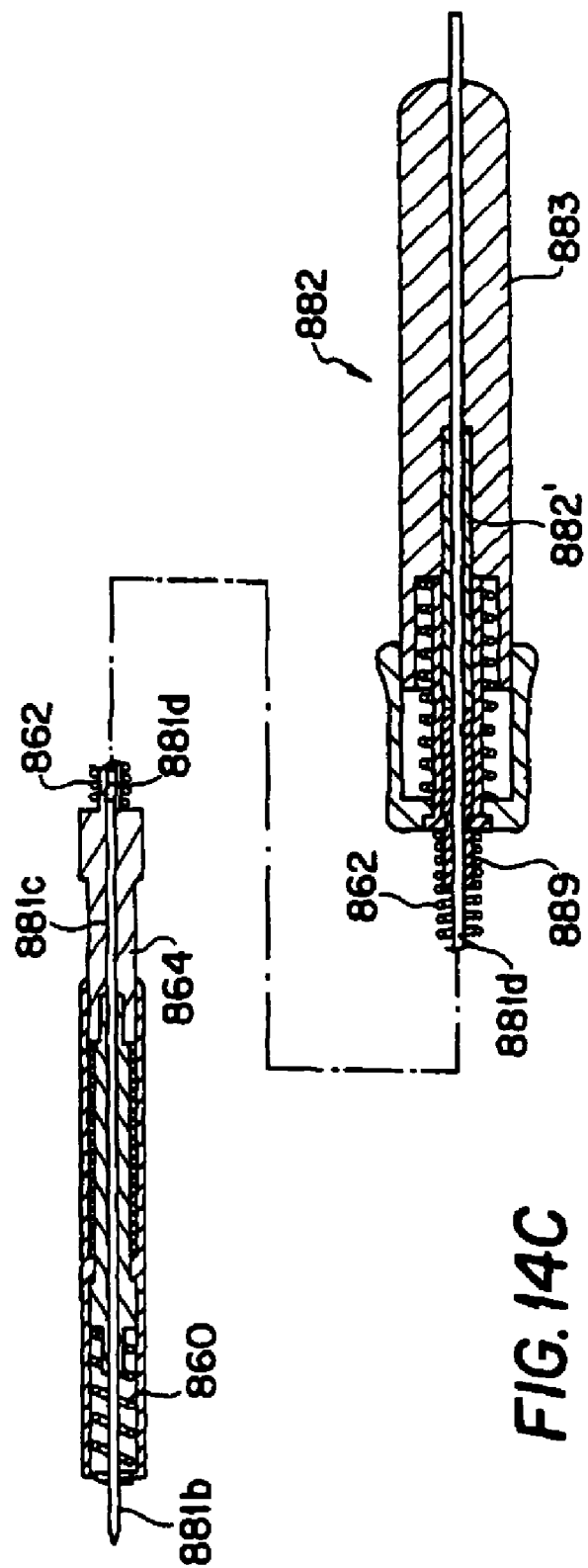
FIG. 14A
FIG. 14B
FIG. 14C

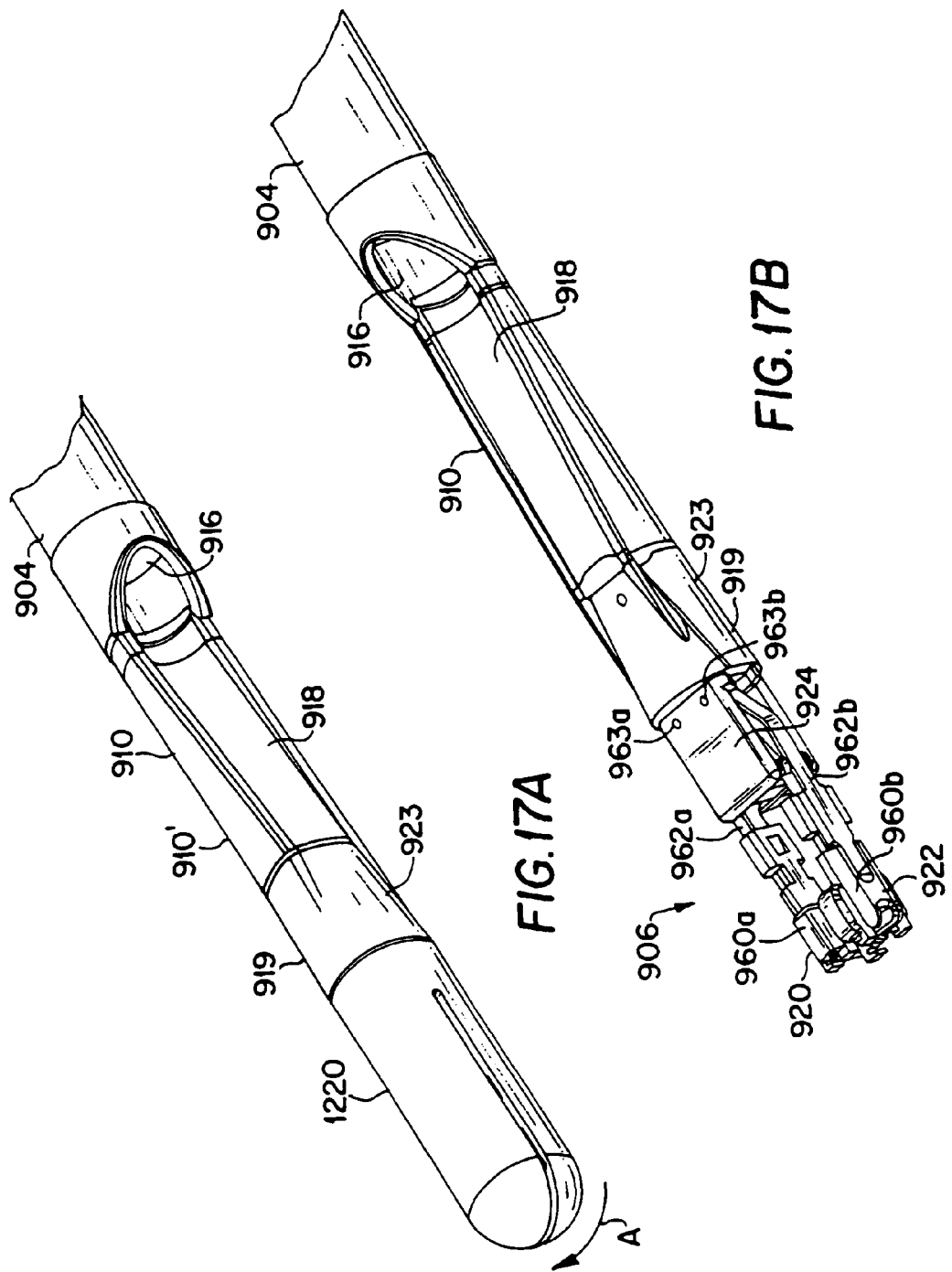

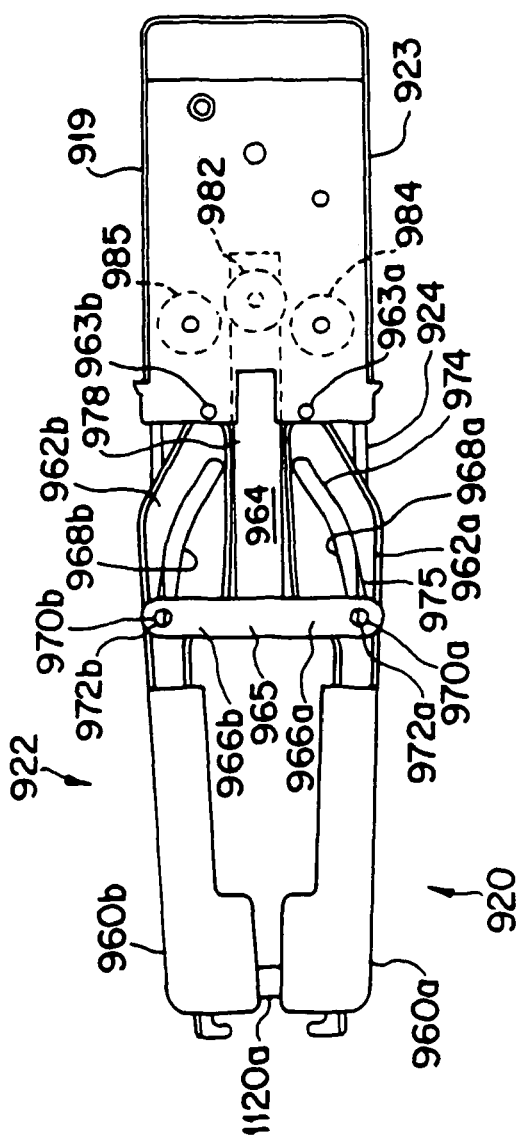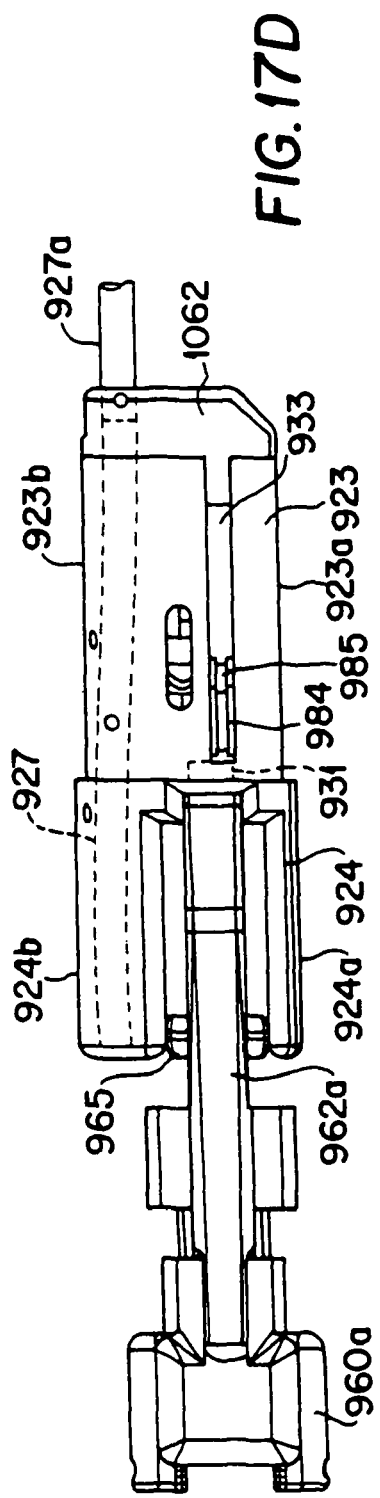

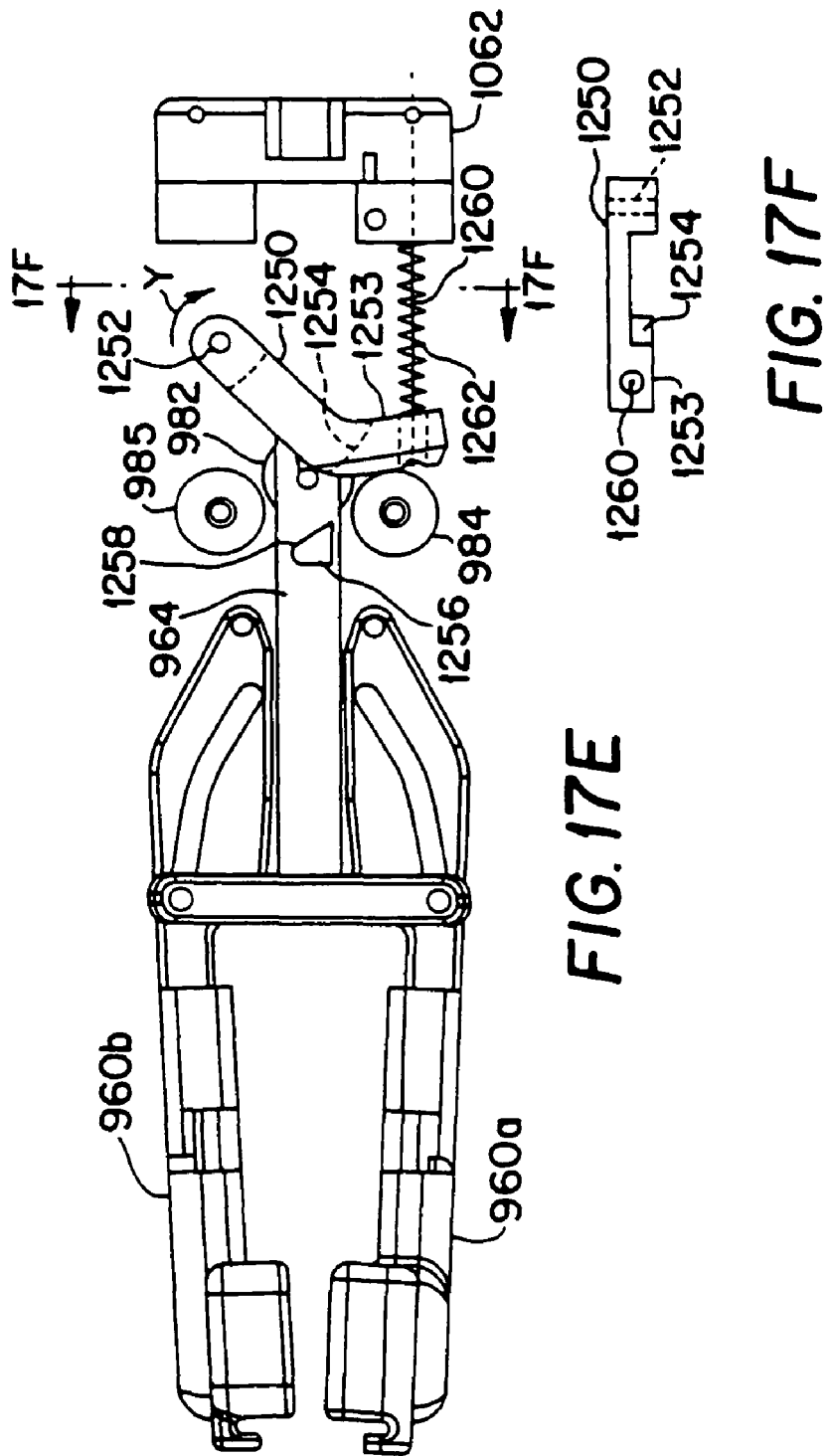

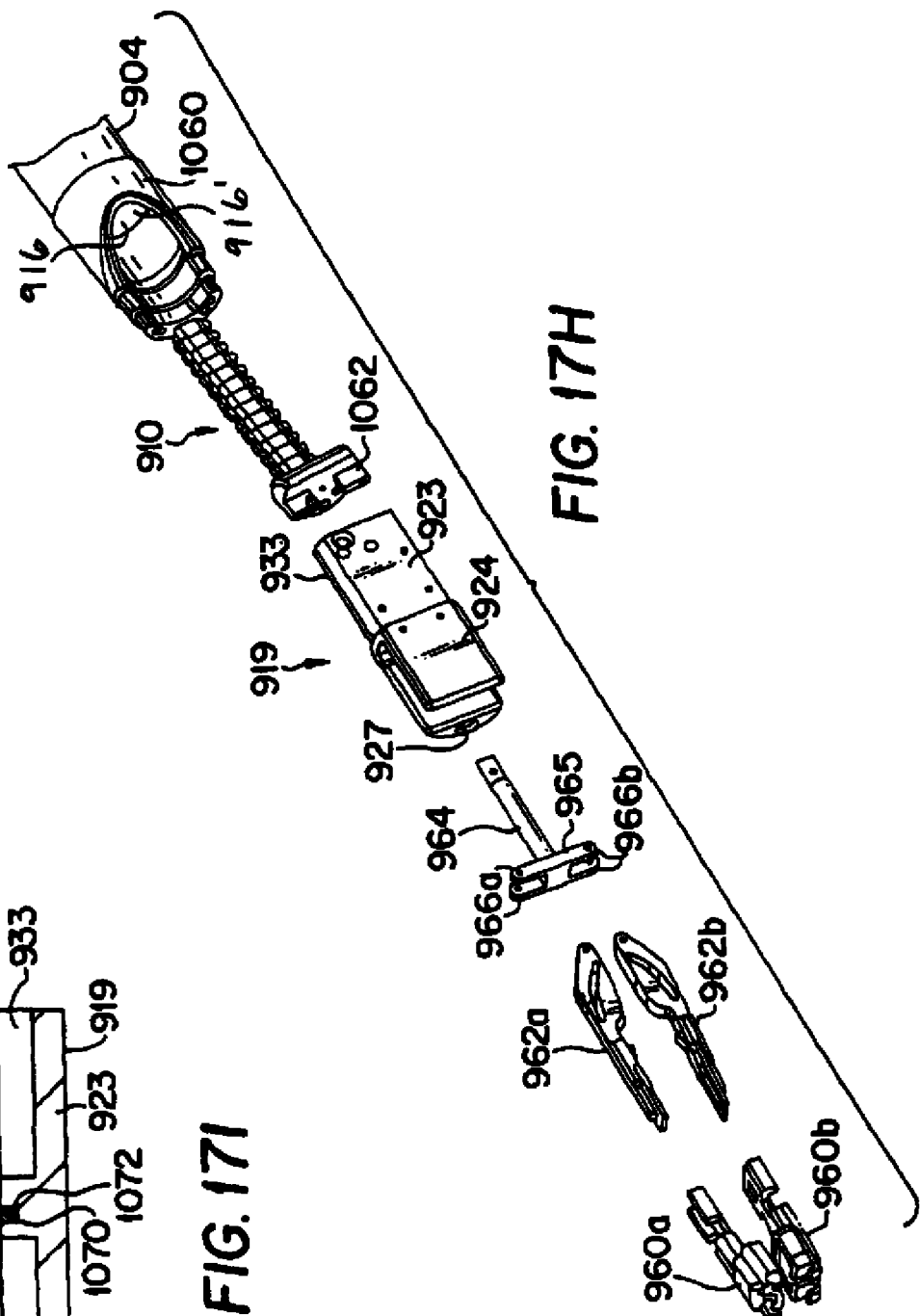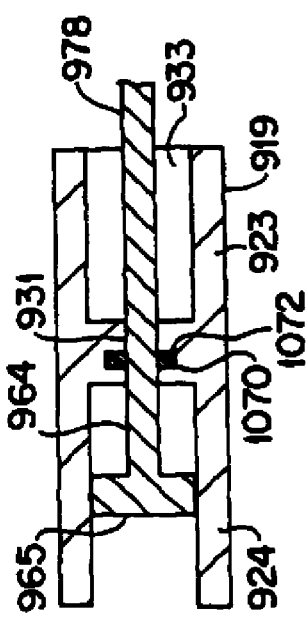

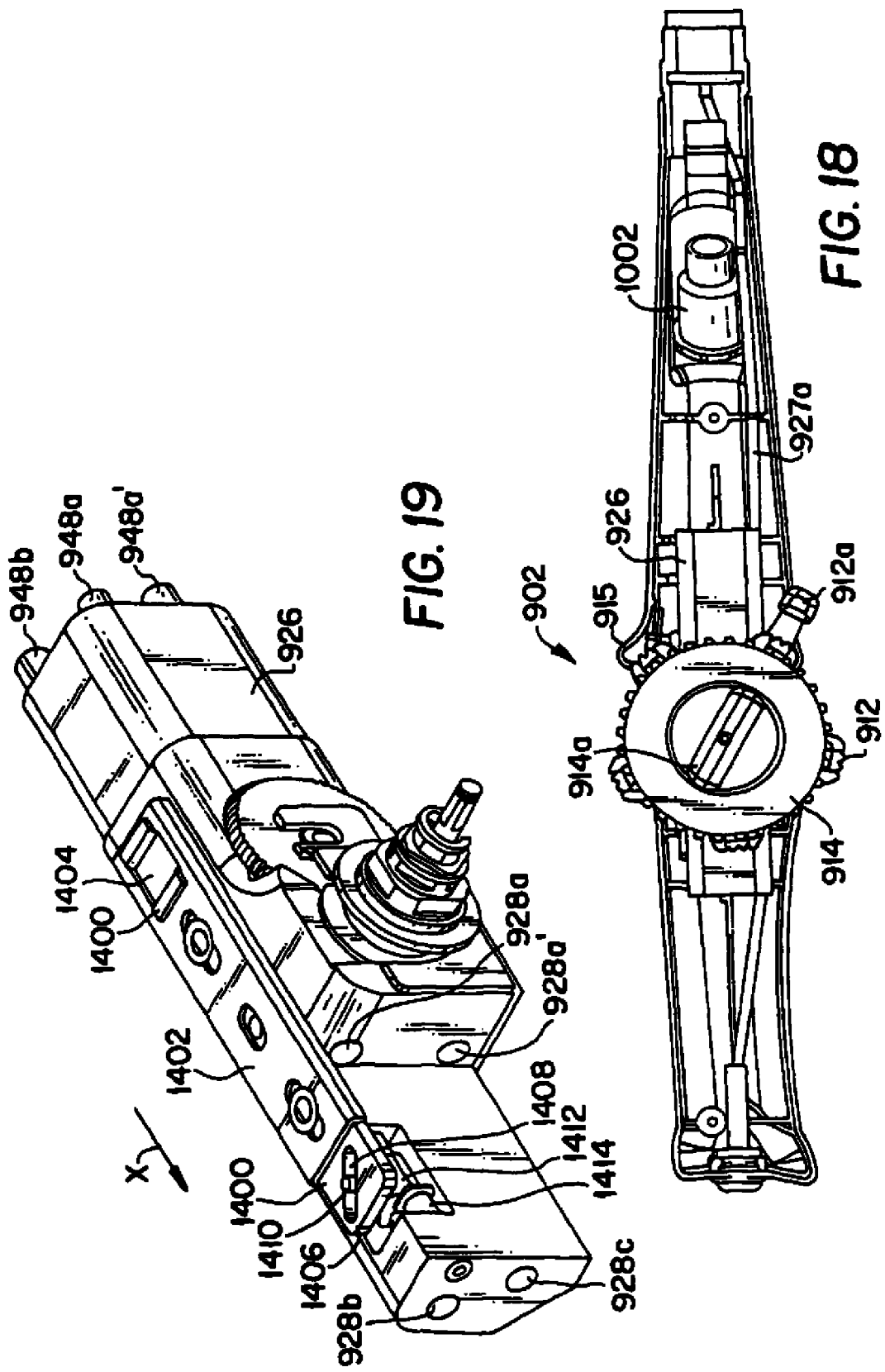

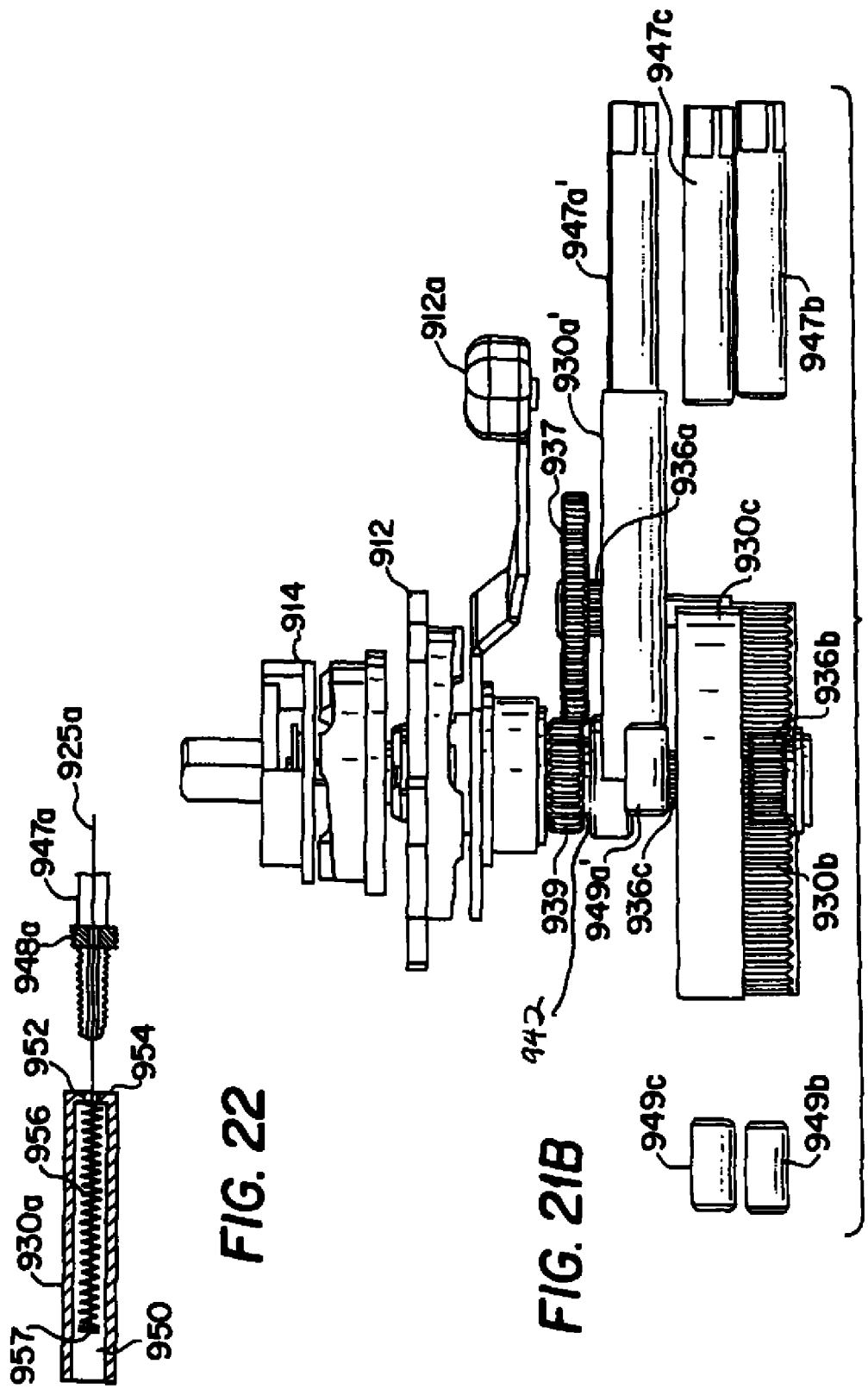

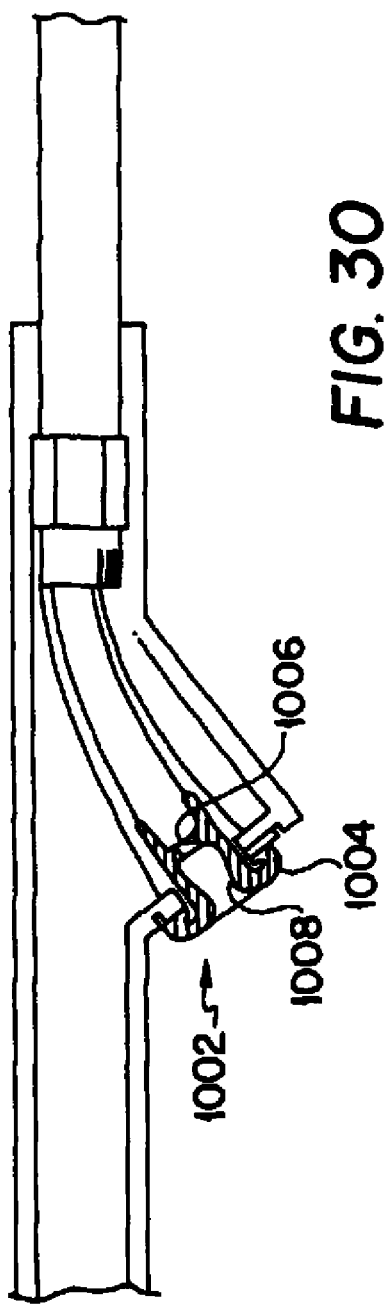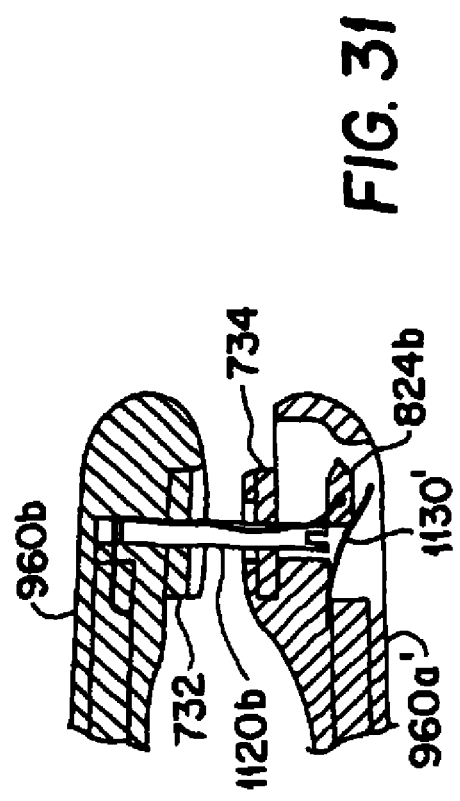

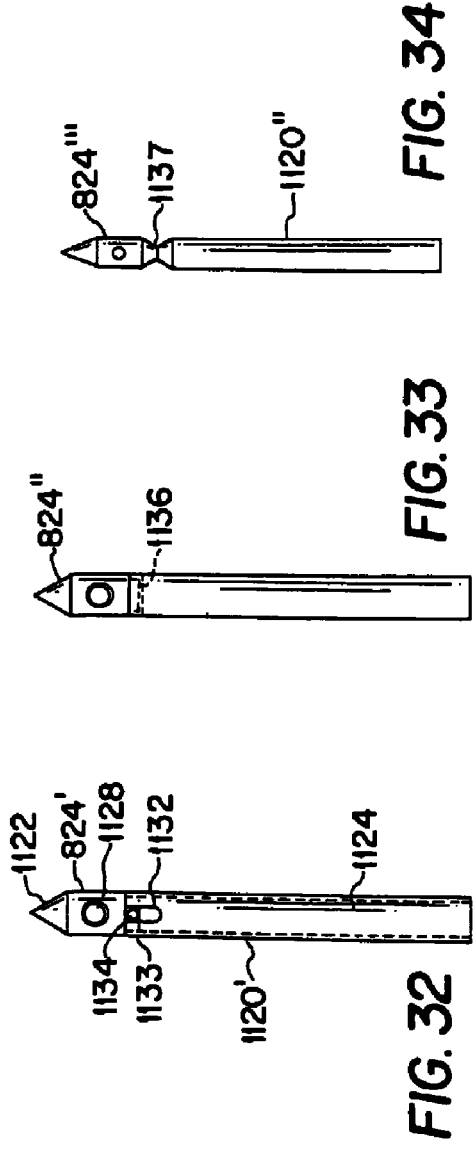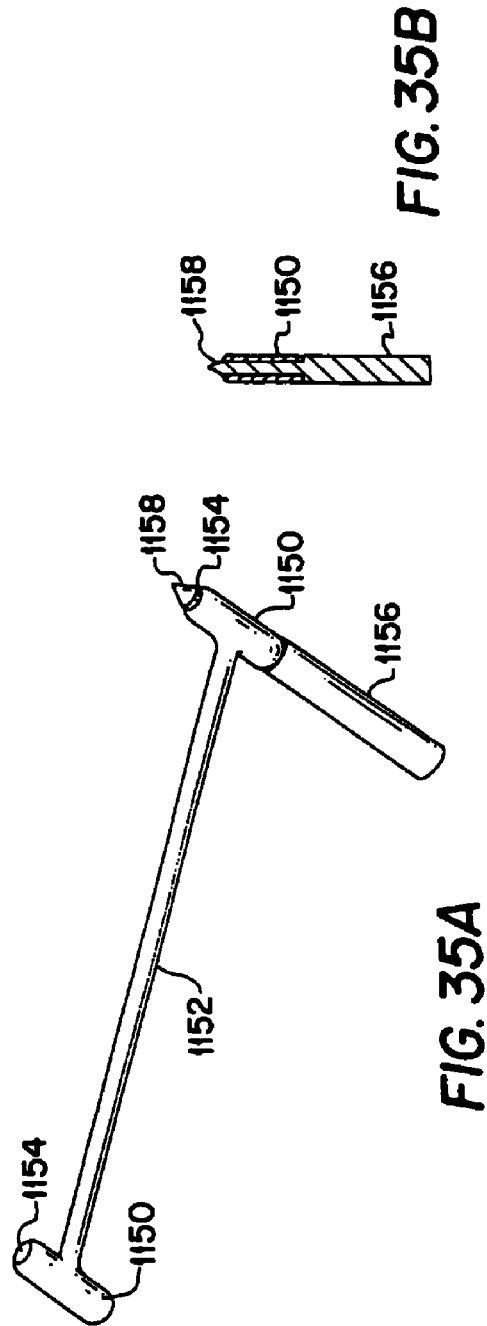

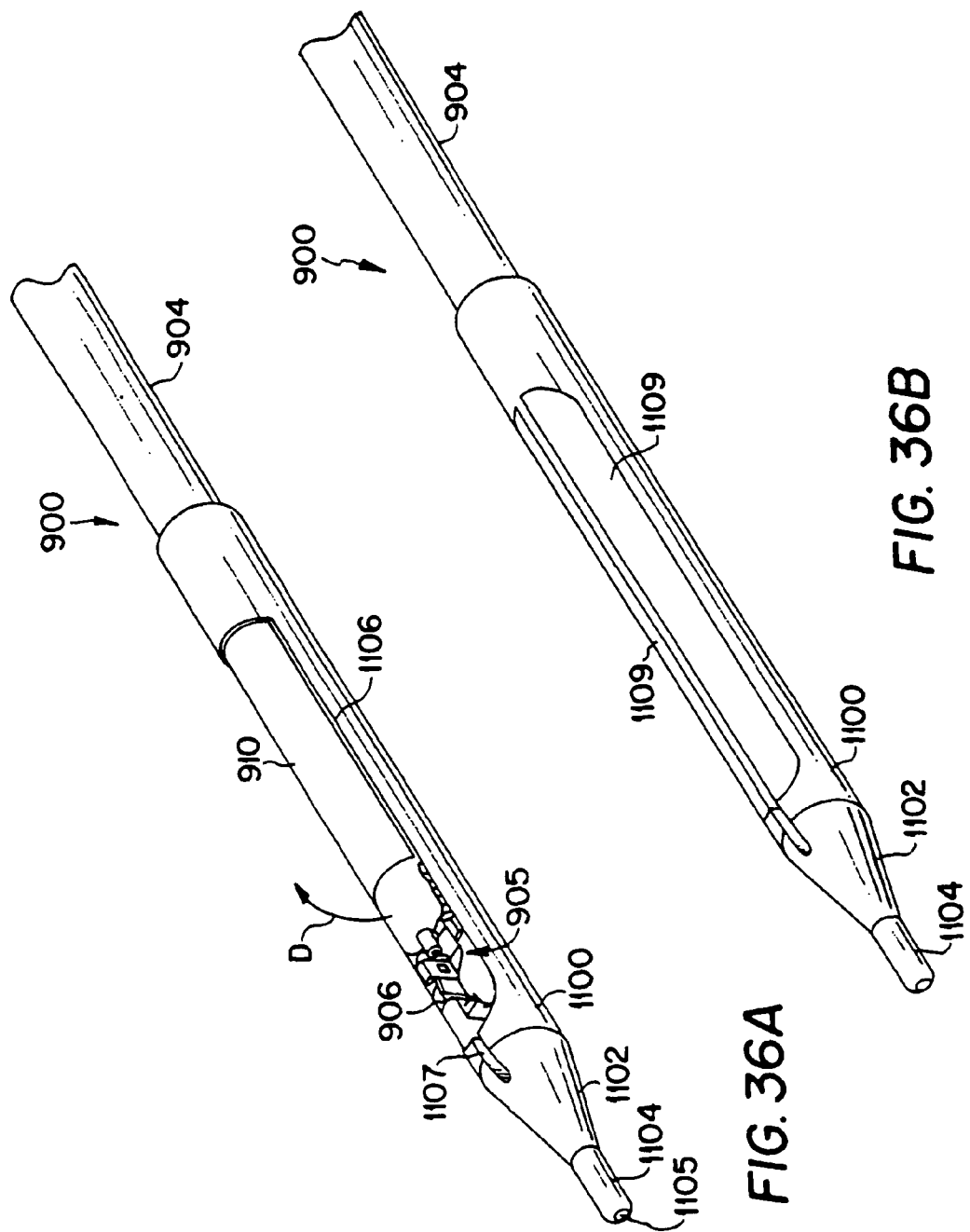

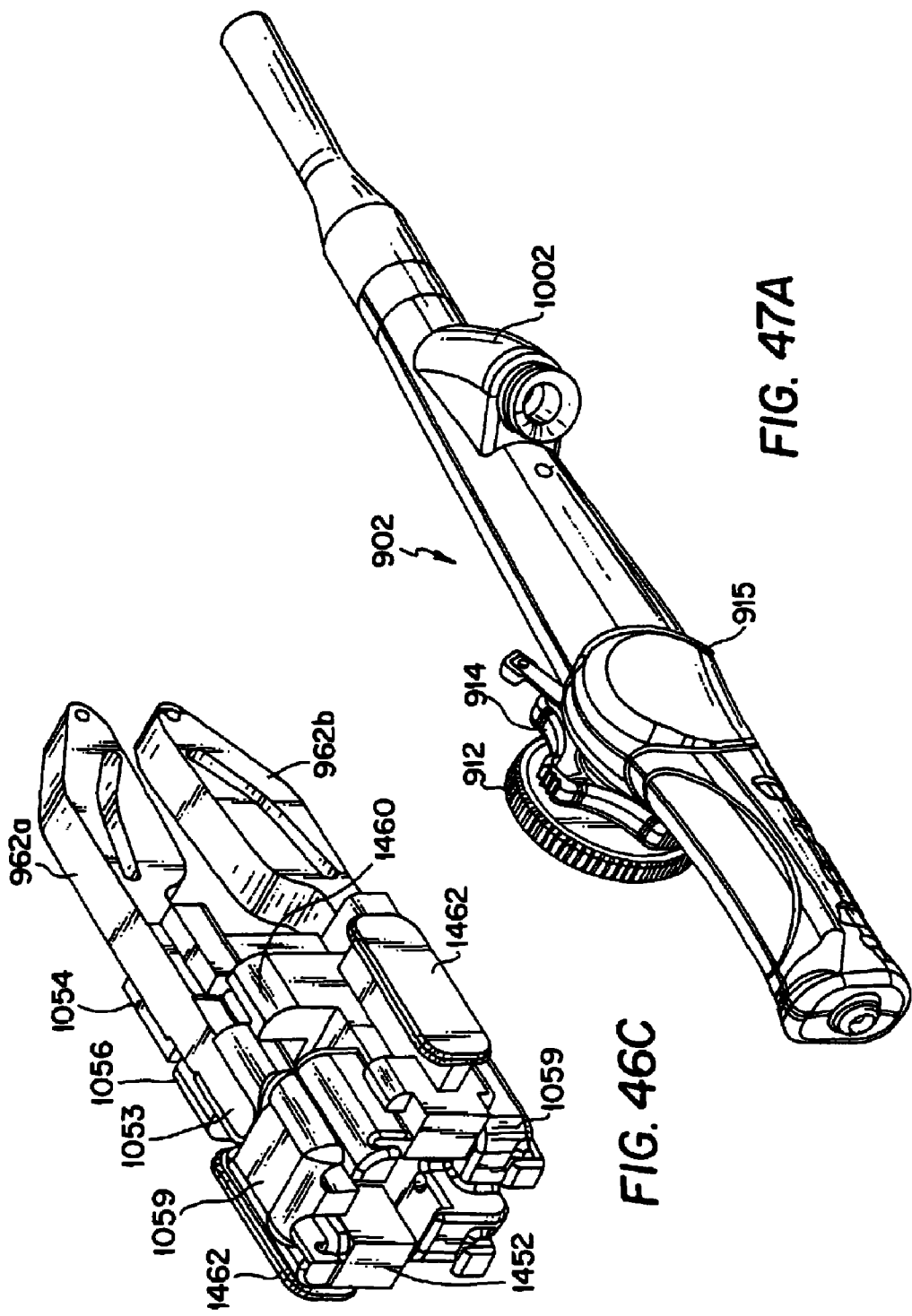

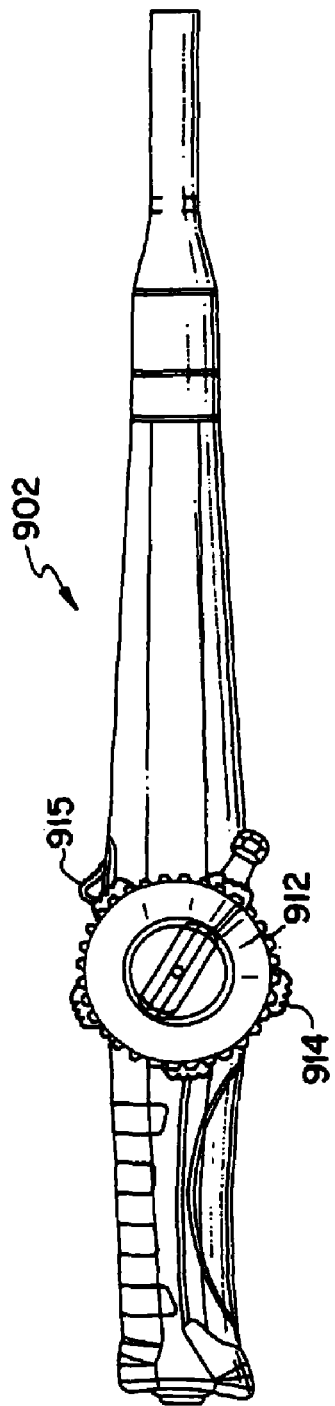
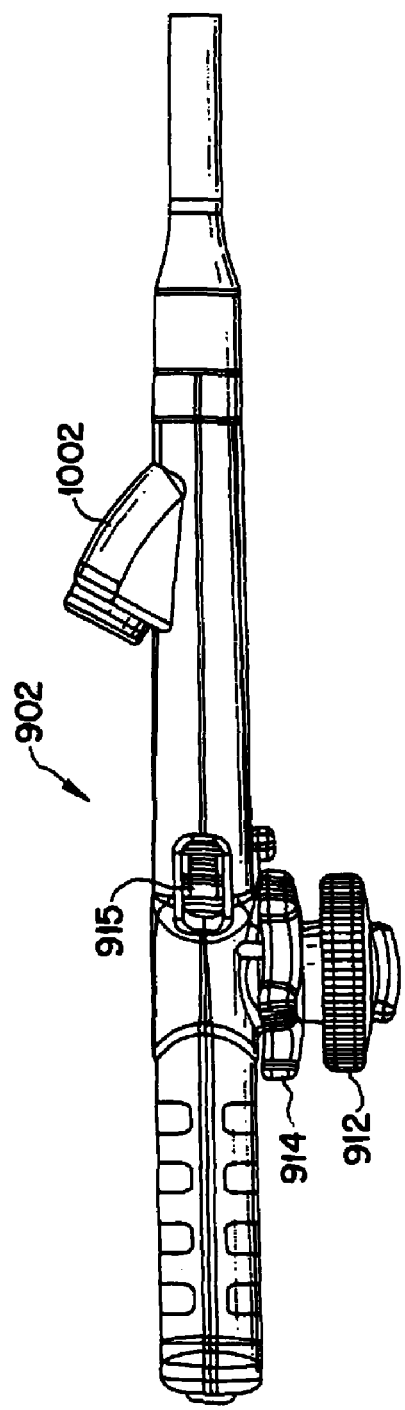

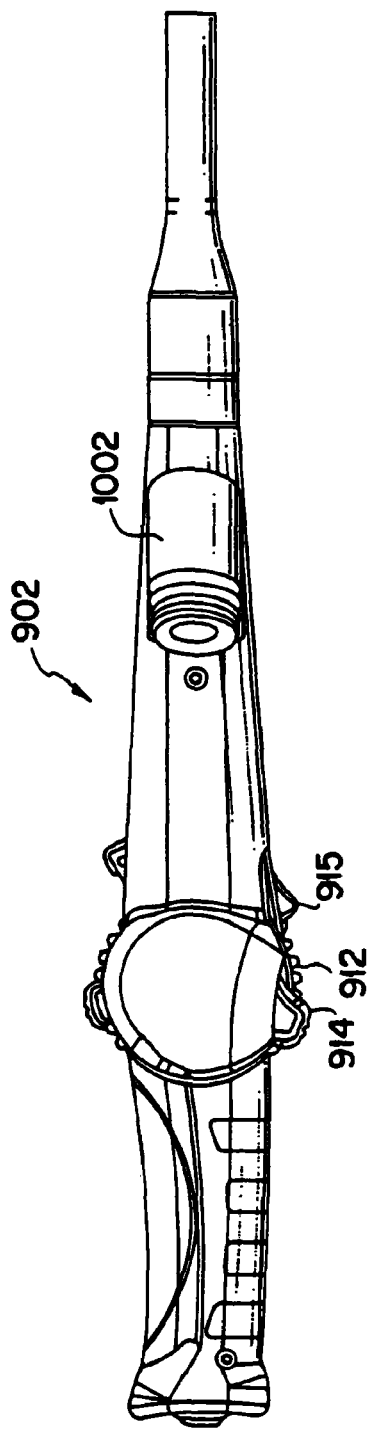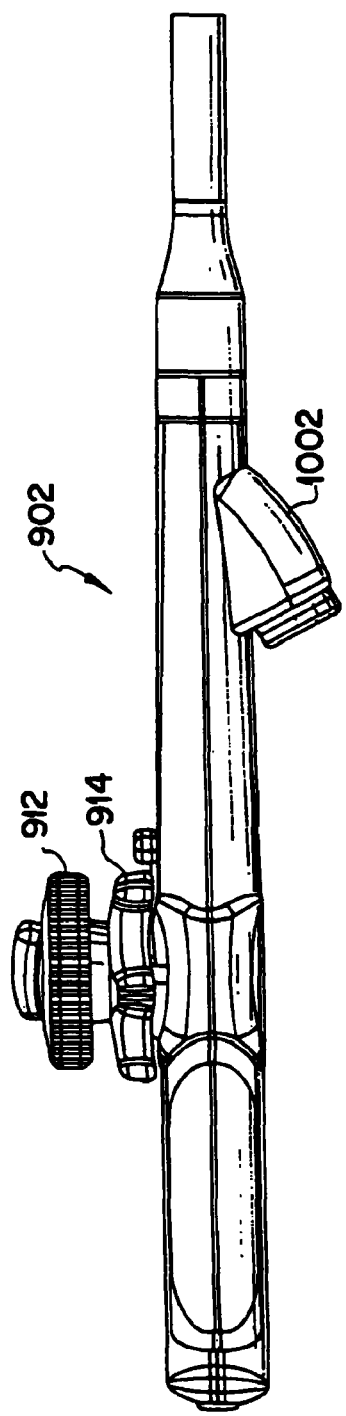
FIG. 47D
FIG. 47E

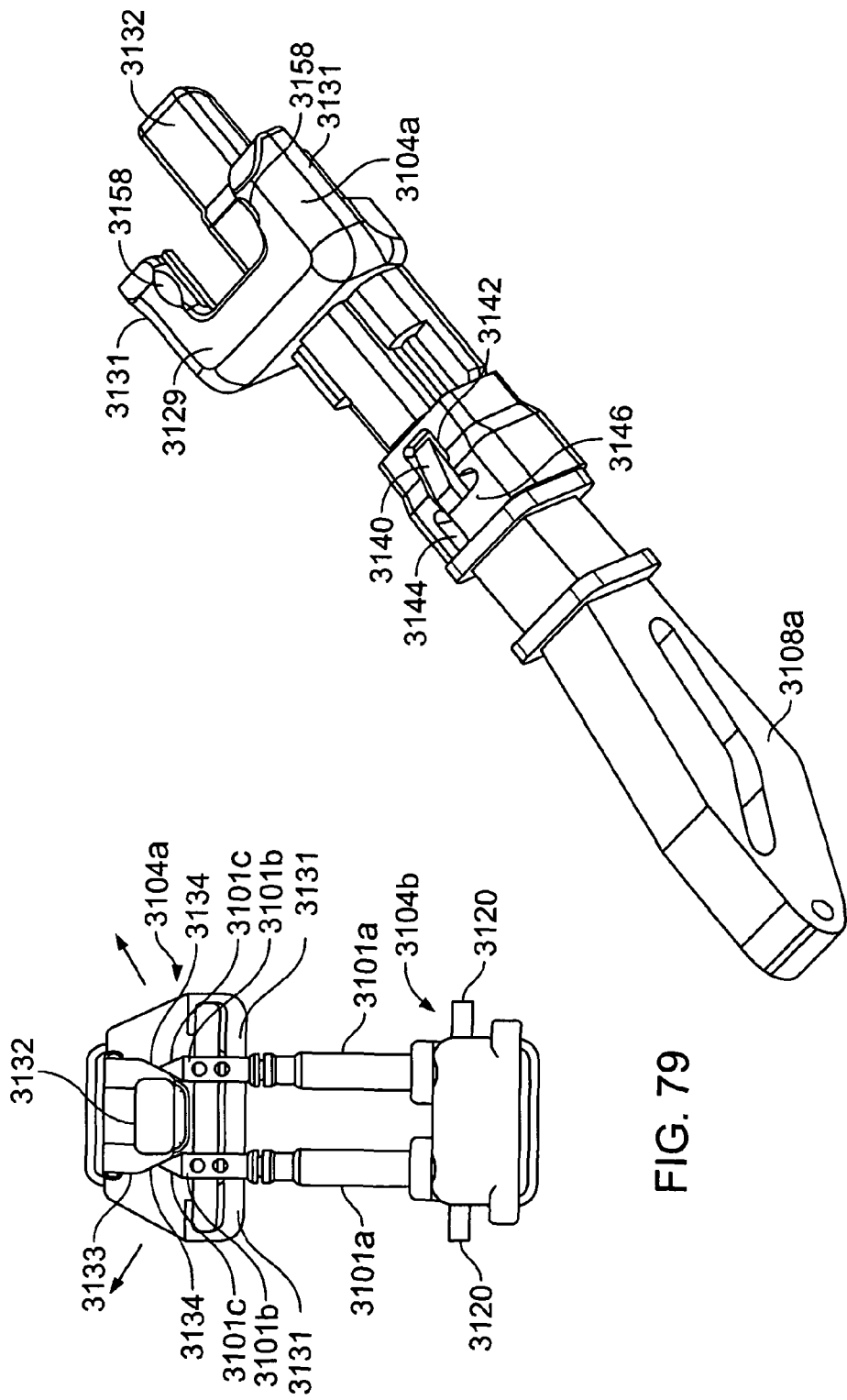

METHOD AND DEVICES FOR TISSUE RECONFIGURATION

CROSS REFERENCES TO RELATED APPLICATIONS

This application claims the priority of U.S. Provisional Application No. 60/459,996, filed Apr. 4, 2003, entitled METHOD AND DEVICES FOR TISSUE RECONFIGURATION, U.S. Provisional Application No. 60/460,308, filed Apr. 4, 2003, entitled TISSUE FIXATION DEVICES AND METHODS OF FIXING TISSUE, and U.S. Provisional Application No. 60/381,539, filed May 17, 2002 now abandoned, entitled ACTUATOR FOR CONTROLLING A MEDICAL INSTRUMENT, which are hereby incorporated by reference in their entirety.

This application is a continuation-in-part of U.S. application Ser. No. 10/197,574, filed Jul. 18, 2002 now U.S. Pat. No. 6,835,200, entitled METHODS AND DEVICES FOR TISSUE RECONFIGURATION, which claims priority to 60/306,652, filed Jul. 18, 2001 now abandoned, and is a continuation-in-part of U.S. application Ser. No. 09/859,579, filed May 18, 2001 now U.S. Pat. No. 6,821,285, entitled TISSUE RECONFIGURATION, which is a continuation-in-part of U.S. application Ser. No. 09/574,424, filed May 19, 2000 now U.S. Pat. No. 6,494,888, entitled TISSUE RECONFIGURATION, which is a continuation-in-part of U.S. application Ser. No. 09/520,273, filed Mar. 7, 2000 now U.S. Pat. No. 6,663,639, entitled METHODS AND DEVICES FOR TISSUE RECONFIGURATION and U.S. application Ser. No. 09/519,945, filed Mar. 7, 2000 now U.S. Pat. No. 6,506,196, entitled DEVICE AND METHOD FOR CORRECTION OF A PAINFUL BODY DEFECT, which claim priority from U.S. Provisional Application No. 60/140,492, filed Jun. 22, 1999, entitled STOMACH ELEVATOR METHOD AND DEVICE, all hereby incorporated by reference in their entirety.

TECHNICAL FIELD

This description relates to methods and devices for use in the treatment of gastroesophageal reflux disease.

BACKGROUND

Gastroesophageal reflux disease (GERD) is a common upper-intestinal disorder in which contents of the stomach flow inappropriately from the stomach into the esophagus. Backflow of gastric contents into the esophagus results when gastric pressure is sufficient to overcome the resistance to flow that normally exists at the gastroesophageal junction (GEJ), or when gravity acting on the contents is sufficient to cause flow through the GEJ. Medication, open surgical procedures, laparoscopic surgical procedures and endoscopic techniques are known for treating GERD.

SUMMARY

In one general aspect, a medical instrument includes a tissue manipulator configured for introduction into a patient, and a sealing member configured to substantially seal a section of the tissue manipulator from contact with bodily fluids. The tissue manipulator includes at least one movable member that is movable within the sealing member and has a portion extending out of the sealing member.

Implementations can include one or more of the following features. For example, the tissue manipulator includes a second movable member that is movable within the sealing member and has a portion extending out of the sealing member. The tissue manipulator includes pivots about which the movable members rotate in opposite directions. The sealing member defines a hole for receiving a guide wire to permit advancement of the tissue manipulator into the patient over the guide wire. The sealing member is a flexible member.

In an illustrated embodiment, the medical instrument includes a flexible linkage coupled to the tissue manipulator, and a sealing portion covering the linkage. The sealing portion abuts the sealing member.

In another general aspect, a medical device includes an apparatus sized to be entirely received within an organ of a patient. The apparatus has a first portion configured for releasable coupling to an actuating member, and a second portion configured to receive an implant to be deployed within the patient, the apparatus defines a through hole for receiving a guide wire to permit advancement of the apparatus into the patient over the guide wire.

Implementation can include one or more of the following features. For example, the second portion is configured to be frangibly connected to the implant. The apparatus includes a pair of jaw members that are configured to move in response to actuation by the actuating member. Each jaw member defines a through hole. The through holes overlap when the jaw members are closed to form the guide wire receiving through hole. The jaw members each include a tissue manipulator and a shell over the tissue manipulator. Each tissue manipulator has a coupler that forms part of the first portion of the apparatus. One tissue manipulator includes a region having a frangible connection to a portion of the implant, and the other tissue manipulator includes a region defining an opening for receiving another portion of the implant. The two regions form the second portion of the apparatus. Each shell defines a through hole that forms part of the guide wire receiving through hole.

In another general aspect, a medical device includes an apparatus sized to be entirely received within an organ of a patient. The apparatus has a first portion configured for releasable coupling to an actuating member, and a second portion configured to receive an implant to be deployed within the patient. The apparatus is configured to decouple from the actuating member when in the patient upon application of an overload to the actuating member.

Implementations can include one or more of the following features. For example, the first portion includes a retainer that moves under application of an overload to decouple the apparatus from the actuating member. The retainer is configured such that the overload applied to the actuating arm is less than a load that causes the implant to be pulled through muscle tissue of the patient. The retainer is configured such that the overload applied to the actuating member is less than or equal to about 27 pounds.

In a further general aspect, a medical device includes a first member having at least two tissue penetrating elements connected thereto by a frangible connection, and a second member having an engaging element configured to deflect the tissue penetrating elements in opposite directions and disengage the tissue penetrating elements from the first member at the frangible connection upon relative movement of the first and second members.

Implementations can include one or more of the following features. For example, the engaging element defines angled surfaces against which the tissue penetrating elements are pushed when the first and second members are moved together. The medical device includes a flexible member coupling the at least two tissue penetrating elements.

In another general aspect, a medical device includes an apparatus sized to be entirely received within an organ of a patient. The apparatus has a first portion configured for releasable coupling to an actuating member, and a second portion configured to receive an implant to be deployed within the patient. The apparatus includes a first member having tissue penetrating elements, and a second member having an engaging element configured to deflect the tissue penetrating elements in opposite directions upon relative movement of the first and second members.

Implementations can include one or more of the following features. For example, the engaging element defines angled surfaces against which the tissue penetrating elements are pushed when the first and second members are moved together. The medical device includes a flexible member coupling the at least two tissue penetrating elements.

In another general aspect, a medical device includes an apparatus sized to be entirely received within an organ of a patient. The apparatus has a first portion configured for releasable coupling to an actuating member, and a second portion configured to receive an implant to be deployed within the patient. The first portion defines a rectangular opening for receiving the actuating member, and a cavity for receiving a coupler of the actuating member, the cavity having a length of at least 0.7 inches.

Implementations can include one or more of the following features. For example, the first portion includes a shaped region configured to receive a corresponding shaped region of the actuating member, and the first portion defines a slot shaped to receive a lip of the actuating member.

In an illustrated embodiment, the apparatus includes a pair of jaw members. One of the jaw members includes a tissue penetrating element positioned relative to the cavity to be supported by the coupler. The other jaw member includes an engaging element positioned relative to the cavity to be supported by the coupler.

In another general aspect, a medical device includes an actuating member, and an end effector configured for releasable coupling to the actuating member. The end effector has a tissue penetrating element. The actuating member includes a tissue penetrating element support positioned to limit bending of the end effector when the tissue penetrating element penetrates tissue.

Implementations can include one or more of the following features. For example, the medical device includes a second end effector including a tip engaging element configured to deflect the tissue penetrating element upon relative movement of the end effectors. The actuating member includes a tip engaging element support positioned to limit bending of the second end effector when the tip engaging element deflects the tissue penetrating element. The actuating member includes two arms. One arm includes the tissue penetrating element support and the other arm includes the tip engaging element support.

In a further general aspect, a medical assembly includes a cartridge configured for releasable attachment to a medical instrument, and a resilient holder configured to receive the cartridge such that the cartridge automatically aligns relative to the medical instrument during attachment of the cartridge to the medical instrument.

Implementations can include the resilient holder having resilient portions that are configured to flex upon attachment of the cartridge to the medical instrument if the cartridge is not aligned with the portions.

In another general aspect, a medical instrument includes a tissue manipulator including first and second members, and an actuating mechanism including a cable that is placed under tension to move at least one of the first and second members toward the other member to engage tissue. The actuating mechanism is configured to limit overtensioning of the cable.

Implementations can include one or more of the following features. For example, the actuating mechanism is configured to limit the application of a tension to the cable of greater than or equal to about 72 pounds. The actuating mechanism includes a clutch configured to slip when an overtension is applied to the cable.

In another general aspect, a medical instrument includes a tissue manipulator including first and second members, and an actuating mechanism including a cable that is placed under tension by an external force to move at least one of the first and second members toward the other member. The actuating mechanism is configured to limit loss of tension on the cable when the external force is removed during deployment.

Implementations can include one or more of the following features. For example, the actuating mechanism includes a knob for applying the external force. The actuating mechanism includes a pawl and a ratchet coupled to the knob. The pawl and the ratchet engage to limit loss of tension on the cable when the external force is removed during deployment.

Aspects of the medical instrument and device may include one or more of the following advantages. For example, the medical instrument and device are designed to facilitate reconfiguration of stomach tissue. Sealing features facilitate cleaning and allow reuse of the instrument. Guide wire receiving holes ease passage of the instrument through the esophagus and into the stomach and minimize trauma. A bailout mechanism allows the instrument to be removed from the patient if the cartridge cannot be disengaged from the tissue. The instrument advantageously deploys the implant using the same mechanism that closes the instrument arms. The instrument is adapted to limit cable breakage if something prevents the instrument arms from closing, for example, if the user attempts to deploy an implant over a previously deployed implant. The instrument also allows the user to deploy the implant with one hand, i.e. when the user lets go of the deployment knob (to reposition the hand to continue turning the knob), the user does not need to hold the knob with their other hand to keep the knob from turning back.

Other features and advantages will be apparent from the description and the drawings.

DESCRIPTION OF DRAWINGS

FIG. 2 shows a tissue fixation device deployed by the instrument of FIG. 1 in use to secure a bulge formed in the tissue;

FIG. 3A is an illustration of the instrument of FIG. 1;

FIG. 5 is a side view of the distal end of the instrument, turned 90 degrees relative to FIG. 4A;

FIG. 6A is an illustration of a first part of the tissue fixation device of FIG. 2;

FIG. 6B is an illustration of the first jaw member with the first part of the tissue fixation device mounted to the jaw member;

FIGS. 9A-9F show the instrument of FIG. 1 in use;

FIG. 12C is a cross-sectional view of the tissue engaging member of FIG. 12A;

FIG. 12D is a cross-sectional view of the tissue engaging member of FIG. 12A shown piercing tissue;

FIG. 13A is an isometric view of a proximal end the tissue engaging member of FIG. 12A and a torque generator;

FIG. 13B is a cross-sectional view of the torque generator of FIG. 13A;

FIG. 14A is an illustration of an alternative tissue engaging member;

FIG. 14B is an illustration of an alternative tissue engaging member including a tissue bulking needle;

FIG. 14C is a further illustration of the tissue engaging member of FIG. 14B;

FIG. 17A is an isometric view of the distal end portion of the instrument of FIG. 16A FIG. 17B shows the distal end portion of the instrument with a hood member removed;

FIGS. 17C-17E are side views of an end effector of the instrument of FIG. 16A;

FIG. 17F is a side view of a lock arm taken along lines 17F-17F in FIG. 17E;

FIG. 17H is an exploded view of the instrument of FIG. 16A;

FIG. 17I is a cross-sectional view of a coupling member of the end effector;

FIG. 18 is a side view of a handle of the instrument of FIG. 16A, shown with a cover removed;

FIG. 19 is an isometric view of a gearbox located in the handle of FIG. 18;

FIGS. 21A and 21B are end and side views, respectively, of the mechanism of FIG. 20;

FIG. 22 is a cross-sectional view of a rack of the mechanism of FIG. 20;

FIG. 30 is an illustration of a seal on the handle of FIG. 18;

FIG. 31 is an illustration of an alternative deployment mechanism;

FIGS. 32-34 are illustrations of alternative means for coupling the implant bar to the tube of the jaw member;

FIG. 35A is an isometric view and FIG. 35B is a cross-sectional view of an alternative tissue fixation device;

FIGS. 36A-40 are illustrations of alternative means for providing an atraumatic distal end on the instrument of FIG. 16A;

FIGS. 46A-46C are illustrations of a cartridge assembly to which the disposable cartridges of FIG. 17F are mounted for handling and attachment to the instrument; and FIGS. 47A-47F are isometric, four side views, and an end view, respectively, of the handle of FIG. 18.

FIG. 79 is an end view of the end effector of FIG. 72;

FIG. 80 is an illustration of the cartridge of FIG. 78 attached to an actuating arm;

FIG. 88b is an illustration of the handle mechanism of FIG. 67 shown with the two closing cables of FIG. 88a;

Like reference symbols in the various drawings indicate like elements.

DETAILED DESCRIPTION

Figure 1:
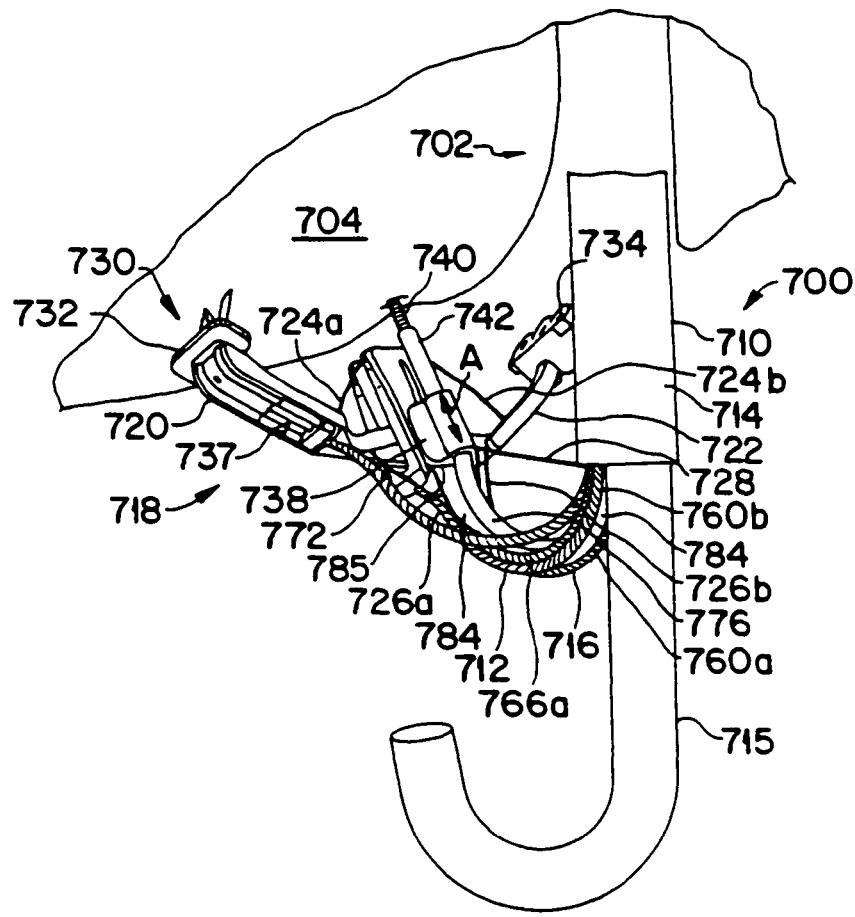
FIG. 1 is a diagrammatic representation of an instrument in use to reconfigure tissue in the vicinity of the gastroesophageal junction of the stomach.

Referring to FIG. 1, an instrument 700 for reconfiguring stomach tissue, for example, stomach tissue in the vicinity of the gastroesophageal junction (GEJ) 702, such as tissue 704 of the lesser curvature of the stomach or any portion of the stomach within about 2 cm of the GEJ, is shown. The GEJ is the region of transition from the esophagus and the stomach. The lesser curvature of the stomach is a portion of the stomach located beyond the GEJ. Instrument 700 includes an elongated shaft 710 dimensioned to permit transoral access to the stomach, and a tissue manipulator 712 for manipulating stomach tissue. Positioned within a lumen 714 defined by shaft 710 is a standard GI endoscope 715 providing visual guidance of the reconfiguring procedure. Instrument 700 is particularly adapted for treating GERD. Using instrument 700, as described below, a bulge, plication or tissue wrap is formed in the vicinity of gastroesophageal junction 702 to reduce reflux of stomach fluids into the esophagus.

Tissue manipulator 712 has an elongated cable assembly 716 housed within lumen 714 of shaft 710, and a distal end effector 718 actuated to perform the various steps in the tissue reconfiguring procedure by cable assembly 716. End effector 718 includes first and second jaw members 720, 722 that engage tissue 704. Cable assembly 716 includes first and second cable pairs 724a, 724b, and 726a, 726b for moving jaws 720, 722 relatively toward and away from one another, respectively, in a first plane, and a third cable 728 for moving end effector 718 relative to shaft 710 in a second plane generally transverse to, and preferably perpendicular to, the first plane, as described further below. During insertion into the stomach, end effector 718 is aligned with shaft 710 (as shown in FIG. 3A). Once positioned in the stomach, cable 728 is actuated to articulate end effector 718 out of alignment with shaft 710 (as shown in FIG. 1).

Cable assembly 716 includes a spring beam 784, formed from, for example, stainless steel or Nitinol, extending into shaft 710. End effector 718 is attached to beam 784 at a distal end 785 of beam 784. Beam 784, in its rest state, is biased toward a straight alignment. Pulling cable 728 bends beam 784. When cable 728 is released, beam 784 returns toward the straight alignment.

Referring also to FIG. 2, mounted to first jaw 720 is a first part 732 of a tissue securement member, for example, a fixation device 730, and mounted to second jaw 722 is a second part 734 of tissue fixation device 730. As described further below, after jaws 720, 722 engage tissue 704 and manipulate the tissue in a wrapping action to create a bulge 736 in, for example, the lesser curvature of the stomach, tissue fixation device 730 is deployed to secure the engaged tissue together. Cable assembly 716 includes a fourth cable 737 for deploying fixation device 730, as described further below.

End effector 718 further includes a tube 738 and a third tissue engaging member or retractor, for example, a coil 740, received within tube 738, for purposes described below. Coil 740 is housed within an overtube 742, and coil 740 and overtube 742 can be moved axially proximally and distally relative to jaws 720, 722, along the axis, A, of cable assembly 716. Coil 740 can be rotatably advanced into tissue.

Figure 3B:
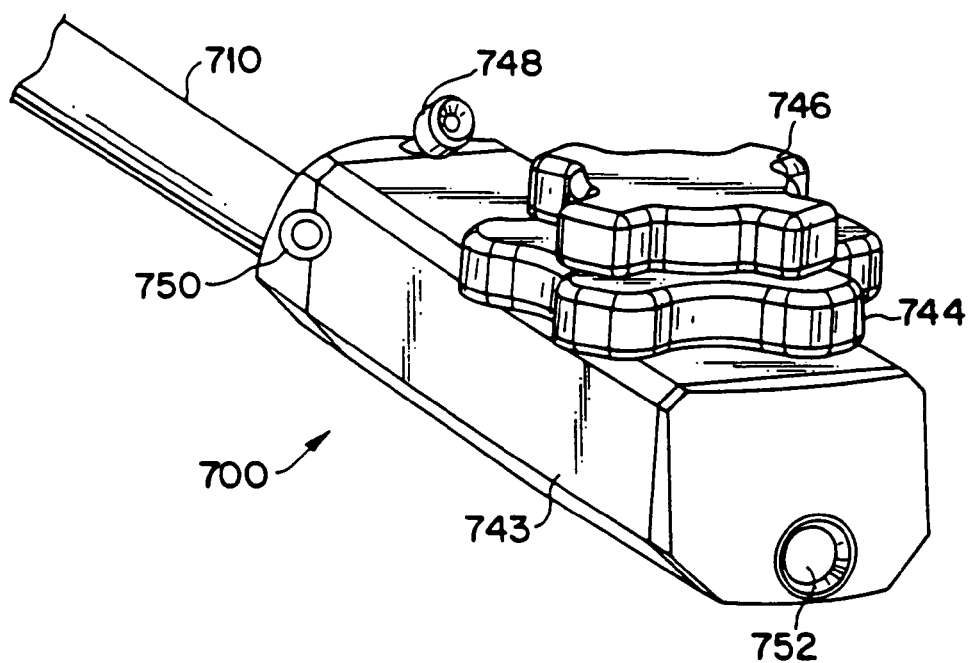
FIG. 3B shows a proximal end of the instrument.

Referring to FIG. 3A, instrument 700 has, at its proximal end 745, a handle 743 with a control knob 744 for controlling cables 724a, 724b, 726a, 726b to close and open jaws 720, 722, and a control knob 746 for controlling cable 728 to move end effector 718. Handle 743 includes a port 748 through which coil 740 and overtube 742 can be introduced into shaft lumen 714, and a pull-knob 750 for deploying tissue fixation device 730, as described below. As shown in FIG. 3B, handle 743 defines a channel 752 through which endoscope 715 is introduced into shaft lumen 714.

Figure 3C:
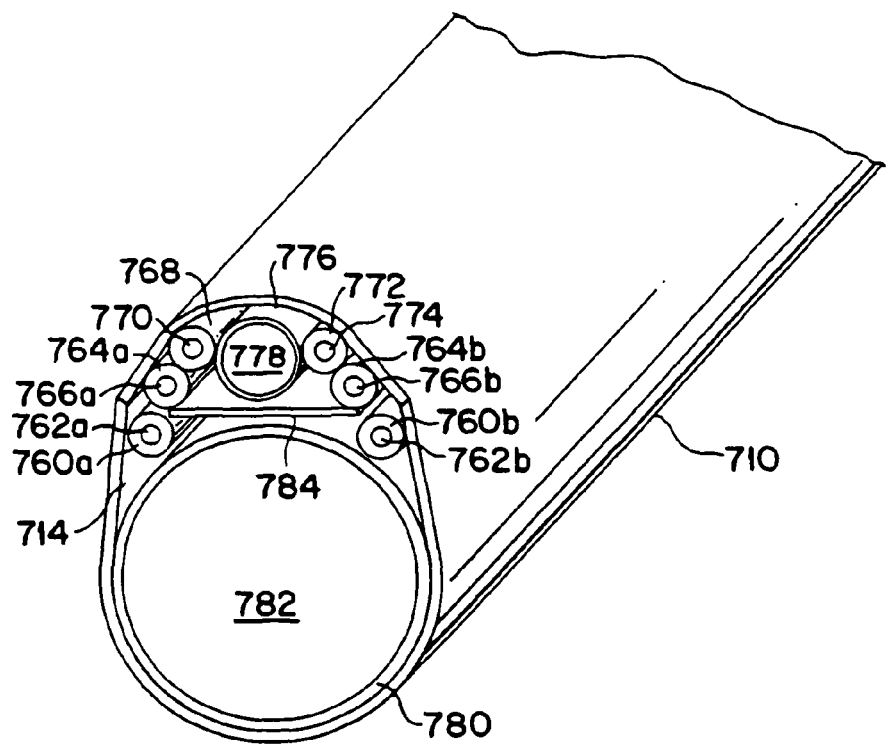
FIG. 3C shows the working channels in a shaft of the instrument.
Figure 3D:
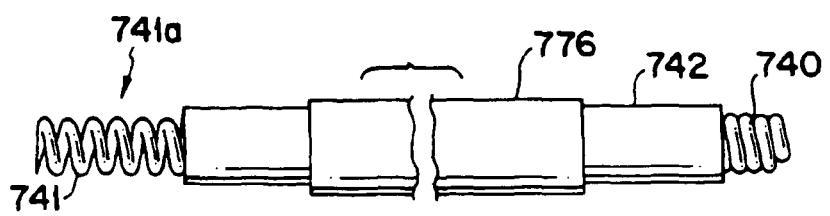
FIG. 3D is an illustration of a coil assembly of the instrument.

Referring to FIGS. 1 and 3C, which shows the working channels in shaft 710 for receiving the various cables, overtube 742 and endoscope 715, within lumen 714 of shaft 710 are cable housings 760a, 760b defining channels 762a, 762b in which cables 724a, 724b for closing jaws 720, 722 are received, and cable housings 764a, 764b defining channels 766a, 766b in which cables 726a, 726b for opening jaws 720, 722 are received. Within lumen 714 are also a cable housing 768 defining a channel 770 in which cable 728 for bending end effector 718 is received, and a cable housing 772 defining a channel 774 in which cable 737 for deploying fixation device 730 is received. Coil 740 and overtube 742 are received in a channel 778 defined in a coil housing 776 in lumen 714. Housing 776 extends from port 748 to tube 738. As shown in FIG. 3D, coil 740 has a tissue penetrating tip 741 and a distal section 740a having a looser wound coil than the remainder of coil 740. Endoscope 715 is received in a channel 782 defined in an endoscope housing 780 in lumen 715.

Spring beam 784 is located generally between cable housing 776 and endoscope housing 780, and extends about 4 inches into shaft 710 from the distal end of the shaft where beam 784 is mounted to shaft 710 by, for example, silicone adhesive/sealant. The various cable housings and spring beam 784 do not move relative to shaft 710 and handle 743. It is the movement of the cables within the cable housings that actuate end effector 718. Shaft 710 is preferably formed from, for example, heat-shrink tubing.

Referring again to FIG. 3A, end effector 718 has a length, L1, of about 2 inches, cable assembly 716 extends axially by a length, L2, of about 2.5 inches from shaft 710, shaft 710 has a length, L3, of about 23.5 inches, and handle 743 has a length, L4, of about 5 inches. Cable assembly 716, spring beam 784, and shaft 710 have the necessary flexibility to permit transoral placement of instrument 700 into the stomach. The length, L1, of relatively rigid end effector 718 is minimized to ensure the necessary flexibility of instrument 700 is maintained. The distance that cable assembly 716 extends axially from shaft 710 is selected to cantilever beam 784 permitting the desired bending of end effector 718 relative to shaft 710 to position jaws 720, 722 against the inner surface of the stomach in the vicinity of the GEJ.

Distal end effector 718 is sized to fit through a 12-16 mm diameter channel (corresponding to the diameter of the esophagus) and shaft 710 has an outer diameter of about 12 to 16 mm to enable transoral passage of instrument 700 into the stomach. Scope channel 782 has a diameter of either about 8 mm or 10 mm. An 8 mm diameter scope channel allows passage of 7.9 mm pediatric gastroscope, and a 10 mm diameter scope channel allows passage of a 9.8 mm adult gastroscope. Channel 778 has a diameter of about 2-3 mm for receiving cable 742.

Figure 4A:
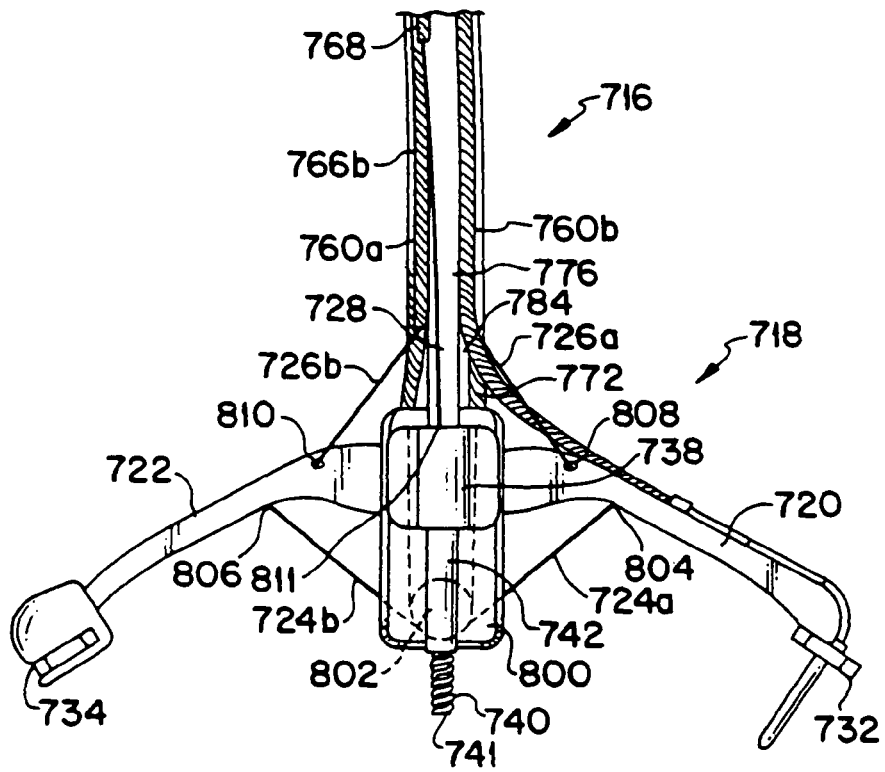
FIG. 4A is a top view of a distal end of the instrument, shown with first and second jaw members in an open position.
Figure 4B:
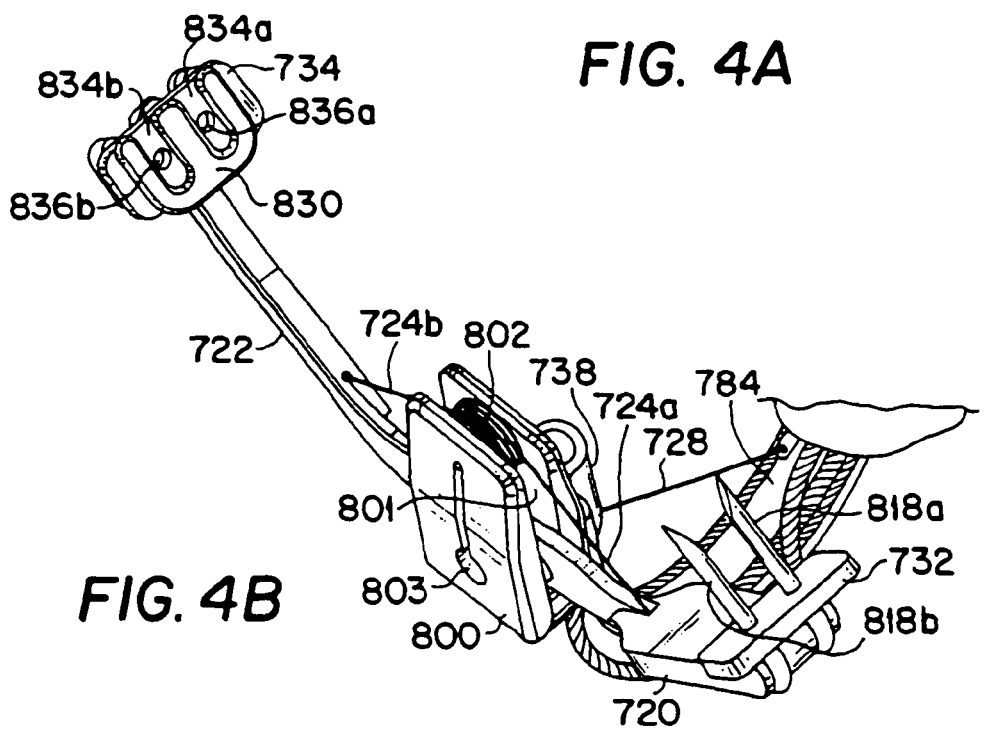
FIG. 4B shows the distal end of the instrument located off-axis relative to a shaft of the instrument.

Distal end effector 718 is shown in more detail in FIGS. 4A and 4B. End effector 718 includes a central mount 800 defining a slot 801. Spanning slot 801 and supported by mount 800 is a pin 803 to which 720, 722 are pivotally mounted. Central mount 800 also houses two pulleys 802 over which cables 724a, 724b are respectively passed for closing jaws 720, 722. Cables 724a, 724b terminate at points 804, 806 on jaws 720, 722, respectively. Cables 726a, 726b for opening jaws 720, 722 terminate at points 808, 810 on jaws 720, 722, respectively, proximal of points 804, 806. Tube 738 of end effector 718 for receiving coil 740 and overtube 742 is attached to mount 800, and cable 728 for bending end effector 718 terminates at point 811 on tube 738.

Pulling cables 724a, 724b proximally moves jaws 720, 722 toward one another generally in a first plane (in the plane of the paper in FIG. 4A). Pulling cables 726a, 726b proximally moves jaws 720, 722 away from one another generally in the first plane. Pulling cable 728 proximally bends beam 784 moving end effector 718 in a second plane (out of the plane of the paper in FIG. 4A) generally perpendicular to the first plane.

Referring also to FIG. 5, jaw 720 includes two guide tubes 816a, 816b and a slider 812 including two push rods 814a, 814b guided within tubes 816a, 816b, respectively. Slider 812 is mounted to jaw 720 to slide relative to jaw 720. Tubes 816a, 816b curve about jaw 720 to terminate in tissue penetrating tips 818a, 818b (FIG. 6B), respectively. Push rods 814a, 814b can be formed from molded plastic such as polyethylene or polypropylene or as a braided stainless steel cable to provide the flexibility to follow the curve of tubes 816a, 816b. Cable housing 772 is attached to slider 812 and cable 737 terminates at a fixed point 739 on jaw 720. Actuation of cable 737 pushes slider 812 distally, as described below.

First part 732 of tissue fixation device 730 is shown in more detail in FIGS. 6A and 6B. First part 732 of tissue fixation device 730 defines through holes 820a, 820b (FIG. 6C), and part 732 is loaded onto jaw 720 with tips 818a, 818b received in through holes 820a, 820b, respectively. Connected to part 732 with a suture 822 are two securing elements, for example, bars 824a, 824b. Each bar 824a, 824b defines two through holes 826a, 826b. Suture 822 is threaded through holes 826a, 826b of the bars and through holes 820a, 820b of part 732, and is tied together forming a knot 823 to secure bars 824a, 824b to part 732. Tubes 818a, 818b each define a channel 827 for receiving one of bars 824a, 824b, and a slot 828 communicating with channel 827 for receiving suture 822 therethrough.

Figure 7:
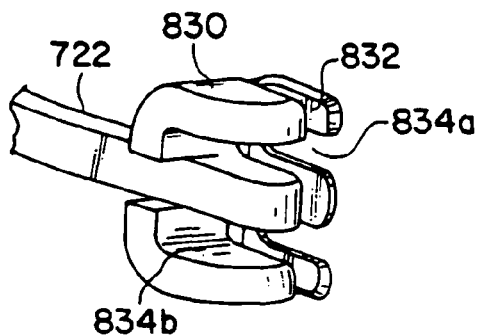
FIG. 7 is an illustration of the second jaw member.
Figure 8:
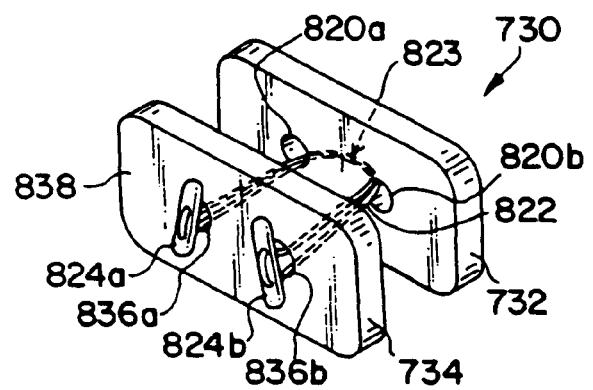
FIG. 8 is an illustration of the tissue fixation device of FIG. 2.

Referring particularly to FIGS. 4B and 7, jaw 722 has a distal member 830 defining a slot 832 for receiving second part 734 of fixation device 730, and slots 834a, 834b for receiving tissue penetrating tips 818a, 818b. Second part 734 of fixation device 730 defines through holes 836a, 836b for receiving tips 818a, 818b. When jaws 720, 722 are closed, tips 818a, 818b pass through slots 834a, 834b and holes 836a, 836b. Actuation of fixation device deployment cable 737 after closing jaws 720, 722 pushes slider 812 and push rods 814a, 814b distally, advancing bars 824a, 824b out of tissue penetrating tips 818a, 818b, and locating bars 824a, 824b on the far side 838 of second part 734 of fixation device 730, as shown in FIG. 8.

Figure 9A:
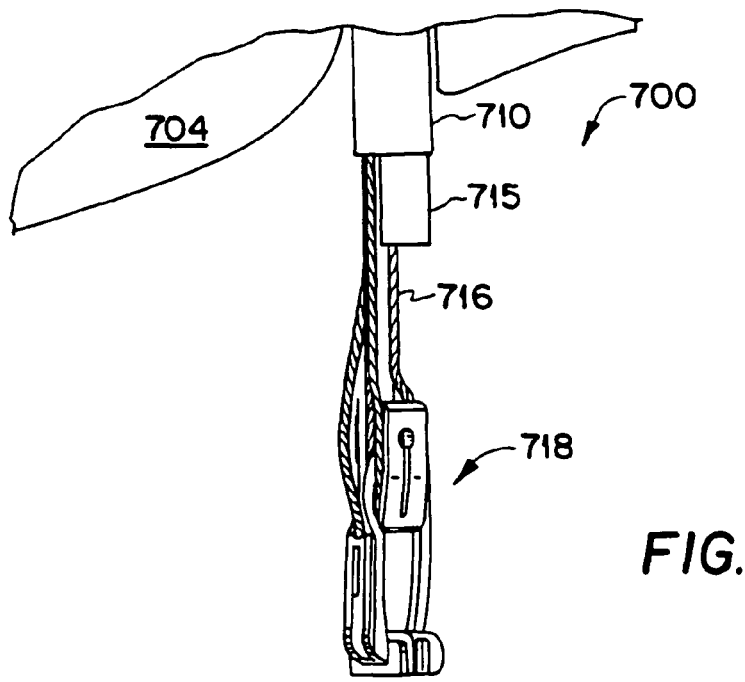

Referring to FIGS. 9A-9F, in use, under endoscopic guidance, the physician advances instrument 700 transorally to position end effector 718 in the stomach. During advancement into the stomach, end effector 718 is generally aligned along the axis of shaft 710, as shown in FIG. 9A. The physician then turns control knob 746 to pull cable 728 proximally, thereby bending beam 784 moving end effector 718 out of alignment with shaft 710 to the position shown in FIG. 9B. By then turning control knob 744 to pull cables 726a, 726b, jaws 720, 722 are pivoted about pins 803 to the open position shown in FIG. 9C.

Figure 9E:
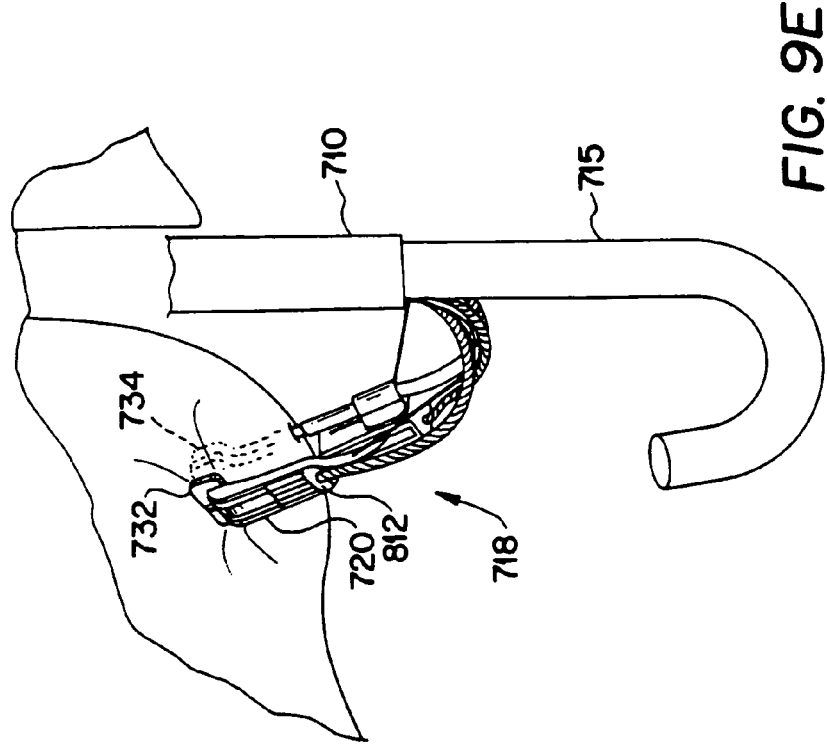
Figure 9D:
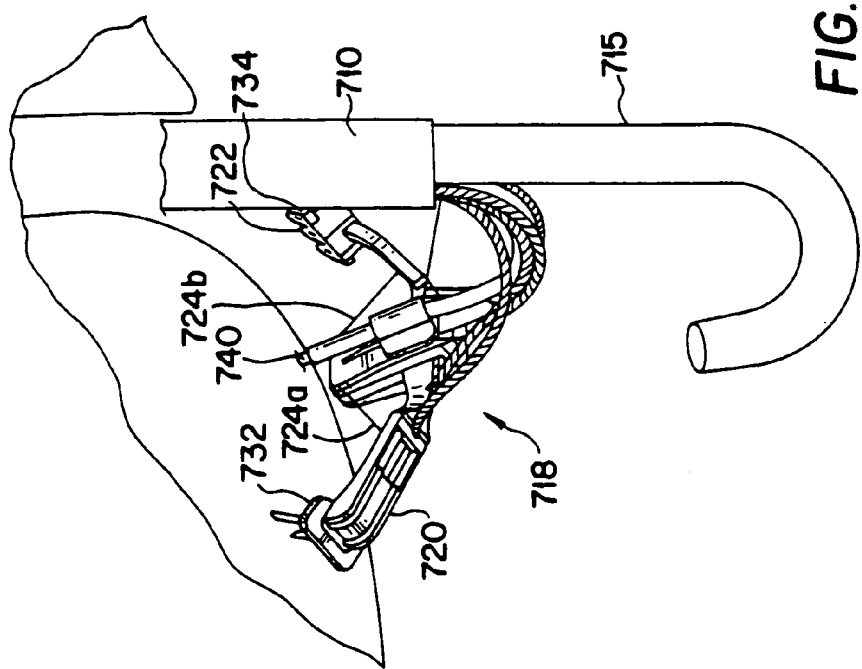

The physician then advances coil 740 and overtube 742 by pushing the coil and overtube distally in channel 778 advancing coil 740 and overtube 742 out of tube 738 and into contact with stomach tissue, preferably stomach tissue beyond the gastroesophageal junction, as shown in FIG. 1. With overtube 742 pressing against the tissue to stabilize the tissue, the physician rotates coil 740 while applying slight distal pressure to advance the coil into the tissue, as shown in FIG. 9D. Coil 740 and overtube 742 are then pulled proximally to pull tissue between jaws 720, 722. Jaws 720, 722 are then closed by turning control knob 744 to pull cables 724a, 724b proximally, as shown in FIG. 9E. The turning of the control knob can also be the action that pulls coil 740 and overtube 742 proximally, ensuring that coil 740 and overtube 742 are positioned out of the way of the closing of the jaws. A lockout can be incorporated to prevent the jaws from closing if coil 740 and overtube 742 are not in their proximal position.

Figure 9F:
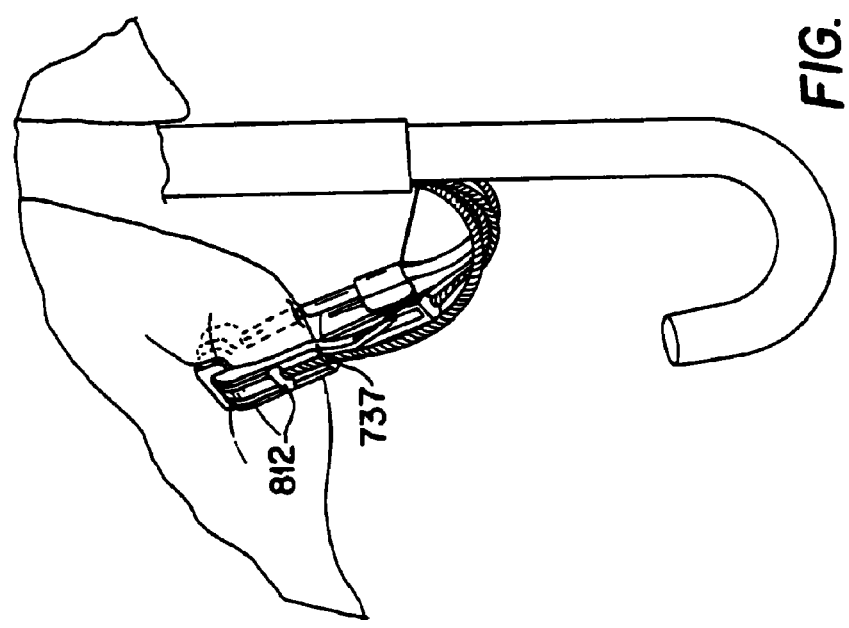

The closing of the jaws places parts 732, 734 of fixation device 730 in contact with two tissue sections, for example, against two spaced tissue surfaces in the stomach, and causes tissue penetrating tips 818a, 818b to penetrate through the tissue and into holes 836a, 836b in second part 734 of fixation device 730. To deploy fixation device 730, the physician pulls cable 737 proximally removing slack from cable 737. Because cable housing 772 is of fixed length and is non-movably attached to the handle, removing slack from cable 737 causes cable housing 772 to move distally, advancing slider 812 to push t-bars 824a, 824b out of tissue penetrating tips 818a, 818b, as shown in FIG. 9F.

Figure 10:
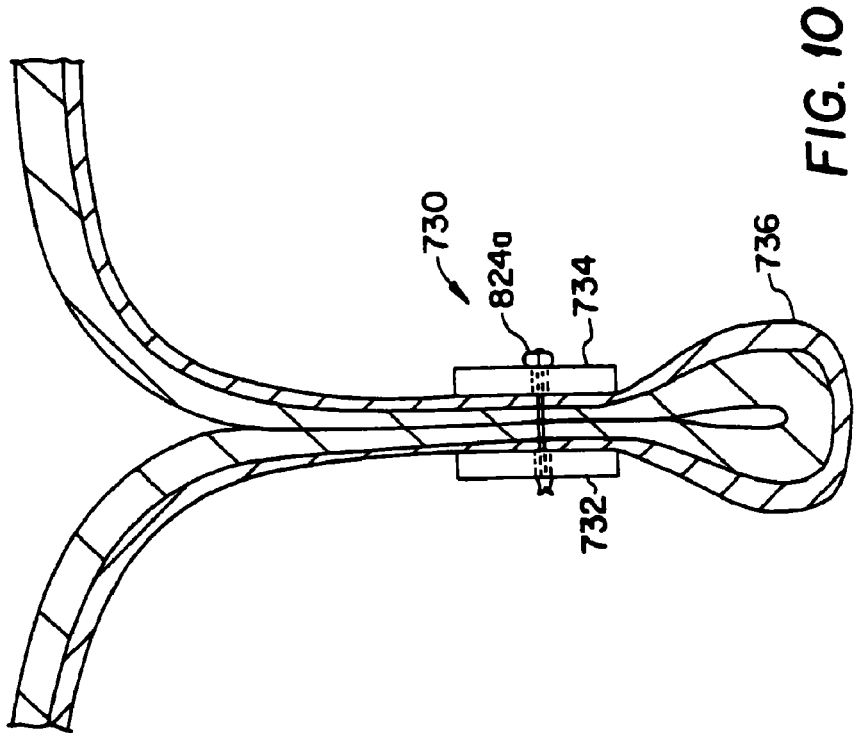
FIG. 10 is an illustration of tissue secured with the tissue fixation device of FIG. 2.

The physician then opens the jaws, disengages jaw 722 from second part 734, returns the distal end effector to its original position generally aligned with shaft 710, closes the jaws and removes instrument 700. FIG. 10 shows a cross-section of the tissue with fixation device 730 in place securing bulge 736.

Other embodiments are within the scope of the following claims.

For example, rather than a coil 740, alternative tissue penetrating or grasping elements such as a T-bar suture or two small grasping jaws can be employed. Instrument 700 can be used without the third tissue engaging member.

Figure 11A:
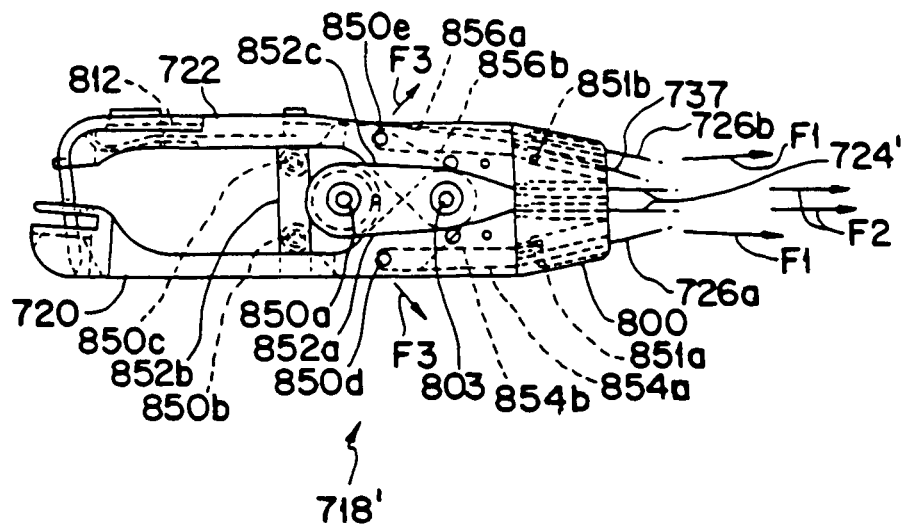
FIGS. 11A and 11B are illustrations of an alternative cable routing for an end effector.
Figure 11B:
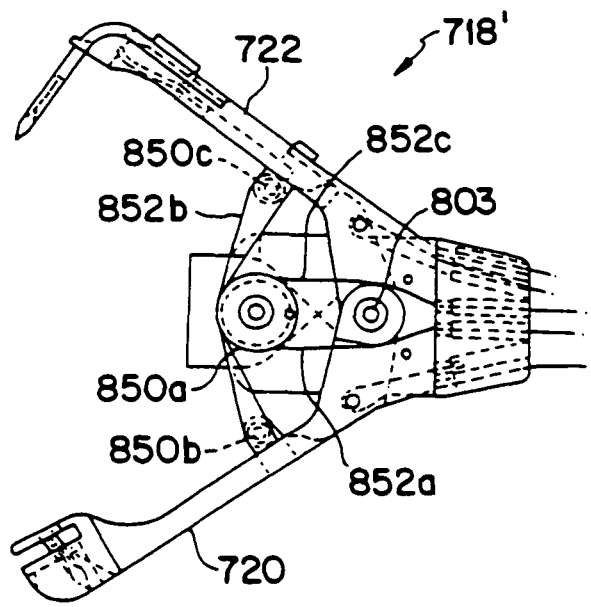

Referring to FIGS. 11A and 11B, an end effector 718' includes an alternative cable routing for actuating jaws 720, 722. End effector 718' includes cables 726a, 726b for opening jaws 720, 722, a single cable 724' for closing jaws 720, 722, and cable 737 for advancing slider 812. End effector 718' also includes pivot 803 and a series of pulleys 850a, 850b, 850c, 850d, and 850e around which the cables are routed.

Cable 724' has a first portion 852a that is routed under (as viewed in FIGS. 11A and 11B) pulley 850a and over pulley 850c; a second portion 852b that extends between pulleys 850c and 850b; and a third portion 852c routed under pulley 850b and over pulley 850a. Cable 726a has a first portion 854a that extends to pulley 850d and a second portion 854b that extends between pulley 850d and anchor 851a fixed to central mount 800. Cable 726b has a first portion 856a that extends to pulley 850e and a second portion 856b that extends between pulley 850d and anchor 851b fixed to central mount 800.

To open jaws 720 and 722, the user applies a tensile force F1 to cables 726a and 726b (by turning control knob 744). The tensile force F1 draws the first portions 854a and 856a of cables 726a and 726b proximally in the same direction as force F1 and draws the second portions 854b and 856b of cables 726a and 726b distally around respective pulleys 850e and 850d. Turning knob 744 also produces slack in cable 724'. A net force F3 results and draws jaws 720, 722 open.

To close jaws 720, 722, the user applies a tensile force F2 to portions 852a and 852b of cable 724' (by turning control knob 744 in the opposite direction, which also relieves tension in cables 726a, 726b). The tensile force F2 acts to shorten portion 852b of cable 724', thereby drawing pulleys 850c and 850b together and jaws 720, 722 closed.

Figure 12A:
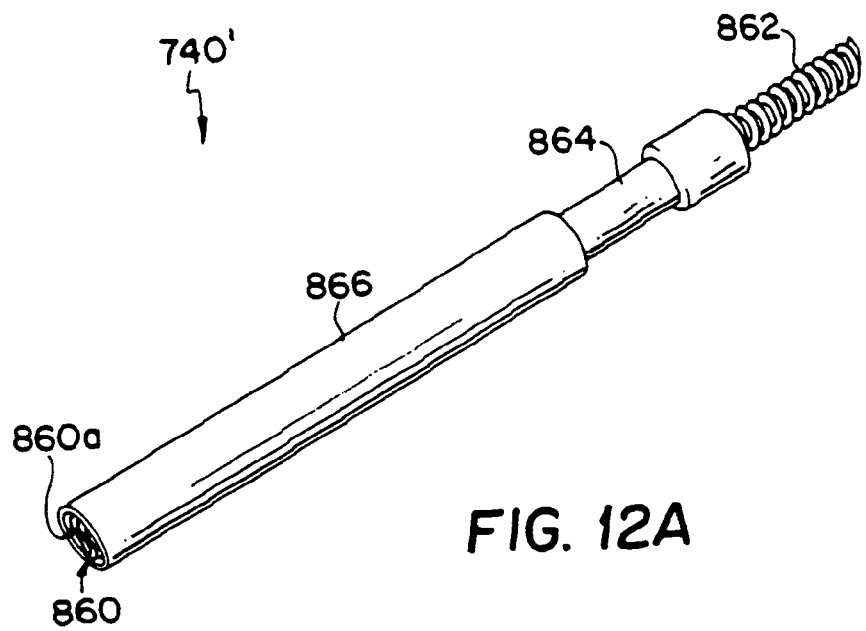
FIG. 12A is an isometric view of a tissue engaging member.

Referring to FIG. 12A, in an alternative embodiment, a third tissue engagement member 740' includes a tissue-engaging coil 860 with a tissue piercing end 860a, a helical drive shaft 862, and a coupling member 864 for translating a torque applied by drive shaft 862 to coil 860. Helical drive shaft 862 is preferably wound in a direction opposite that of tissue engaging coil 860, for reasons described below. Positioned over and axially movable relative to coupling member 864 is a sprung sheath 866. Tissue engagement member 740' can be used alone or can replace tissue engagement member 740 of FIG. 1. Coil 860 has, for example, six loops with a pitch of 1½ mm from loop-to-loop and a diameter of 2 mm. Other configurations can be used, for example, one loop and greater with the number of loops times the pitch corresponding to the desired penetration depth into the tissue.

Figure 12B:
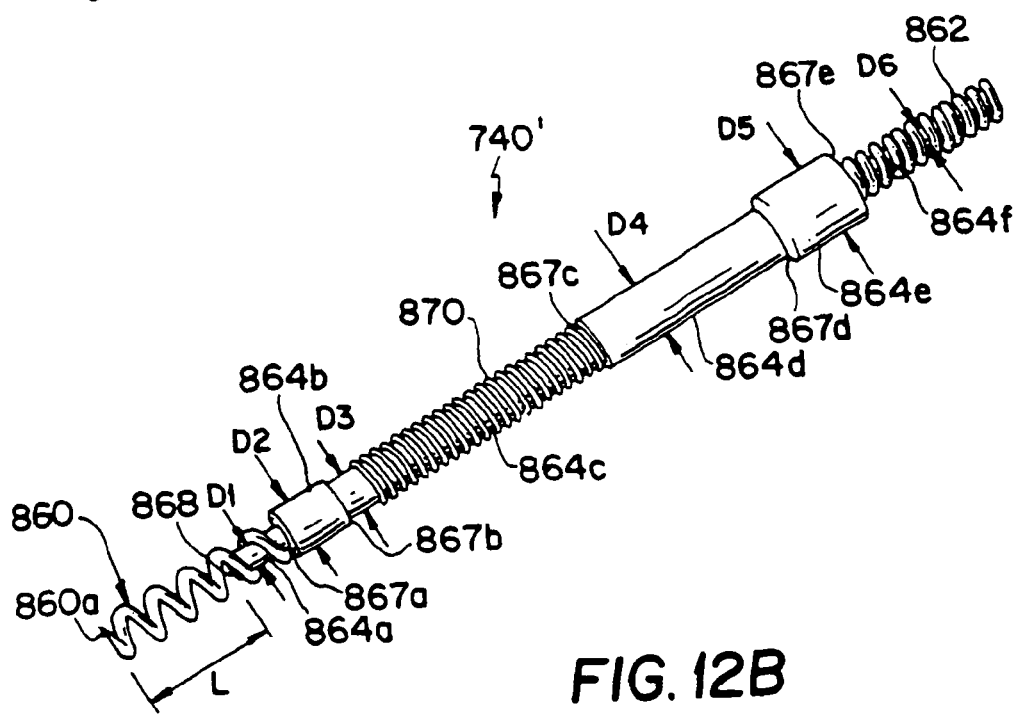
FIG. 12B is an isometric view of the tissue engaging member of FIG. 12A shown with an outer sheath removed.

Referring to FIG. 12B, in which tissue engagement member 740' is shown without sprung sheath 866, coupling member 864 includes a first, distal-most section 864a with a diameter, D1; a second section 864b with a diameter D2 larger than D1; a third section 864c with a diameter D3 between D1 and D2; a fourth section 864d with a diameter D4 about equal to D2; a fifth section 864e with a diameter D5 larger than D4; and a proximal-most section 864f having a diameter D6 about equal to D1. Diameters D1-D6 are, for example, about 0.04", 0.09", 0.06", 0.09", 0.12" and 0.04", respectively. Defined between sections 864a and 864b is a shelf 867a; defined between sections 864b and 864c is a shelf 867b; defined between sections 864c and 864d is a shelf 867c; defined between sections 864d and 864e is a shelf 867d; and defined between sections 864e and 864f is a shelf 867e. Drive shaft 862 is received over coupling member section 864f and coil 860 is received over coupling member section 864a. Drive shaft 862 and coil 869 are attached to coupling member 864 by, for example, soldering. Coil 860 has a coil length, L, of, for example, about 0.2", extending beyond the distal end 868 of section 864a. Positioned on coupling member section 864c between shelves 867b and 867c is a spring 870 that biases sprung sheath 866 distally.

Referring to FIG. 12C, sprung sheath 866 defines a lumen 872 and has a first section 866a with an inner diameter d1, a second hub section 866b with an inner diameter d2 less than d1, and a third section 866c with an inner diameter d3 about equal to d1. Coil 860 is received within lumen 872 in sheath section 866a. Spring 870 is located within lumen 872 radially between coupling member section 864c and section 866c of sheath 866 and axially between hub 866b and shelf 867c. Sheath hub 866b is biased against shelf 867b by spring 870. The spacing between coupling member shelf 867d and a proximal end 874b of sheath 866 permits axial, proximal movement of sheath 866 against the action of spring 870.

To facilitate assembly of tissue engaging member 740', coupling member 864 is formed from two parts 876a, 876b having mating fingers 878 joined, for example, by compression fitting. This configuration permits sheath 866 to be slid over part 876a prior to joining part 876b to 876a.

Referring also to FIG. 12D, in operation, the user places distal end 874a of sheath 866 against tissue T to be pierced to stabilize the tissue. The user then applies distal and rotational forces to drive shaft 862, which causes coupling member 864 and coil 860 to move distally and rotate into the tissue, for example, the mucosal layer of tissue. As coil 860 advances into the tissue, distal end 874a of sheath 866 remains on the surface of the tissue, spring 870 is compressed, and shelf 867d advances toward sheath proximal end 874a. When coil 860 has been anchored in the tissue, for example, the muscle layer of tissue underlying the mucosal layer (which takes about 3 or 4 turns of the coil into the tissue), the user can manipulate the tissue with tissue engaging member 740'. By engaging multiple layers of tissue, member 740' provides a secure grasp on the tissue.

Sprung sheath 866 acts to stabilize both the tissue and coil 860 when coil 860 is advanced into the tissue. Sheath 866 compresses the tissue, facilitating initial penetration of the coil into the tissue, and helps keep the tissue from twisting as the coil rotates. Furthermore, the coil 860 tends to want to go off-axis as it rotates into the tissue. Sprung sheath 866 provides enough force against the tissue and has enough friction against the tissue surface to limit movement of sheath 866 as coil 860 is advanced into the tissue. This counteracts the tendency of the coil to want to go off-axis.

Due to the opposed winding of drive shaft 862 and coil 860, the rotational force applied to drive shaft 862 causes a decrease in the diameter of drive shaft 862 upon encountering torsional resistance. This decrease in the diameter of drive shaft 862 limits contact of drive shaft 862 with the wall of an associated working channel in which drive shaft 862 is located and thus possible jamming in the working channel.

Referring to FIGS. 13A and 13B, to apply the distally and rotationally directed forces to drive shaft 862, a torque generator 882 held by the user and a drive rod 880 releasably attached to torque generator 882 and extending through handle 743 are coupled to drive shaft 862. Drive rod 880 runs a majority of the length of instrument 700 to provide high torque, with drive shaft 862 extending in the area of the retroflex region to provide high flexibility. Drive rod 880 and drive shaft 862 are coupled, for example, by soldering. Torque generator 882 includes a handle 883, a collet 885, and a spring loaded cap 887. Collet 885 includes a circumferential section 885' and four legs 885a extending from section 885', each with an enlarged end 885b. Each leg 885a has a flat, inner facing surface 885c that together define a square opening 886. Drive rod 880 has a coupling member 889 with four flat sides 889a. Coupling member 889 is received within opening 886 with flat sides 889a aligned with surfaces 885c such that when closed, torque generator 882 and drive rod 880 are rotationally locked.

Handle 883 defines a bore 881' in which a pin 882' is received, and a larger diameter bore 883' in which pin 882', collet 885 and a spring 887' are received. Cap 887 is biased distally by spring 887'. Pin 882' is press fit into bore 881' and into circumferential section 885' of collet 885. To attach drive rod 880 to torque generator 882, cap 887 is moved proximally against the force of spring 887', which allows legs 885a to be flexed outward permitting coupling member 889 to be positioned in opening 886. The user releases cap 887, and spring 887' acts to move cap 887 distally closing legs 885a around coupling member 889. Distal motion of cap 887 is limited by contact of a shelf 880' of cap 887 against enlarged leg ends 885b.

Tissue engaging member 740' is preferably a single use disposable product supplied sterile to the user. Member 740' can be loaded into the instrument from the distal end of the instrument and then attached to torque generator 882. This preserves the sterility of the distal end of member 740'.

Referring to FIG. 14A, in an alternative embodiment, rather than stabilizing tissue with sprung sheath 866 of FIG. 12A, positioned within coil 860 is a solid needle 881a. Needle 881a extends from coupling member 864. Needle 881a facilitates the initial engagement of coil 860 with the tissue, and is particularly applicable to situations in which coil 860 approaches the tissue surface at an angle. Referring to FIGS. 14B and 14C, rather than a solid needle, positioned within coil 860 and extending to the proximal end of the tissue engagement member is a matter injector needle 881b, which can be advanced through coil 860. Matter injector needle 881b has a metal tip 881c on a flexible, plastic tube 881d. Coupling member 864, coupling member 889, pin 882', and hand grip 883 define aligned through bores that slidably receive needle 881b. Needle 881b replaces drive rod 880, and drive shaft 862 extends the length of the instrument.

Matter injector needle 881b can be used in "bulking" procedures to augment tissue in a selected region by injecting a biocompatible material, such as described, for example, in U.S. Pat. No. 5,336,263 to Ersek et al., hereby incorporated by reference in its entirety. In use, coil 860 acts to anchor needle 881b in the tissue to counteract pressure created by the material injection, which would tend to push needle 881b out of the tissue. For matter injection, the tissue engaging instrument can be used through a working channel of an endoscope, or in conjunction with instrument 700. Alternatively, the wire forming coil 860 can define a lumen and matter injected through the wire lumen.

Figure 15A:
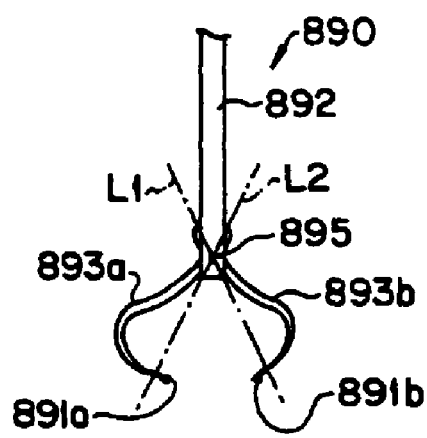
FIGS. 15A-15D are illustrations of an additional alternative tissue engaging member.
Figure 15B:
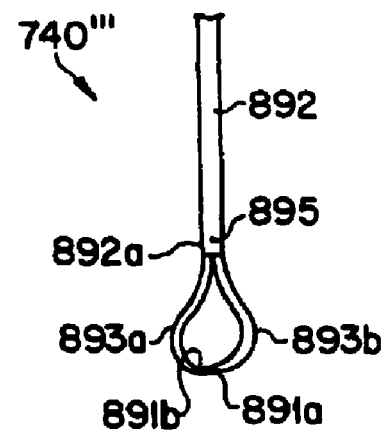

Referring to FIGS. 15A and 15B, an alternative third tissue engagement member 740''' includes an elongate member 892 that passes through a working channel of instrument 700 and a pair of pincers 893a and 893b pivotably mounted at a pivot 895 to the distal end 892a of elongate member 892. Pincers 893a and 893b each include a respective pincer tip 891a and 891b suitable for piercing tissue. Pincers 893a and 893b are actuated, for example, by one or more guide wires (not shown), as is described, for example, in U.S. Pat. No. 5,613,499 to Palmer et al., hereby incorporated by reference in its entirety.

Pincers 893a and 893b are generally arcuate in shape with pincer tips 891a and 891b oriented substantially normal to lines L1, L2 defined by pivot point 895 and the end of each respective pincer tip. Pincers 893a and 893b are made from a rigid, sterilizable material capable of maintaining pincer tips 891a and 891b suitable for puncturing tissue and withstanding at least short term exposure to operating environments such as the stomach. As such, pincers 893a and 893b can be made from metals such as stainless steel and Co—Cr alloys.

Figure 15C:
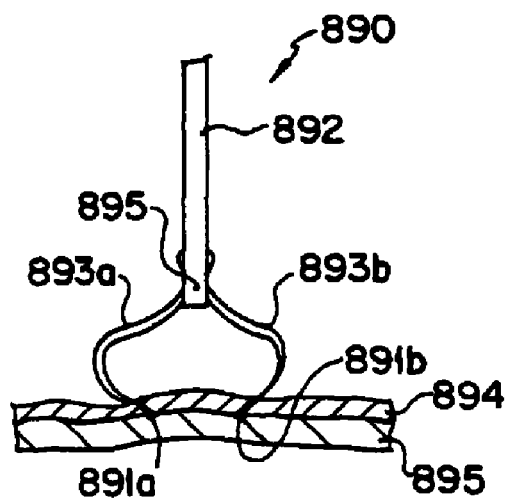
Figure 15D:
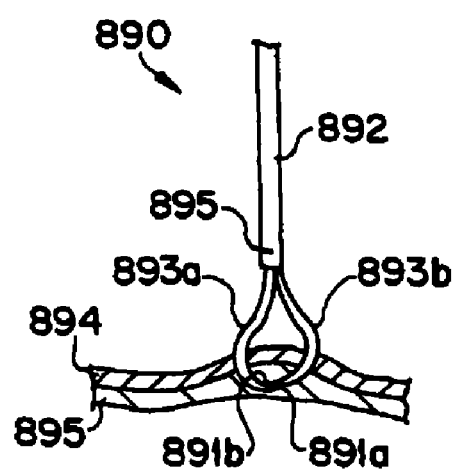

Referring to FIGS. 15C and 15D, in operation, with pincers 893a and 893b in their opened position, the user advances tissue engagement member 740''' into contact with a tissue surface such as a mucosal layer 894 on a muscle layer 895 in the stomach. The user then closes pincers 893a and 893b such that the pincer tips 891a and 891b penetrate through the mucosal layer 894 and into muscle layer 895. Once the pincer tips 891a and 891b have been drawn together, the user retracts the pincers 893a and 893b from the engaged tissue using the elongate member 892. Plication and/or bulking of the retracted tissue can follow as described elsewhere herein.

Due to the arcuate shape of pincers 893a and 893b, the initial closing of the pincers results in substantially distal translation of pincer tips 891a, 891b, with further closing of the pincers resulting in substantially transverse motion of pincer tips 891a, 891b. This distributes the retraction load applied by the pincers 893a and 893b for plication over a relatively large area of tissue, limiting the possibility of tearing the tissue during retraction.

Figure 16A:
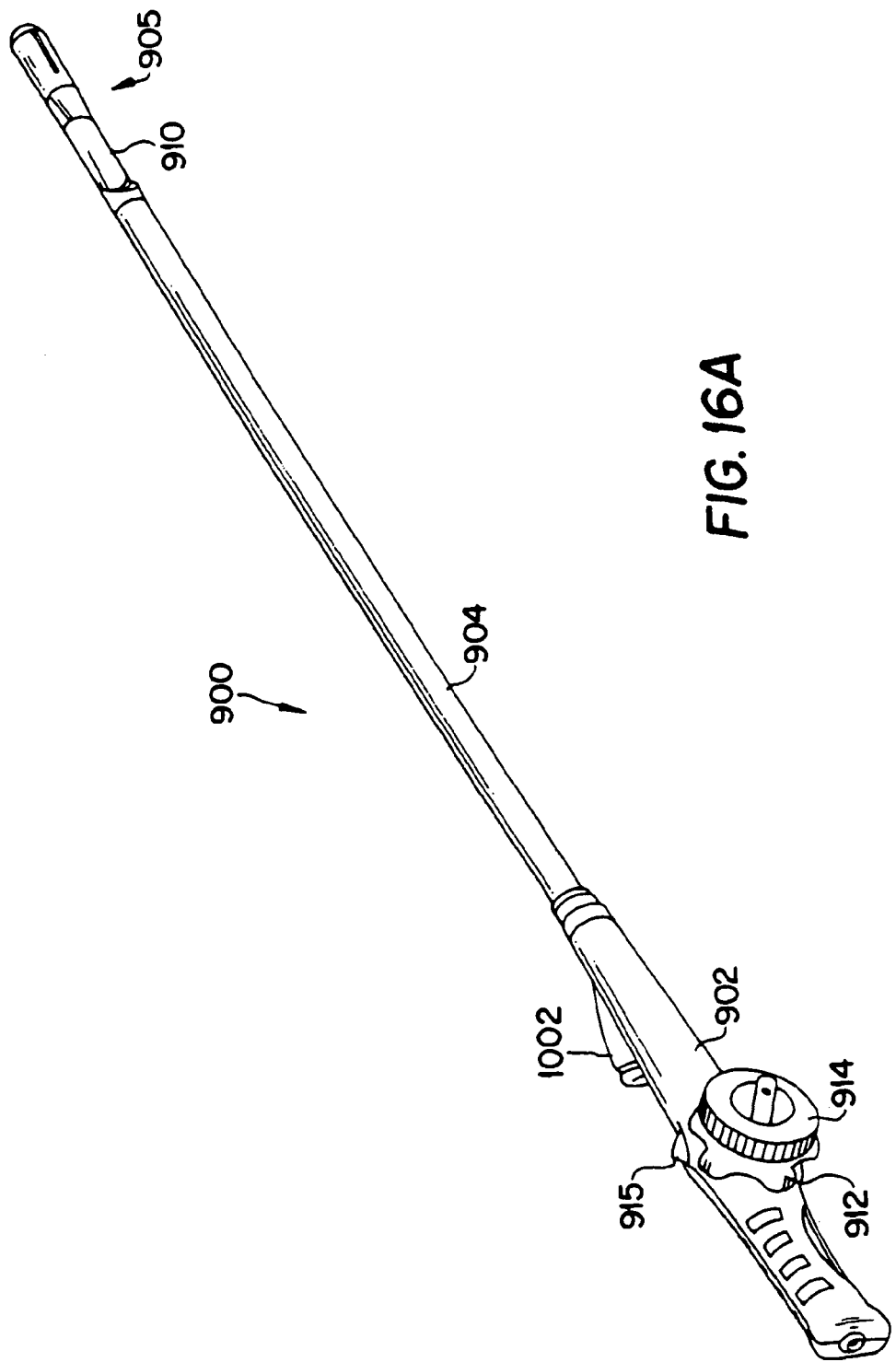
FIG. 16A is an isometric view of an instrument for reconfiguring tissue.
Figure 16B:
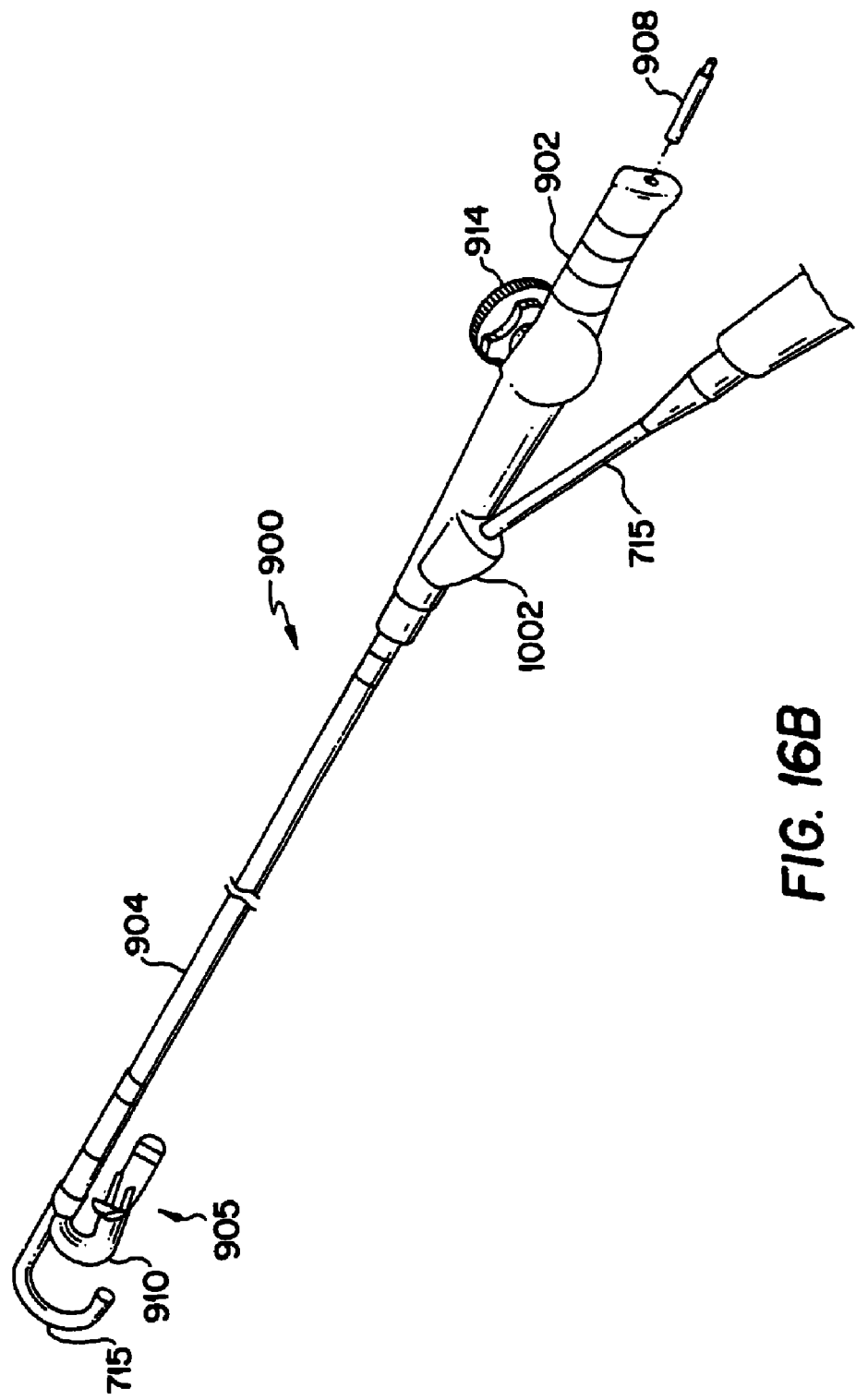
FIG. 16B shown the instrument of FIG. 16A receiving a gastroscope.

Referring to FIGS. 16A and 16B, in accordance with another embodiment of the invention, an instrument 900 for reconfiguring stomach tissue includes a handle 902, an elongated instrument shaft 904, and a distal actuating assembly 905. As discussed below, the configuration of assembly 905, and the means of attachment of assembly 905 to instrument shaft 904, substantially seals a lumen of shaft 904 that houses the actuating cables from contact with bodily fluids. As a result, only a disposable portion of assembly 905 need be supplied to the user in a sterile condition. The remainder of the instrument can simply be disinfected by manual cleaning and soaking in a disinfecting solution between procedures.

As in embodiments discussed above, instrument 900 receives gastroscope 715 and a tissue engagement member 908 (such as coil 740 or 740' described above). Assembly 905 includes a retroflex portion 910 that is manipulated by the user to orient assembly 905 (as shown in FIG. 16B). Handle 902 includes control knobs 912, 914 that actuate assembly 905, and a switch 915 that disengages a lock mechanism, as described below.

Referring to FIGS. 17A and 17B, shaft 904 defines a lumen 916 through which the end of gastroscope 715 protrudes. Retroflex portion 910 has a sloping curved wall section 918 against which the end of gastroscope 715 is received. When flexed, retroflex portion 910 is bent in a direction away from section 918 (arrow A). Assembly 905 further includes a coupling member 919 and an end effector 906. Coupling member 919 includes a first portion 923 that attaches to retroflex portion 910, and a mount 924 to which end effector 906 is pivotally mounted. End effector 906 includes jaw members 920, 922, each of which includes a tissue manipulating cartridge 960a, 960b, respectively, releasable mounted to a respective actuating arm 962a, 962b.

Covering retroflex portion 910 and coupling member portion 923 is a cover 910', and covering mount 924 and end effector 906 is a hood 1220, discussed further below. Hood 1220 provides an atraumatic distal end for transoral placement of instrument 900, and cover 910' seals retroflex portion 910 and coupling member portion 923 from contact with bodily fluids.

In use, with gastroscope 715 in instrument lumen 916 and the end of the gastroscope residing in section 918, the user advances instrument 900 transorally into the stomach. Once in the stomach, gastroscope 715 is independently manipulated to obtain the desired view. The user flexes instrument 900 (as shown in FIG. 16B), opens jaws 920, 922, advances the tissue engagement member into engagement with the tissue to stabilize the tissue, closes jaws 920, 922 such that cartridges 960a, 960b manipulate the tissue into a bulge, and deploys an implant, as described further below.

Referring to FIG. 17C (coupling member 919 has been partially removed from FIG. 17C for clarity), actuating arms 962a, 962b are pivotally coupled to mount 924 at pivots 963a, 963b, respectively. A pair of cables, discussed below, for opening and closing jaws 920, 922 are coupled to the jaws via a yoke 964. Yoke 964 has a generally H-shaped section 965 with two legs 966a straddling arm 962a, and two legs 966b straddling arm 962b. Each arm 962a, 962b defines a slot 968a, 968b, and each leg 966a, 966b defines a through hole 970a, 970b. Received within slot 968a and holes 970a is a pin 972a, and received within slot 968b and holes 970b is a pin 972b. Slots 968a, 968b each have first and second sections 974, 975. Slot sections 974 are orientated at a greater angle relative to the axis of the instrument than that of slot sections 975, for purposes described below. Yoke 964 includes a post 978 extending proximally from section 965. Post 978 extends into coupling member 919. Mounted to post 978 is a first pulley 982, and mounted to coupling member 919 are two pulleys 984, 985, which a jaw closing cable is routed over, as described below.

Portion 923 and mount 924 of coupling member 919 have flat sides 923a, 924a and rounded sides 923b, 924b, as shown in FIG. 17D. Rounded sides 923b, 924b define a through bore 927 for passage of the tissue engagement member. Mount 923 also defines a through bore 931 through which yoke 964 extends.

Referring to FIGS. 17E and 17F, located in portion 923 is a lock arm 1250 pivotally mounted at 1252. Lock arm 1250 has a ridge 1253 with curved wall 1254 and yoke 964 defines a notch 1256 with a correspondingly shaped curved wall 1258. After a predetermined amount of distal travel of yoke 964, curved wall 1254 of ridge 1253 engages with curved wall 1258 of notch 1256 to limit further distal travel of yoke 964. Lock arm 1250 is biased by a compression spring 1262 to rotate clockwise about pivot 1252 (arrow Y) such that when notch 1256 passes under lock arm 1250, lock arm 1250 is rotated under the force of spring 1262 to engage curved walls 1254, 1258. Attached to lock arm 1250 is a cable 1260 for moving arm 1250 out of engagement with yoke 964 to allow further distal travel of yoke 964.

Figure 17G:
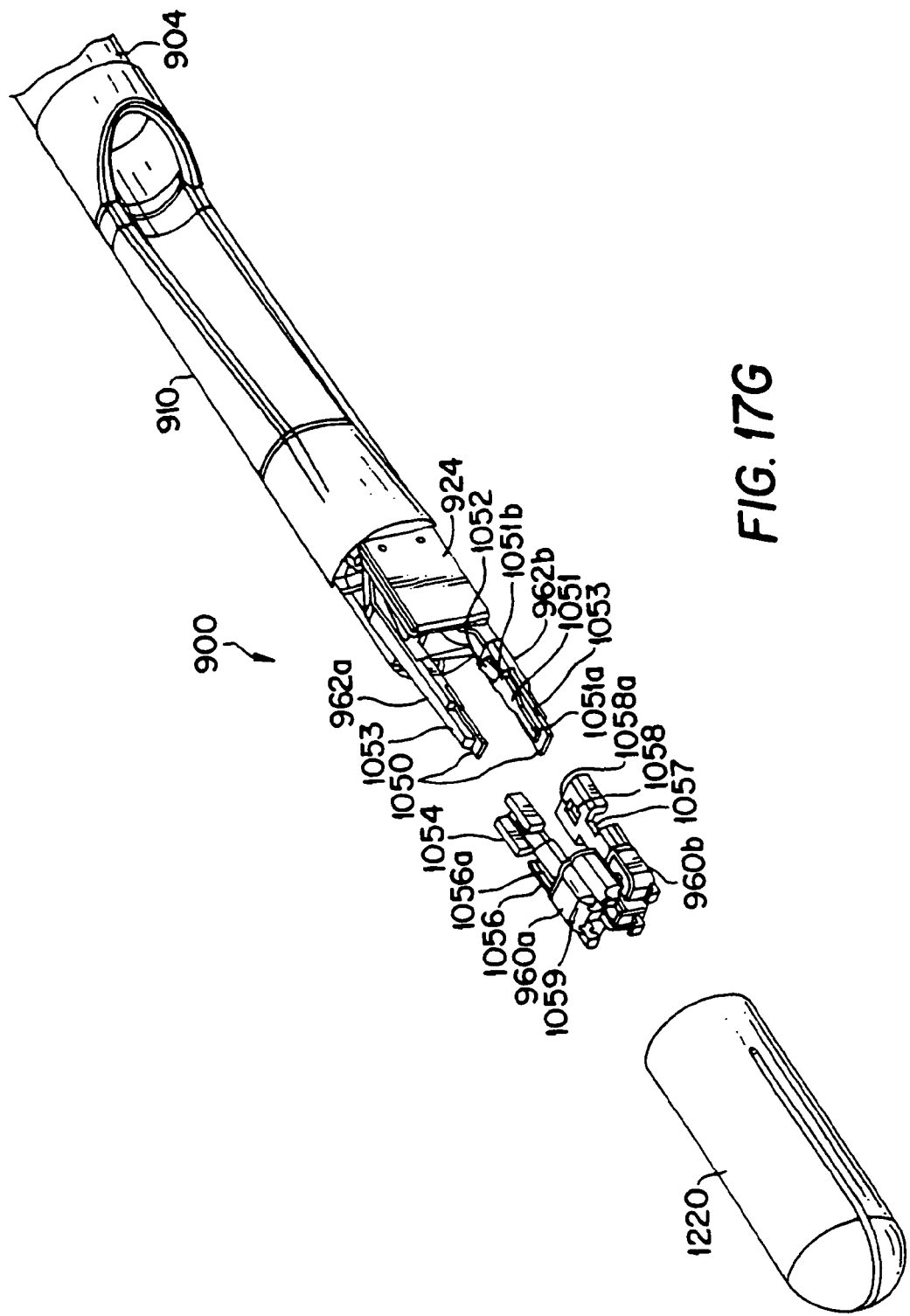
FIG. 17G is an illustration of disposable components of the instrument of FIG. 16A.

FIG. 17G illustrates the replaceable nature of cartridges 960a, 960b. Arms 962a, 962b each include a flat, rectangular member 1050 and a clip 1052. Member 1050 has formations 1051, 1053 extending from either side of member 1050. Formations 1051 have a thin distal section 1051a that slopes to a wider proximal section 1051b, for purposes described below with reference to FIG. 46. Cartridges 960a, 960b each include a first pair of side walls 1054, a second pair of side walls 1056 defining slots 1056a, an opening 1058, and a head 1059. Opening 1058 is rectangular in shape, here shown square, though other shapes are suitable that have a mating contour with a flat proximal edge 1058a. Instead of an opening 1058, an indentation in the cartridge that corresponds to the shape of clip 1052 can be employed. Side walls 1054, 1056 are separated by a thin section 1057 that allows the cartridge to flex.

To attach cartridges 960a, 960b to arms 962a, 962b, respectively, the cartridge is slid over the arm with side walls 1054 aligning the cartridge to the arm. Rectangular member 1050 is received in slots 1056a while the cartridge flexes over clip 1052 such that clip 1052 is received within opening 1058 to lock the cartridge to the arm. To remove the cartridge, the user pushes on side walls 1054 to flex the cartridge away from clip 1052, and the cartridge is then slid off the arm.

Referring to the exploded view of FIG. 17H, retroflex portion 910 has a proximal mount 1060 that is, for example, glued onto the end of shaft 904, and a distal mount 1062 that is received within a slot 933 in mount 923. Mounts 1062, 923 are attached, for example, by screws. Mount 1062 is preferably metal and coupling member 919 is preferably plastic.

Referring to FIG. 17I, the only member of instrument 900 that extends from retroflex region 910 through the sealed section formed by cover 910' is yoke 964. To limit access of bodily fluids to retroflex portion 910, coupling member portion 923 defines a space 1070 in which an o-ring 1072 is positioned to seal off through bore 931.

Figure 20:
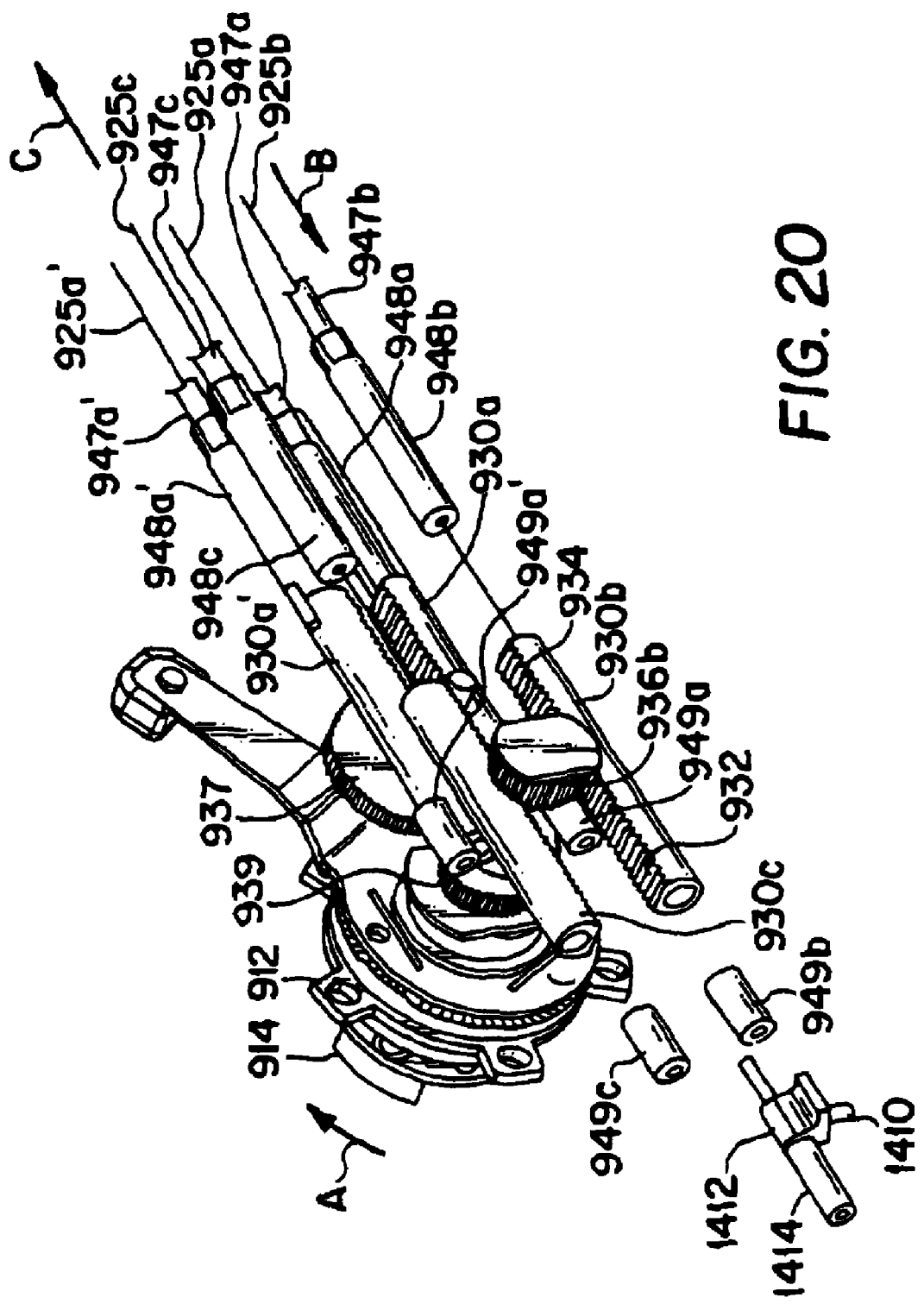
FIG. 20 is an illustration of the mechanism inside the gearbox of FIG. 19.
Figure 21A:
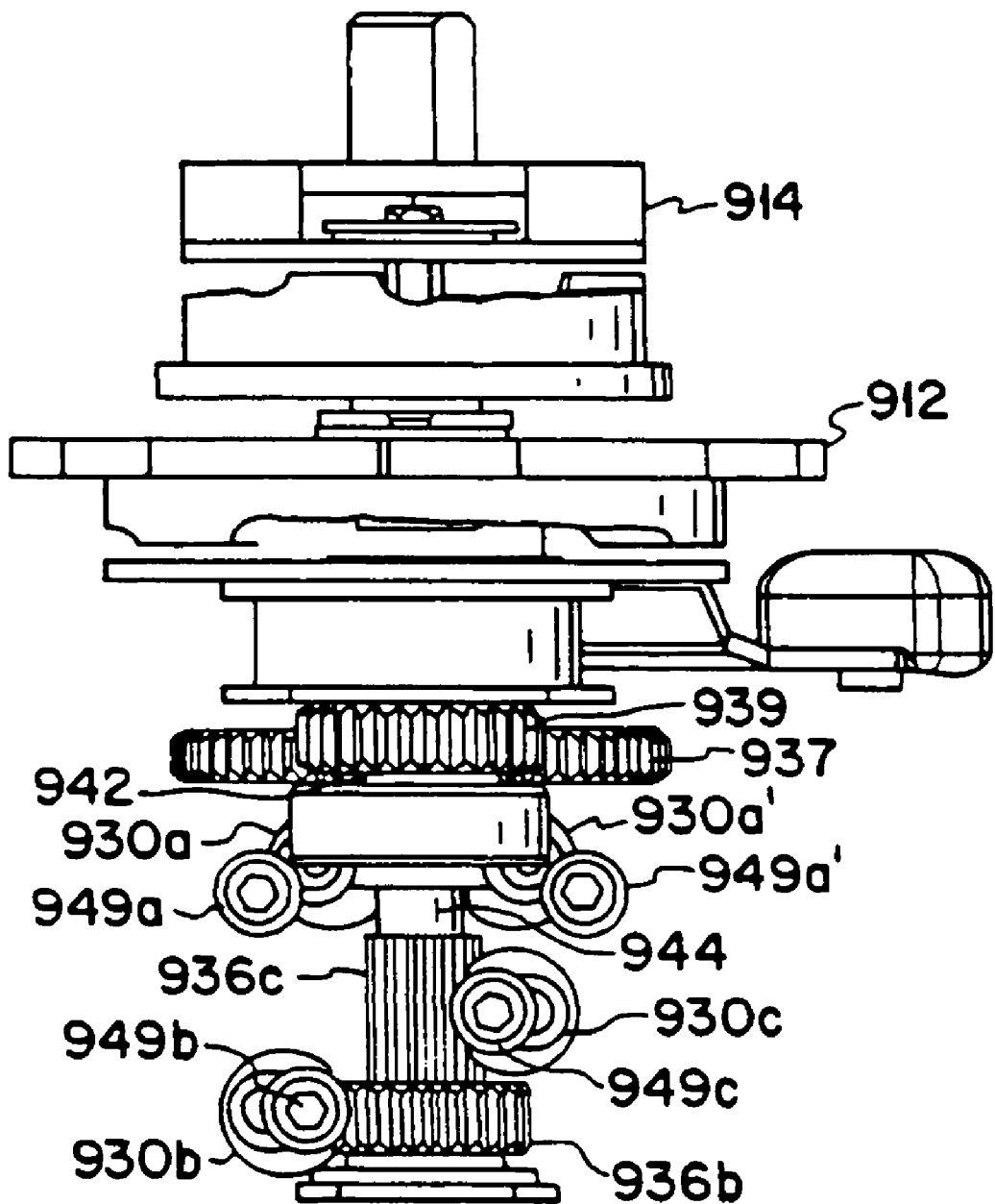

Referring to FIGS. 18-20, to control retroflex portion 910 and end effector 906, knobs 912, 914 interface with a series of cables 925a, 925a', 925b, 925c (FIG. 20) through a gear block mount 926 located in handle 902. Block mount 926 defines through bores 928a, 928a', 928b, 928c within each of which a rack 930a, 930a', 930b, 930c, respectively, is located. Each rack 930a, 930a', 930b, 930c is connected to a respective cable 925a, 925a', 925b, 925c, as described below, and has a flat side 932 defining teeth 934. Referring particularly to FIGS. 21A and 21B, associated with racks 930a, 930a' is a pinion 936a, and associated with each rack 930b, 930c is a respective pinion 936b, 936c. Racks 930a, 930a' are on opposite sides of pinion 936a, and racks 930b, 930c are on opposite sides of pinions 936b, 936c. Pinion 936b is preferably twice the diameter of pinion 936c, for reasons discussed below. Pinion 936a is driven by a reduction gear set 937, 939. Gear 939 is mounted to a shaft 942 that is integral with retroflex knob 912. Pinions 936b, 936c are mounted to a shaft 944 that is integral with jaw actuating knob 914, and passes through shaft 942.

To manipulate retroflex portion 910, the user turns knob 912, which causes shaft 942 and pinion 936a to turn. Since racks 930a, 930a' are on opposite sides of shaft 942, rotation of pinion 936a causes opposed linear motion of racks 930a, 930a', which moves cables 925a, 925a' to flex and straighten retroflex portion 910, as described further below. To manipulate the jaws, the user turns knob 914, which causes shaft 944 and pinions 936b, 936c to rotate. Since racks 930b, 930c are on opposite sides of shaft 944, rotation of pinions 936b, 936c causes opposed linear motion of racks 930b, 930c, which moves cables 925b, 925c to open and close the jaws, as described further below. Associated with knob 912 is a tension adjustment lever 912a, and associated with knob 914 is a tension adjustment knob 914a, as is well known in the art.

Referring to FIGS. 20 and 22, mounted over each cable 925a, 925a', 925b, 925c is a cable housing 947a, 947a', 947b, 947c, respectively, and a cable housing adjustment screw 948a, 948a', 948b, 948c, respectively. Cable housing adjustment screws 948a, 948a', 948b, 948c are threadably received within respective block through bores 928a, 928a', 928b, 928c (as shown in FIG. 19). Rotation of screws 948a, 948a', 948b, 948c translates cable housings 947a, 947a', 947b, 947c distally and proximally along respective cables 925a, 925a', 925b, 925c to provide an optimal working length for transmitting actuating forces. Cables 925a, 925a', 925b, 925c move freely through their respective housings and screws.

On the opposite side of racks 930a, 930a', 930b, 930c from screws 948a, 948a', 948b, 948c are stops 949a, 949a', 949b, 949c received within respective block through bores 928a, 928a', 928b, 928c. Stops 949a, 949a', 949b, 949c limit the travel of racks 930a, 930a', 930b, 930c, respectively.

Referring particularly to FIG. 22, cable 925a is received within a bore 950 defined in rack 930a. Cable 925a extends through a hole 952 defined in an end wall 954 of rack 930a into bore 950. Located within bore 950 is a spring 956. Cable 925a extends through spring 956 and has an enlarged terminal end 957 that maintains the position of cable 925a relative to spring 956. Spring 956 acts to continually exert a slight tensile force upon cable 925a to keep the cable taught. Cables 925b, 925c are likewise coupled to racks 930b, 930c, respectively.

Referring again to FIG. 19, attached to block mount 926 is a slide lever 1400 mounted within a bracket 1402. Switch 915 is received within an opening 1404 in lever 1400 such that movement of switch 915 moves lever 1400. Lever end 1406 defines a diagonal slot 1408 in which a pin 1410 is received. Pin 1410 is attached to a stop member 1412 that contacts a stop 1414 after jaw closing rack 930b has traveled a pre-set distance. Movement of lever 1400 in the direction of arrow X causes pin 1410 and stop member 1412 to rotate about the axis of stop member 1412, disengaging stop member 1412 from stop 1414 to allow further movement of rack 930b. Cable 1260 attached to lock arm 1250 is attached at its opposite end to switch 915. When switch 915 is moved in the direction of arrow X, cable 1260 moves lock arm 1250 to disengage lock arm 1250 from yoke 964 (discussed further below with reference to FIG. 23). Bracket 1402 can be adjusted to fine tune the positioning of switch 915 relative to pin 1410 and lock arm 1250.

As shown in FIGS. 23A-23D, jaw closing cable 925b is wound around pulleys 984, 985, and 982, and terminates at a fixed point 986 connected to distal mount 1062 (FIG. 17E). Jaw opening cable 925c is connected in a fixed relationship to post 978. To close jaws 920, 922, the user turns knob 914 in the direction of arrow, A (FIG. 20), which moves cable 925b in the direction of arrow, B, and permits slack in cable 925c allowing yoke 964 to move distally, in the direction of arrow, C. Due to the 2:1 ratio between pinions 936b and 936c, cable 925b moves twice the distance of cable 925c. (This is required due to the routing of cable 925b around pulleys 982, 984, and 985.) Pins 972a, 972b slide along slots 968a, 968b causing jaws 920, 922 to close. To open the jaws, the user turns knob 914 in the direction opposite arrow, A, which tensions cable 925c and permits slack in cable 925b. The tension on cable 925c moves yoke 964 proximally (opposite arrow C) opening jaws 920, 922.

Due to the orientation of slot sections 974, 975, during the initial stage of jaw closing (FIG. 23B) when the yoke is sliding along slot section 974, there is a greater ratio of jaw closing for the distance the piston moves than during the later stage (FIG. 23C) when the yoke is sliding along slot section 975. Such a configuration provides faster jaw closing with lower mechanical advantage when less closing force is needed (because the jaws are not yet contacting the tissue), and slower jaw closing with higher mechanical advantage when more closing force is needed as the jaws grasp the tissue and pierce through the tissue. After the jaws have reached the position of FIG. 23C, pin 1410 hits stop 1414 in handle 902 and lock arm notch 1254 and yoke notch 1256 engage to limit further closing of the jaws. The user then pushes switch 915 proximally to move stop member 1412 out of the way and to disengage lock arm 1250 from yoke 964, this permits knob 914 to be further turned to completely close the jaws and deploy the implant (FIG. 23D).

Referring to FIGS. 24A-24D, retroflex portion 910 includes a series of links 990 that are hinged together with pins 991. Each link 990 includes a generally U-shaped body 992 with a first section 992a defining a U-shaped opening and second section 992b defining a larger U-shaped opening. Extending from body 992 are two mating prongs 994. Body 992 defines two transverse holes 996 (only one hole 996 being shown in FIG. 24B), and each prong 994 defines a transverse hole 998. When two links 990 are mated, prongs 994 lie within the U-shaped opening defined by section 992b. Holes 996, 998 are aligned, and pin 991 is passed through holes 996, 998 to join the two links. Body 992 has a side wall 1000 with a portion 1001 of the side wall set at an angle to allow the joined links to flex. Links 990 also define axial holes 1002, 1003 for receiving cables 924a', 924a, respectively. Cables 924a, 924a' terminate on mount 1062. Pulling cable 924a flexes portion 910, and pulling cable 924a' straightens portion 910. Cover 910' (FIG. 17A) covers the links.

Figure 25:
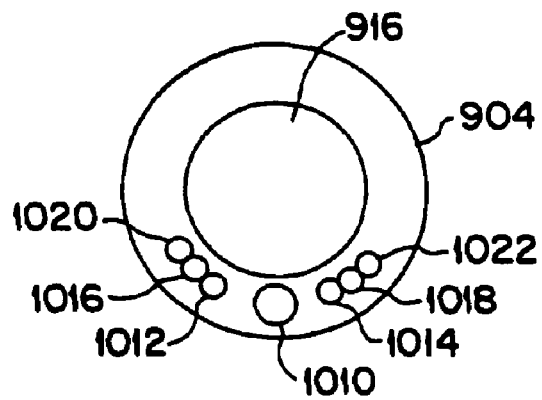
FIG. 25 is a cross-sectional view of a shaft of the instrument of FIG. 16A.

Referring also to FIG. 25, in addition to lumen 916 for receiving gastroscope 715, shaft 904 and mount 1060 define a lumen 1010 for receiving tissue engaging member 908, a lumen 1012 for receiving flexing cable 924a, a lumen 1014 for receiving straightening cable 924a', a lumen 1016 for receiving closing cable 925b, a lumen 1018 for receiving opening cable 925c, a lumen 1020 for receiving locking cable 1260, and an extra lumen 1022 if needed. Mount 1062 includes holes 1024 and 1026 for passage of cables 925b, 925c, respectively, a hole 1028 at which the end of closing cable 925b terminates, and a hole 1030 for passage of locking cable 1260.

Tissue engaging member 908 is located in the U-shaped openings defined by U-shaped bodies 992 in retroflex portion 910. Pins 991 are centered along the central axis of tissue engaging member 908 such that when flexed, tissue engaging member 908 is flexed along is central axis. Tissue engaging member 908 is surrounded by a sheath 927a (FIGS. 17D and 18). Sheath 927a runs from handle inlet 1002 to the proximal end of through bore 927 in coupling member 919. Sheath 927a is sealed at one end to handle 902 and at the other end to coupling member 919. This effectively seals the remainder of the instrument from contact with fluid that enters tissue engaging member 908. Shaft lumen 916 likewise is lined with a sheath 916' that seals the remainder of the instrument from contact with bodily fluids that enter lumen 916.

Figure 26:
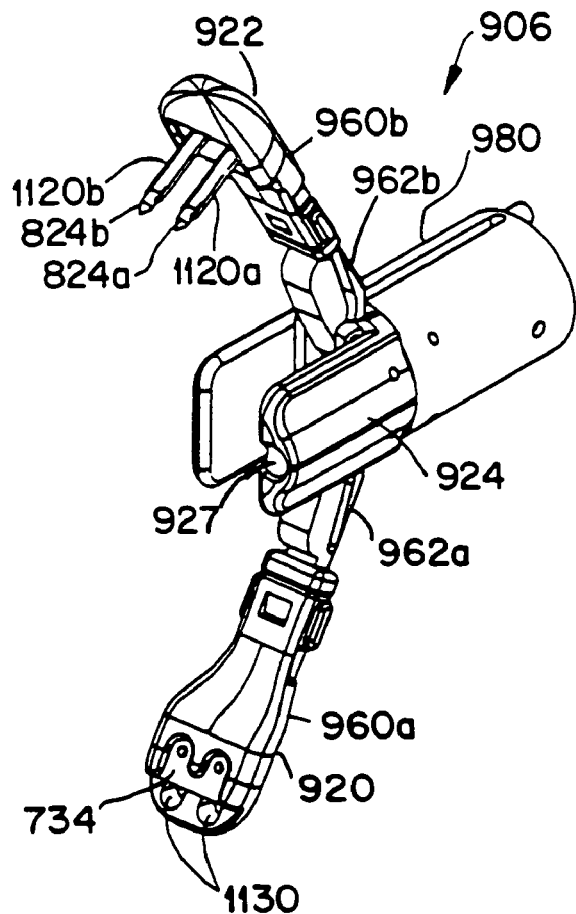
FIG. 26 is an isometric view of the distal end portion with the jaw members open.
Figure 27:
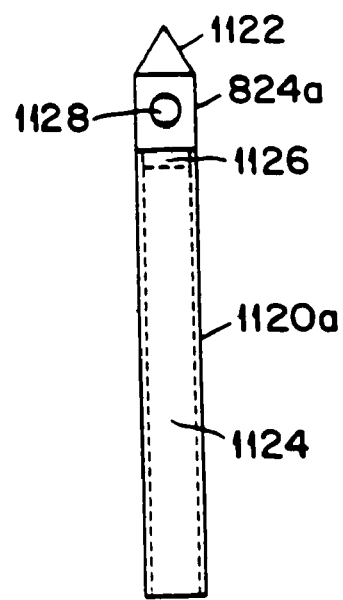
FIG. 27 is an illustration of an implant bar of a tissue fixation device shown coupled to a tube of the jaw member.

Referring to FIGS. 26 and 27, end effector 906 is configured for deployment of a tissue fixation member upon closing of jaws 920, 922 without requiring further actuation. Cartridge 960b of jaw 922 includes tissue passing tubes 1120a, 1120b. Removably coupled to each tube 1120a, 1120b is a tissue fixation bar 824a, 824b having a pointed tip 1122 for penetrating tissue. Each tube 1120a, 1120b defines a through bore 1124, and each bar 824a, 824b has a hub 1126 that fits within bore 1124. Tubes 1120a, 1120b and bars 824a, 824b have the same outer diameter for ease of penetrating tissue. Bars 824a, 824b each define a through hole 1128 for receiving, for example, a suture (not shown), which is passed through both holes and tied off to itself. Bars 824a, 824b can be coupled to tubes 1120a, 1120b, respectively by a press fit, crimp, or spot laser welding. Crimping can be done around the entire perimeter of the bar, at two (opposing) sides of the bar, or at a single point along the perimeter of the bar.

Figure 28A:
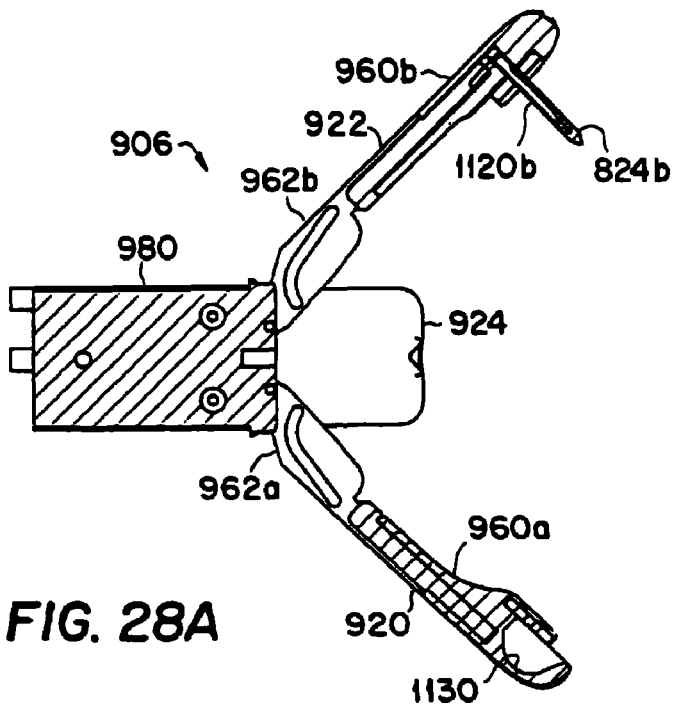
FIGS. 28A-28C illustrate deployment of the implant bar of FIG. 27.
Figure 28B:
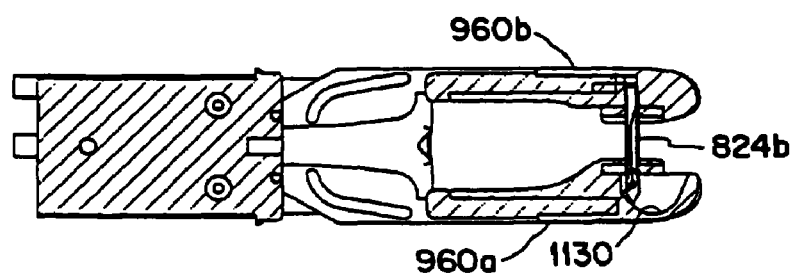
Figure 28C:
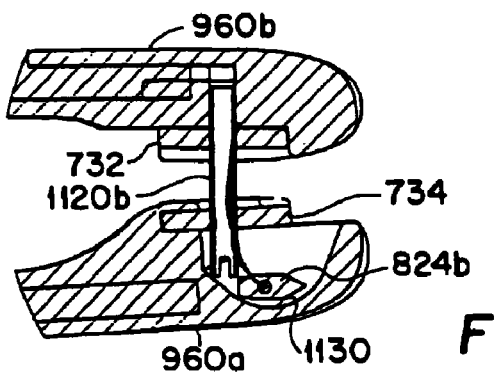

Bars 824a, 824b are configured to detach from tubes 1120a, 1120b under the force applied by the closing of jaws 920, 922. Referring to FIGS. 26 and 28A-28C, cartridge 960a defines two arcuate walls 1130 against which bars 824a, 824b are positioned upon closing of jaws 920, 922. As shown in FIG. 28C, upon closure of jaws 920, 922, the arcuate walls 1130 apply a lateral force (that is, substantially normal to the long axis of the tubes) to bars 824a, 824b, which causes the bars to be released from the respective tubes. When jaws 920, 922 are opened, and instrument 900 pulled proximally, bars 824a, 824b and parts 732, 734 (discussed above with reference to FIG. 8) of the tissue fixation member are released from jaws 920, 922.

Figure 29A:
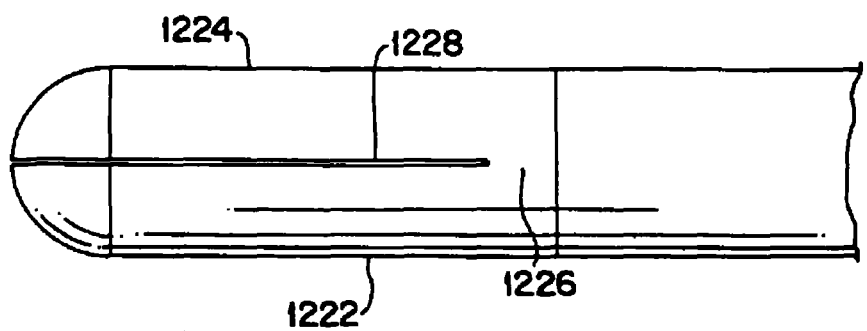
FIGS. 29A and 29B are illustrations of the hood member with the jaw members closed and open, respectively.
Figure 29B:
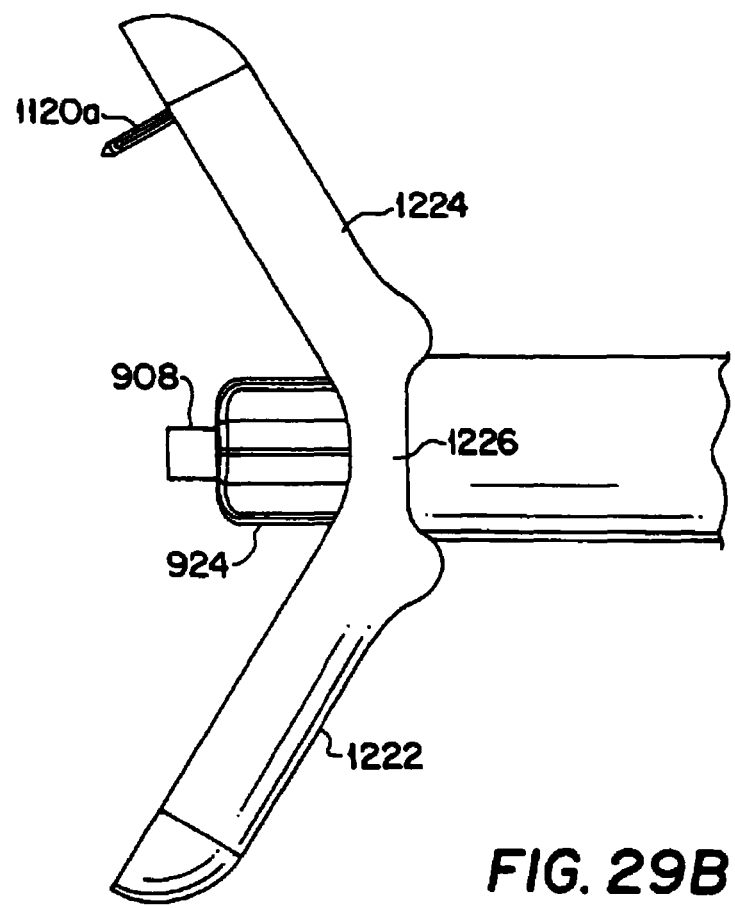

Referring to FIGS. 29A and 29B, jaws 920, 922 are covered with hood 1220 formed from halves 1222 and 1224 connected at a region 1226 and defining a seam 1228 therebetween. Each half 1222, 1224 covers a respective jaw 920, 922. When the jaws are closed, as shown in FIG. 29A, hood 1220 provides an atraumatic distal end for delivery through the esophagus. When the jaws are opened, as shown in FIG. 29B, halves 1222, 1224 separate at seam 1228. Hood 1220 limits trauma to the tissue during transoral insertion of the instrument and eliminates the need for an outer sheath extending the length of the instrument.

Referring to FIG. 30, handle 902 defines an inlet 1002 through which gastroscope 715 is introduced. Located at inlet 1002 is a seal 1004 for providing a hermetic seal between handle 902 and gastroscope 715. Seal 1004 has a sealing area 1006 of restricted diameter, and an alignment area 1008 of restricted diameter spaced about 10 mm from area 1006. Area 1006 has a diameter of about 9 mm, which is about the same or slightly smaller than (about 90% of) the diameter of gastroscope 715 (typically about 10 mm). Area 1008 has a diameter of about 11 mm, which is also about the same or slightly larger than (about 110% of) the diameter of gastroscope 715. Alignment area 1008 provides support for gastroscope 715 to maintain a hermetic seal at sealing area 1006 during motion of the gastroscope. Seal 1004 is made from, for example, rubber or other deformable material.

Other embodiments are within the scope of the following claims.

For example, referring to FIG. 31, instead of curved surfaces 1130 of FIG. 28, cartridge 960a' includes a spring member 1130'. When bars 824a, 824b contacts members 1130', member 1130' deflects forming a curved surface resulting in a lateral force being applied to bars 824a, 824b that acts to dislodge the bars from tubes 1120a, 1120b.

Referring to FIG. 32, in an alternative embodiment, tubes 1120' include a pair of radially opposed slots 1132 that impart flexibility to end 1133 of the tube to aid in release of the bars from the tubes. Bars 824' can include a pair of guide nubs 1134 received in slots 1132 to radially orients bars 824' relative to tubes 1120'. Referring to FIG. 33, bars 824" include a bump or undercut 1136 that determine the force needed to remove the bars from the tubes. The tubes can be formed from plastic and molded as an integral component of the cartridges, and the bars can be insert molded into the tubes. Referring to FIG. 34, bars 824''' are connected to tubes 1120" by a weak, frangible area 1137 of decreased diameter that breaks upon application of lateral force to bars 824'''.

Referring to FIGS. 35A and 35B, instead of bars attached by suture, the tissue fixation member includes bars 1150 connected by a flexible spanning member 1152. Bars 1150 define through bores 1154 and are received on members 1156 having tissue penetrating tips 1158. Members 1156 replace tubes 1120.

Referring to FIG. 36A, to aid in insertion of instrument 900 through the esophagus, end effector 906 and retroflex portion 910 are partially covered with an atraumatic hood 1100. Hood 1100 has a tapered distal end 1102 terminating in a small diameter lead portion 1104. Hood 1100 includes an opening 1106 through which end effector 906 and retroflex portion 910 are deployed, in the direction of arrow, D, after insertion of instrument 900 through the esophagus. Distal end 1102 defines a channel 1105 extending from lead portion 1104 to a slot 1107. Instrument 900 can be introduced transorally over a guide wire (not shown) by threading the guide wire through channel 1105 entering at lead portion 1104 to exiting at slot 1107. Hood 1100 is made from, for example, metal, plastic, or elastomeric materials such as rubber, polyurethane or silicone.

As shown in FIG. 36B, to further ensure trauma to tissue as the instrument is introduced transorally is avoided, a pair of flaps 1109 are provided covering assembly 905. The flaps part when retroflex portion 910 is deployed.

Figure 37:
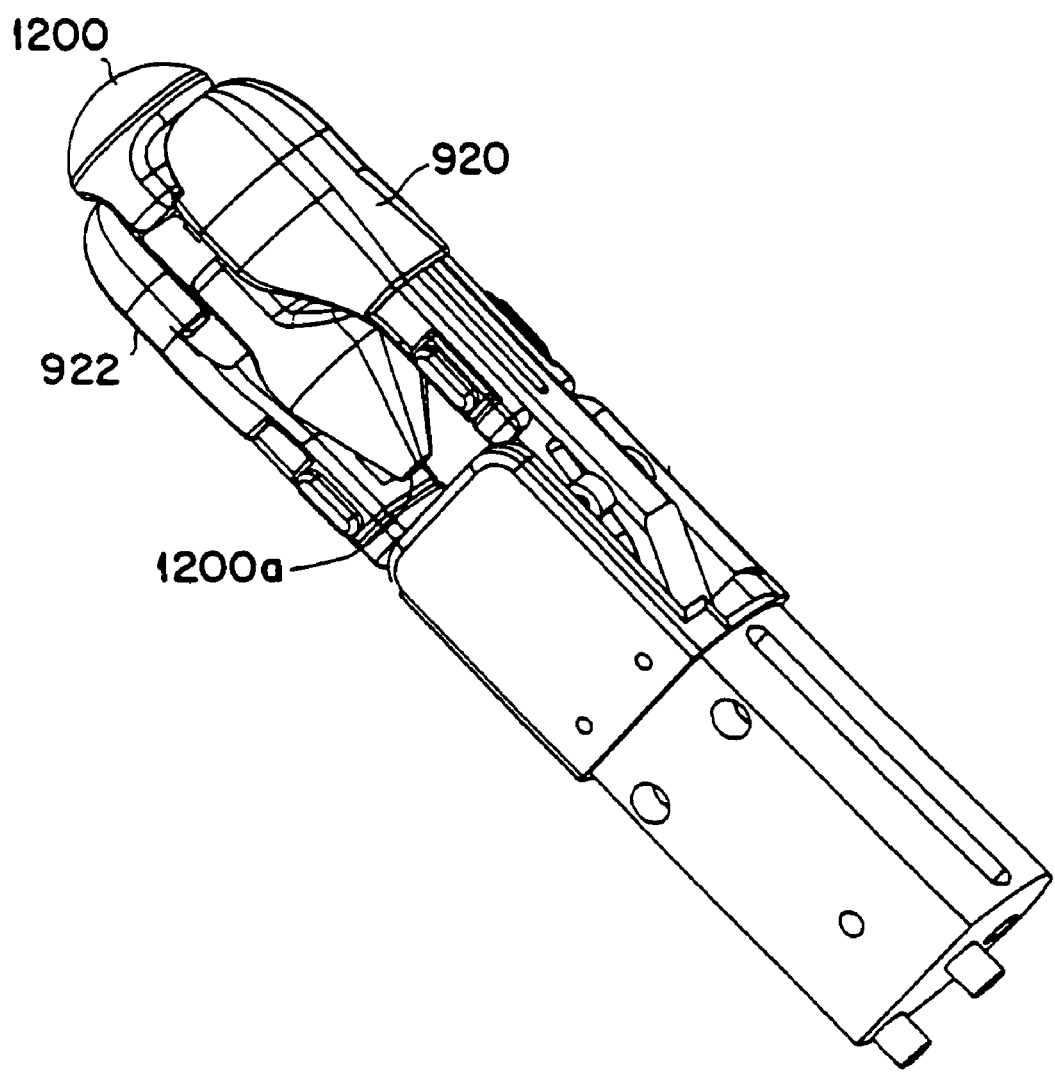

Referring to FIG. 37, rather than a hood covering end effector 906, placed between jaws 920, 922 is volume-filling bullet 1200 that creates a relatively smooth surface at the distal end of the instrument to facilitate insertion of the instrument into a patient. Bullet 1200 defines a through hole 1200a for delivery over a guide wire. Volume-filling bullet 1200 can be dissolvable in the operating environment, retrievable from the operating environment, or abandonable in the operating environment. For example, the guide wire can have a tip with a larger diameter than hole 1200a such that bullet 1200 is retained on the guide wire and removable therewith.

Figure 38:
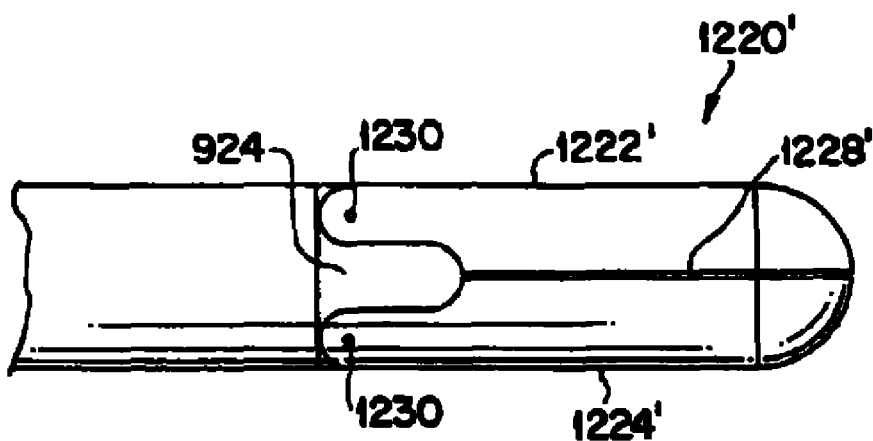
Figure 39:
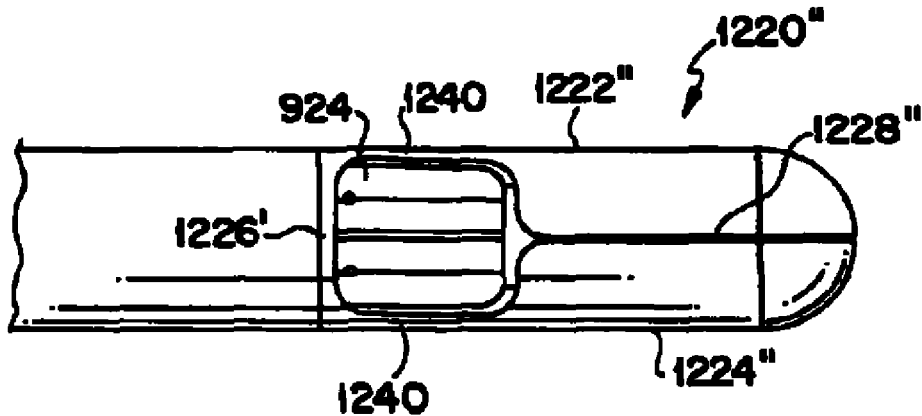

Referring to FIG. 38, in another embodiment, a hood 1220' includes halves 1222', 1224' that are connected to mount 924 at pivots 1230. When the jaws are opened, halves 1222', 1224' pivot about pivots 1230 to separate at seam 1228'. In FIG. 39, halves 1222", 1224" of a hood 1220" include spring beams

1240 joined in a region 1226'. When the jaws are opened, halves 1222", 1224" separate at seam 1228" and spring beams 1240 deform.

Figure 40:
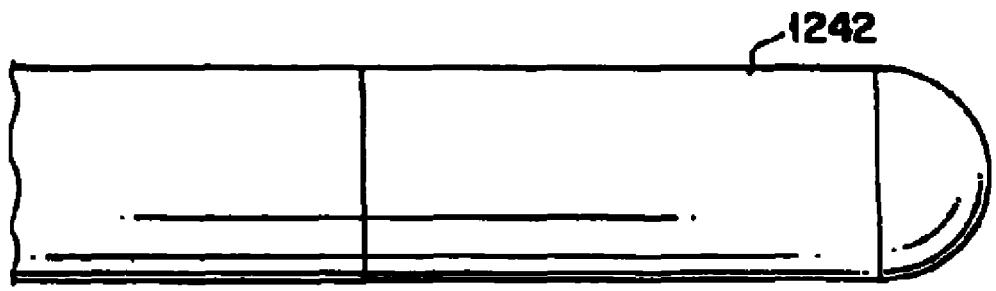

Alternatively, as shown in FIG. 40, to provide an atraumatic distal end, an end cap 1242 is placed over the jaws. End cap 1242 can be removed by pushing it off distally using the tissue engagement member, can be dissolvable (for example, made out of starch or gelatin), or can "break-away." when the jaws are opened. Providing a perforation along the length of cap 1242 can aid in break-away. After removal, cap 1242 can be abandoned in the operating environment, where it is dissolved or passed, or it can be retained by a guide wire so that it is withdrawn when the instrument is withdrawn.

Figure 41A:
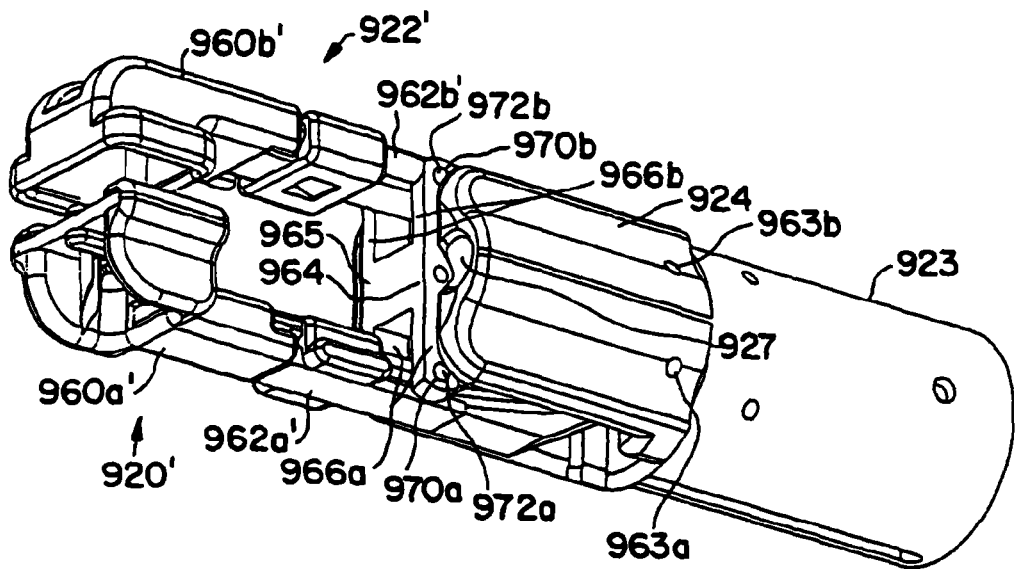
FIG. 41A is an isometric view and FIG. 41B is a side view in partial cross-section of an alternative embodiment of an end effector.
Figure 41B:
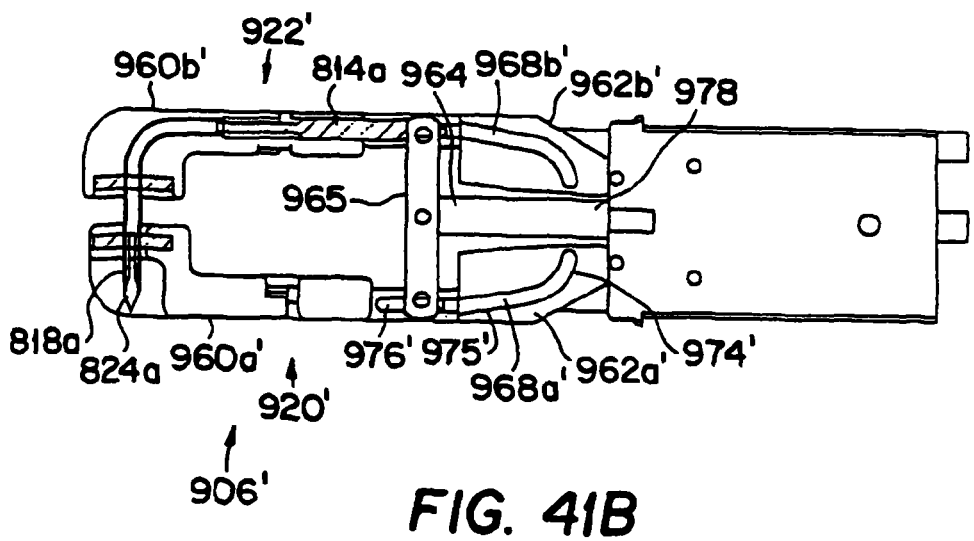

Referring to FIGS. 41A and 41B, in an alternative embodiment, an end effector 906' includes jaw members 920', 922', each of which includes a tissue manipulating cartridge 960a', 960b', respectively, releasably mounted to a respective actuating arm 962a', 962b'. Jaw 922' contains a pusher rods 814a, 814b for deploying bars 824a, 824b as described above with reference to FIG. 5. However, rather than employing a separate mechanism for actuating pusher rods 814a, 814b, pusher rods 814a, 814b are actuated by yoke 964. Each arm 962a', 962b' defines a slot 968a', 968b" having a first arcuate section 974', a second generally linear, angled section 975', and a third generally linear, parallel section 976'. Movement of yoke 964 along slot sections 974' and 975' closes jaws 920', 922'. To deploy tissue fixation device 730 (FIG. 2), movement of yoke 964 along section 976' of slots 968a, 968b moves pusher rods 814a, 814b distally advancing bars 824a, 824b out of tissue penetrating tips 818a, 818b to deploy fixation device 730, as described above with reference to FIGS. 4A and 4B.

Figure 42:
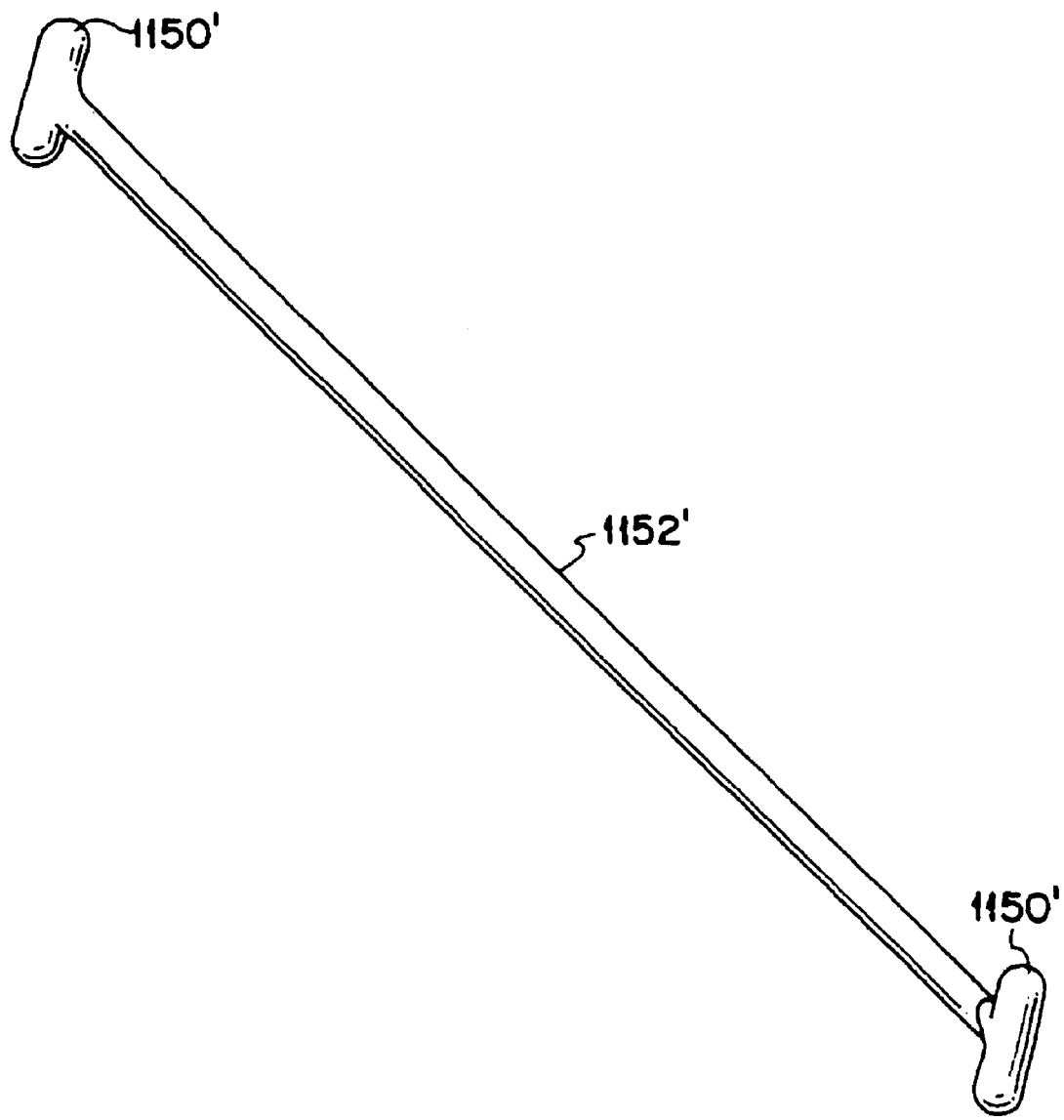
FIG. 42 is an illustration of a tissue fixation device for use with the end effector of FIG. 41.

Referring to FIG. 42, an alternative tissue fixation member for use with the embodiments of FIGS. 2 and 41, includes bars 1150' connected by a flexible spanning member 1152.' Bars 1150' replace bars 824a, 824b.

Figure 43:
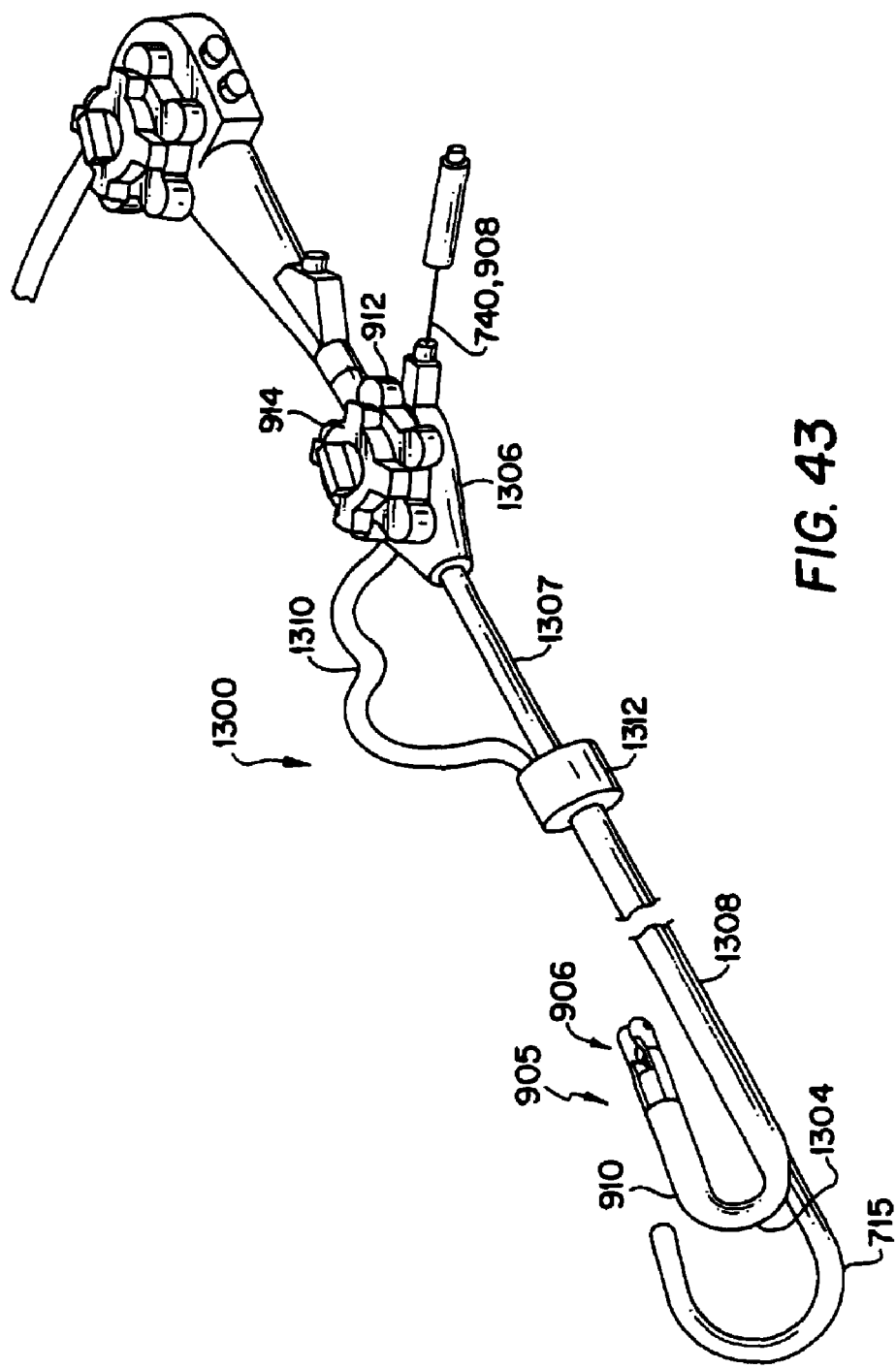
FIGS. 43-45 are illustrations of alternative configurations of an instrument for reconfiguring tissue.
Figure 44:
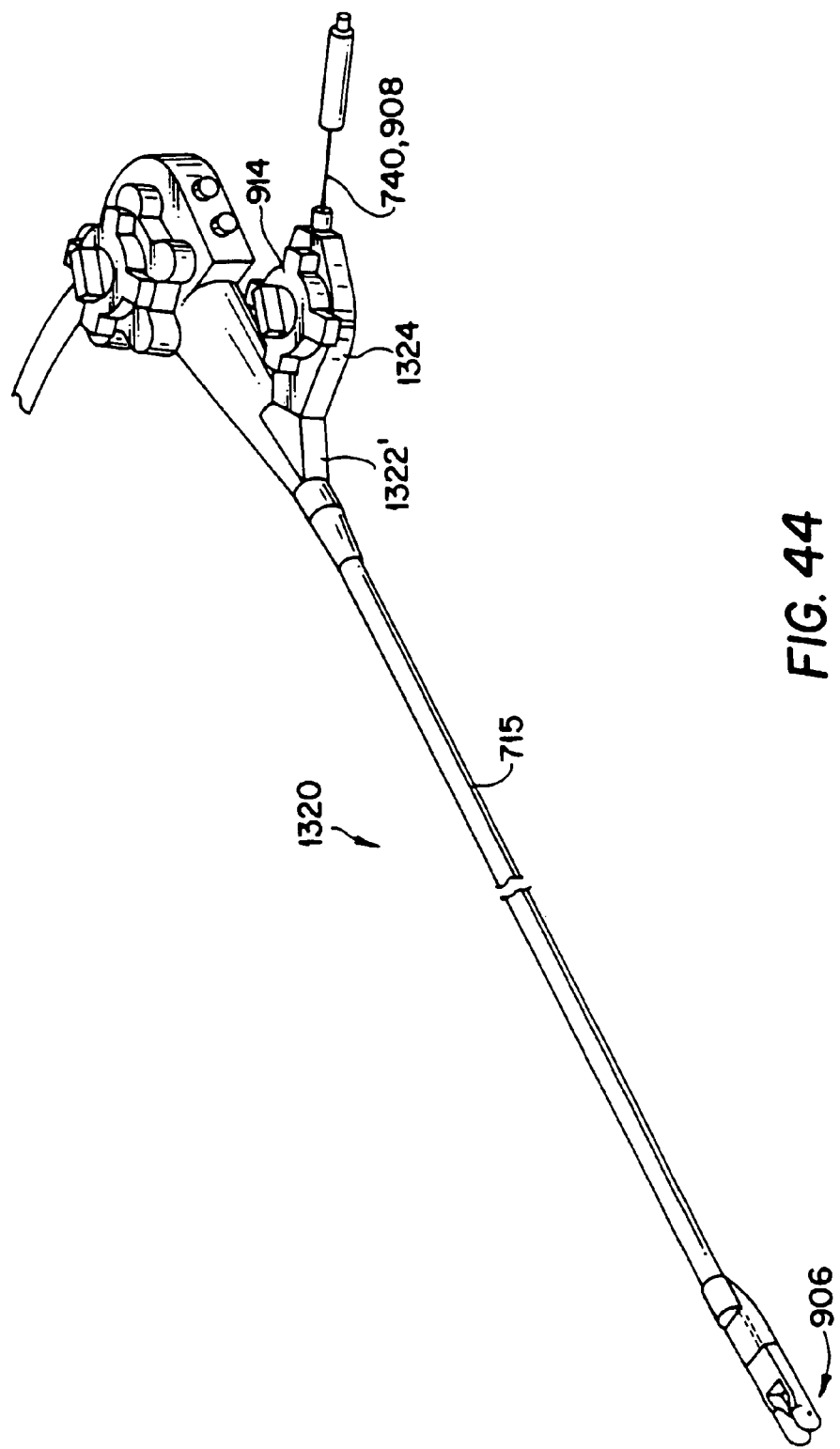
Figure 45:
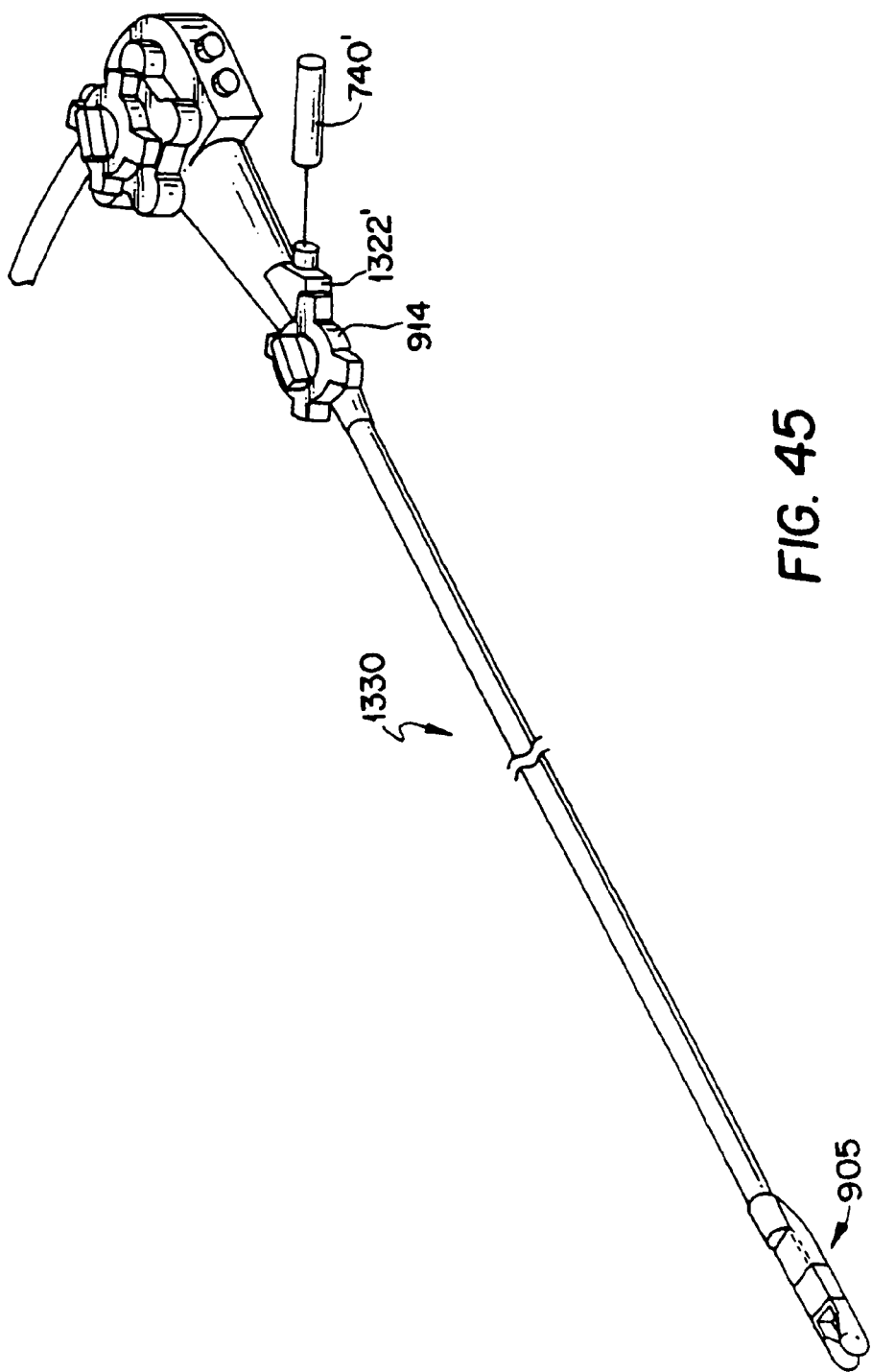

The instruments embodied in FIGS. 43-45 are configured to allow one person to control both the gastroscope and the tissue reconfiguring instrument. Referring particularly to FIG. 43, an instrument 1300 for reconfiguring tissue includes a standard gastroscope 715 and a tissue manipulator 1304 mounted to gastroscope 715. Tissue manipulator 1304 includes a control mount 1306 that the user mounts to gastroscope tube 1307 by, for example, a friction fit. Control mount 1306 includes knobs 912, 914, described above. End effector 906 and retroflex portion 910 of assembly 905 are mounted to a sleeve 1308 through which gastroscope tube 1307 extends. Sleeve 1308 defines conduits for the control cables as described above. Connecting control mount 1306 and sleeve 1308 is a flexible conduit 1310 enclosing the various cables for controlling end effector 906 and retroflex portion 910, as discussed above. Sleeve 1308 includes a hand grip 1312. Conduit 1310 permits axial movement of gastroscope 1302 relative to tissue manipulator 1304. In use, the operator holds the gastroscope handle with one hand, and operates all the controls and manipulates grip 1312 with the other hand, permitting a single operator to control all functions.

Referring to FIG. 44, an instrument 1320 for reconfiguring tissue includes a standard gastroscope 715 to which the user mounts end effector 906. Cables for actuating the jaws are attached to a jaw control mount 1324. The cables are received in the standard biopsy channel 1322' of the gastroscope. Retroflexing action is provided by gastroscope 715 and is controlled by the gastroscope controls. Jaw control mount 1324 includes knob 914 for actuating the jaw control cables. In the embodiment of FIG. 45, rather than mounting the tissue reconfiguring instrument to a standard gastroscope, an integral instrument 1330 includes a knob 914 mounted directly to gastroscope 1330. The control cables for actuating the jaws are integrated with the gastroscope control cables. The tissue engaging member, for example, member 740' of FIG. 12, is introduced through the gastroscope channel 1322'.

Figure 46A:
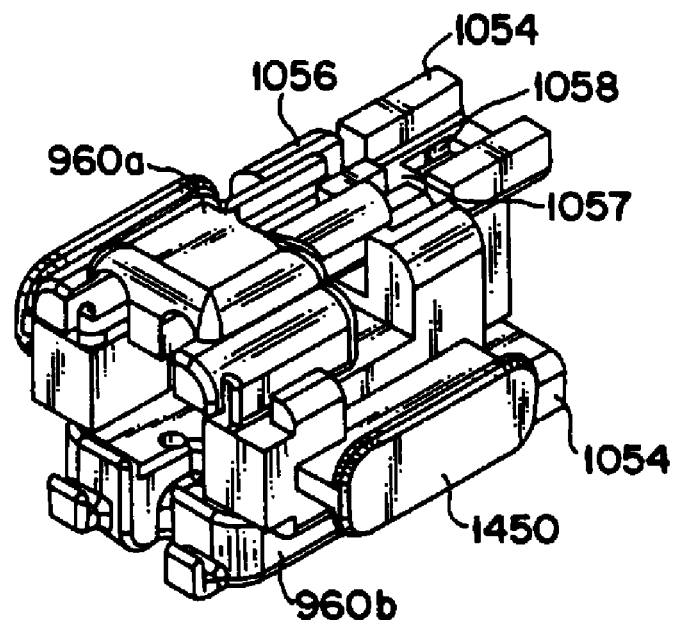
Figure 46B:
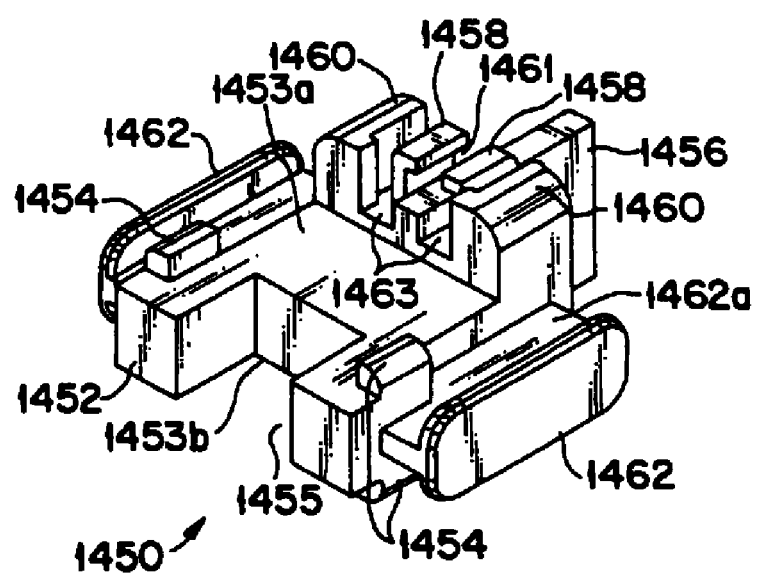
Figure 47F:
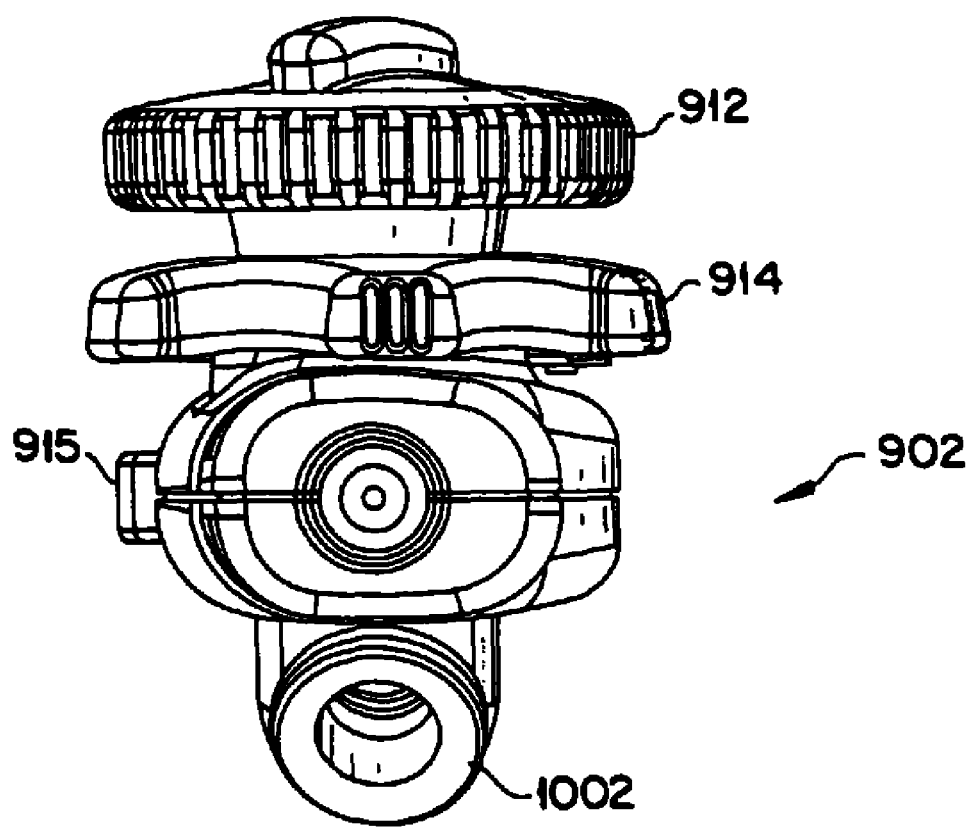

Referring to FIGS. 46A and 46B, cartridges 960a, 960b are supplied to the medical personnel in a holder 1450. Holder 1450 includes a base section 1452 having a first side 1453a for receiving head 1059 of cartridge 960a, and a second side 1453b for receiving head 1059 of cartridge 960b. Base section 1452 defines an opening 1455 where tubes 1120a, 1120b are located. Extending from either side of base section 1452 are two sets of detents 1454 that are positioned on either side of the cartridge head 1059. Extending proximally from base section 1452 is a fin 1456 with spring beams 1458 on either side of fin 1456 on both sides of base section 1452. Located on either side of spring beams 1458 are guide rails 1460. Between the spring beams is a slot 1461 and between each spring beam 1458 and guide rail 1460 is a slot 1463. Holder 1450 includes finger grips 1462 for ease of handling. Hood 1220 is provided to the user with holder 1450. To allow the user to hold finger grips 1462, finger grips 1462 are attached to the remainder of the holder by a thin section 1462a over which the slot in the hood is positioned.

To load cartridges 960a, 960b in holder 1450, each cartridge is in turn positioned over base section 1452 with thin section 1057 of the cartridge aligned with slot 1461. By pushing down on the cartridge, spring beams 1458 are forced apart and thin section 1057 snaps into place in slot 1461, with spring beams 1458 holding the cartridge in place. Cartridge head 1059 is located between detents 1454, and side walls 1056 are partially within slots 1463 to align the cartridge and help hold the cartridge in position. With base section 1452 located between cartridges 960a, 960b, the cartridges are spaced such that the implant will not deploy (corresponding to the position shown in FIG. 23C).

Figure 23A:
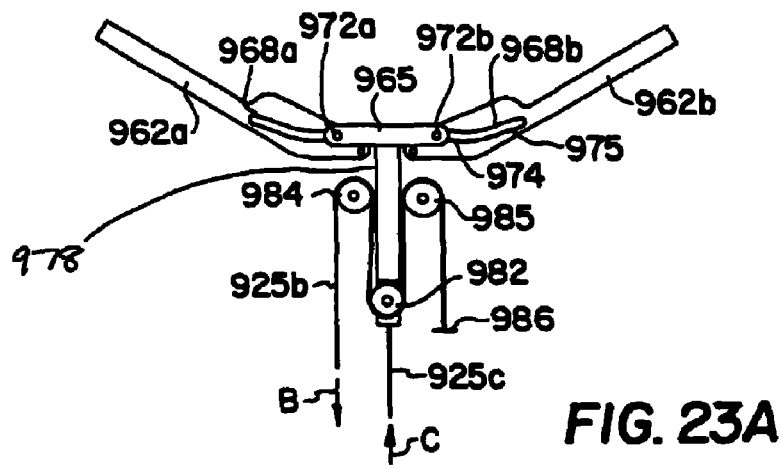
FIGS. 23A-23D illustrate the closing of jaw members of the end effector.
Figure 23B:
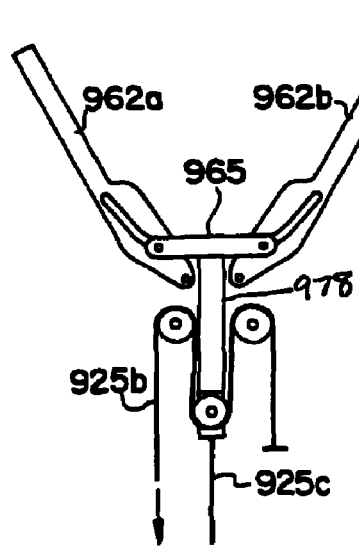
Figure 23C:
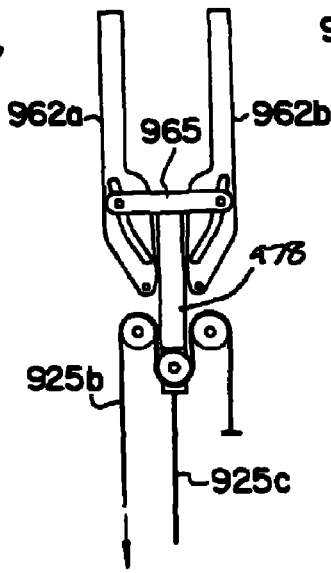
Figure 23D:
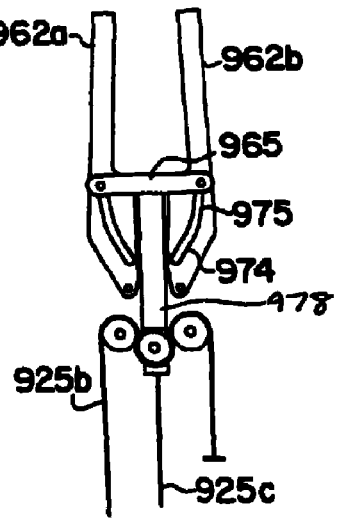
Figure 24A:
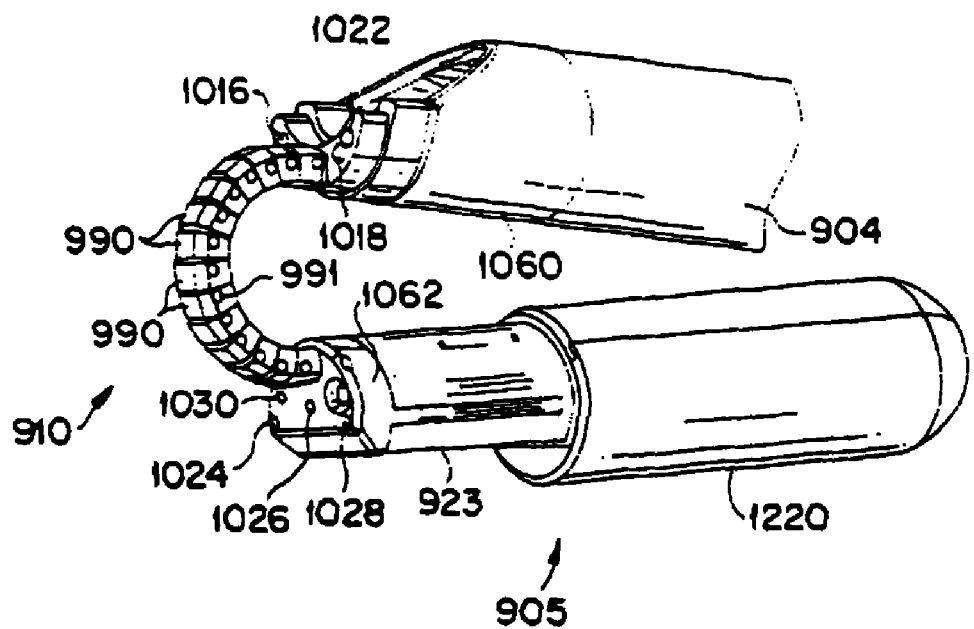
FIG. 24A is an illustration of the distal end portion in a flexed position.
Figure 24B:
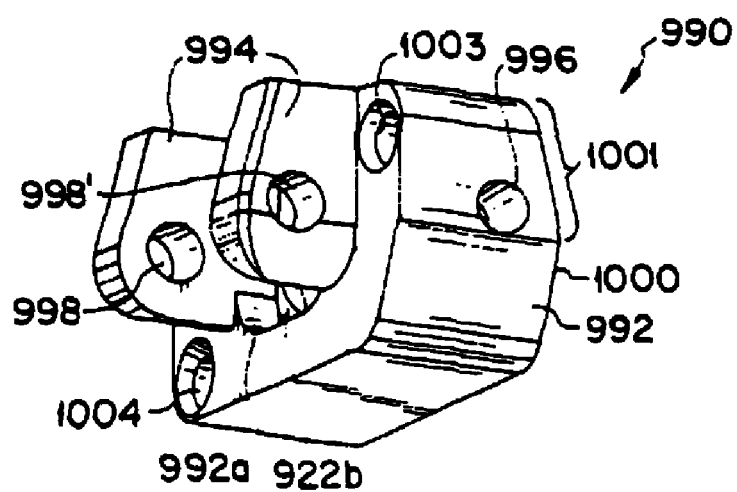
FIG. 24B is an isometric view of a link of a retroflex portion of the distal end portion.
Figure 24C:
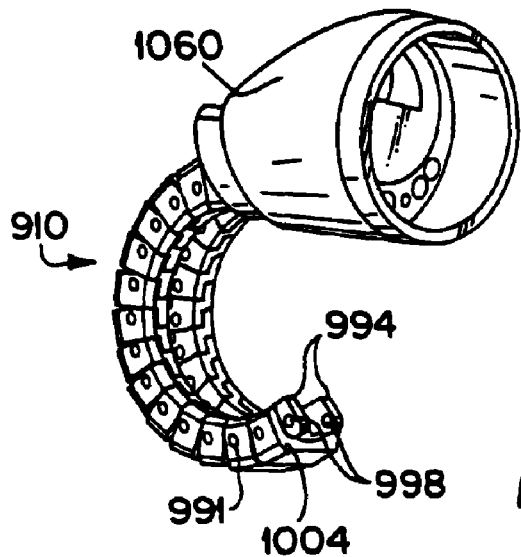
FIGS. 24C and 24D show the retroflex portion flexed and straight, respectively.
Figure 24D:
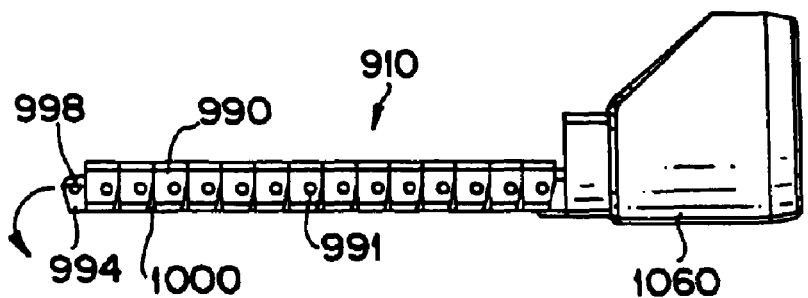

Referring also to FIG. 46C, to attach cartridges 960a, 960b to arms 962a, 962b, respectively, while holding finger grips 1462, the user slides the cartridges over the arms (with the arms positioned as shown in FIG. 23C). Initially, formation 1051 on the inner surfaces of the arms slide between spring beams 1458 forcing the spring beams apart. Further sliding of the cartridge over the arms, positions rectangular member 1050 under arms 1056 and locates clip 1052 in hole 1058. The cartridges are now attached to the arms. Because spring beams 1458 have been forced apart by formation 1051, holder 1450 can now be released from cartridges 960a, 960b by opening the jaws and the instrument is ready for use.

Holder 1450 is preferably formed from plastic, and holder 1450 with cartridges 960a, 960b, hood 1220 and the implant are supplied to the surgical personnel in a sterile condition.

FIGS. 47A-47F are various views of handle 902.

Referring to FIGS. 48-55, an instrument 2010 has a proximal end (not shown), a shaft 2012, a retroflexing portion 2014, and a distal end effector 2015 including movable arms 2016, a retractor 2020, and an implant 2022. The function of the instrument is controlled by the user by controls at the proximal end, as disclosed herein.

Figure 48:
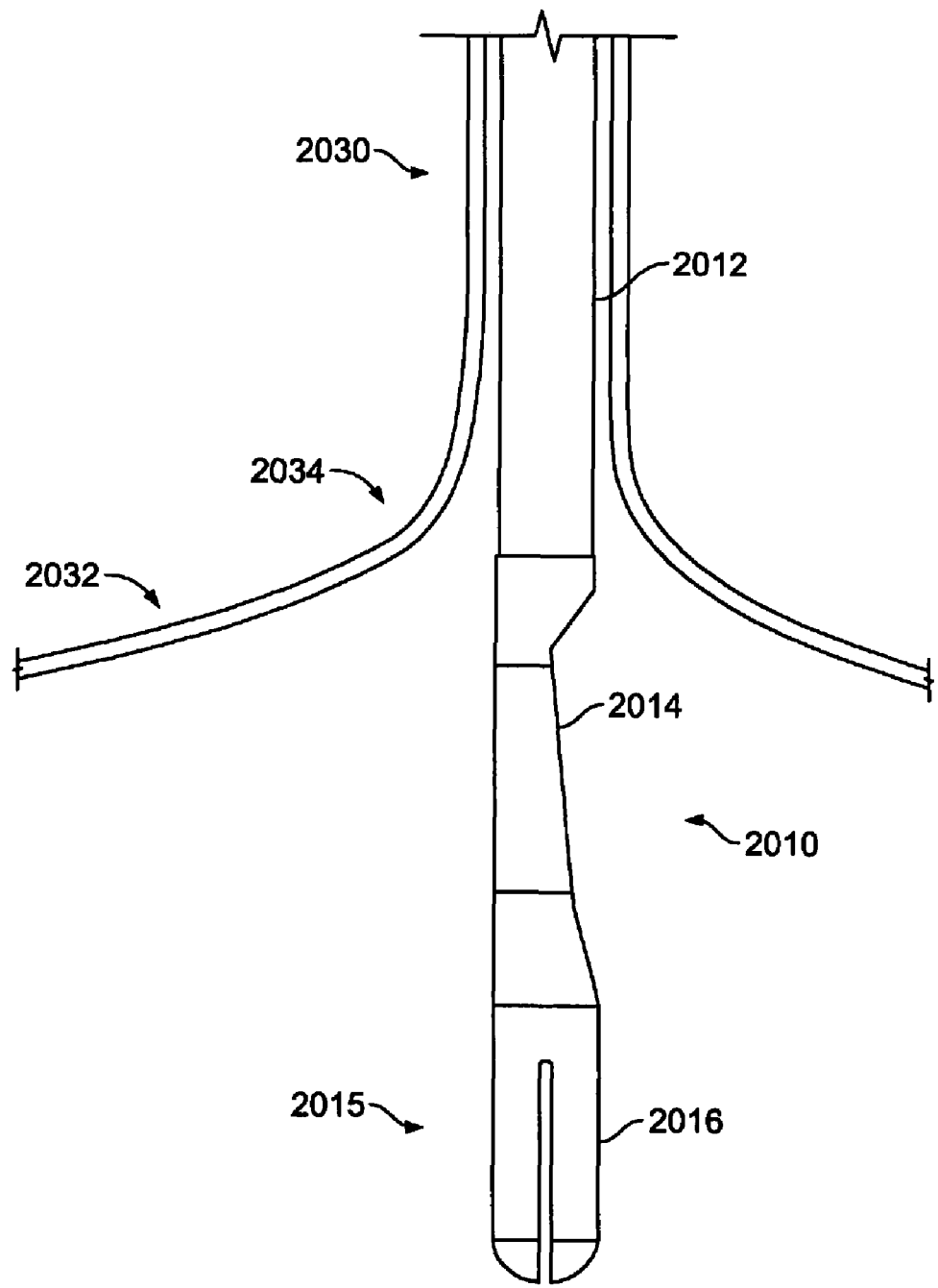
FIG. 48 is a side cross sectional view of a portion of an esophagus and a portion of a stomach, and a side view of an instrument in place in the esophagus and stomach.
Figure 49:
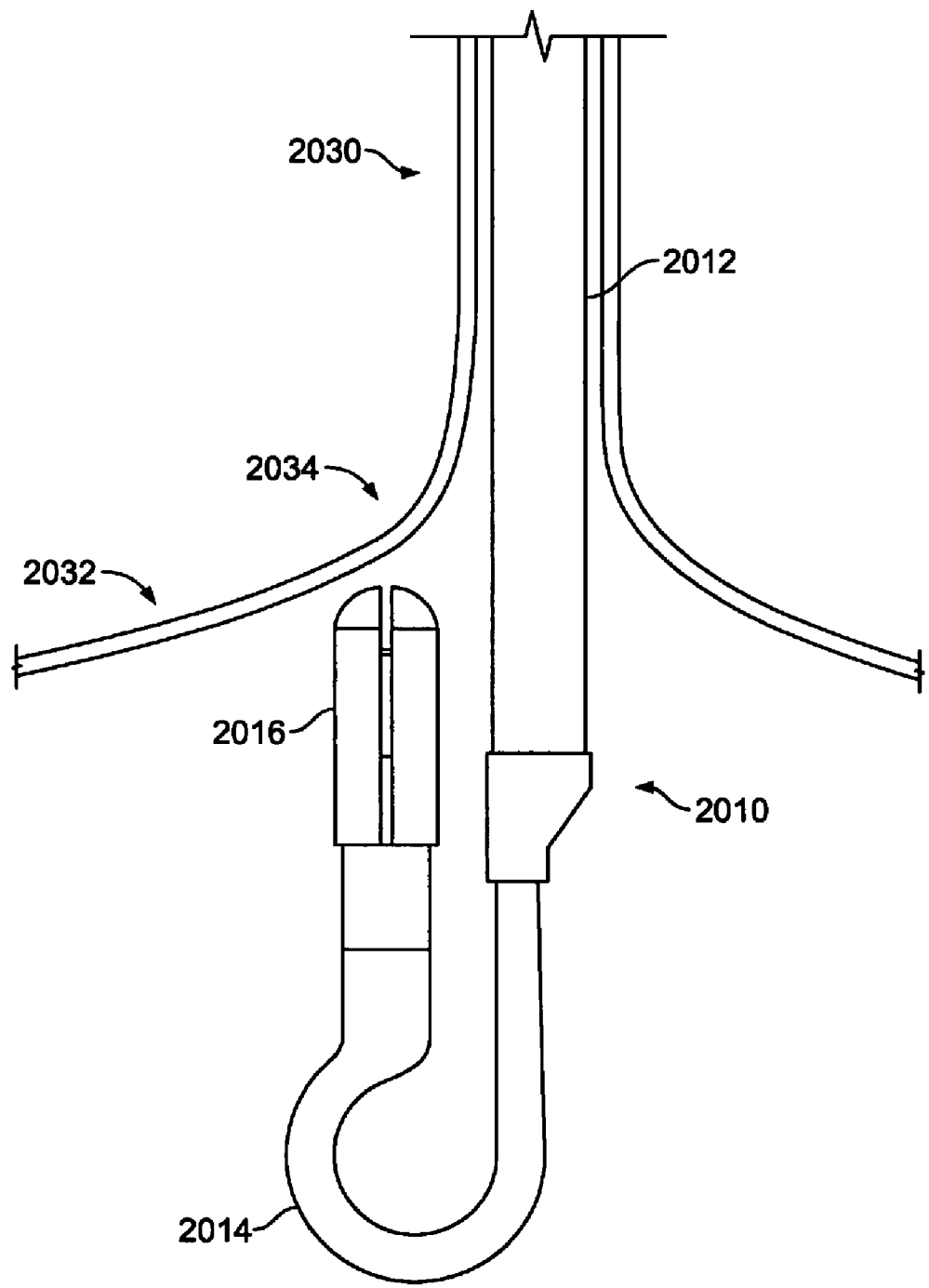
FIG. 49 is a side cross sectional view of a portion of the esophagus and a portion of the stomach, and a side view of the instrument in place in the esophagus and stomach, showing the instrument in a retroflexed position.

FIG. 48 shows the instrument 2010 in place in the esophagus 2030 and the stomach 2032. The instrument is in a straight configuration, which is the configuration in which it is inserted into the esophagus and stomach FIG. 49 shows the instrument 2010 in place in the esophagus 2030 and the stomach 2032, with the instrument 2010 in a retroflexed position. Retroflexion of retroflexing portion 2014 is accomplished as disclosed in the referenced patent applications. In this position, the distal end of the movable arms 2016 of distal end effector 2015 is located near the junction 2034 of the esophagus 2030 and the stomach 2032.

Figure 50:
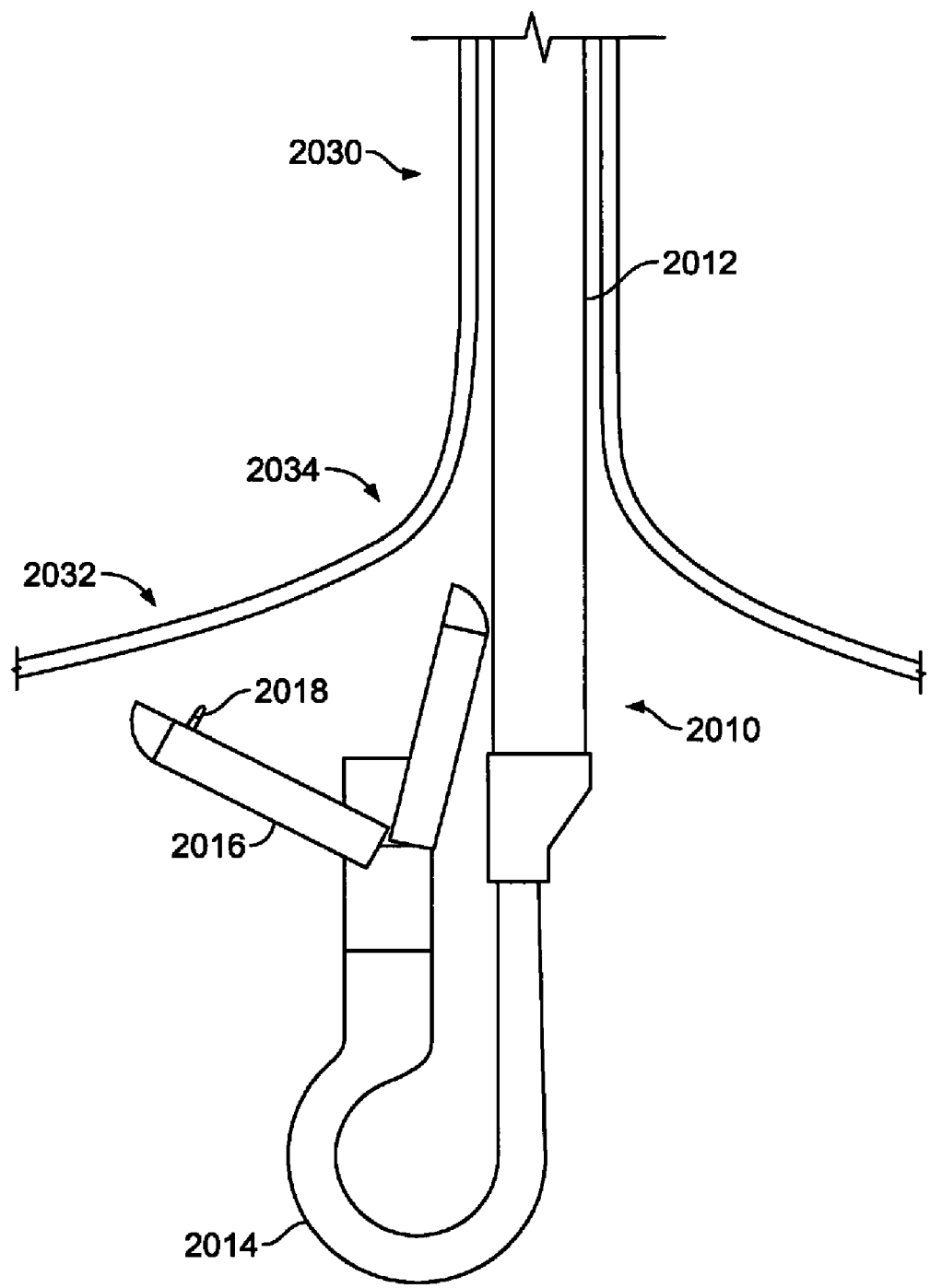
FIG. 50 is a side cross sectional view of a portion of the esophagus and a portion of the stomach, and a side view of the instrument in place in the esophagus and stomach, showing the movable arms open.
Figure 54:
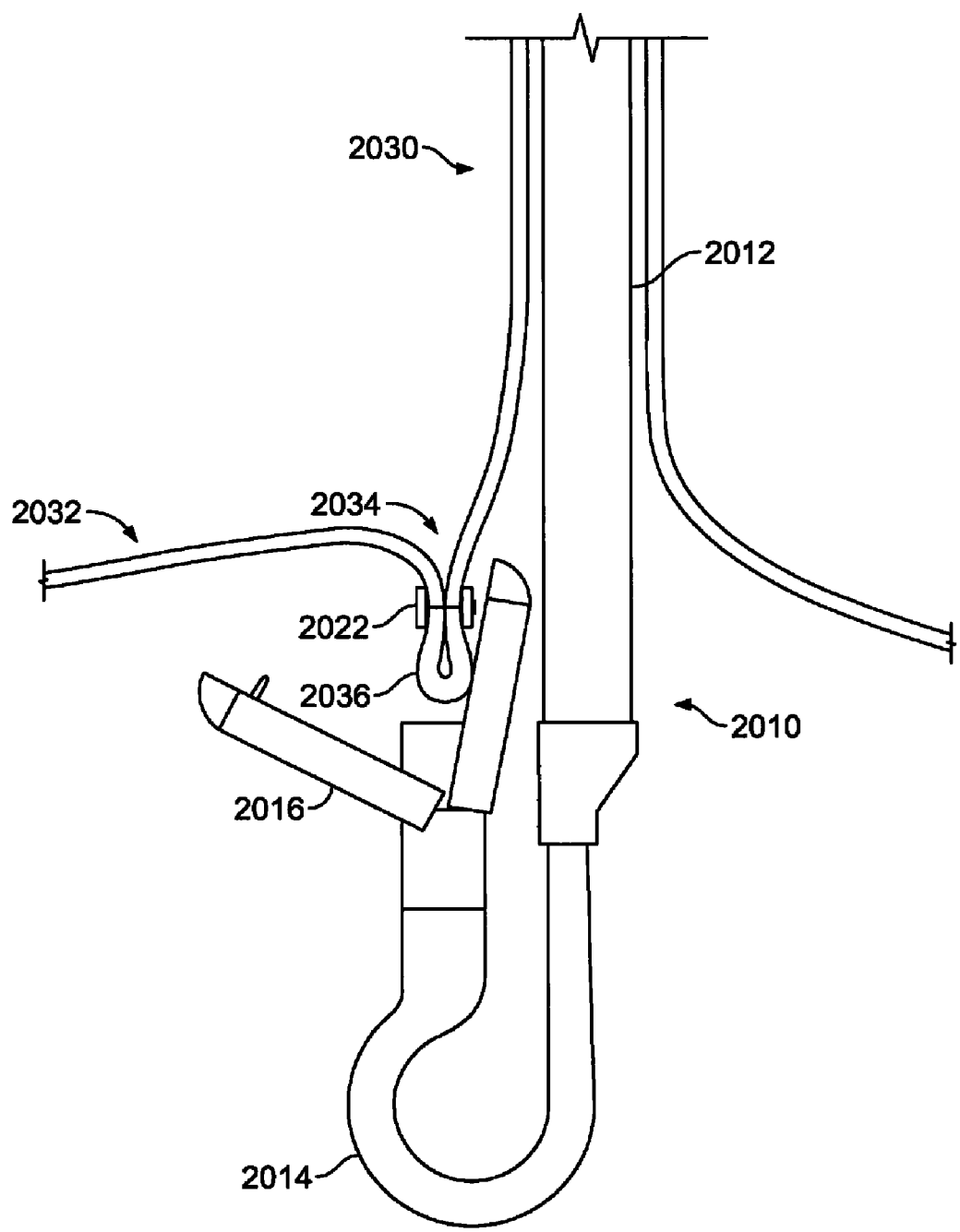
FIG. 54 is a side cross sectional view of a portion of the esophagus and a portion of the stomach, and a side view of the instrument in place in the esophagus and stomach, showing the movable arms open and an implant fixating the tissue fold.

FIG. 50 shows the instrument 2010 in place in the esophagus 2030 and the stomach 2032, with the instrument 2010 in a retroflexed position and the movable arms 2016 in an open position revealing a portion 2018 of an implant 2022 (FIG. 54). It is important to note that the moveable arms 2016 are oriented relative to the retroflexing portion 2014 to grasp the tissue at the junction 2034 of the esophagus 2030 and the stomach 2032. The movable arms 2016 open and close in the same plane within which the retroflexing portion 2014 moves. The actuating mechanism used to open movable arms 2016 is substantially the same as the mechanisms described herein, with the movable arms rotated 90° with respect to the configuration described herein such that the arms 2016 open and close in the same plane within which the retroflexing portion 2014 moves.

Figure 51:
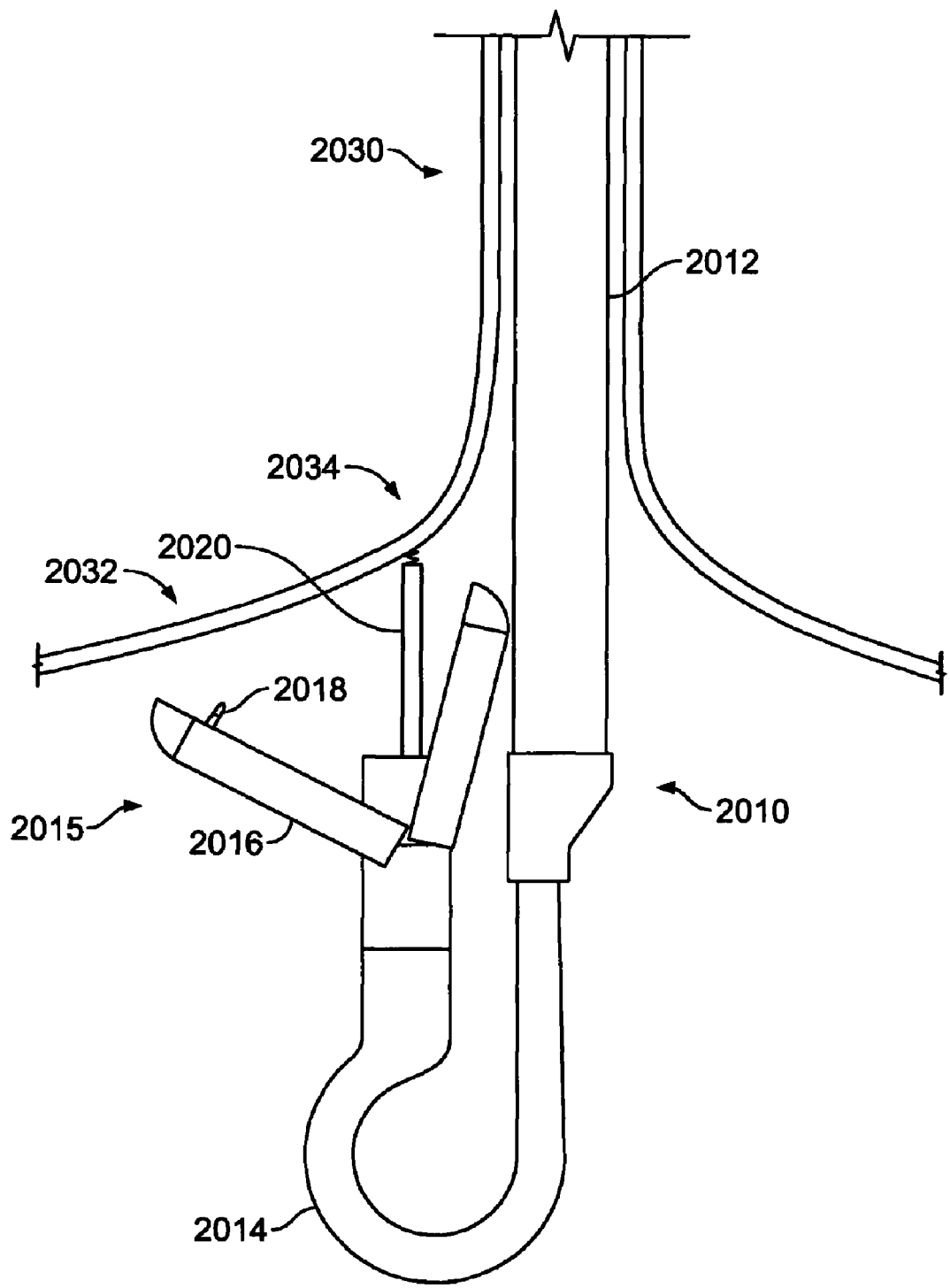
FIG. 51 is a side cross sectional view of a portion of the esophagus and a portion of the stomach, and a side view of the instrument in place in the esophagus and stomach, showing a retractor engaging tissue.

FIG. 51 shows the instrument 2010 in place in the esophagus 2030 and the stomach 2032, with the instrument 2010 in a retroflexed position, the movable arms 2016 in an open position, and the retractor 2020 engaged with the tissue at or near the junction 2034 of the esophagus 2030 and the stomach 2032. Engagement of the retractor 2020 with the tissue at or near the junction 2034 is accomplished as is described herein.

Figure 52:
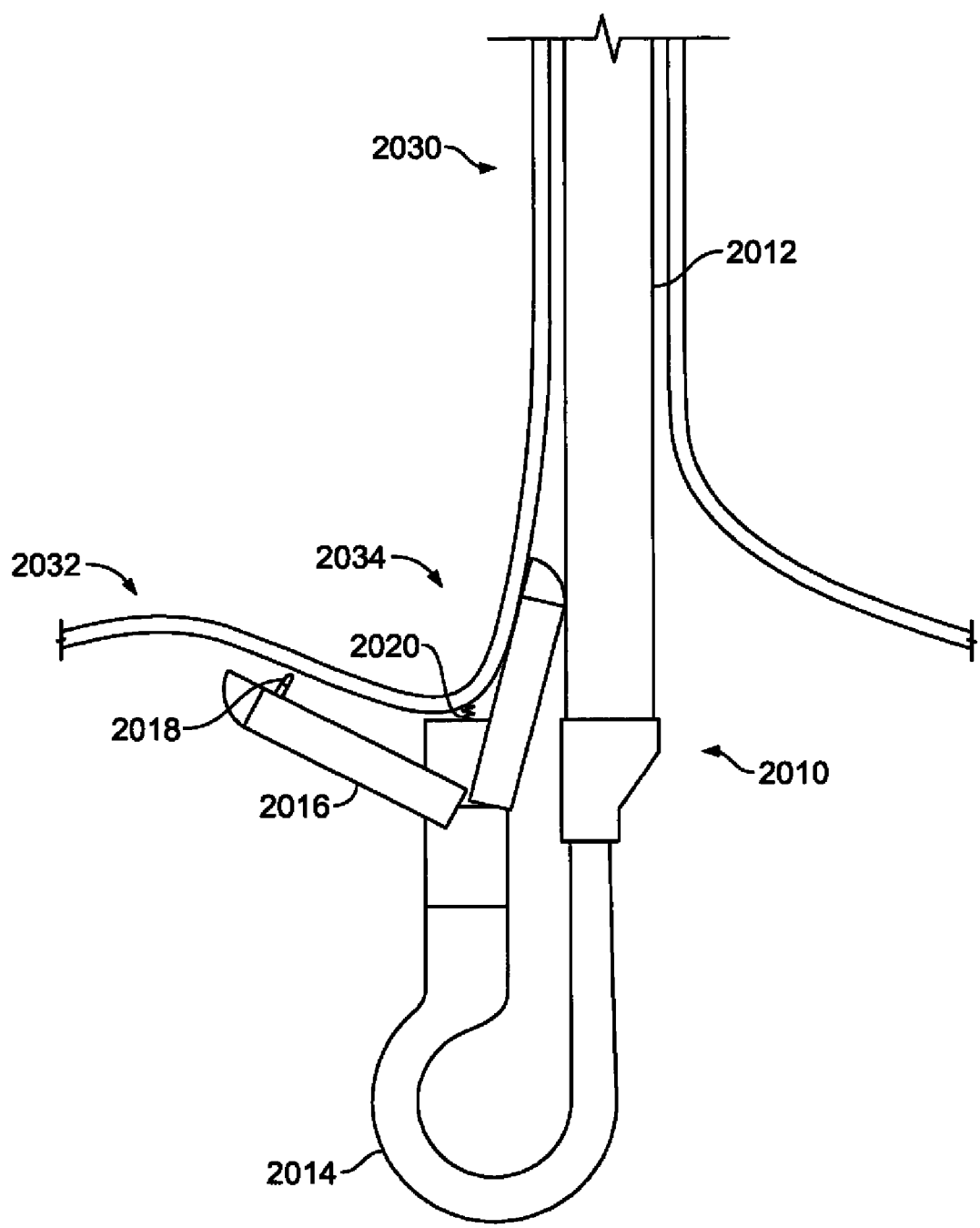
FIG. 52 is a side cross sectional view of a portion of the esophagus and a portion of the stomach, and a side view of the instrument in place in the esophagus and stomach, showing the retractor retracting the tissue.

FIG. 52 shows the instrument 2010 in place in the esophagus 2030 and the stomach 2032, with the instrument 2010 in a retroflexed position, the movable arms 2016 in an open position, and the retractor 2020 retracting the tissue at or near the junction 2034 of the esophagus 2030 and the stomach 2032 into the space between the movable arms 2016.

Figure 53:
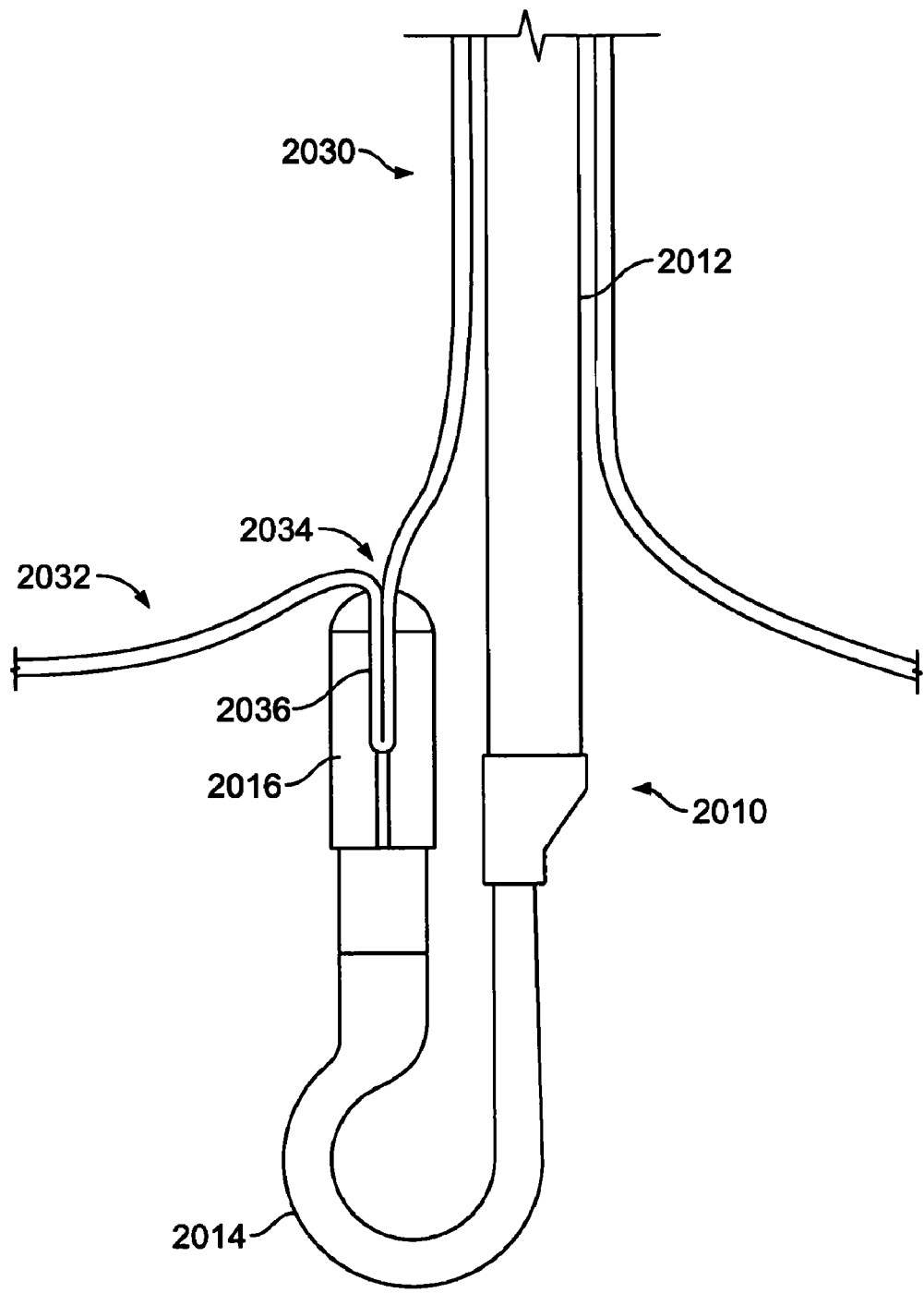
FIG. 53 is a side cross sectional view of a portion of the esophagus and a portion of the stomach, and a side view of the instrument in place in the esophagus and stomach, showing the movable arms closed, forming a tissue fold.

FIG. 53 shows the instrument 2010 in place in the esophagus 2030 and the stomach 2032, with the instrument 2010 in a retroflexed position, and the movable arms 2016 closed, to create a fold 2036 of tissue at or near the junction 2034 of the esophagus 2030 and the stomach 2032. The mechanism to close the movable arms is as is described herein.

FIG. 54 shows the instrument 2010 in place in the esophagus 2030 and the stomach 2032, with the instrument 2010 in a retroflexed position, and the movable arms 2016 opened. An implant 2022 has been placed through the tissue to maintain fixation of the tissue fold 2036. Placement of the implant is accomplished as is described herein.

Figure 55:
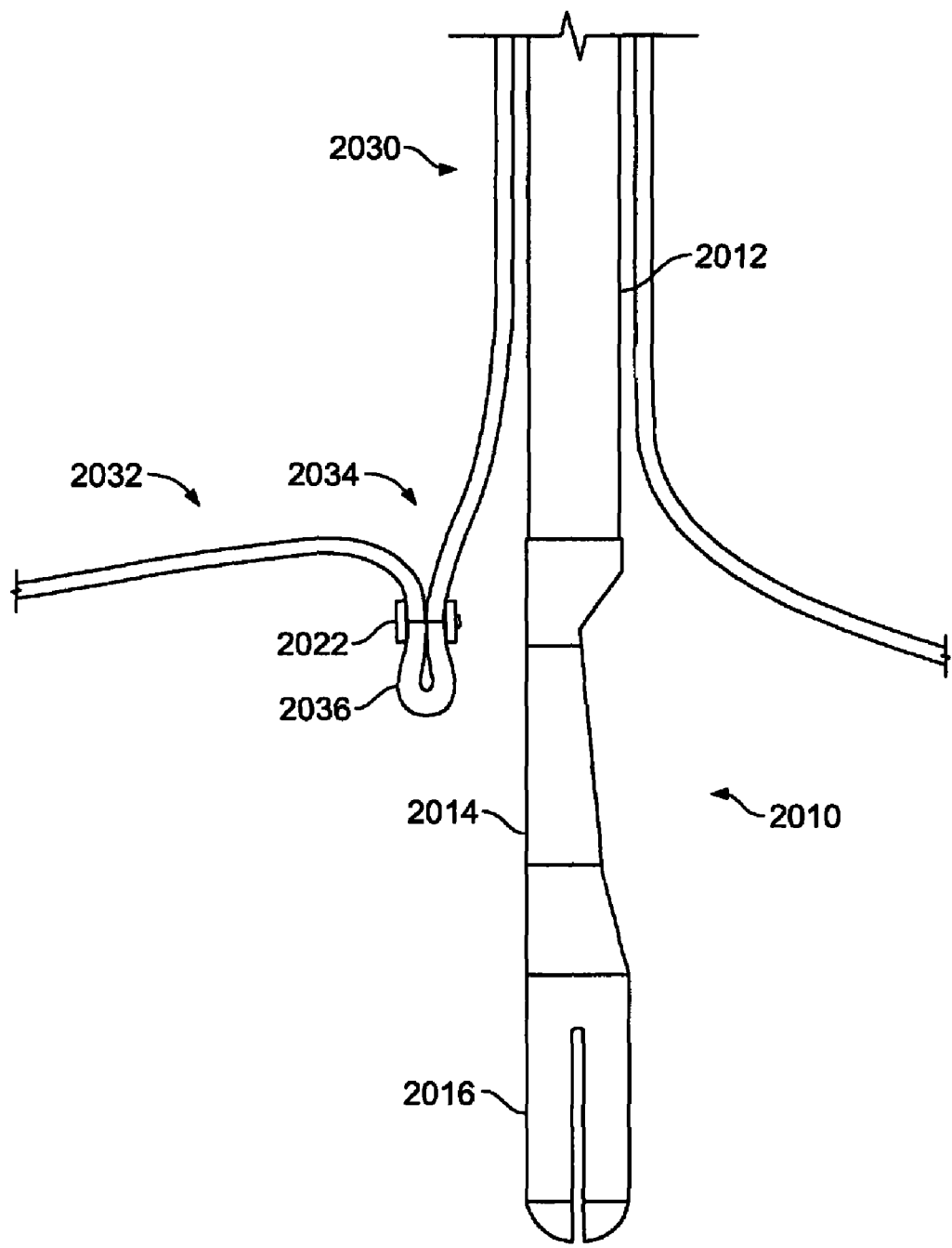
FIG. 55 is a side cross sectional view of a portion of the esophagus and a portion of the stomach, and a side view of the instrument in place in the esophagus and stomach, showing the tissue fold, with the instrument in a straight configuration for removal from the patient.

FIG. 55 shows the instrument 2010 in place in the esophagus 2030 and the stomach 2032, with the instrument 2010 in a straight position, and the movable arms 2016 closed. The tissue fold 2036 is shown, fixated by implant 2022. The instrument 2010 is in position for removal from the patient.

The device and method can be used to treat GERD by creating and fixating a fold of tissue at or near the junction of the esophagus and the stomach, thereby fixating the wall of the stomach to the wall of the esophagus. The fold can be created and fixated via a completely endoluminal technique. More than one fold can be created in the tissue at or near the junction of the esophagus and the stomach. The movable arms can be attached to the retroflexing portion in a manner that allows the operator to rotate the position of the movable arms relative to the retroflexing portion about the center axis of the movable arms, thus allowing the operator to vary the orientation of the tissue fold.

Figure 56:
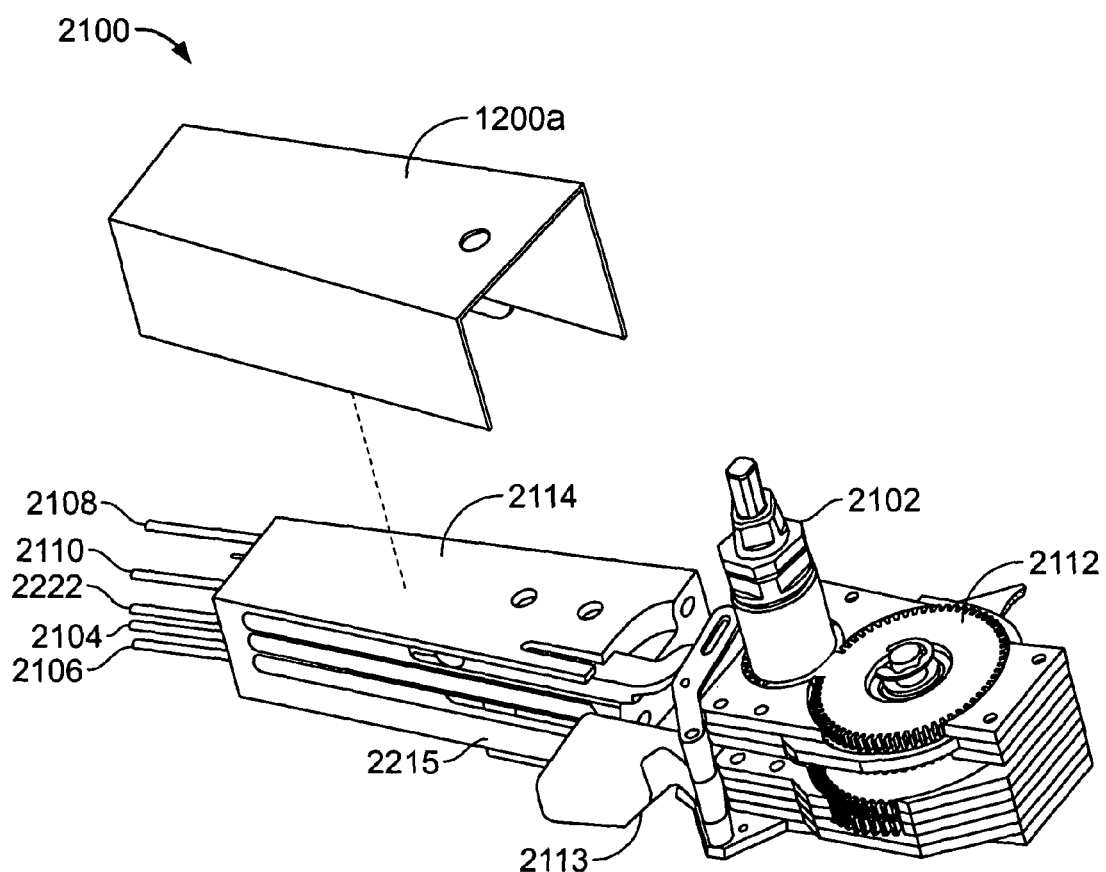
FIG. 56 is an illustration of a cable actuation mechanism.

Referring to FIG. 56, a cable actuation mechanism 2100 is used to control a retroflex portion and an end effector of a trans-oral medical device for treating GERD, such as described herein. Mechanism 2100 includes a knob assembly 2102, a gear assembly 2112 controlled by knob assembly 2102, and a series of cables 2104, 2106, 2108, 2110 attached to gear assembly 2112 for controlling movement of the retroflex portion and end effector of the medical device. Mechanism 2100 also includes a lever lock button assembly 2113, which is actuated to allow deployment of an implant coupled to the end effector of the medical device, and an adjust block assembly 2114 through which the cables are guided and which is used to adjust the cables during assembly for proper operation. When assembled, a cover 1200a is positioned over assembly 2114.

Figure 57:
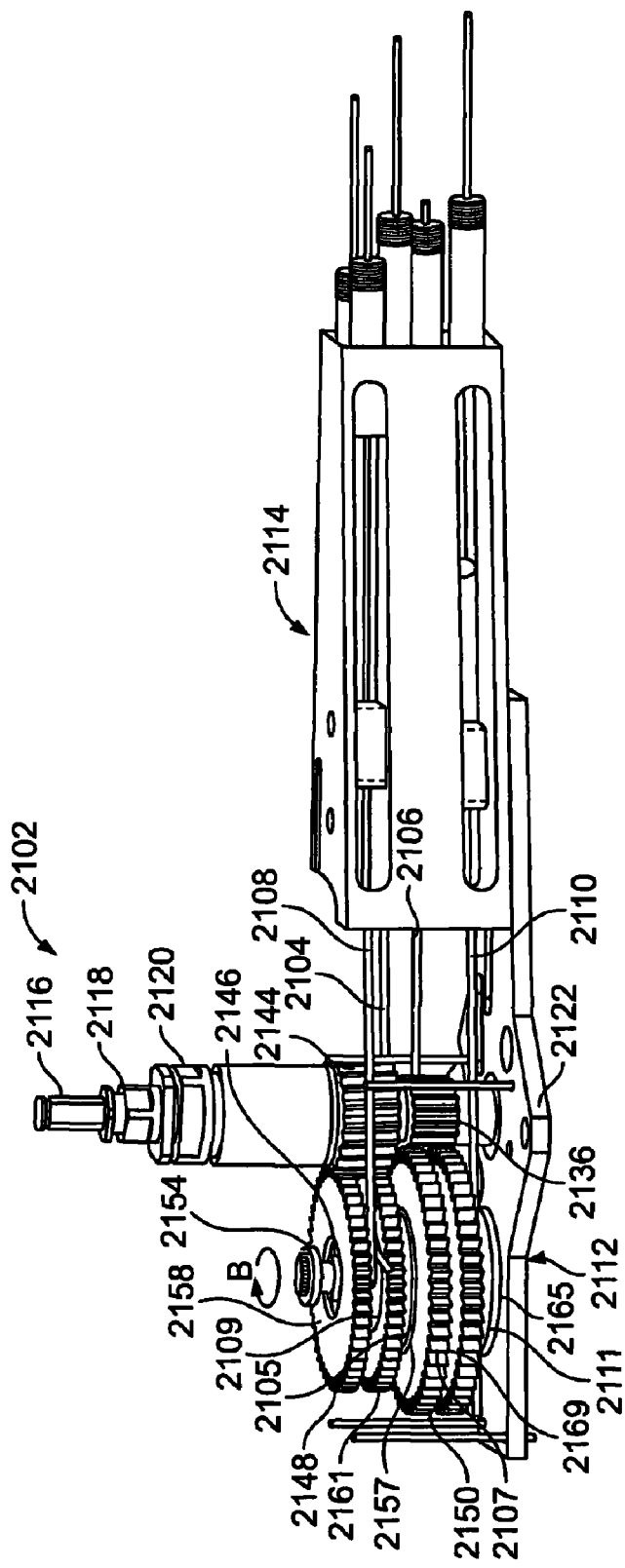
FIG. 57 is an illustration of the mechanism of FIG. 56 with a lever lock button assembly of the mechanism removed.

Referring to FIG. 57, knob assembly 2102 includes a fixed center shaft 2116 surrounded by a rotatable shaft 2118 that is, in turn, surrounded by a rotatable shaft 2120. Shaft 2118 includes a gear 2136 that engages a gear-pulley 2150 of gear assembly 2112. Cables 2106, 2110 are coupled to gear-pulley 2150 and the end effector such that rotation of gear-pulley 2150 controls opening and closing of jaws of the end effector. Shaft 2120 includes a gear 2144 that engages a gear-pulley 2148 of gear assembly 2112. Cables 2104, 2108 are coupled to gear-pulley 2148 and the retroflex portion such that rotation of gear-pulley 2148 controls bending and straightening of the retroflex portion.

Figure 58:
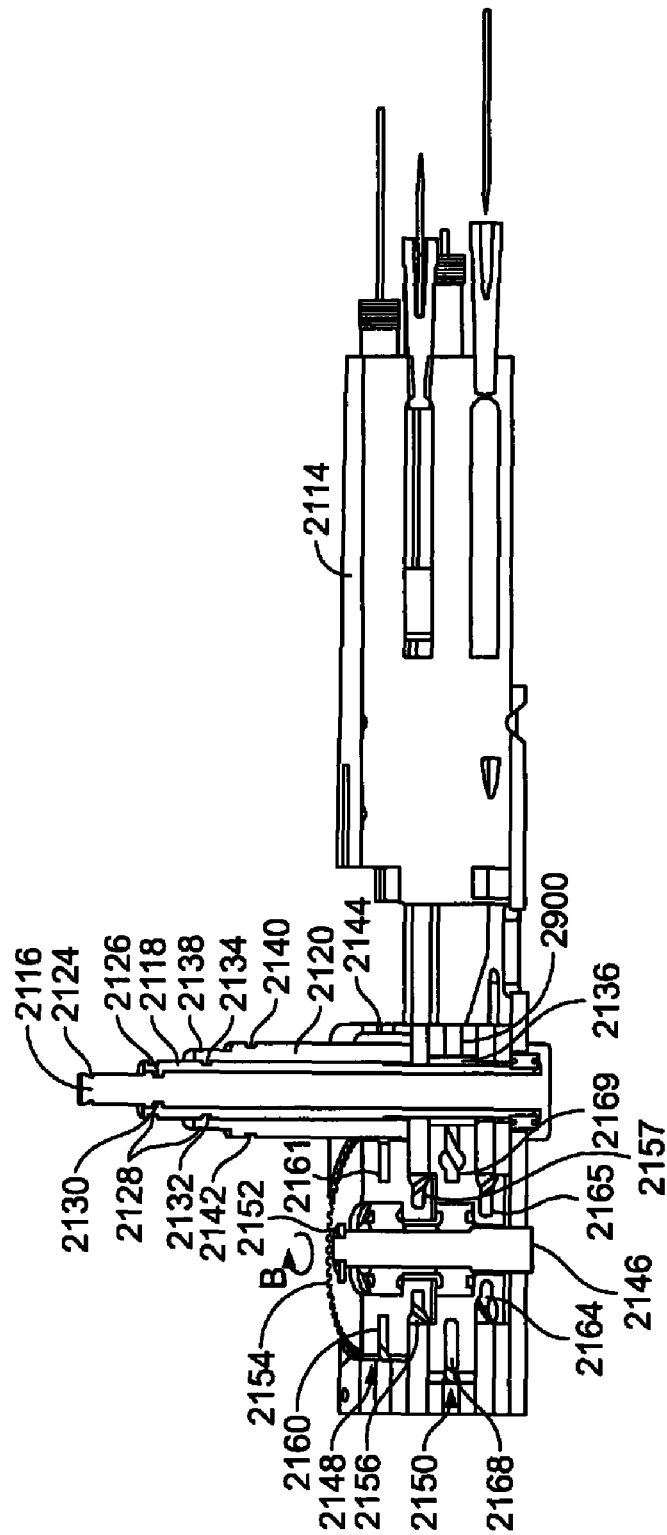
FIG. 58 is a cross-sectional view of the mechanism of FIG. 56 with the lever lock button assembly of the mechanism removed.

Referring to FIG. 58, gear-pulleys 2148, 2150 are mounted to rotate about a fixed shaft 2146. Fixed shaft 2146 includes a groove 2152 for receiving a clip 2154 used to secure gear-pulleys 2148 and 2150 to fixed shaft 2146. Gear-pulley 2148 includes a first groove 2160 for receiving cable 2108 and a second groove 2156 for receiving cable 2104. As shown in FIG. 57, the ends 2109, 2105 of cables 2108, 2104 are attached to groove walls 2161, 2157, respectively, for example, by including ball crimps on the end of the cables with the ball crimps being received in openings in the groove walls, such that rotation of gear-pulley 2148 in the direction of arrow, B, pulls cable 2108 to bend the retroflex portion, and rotation in the opposite direction pulls cable 2104 to straighten the retroflex portion. The diameter of groove wall 2161 is approximately twice the diameter of wall 2157 such that the displacement of cable 2108 is approximately twice the displacement of cable 2104. In addition, a mechanical advantage is obtained by having a gear ratio of gear 2148 to gear 2144 of approximately 2:1.

Gear-pulley 2150 includes a first groove 2168 for receiving cable 2106 and a second groove 2164 for receiving cable 2110. As shown in FIG. 57, the ends 2107, 2111 of cables 2106, 2110 are attached to groove walls 2169, 2165, respectively, for example, by including ball crimps on the end of the cables with the ball crimps being received in openings in the groove walls, such that rotation of gear-pulley 2150 in the direction of arrow, B, pulls cable 2110 to open the jaws of the end effector, and rotation in the opposite direction pulls cable 2106 to close the jaws. The diameter of groove wall 2169 is approximately twice the diameter of wall 2165 such that the displacement of cable 2106 is approximately twice the displacement of cable 2110. In addition, a mechanical advantage is obtained by having a gear ratio of gear 2150 to gear 2136 of approximately 4:1.

Center shaft 2116 includes a groove 2124 for receiving a snap-ring (not shown) for coupling shaft 2116 to a lock mechanism (not shown), and a groove 2126 for receiving an o-ring 2128 for creating a seal between shaft 2116 and shaft 2118. Shaft 2118 includes a groove 2130 for receiving a snap-ring (not shown) for coupling shaft 2118 to a knob (not shown), and a groove 2132 for receiving an o-ring 2134 for creating a seal between shaft 2118 and shaft 2120. Shaft 2120 includes a groove 2138 for receiving a snap-ring (not shown) for coupling shaft 2120 to a knob (not shown), and a groove 2140 for receiving an o-ring 2142 for creating a seal between shaft 2120 and a handle housing (not shown).

Figure 59:
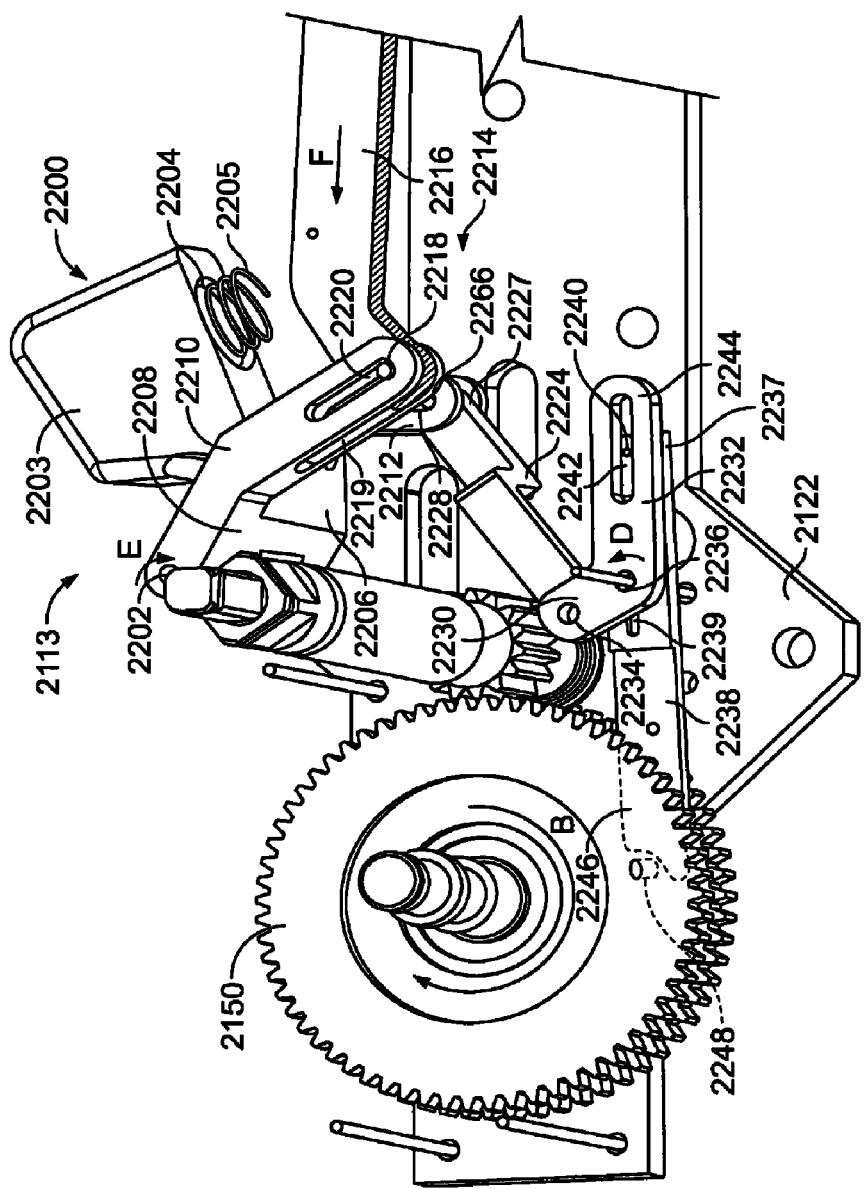
FIG. 59 is an illustration of the lever lock button assembly.

Referring to FIG. 59, lever lock button assembly 2113 includes a button assembly 2200 coupled to a slide 2216 and a locking mechanism 2214. Slide 2216 has a cable 2222 (FIG. 56) attached thereto, which actuates a distal lock (not shown) of the end effector. Locking mechanism 2214 limits rotation of gear-pulley 2150 to limit the extent of closing of the jaws until the user wants to deploy the implant. To deploy the implant, the user pushes on button assembly 2200, which simultaneously acts to pull cable 2222 to release the distal lock, and actuate locking mechanism 2214 to allow further rotation of gear-pulley 2150, and thus further closing of the jaws.

Figure 60:
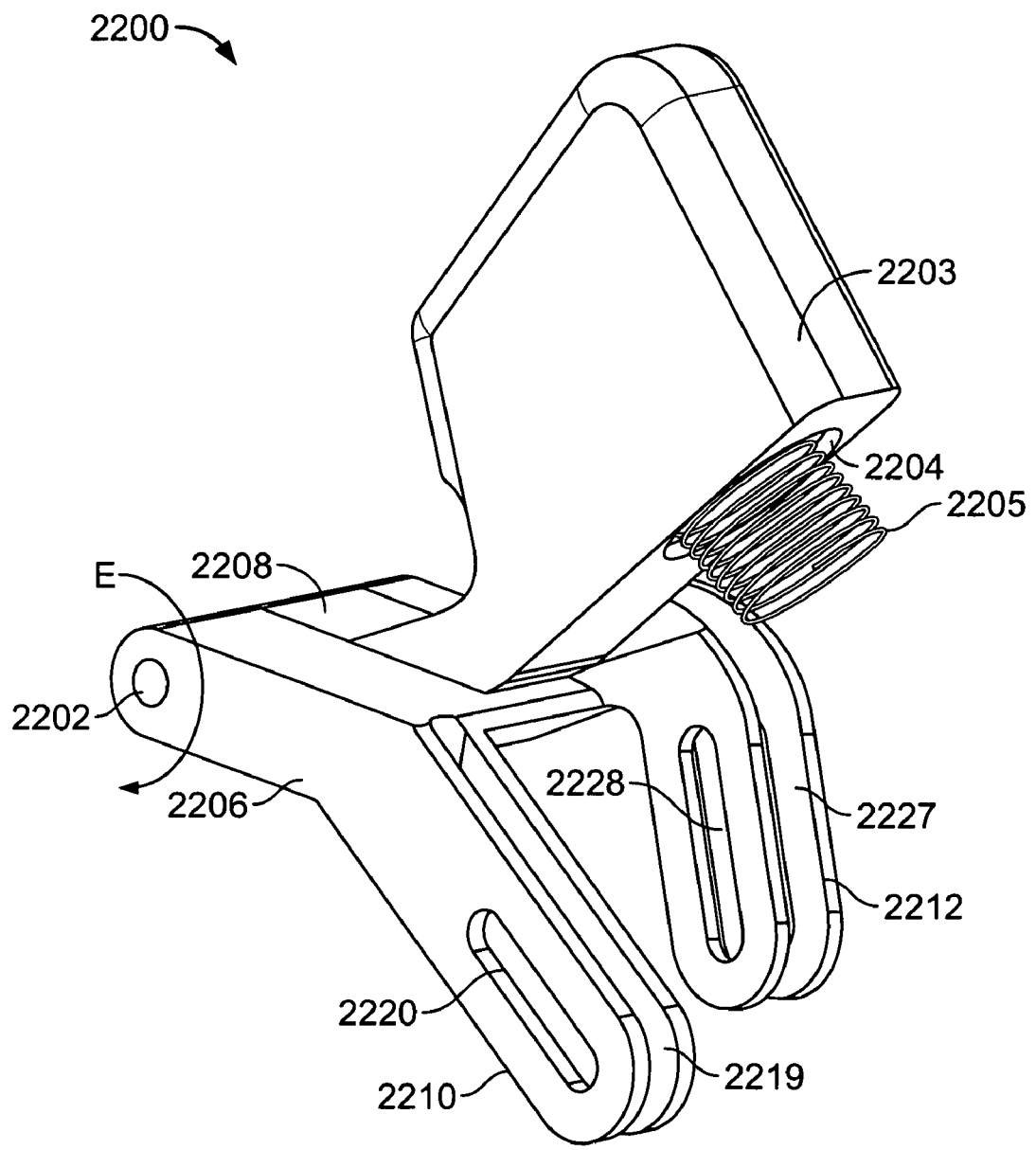
FIG. 60 is an illustration of a button assembly of the lever lock button assembly.
Figure 61:
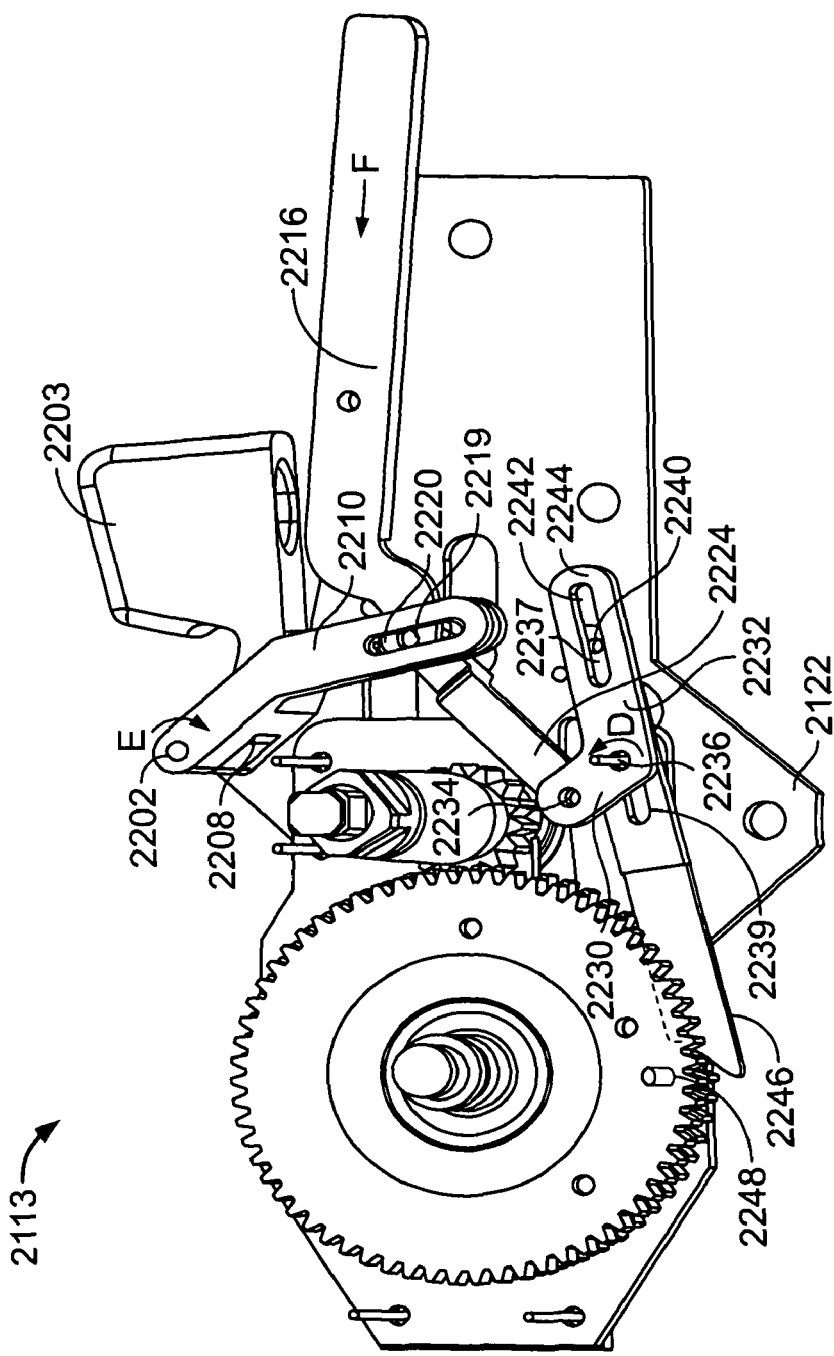
FIG. 61 is an illustration of the lever lock button assembly of FIG. 59 showing the assembly actuated.
Figure 62:
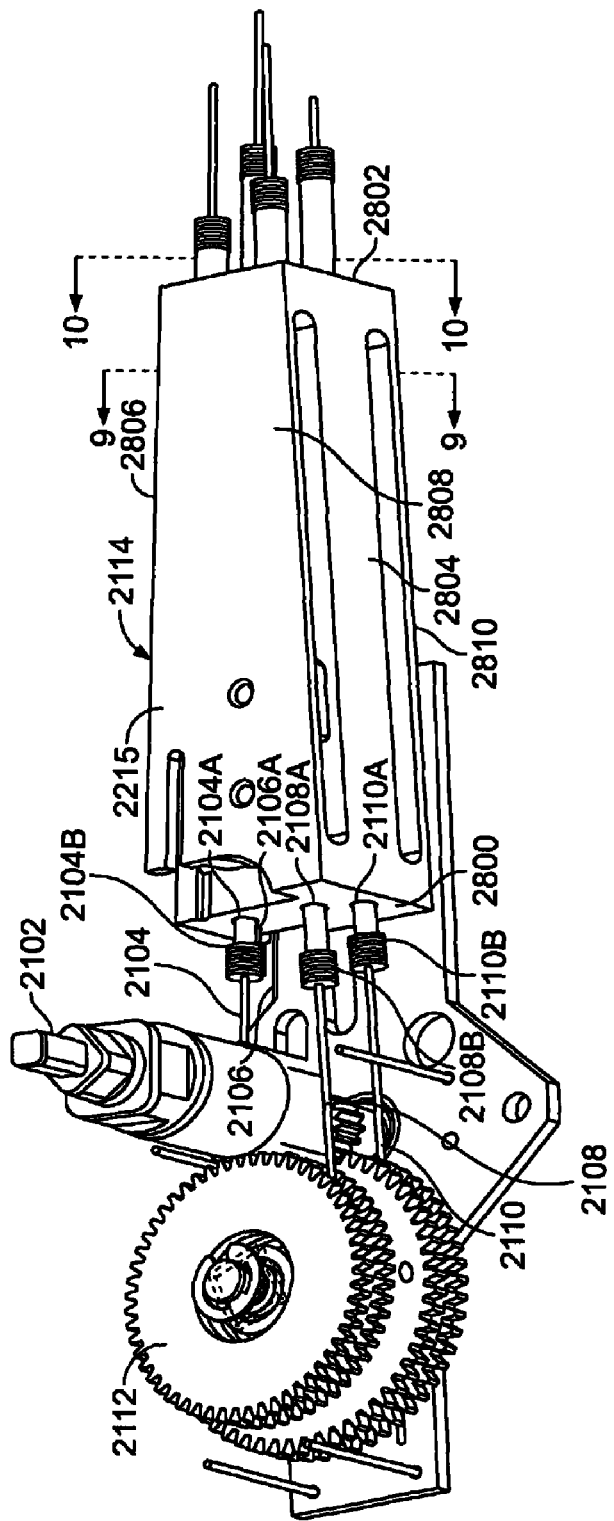
FIG. 62 is an illustration of the mechanism of FIG. 56 shown with a second set of optional cable adjusters.
Figure 63:
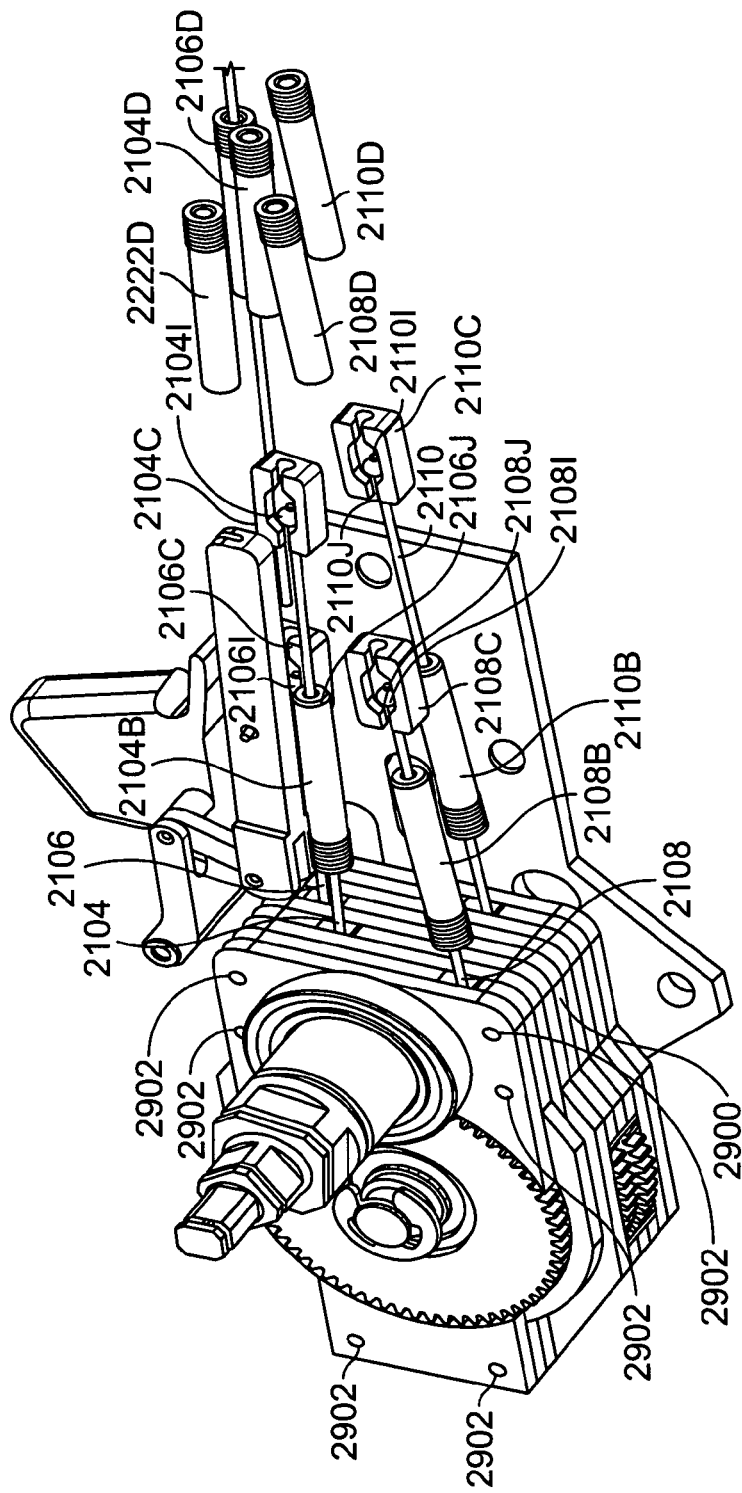
FIG. 63 is an illustration of the mechanism of FIG. 62 shown with a housing removed.
Figure 64:
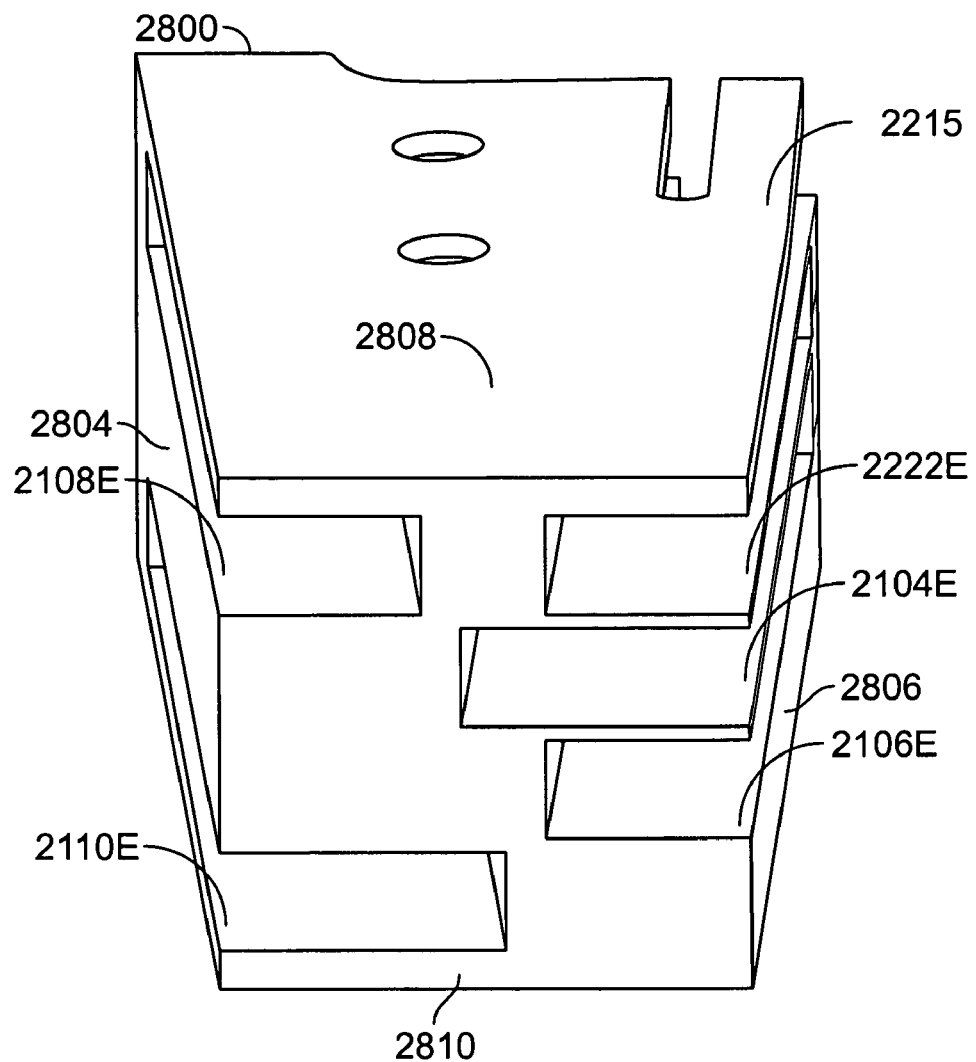
FIG. 64 is an isometric view of the housing taken along lines 9-9 of FIG. 62.
Figure 65:
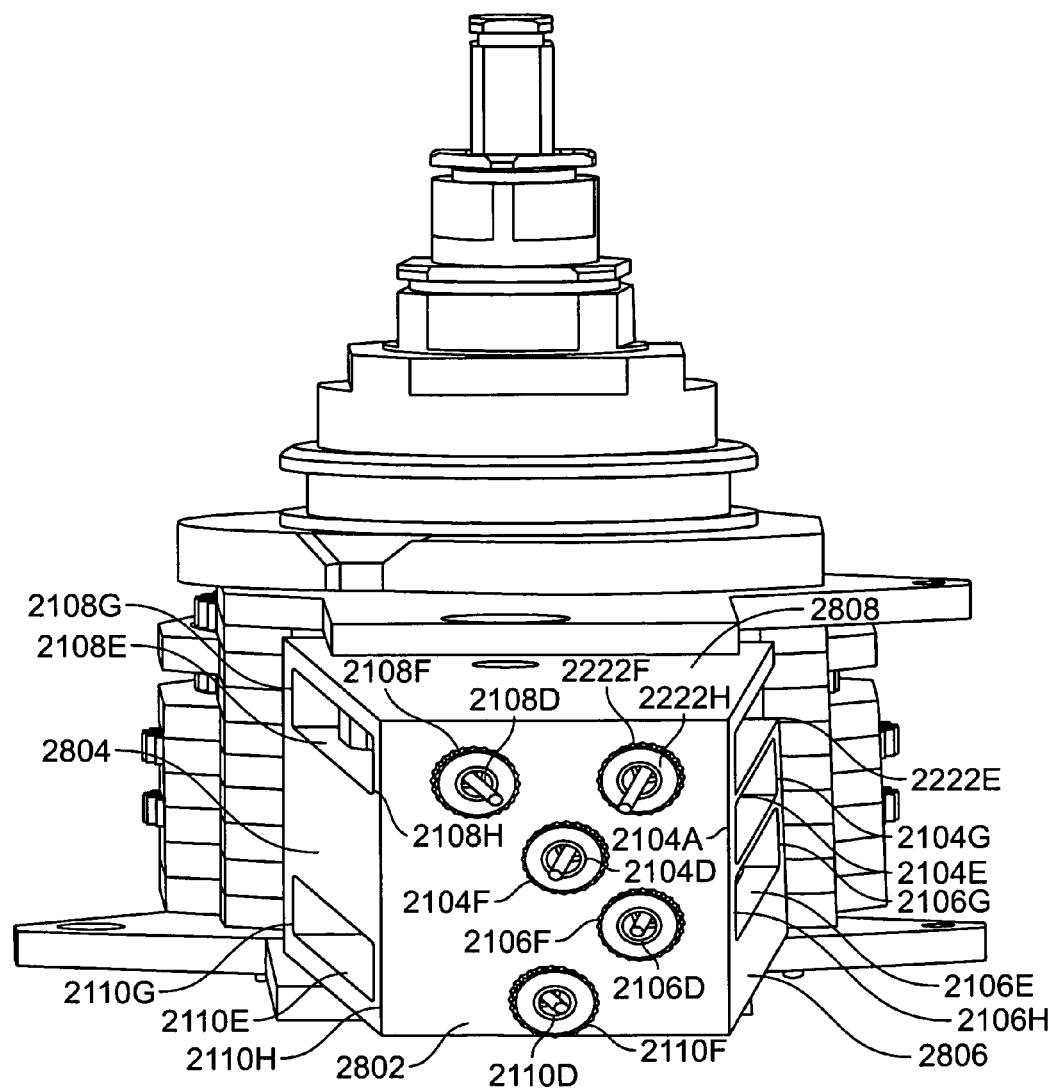
FIG. 65 is an end view of the mechanism of FIG. 62 taken along lines 10-10 of FIG. 62.

Button assembly 2200 is connected to a bottom plate 2122 and to a top plate (not shown) by a pin 2202. Referring also to FIGS. 60 and 61, button assembly 2200 includes a button element 2203 defining a hole 2204 in which a spring 2205 is inserted, and a forked element 2206 that includes a cross bar 2208 that receives pin 2202 and from which extend two arms 2210 and 2212. Spring 2205 acts between button element 2203 and a housing 2215 of adjust block 2114 (FIG. 56) to bias button assembly 2200 toward a locking position.

Arm 2210 defines a slot 2219 for receiving slide 2216, and a slot 2220 for receiving a pin 2218 attached to slide 2216 for slidably coupling slide 2216 to arm 2210. When the user presses button element 2203, button assembly 2200, and thus arm 2210, pivots about pin 2202 in the direction of arrow E. This motion of arm 2210 pulls slide 2216 in the direction of arrow F, with pin 2218 sliding within slot 2220 (FIG. 61), and thus pulls cable 2222 in the direction of arrow F to release the distal lock.

Arm 2212 defines a slot 2227 for receiving a bent arm 2224 of locking mechanism 2214, and a slot 2228 for receiving a pin 2266 attached to bent arm 2224 for slidably coupling bent arm 2224 to arm 2212. Bent arm 2224 is also coupled to a first portion 2230 of a L-shaped arm 2232 by a pin 2234. L-shaped arm 2232 is coupled to base plate 2122 by a post 2236 about which arm 2232 can rotate. L-shaped arm 2232 is also fixed to a first end 2237 of a stop lever 2238 by a screw 2240 inserted in a slot 2242 defined by a second portion 2244 of L-shaped arm 2232. Stop lever 2238 defines a slot 2239 that receives post 2236 about which lever 2238 rotates with arm 2232 (FIG. 61). Lever 2238 has a second end 2246 shaped to engage a pin 2248 of gear-pulley 2150.

The engagement of lever 2238 with pin 2248 limits the extent to which the jaws can be closed, such that the implant is not deployed until the button mechanism is activated to disengage the lever and pin. When the user presses button element 2203, arm 2212 rotates about pin 2202 in the direction of arrow E, moving bent arm 2224 and L-shaped arm 2232 such that L-shaped arm 2232 rotates about post 2236 in the direction of arrow D (FIG. 61). This motion causes stop lever 2238 to also rotate about post 2236, disengaging lever 2238 from pin 2248 such that gear-pulley 2250 can be further rotated to deploy the implant. Stop lever slot 2242 facilitates assembly and calibration of cable actuation mechanism 2100 by allowing the position of stop lever 2238 relative to the closing of the jaws to be set during assembly.

Referring to FIGS. 62-65, adjust block assembly 2114 includes housing 2215 with a front end 2800, a back end 2802, a first side 2804, a second side 2806, a top 2808, and a bottom 2810. Housing 2215 defines five slots 2110E, 2108E, 2104E, 2106E, and 2222E, four holes 2110A, 2108A, 2104A, and 2106A at front end 2800, and five holes 2110F, 2108F, 2104F, 2106F, and 2222F at back end 2802. Holes 2110A, 2110F communicate with slot 2110E for receiving cable 2110 therethrough, holes 2108A, 2108F communicate with slot 2108E for receiving cable 2108 therethrough, holes 2104A, 2104F communicate with slot 2104E for receiving cable 2104 therethrough, and holes 2106A, 2106F communicate with slot 2106E for receiving cable 2106 therethrough. Slot 2222E is open at front end 2800 for receiving slide 2216, and communicates with hole 2222F at back end 2802 for receiving cable 2222.

Within each hole 2110F, 2108F, 2104F, 2106F, and 2222F in back end 2802, a cable adjuster 2110D, 2108D, 2104D, 2106D, and 2222D, respectively, is received. Cables 2110, 2108, 2104, 2106, and 2222 each pass through one of the cable adjusters and the cable adjusters are used to set the length of the cables during assembly. Within each hole 2110A, 2108A, 2104A, and 2106A in front end 2800, a cable adjuster 2110B, 2108B, 2104B, and 2106B, respectively, can optionally be received to aid in setting the length of the cables.

For ease of assembly, each of cables 2110, 2108, 2104, and 2106 is preferably formed from two cable pieces joined by a coupler 211C, 2108C, 2104C, and 2106C, respectively. The cable ends each have a ball crimp 21101, 21081, 21041, and 21061 (only one end and ball crimp of each cable being shown in FIG. 63) removably received within a slot 2110J, 2108J, 2104J, and 2106J defined by the coupler. Couplers 2110C, 2108C, 2104C, and 2106C are received within slots 2110E, 2108E, 2104E, 2106E, respectively. Slots 2110E, 2108E, 2104E, and 2106E include front stops 2110G, 2108G, 2104G, and 2106G, respectively, and back stops 2110H, 2108H, 2104H, and 2106H, respectively. The stops restrict the movement of couplers 2110C, 2108C, 2104C, and 2106C, respectively. The stops limit the movement of the couplers and therefore limit the maximum amount of distance that the cables 2110, 2108, 2104, and 2106 can be pulled.

Referring again to FIGS. 58 and 63, knob assembly 2102 and gear assembly 2112 are enclosed in a stack of plates 2900 such that possible slipping of cables 2110, 2108, 2104, and 2106 from grooves 2164, 2160, 2156, and 2168 is limited. The plates have slots as necessary to allow the cables to pass out of the stack of plates 2900 and connect to the adjust block assembly 2114. The stack of plates 2900 are aligned and connected to bottom plate 2122 and top plate (not shown) by posts 2902.

Figure 66:
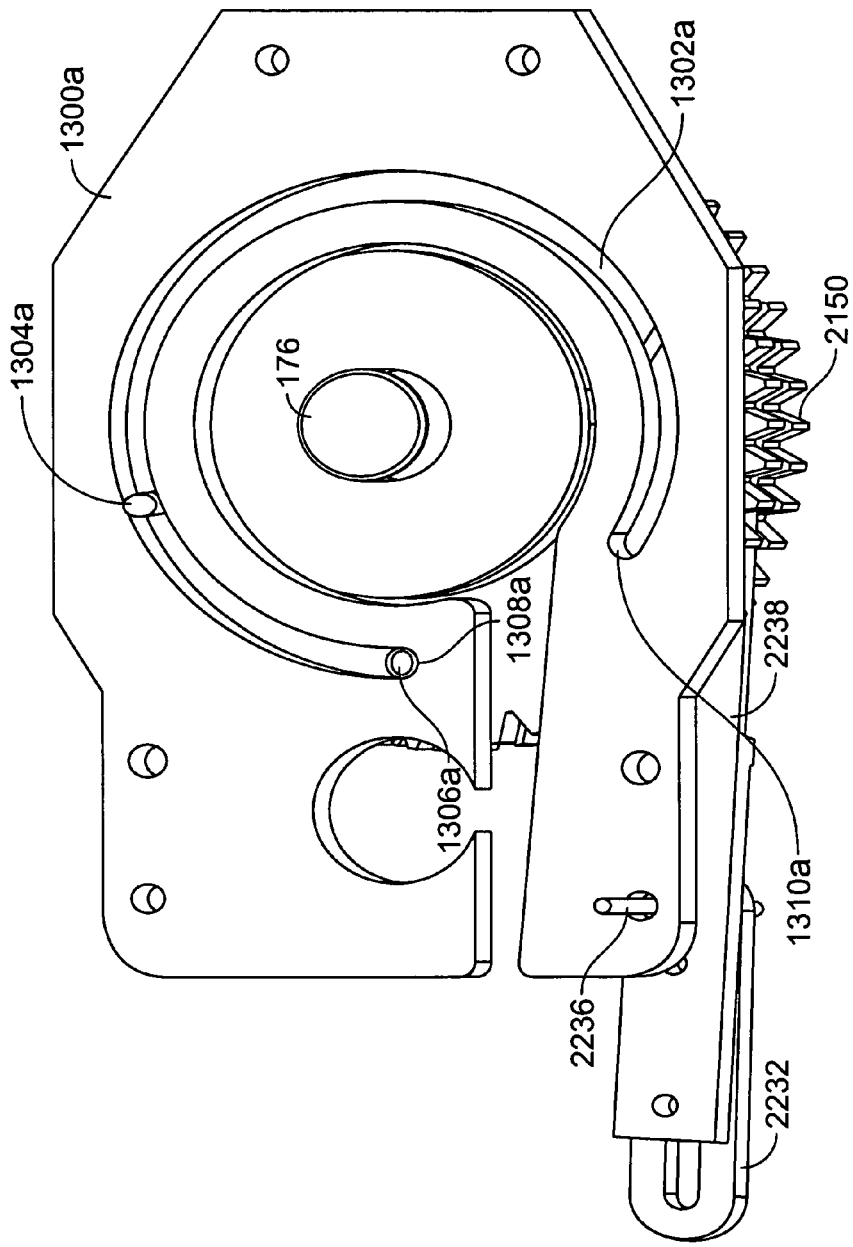
FIG. 66 is an illustration of a plate assembly used to bind the movement of the cables.

Referring to FIG. 66, an alternative embodiment to using contact of the couplers with the ends of the slots in the housing 2215 to bound the movement of the cables includes providing a concentric slot 1302a in a plate 1300a of the plate stack, and pins 1304a and 1306a attached to gear-pulley 2150 that extend into slot 1302a. Slot 1302a has a first end 1308a and a second end 1310a. The rotation of gear-pulley 2150 is bounded by pins 1304a, 1306a abutting against ends 1308a, 1310a. Likewise, another concentric slot can be providing in another plate, and pins provided on gear-pulley 2148 to bound rotation of gear-pulley 2148.

Figure 67:
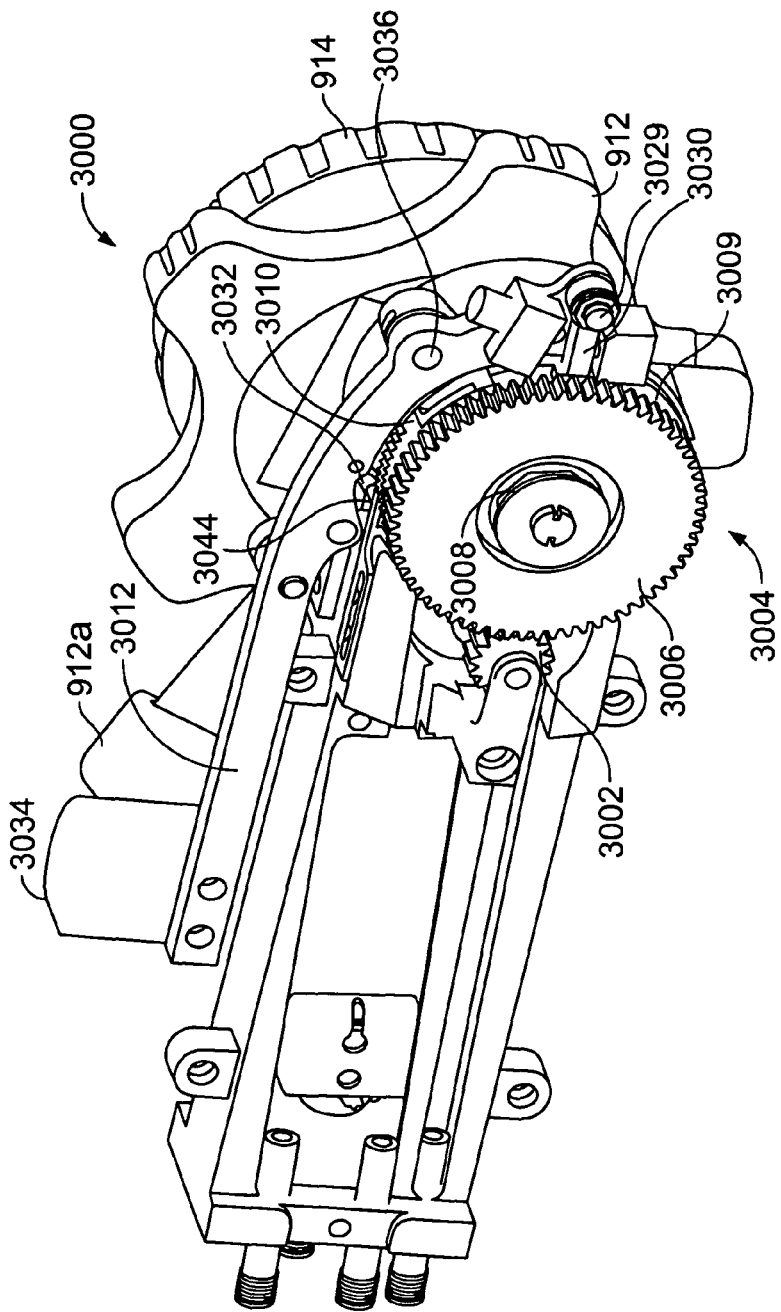
FIG. 67 is an illustration of an alternative embodiment of a handle mechanism.

Referring to FIG. 67, a handle mechanism 3000 includes a gear 3002 coupled to actuating control knob 914 via shaft 2118 (FIG. 57) to rotate therewith. Gear 3002 drives a transmission assembly 3004. Transmission assembly 3004 includes a drive gear 3006, a clutch 3008, a ring 3009, a pulley 3010, and a control arm 3012. Rotation of gear 3002 causes rotation of drive gear 3006, ring 3009, and pulley 3010 (as discussed below with respect to FIG. 96). The various components of assembly 3004 interact, as described below, to determine fully open and closed positions of the actuating arms 962a, 962b, which are coupled to the pulley 3010 (FIG. 17G), to determine a cartridge loading position for the actuating arms, to provide a mechanism for holding the actuating arms in a fixed position for insertion through the esophagus, and to provide a mechanism for holding the actuating arms open when no torque is being applied to knob 914. In addition, a ratchet formed on the pulley 3010 interacts with the control arm 3012 to keep the arms from being pushed apart by the tissue during closing of the actuating arms 962a, 962b if the operator lets go of knob 914. When knob 914 is turned to close actuating arms 962a, 962b, clutch 3008 slips before the tension applied to the cables reaches a level that could damage the cables, as described further below, which can occur, for example, if something is jamming the actuating arms apart.

Figure 68:
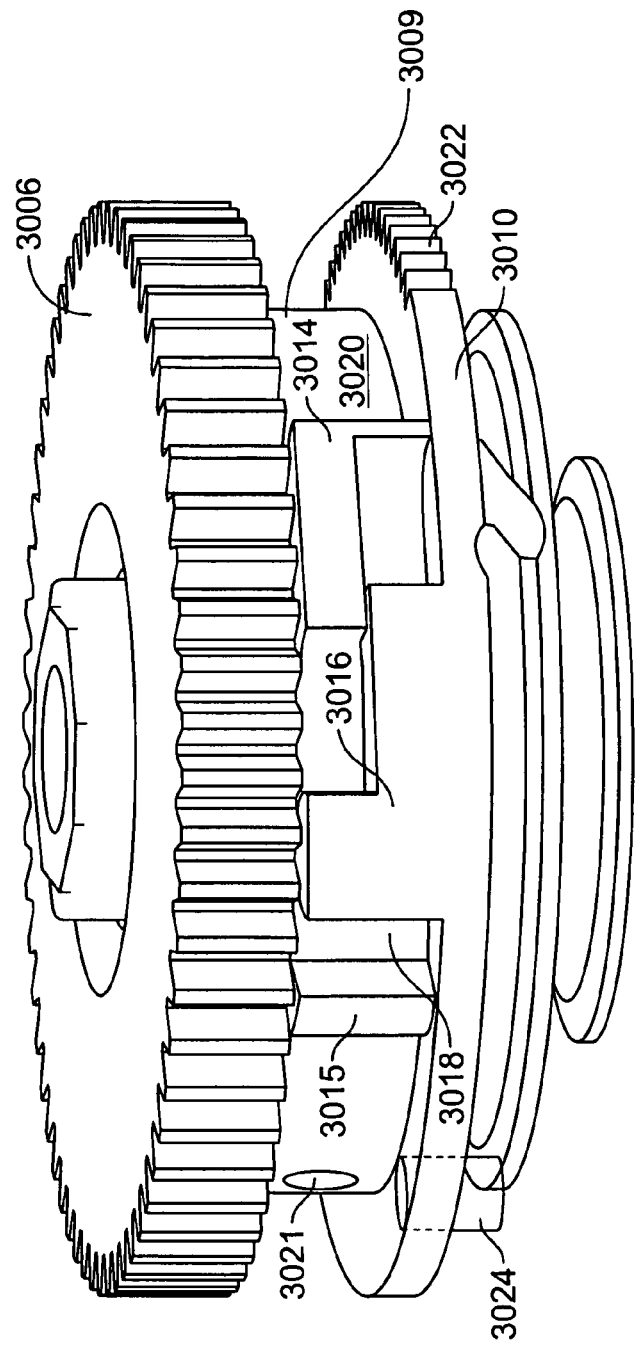
FIG. 68 is an illustration of a transmission assembly of the handle mechanism of FIG. 67.
Figure 69:
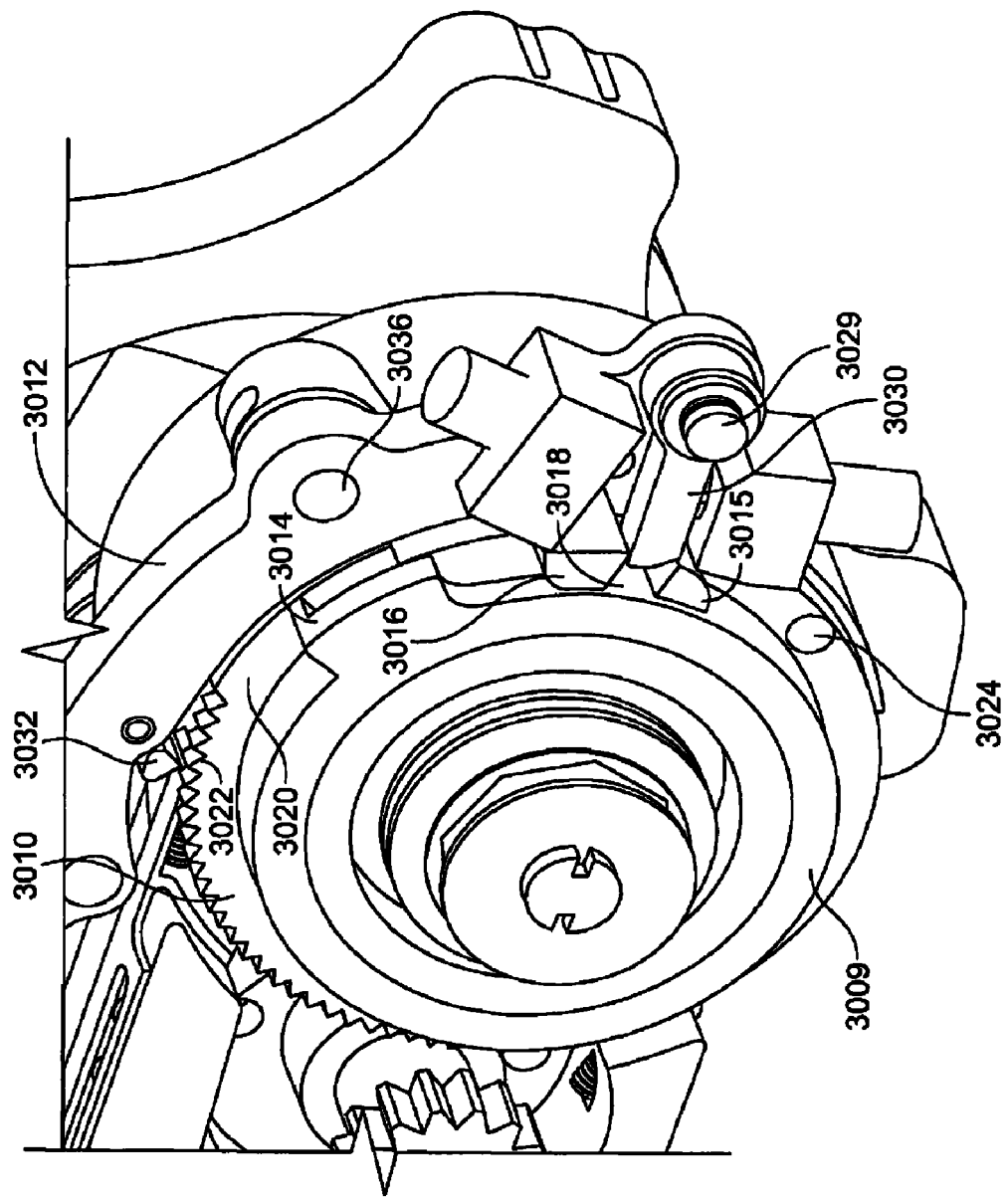
FIG. 69 shows a portion of the handle mechanism of FIG. 67 with a gear removed.

Referring to FIG. 68, ring 3009 includes a ramp 3014, and pulley 3010 includes a first ramp 3015 and a second ramp 3016. Defined between ramps 3015 and 3016 is a first recess 3018, and at the end of ramp 3014 is a second recess 3020. The position of recess 3020 relative to recess 3018 is adjustable by rotating ring 3009 relative to pulley 3010, and is fixed using a set screw 3021. Pulley 3010 also has a section of ratchet teeth 3022 and a stop pin 3024. As shown in FIGS. 67 and 69, arm 3012 includes a post 3030 rotatably mounted to arm 3012 at pin 3029. When knob 914 is rotated to close the actuating arms, post 3030 travels over ramp 3015 and into recess 3018. This position of post 3030 sets the position of the actuating arms that corresponds to the desired position for loading the cartridges to the actuating arms, as well as for passing the distal end of the instrument though the esophagus.

Figure 70:
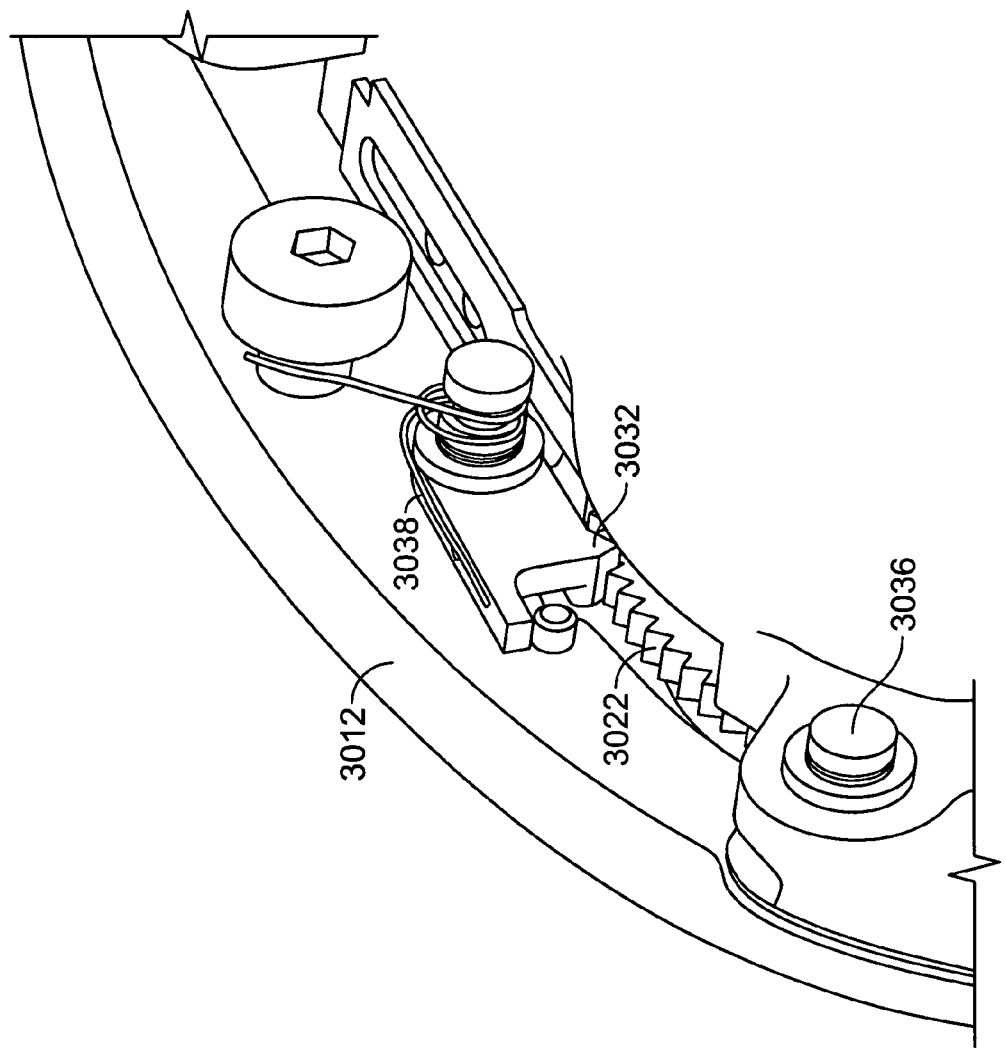
FIG. 70 is a view of the handle mechanism taken from the opposite side of the view of FIG. 69.

Referring also to FIG. 70, arm 3012 has a pawl 3032 mounted thereto that rides along ratchet teeth 3022. When closing the actuating arms from the cartridge loading position to the deployed position, the operator pushes a button 3034 (FIG. 67) of arm 3012, causing the arm 3012 to rotate about a pivot point 3036 to remove post 3030 from recess 3018. Continued rotation of knob 914 causes post 3030 to ride along ramps 3016 and 3014, which also causes arm 3012 to pivot about a pivot point 3036 such that pawl 3032 engages ratchet teeth 3022. Pawl 3032 includes a torsion spring 3038 that biases the pawl into engagement with teeth 3022. The engagement of pawl 3032 with ratchet teeth 3022 as the actuating arms are closed limits the tendency of the actuating arms to be pushed apart by tissue located therebetween if the user lets go of knob 914, such as when the user lets go of knob 914 between repeated turnings of the knob to close the actuating arms. When the actuating arms are fully deployed, that is, when the arms are in the position at which they have deployed the implant, post 3030 drops into recess 3020, disengaging pawl 3032 from ratchet teeth 3022, and the button 3034 pops up, providing the user with visual, tactile, and/or audible feedback that the implant is deployed. To open the actuating arms, the operator turns knob 914 in the opposite direction. When post 3030 rides along the edge of ramp 3014, post 3030 pivots about pin 3029 and engages upper ball plunger 3030a, allowing arm 3012 to remain in position such that pawl 3032 remains disengaged from ratchet teeth 3022 during the opening of the actuating arms.

Figure 71:
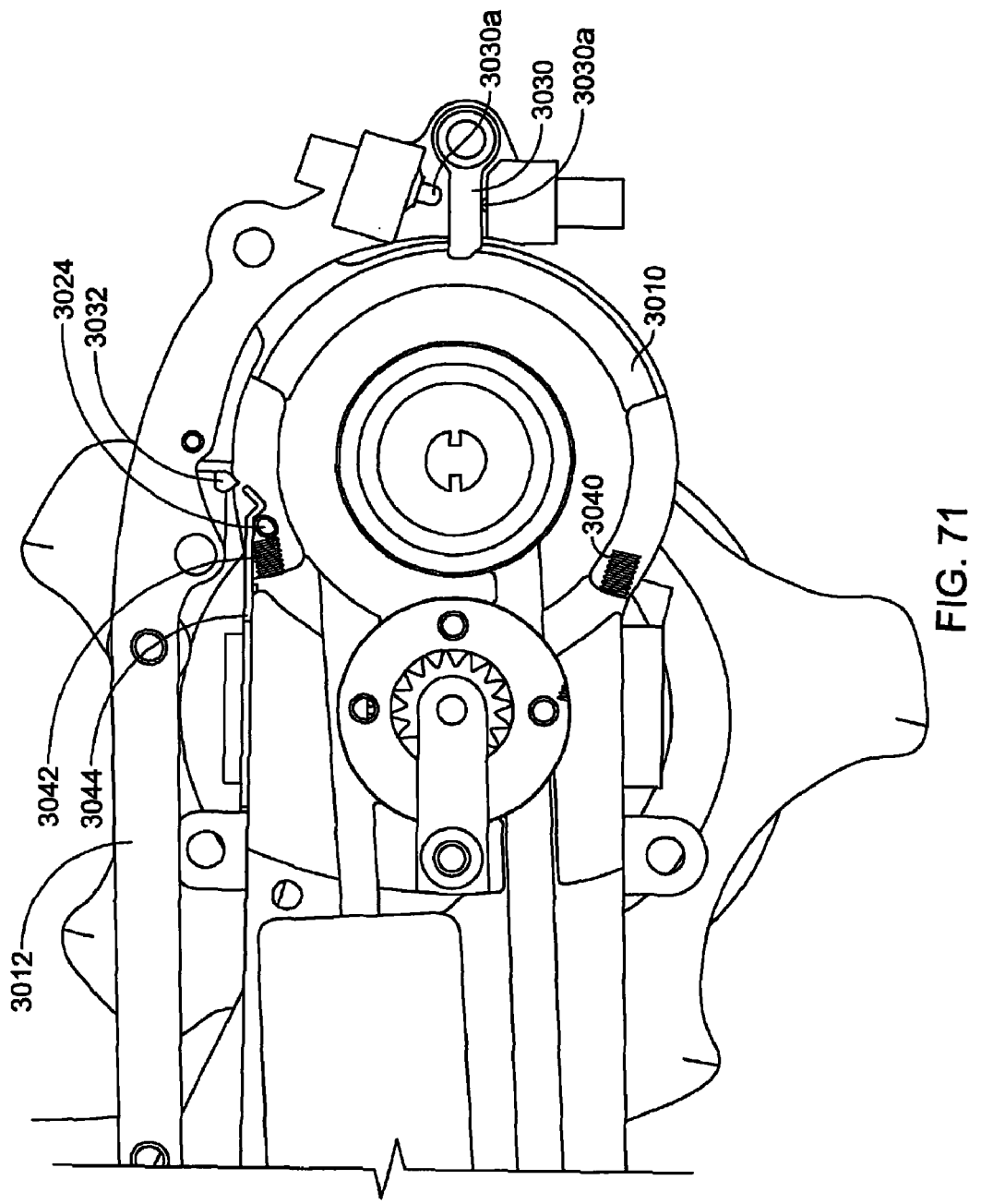
FIG. 71 is an illustration of the handle mechanism of FIG. 67 with the transmission assembly of FIG. 68 removed.

Referring to FIG. 71, assembly 3004 includes a deploy stop 3040 and an open stop 3042. The stops 3040 and 3042 are threaded, so that their position is adjustable. Pin 3024 of ratchet 3010 hits stop 3040 when the actuating arms are deployed (corresponding to the position in which post 3030 enters recess 3020), and pin 3024 hits stop 3042 when the actuating arms are in their fully open position. In the fully open position, pin 3024 also interacts with a detent 3044 such that the actuating arms are held open until a torque is applied to knob 914. Also shown in FIG. 71 are a pair of spring-loaded ball plungers 3030a that act against post 3030 to limit travel of post 3030 and bias the post into a neutral position.

Figure 92:
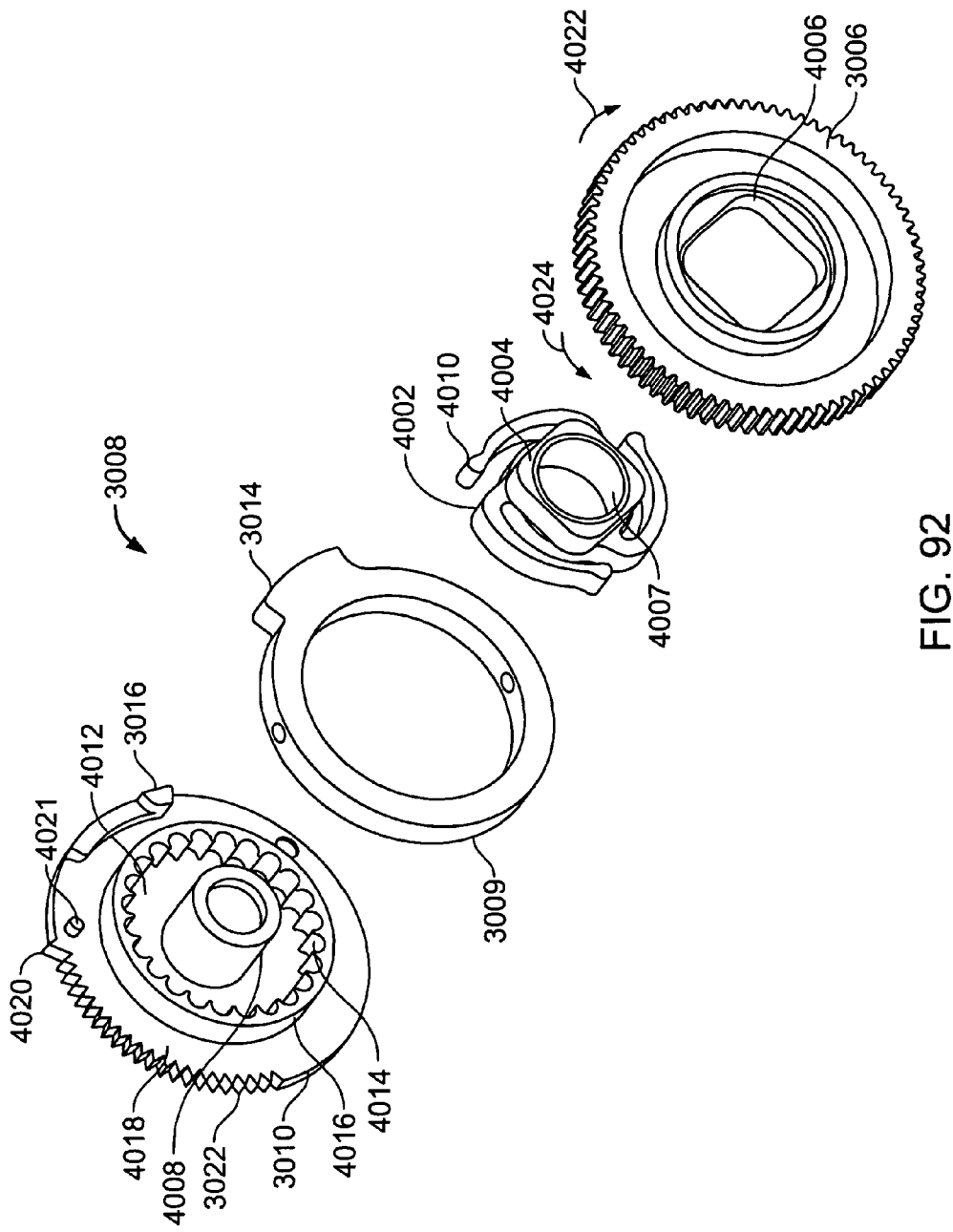
FIGS. 92 and 93 are exploded perspective views of a clutch of the transmission assembly of FIG. 67.
Figure 93:
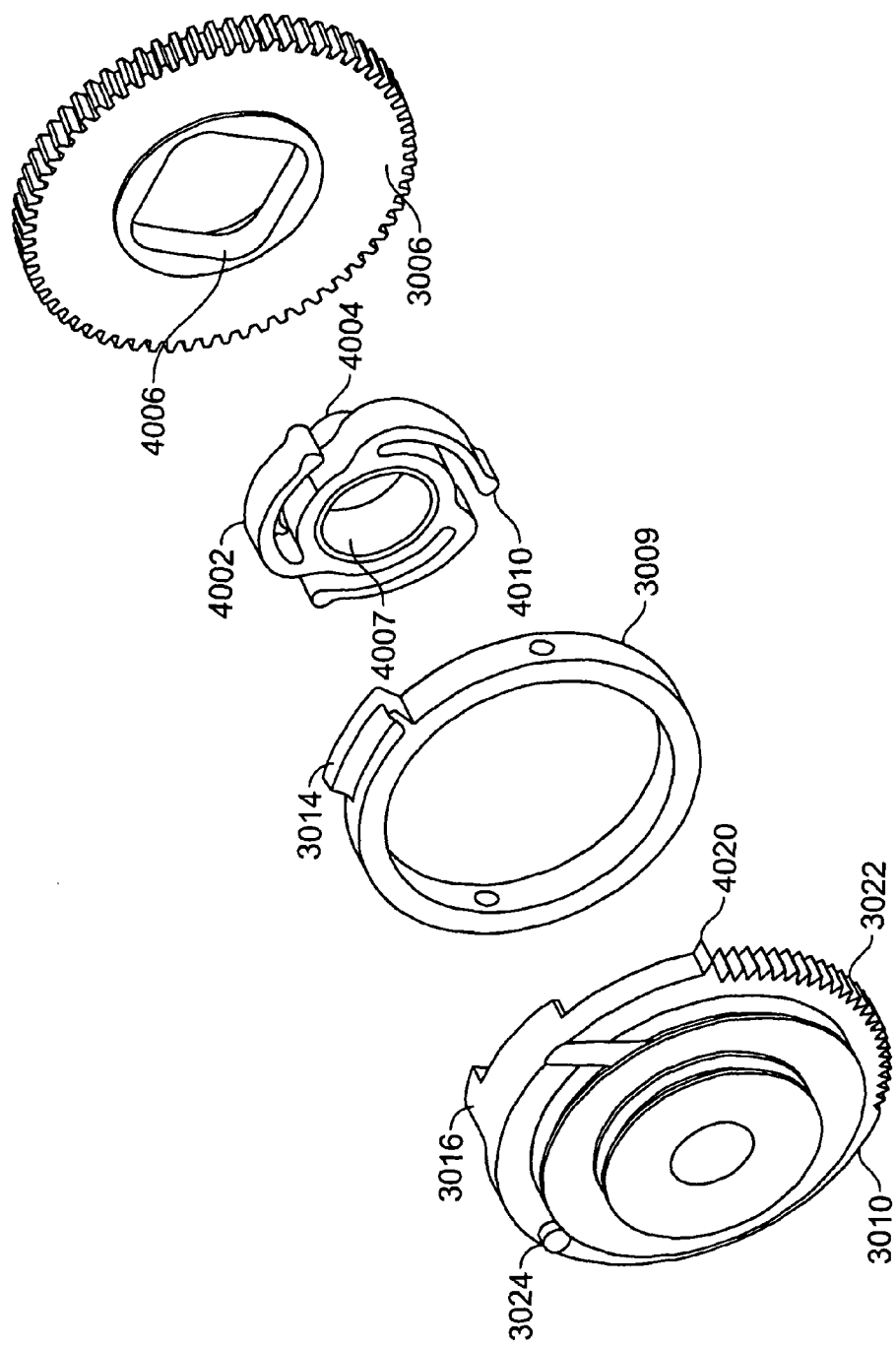

Referring to FIGS. 92 and 93, the transmission assembly clutch 3008 includes a clutch spring 4002 positioned between the gear 3006 and the pulley 3010 within a recess 4006 in the gear 3006 and a recess 4012 in the pulley 3010. The clutch spring 4002 includes a post 4004 shaped to fit within the recess 4006 of gear 3006. The clutch spring 4002 defines a through hole 4007 that receives a post 4008 of the pulley 3010. The pulley recess 4012 is defined by an inner, waved surface 4014 of a wall 4016 extending from surface 4018 of the pulley 3010. Clutch spring 4002 includes legs 4010 that interact with the waved surface 4014 to form a one-way clutch. In this embodiment of the pulley 3010, the pulley 3010 includes a protrusion 4020 formed at one end of the set of ratchet teeth 3022 and a stop 4021 formed at the surface 4018. When the ring 3009 is slid over the wall 4016, the ramp 3014 fits snugly between the stop 4021 and the ramp 3016 (FIGS. 94 and 95).

Figure 94:
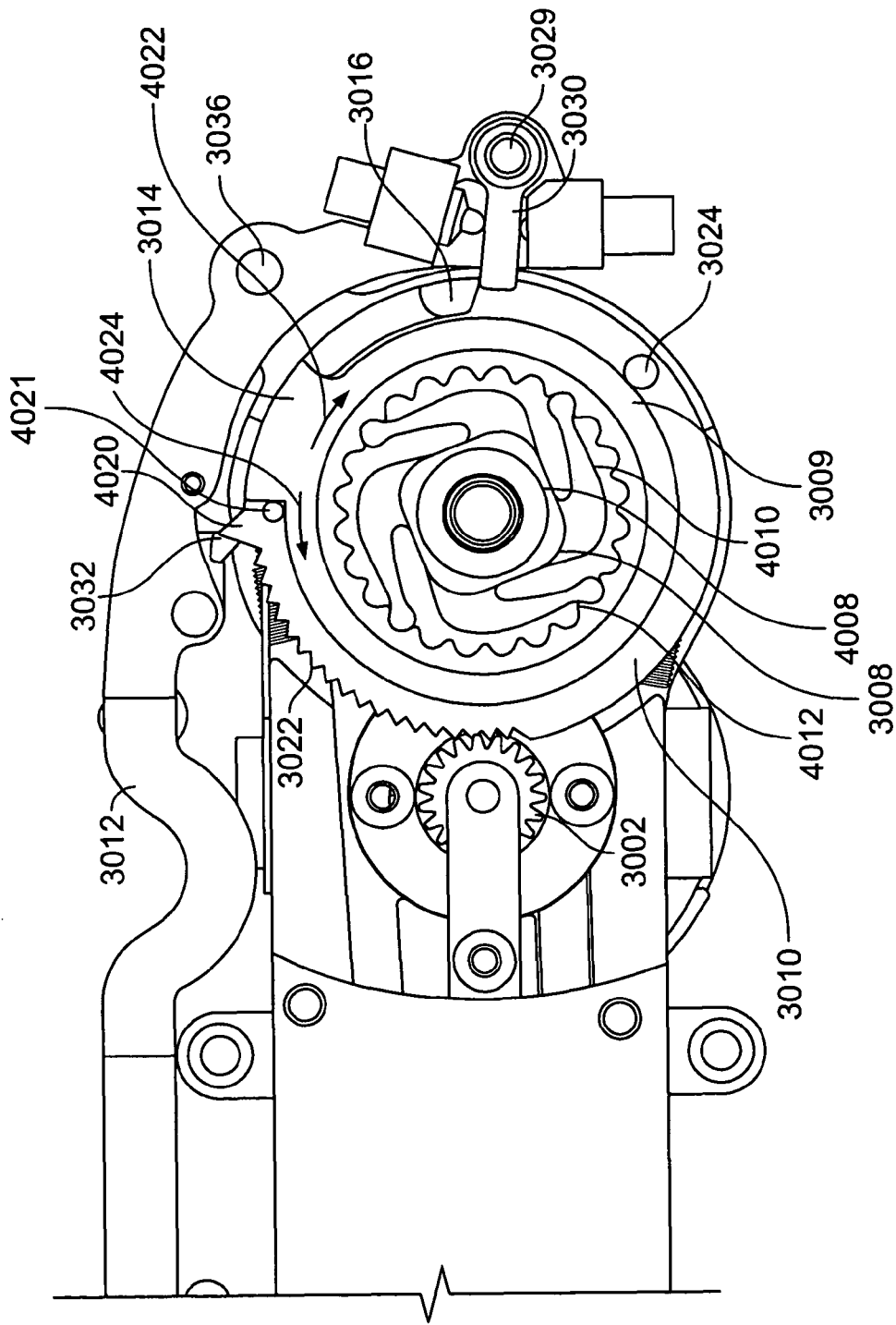
FIGS. 94 and 95 show a portion of the transmission assembly of FIG. 67 with a gear removed.
Figure 95:
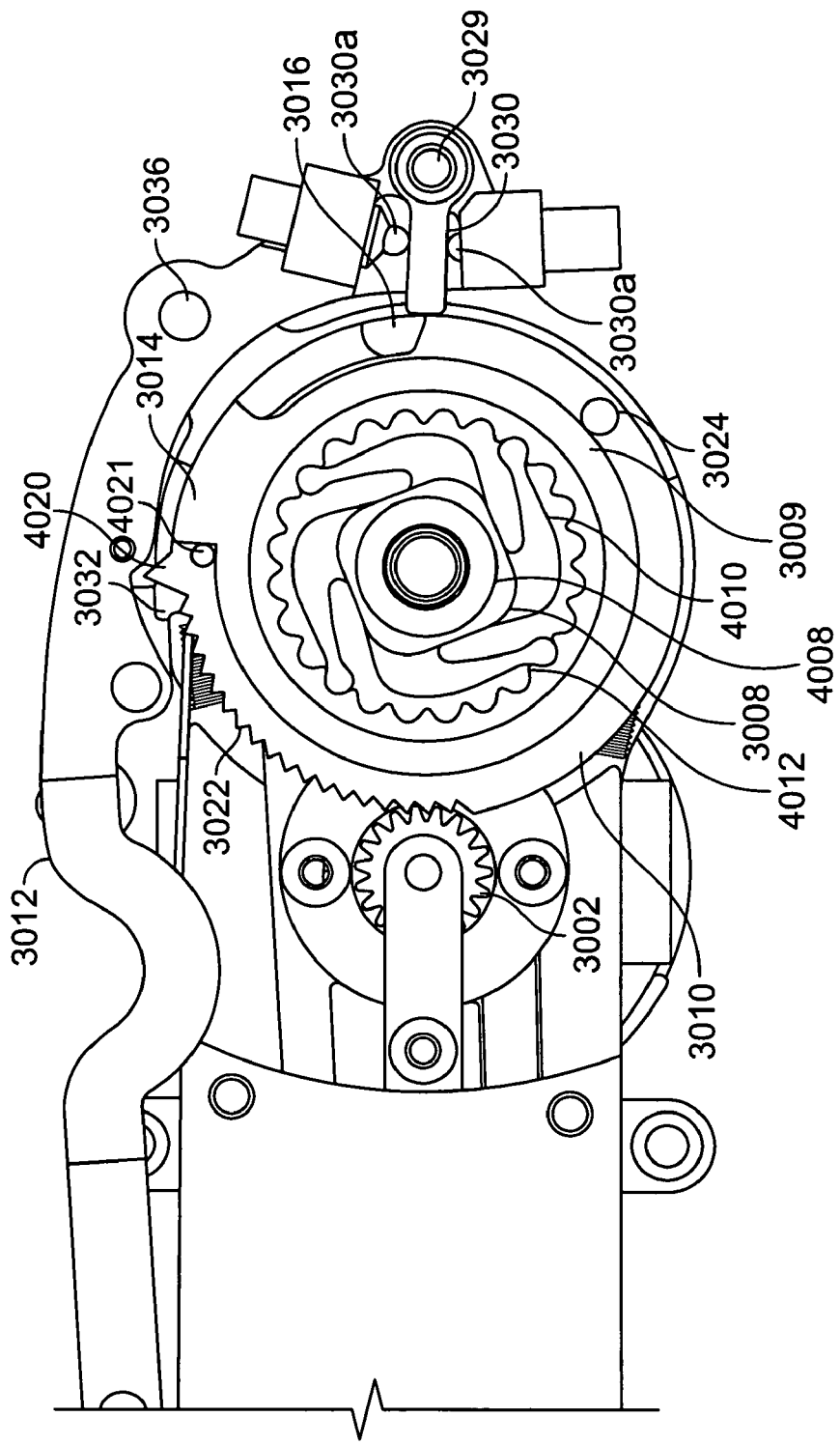

FIG. 94 shows the transmission assembly 3004 in position corresponding to when jaw members 3102a, 3102b are closed but the implant is not deployed. This position is used during loading of the cartridge and during insertion of the instrument into the patient to prevent damage to surrounding tissue. As the knob 914 is turned to close the actuating arms 962a, 962b, the gear 3002 rotates the gear 3006 in the direction of arrow 4022. Because the gear 3006 is keyed to the clutch spring 4002 at the interface of the post 4004 with the recess 4006, the spring 4002 rotates in the direction of 4022. Under normal operating conditions, rotation of the clutch spring 4002 rotates the pulley 3010 by the interaction of the legs 4010 with the waved surface 4014, that is, the clutch spring 4002 does not slip relative to the pulley 3010. If the actuating arms 962a, 962b experience an abnormally high resistance to closing, the legs 4010 of the clutch spring 4002 bend inward as the clutch spring 4002 is rotated, thus permitting the clutch spring 4002 to slip relative to the pulley 3010 such that additional tension that could damage the cable is not placed on the actuating arm closing cable attached to the pulley 3010. For example, clutch spring 4002 may begin to slip relative to the pulley 3010 when the cable experiences a tension greater than 72 pounds, at which point the cable would be overtensioned.

As the knob 914 is turned to open the actuating arms 962a, 962b, the gear 3002 rotates the gear 3006 in the direction of arrow 4024, which causes the clutch spring 4002 and the pulley 3010 to rotate in the direction of arrow 4024. Because of the orientation of the legs 4010 relative to the waved surface 4014, the clutch spring 4002 does not slip relative to the pulley 3010 when the clutch spring 4002 rotates in the direction of arrow 4024. Thus, a larger torque can be applied by the pulley 3010 in the opening direction (in the direction of arrow 4024) than in the closing direction (in the direction of arrow 4022).

In the closed position, the pawl 3032 engages the protrusion 4020 of the pulley 3010 such that pulley 3010 is retained in its closed position and post 3030 is biased in the position shown in FIG. 94. When the button 3034 is pressed (FIG. 95), the arm 3012 rotates about the pivot 3036 and the post 3030 clears the ramp 3016 and rotates out of the biased position of FIG. 94 and into a neutral position due to the force of the spring-loaded ball plunger 3030a. Since the post 3030 is now pushing against the ramp 3016, the button 3034 remains in its pressed position and the pawl 3032 engages the ratchet teeth 3022. The knob 914 can now be rotated to further close the actuating arms. If the knob 914 is rotated to open the actuating arms 962a, 962b beyond the position depicted in FIG. 94, the pulley 3010 rotates in the opening direction (in the direction of arrow 4024) and the pawl 3032 is slid across and pushed over the protrusion 4020 because the force of the pulley 3010 is great enough to overcome the biasing force applied to the pawl 3032 by the torsion spring 3038.

Figure 96:
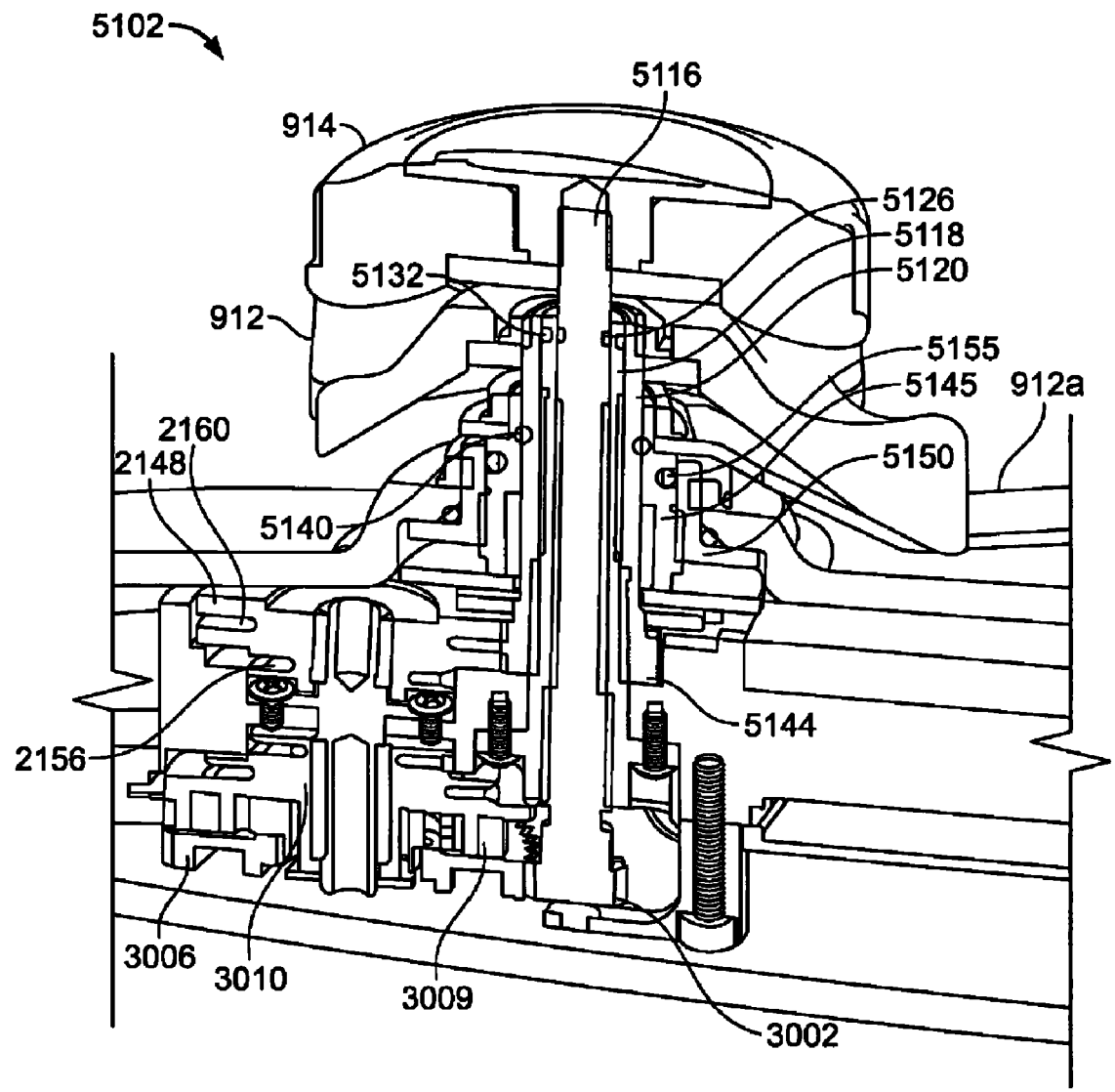
FIG. 96 shows a cross-sectional perspective view of a knob assembly of FIG. 67.

Referring also to FIG. 96, the cable actuation mechanism includes a knob assembly 5102 that is designed with a rotatable center shaft 5116 surrounded by a fixed shaft 5118 that is, in turn, surrounded by a rotatable shaft 5120. The shaft 5120 includes a gear 5144 that engages the gear pulley 2148 of gear assembly 2112 (FIGS. 57 and 58). The shaft 5118 includes the gear 3002 that engages the gear 3006 of the transmission assembly 3004 (FIGS. 67 and 92-95). The gear 3006 actuates the pulley 3010, which includes a first groove 5168 for receiving cable 2106 coupled to end effector and a second groove 5164 for receiving cable 2110 coupled to end effector.

The center shaft 5116 includes a groove 5126 for receiving an o-ring for creating a seal between the shaft 5116 and the shaft 5118. The shaft 5118 includes a groove 5132 for receiving an o-ring for creating a seal between the shaft 5118 and the shaft 5120. The shaft 5120 includes a groove 5140 for receiving an o-ring for creating a seal between the shaft 5120 and a shaft 5145. The lever 912a associated with retroflex knob 912 turns the shaft 5145, which is threaded to a collar 5150 so when the shaft 5145 is turned it engages and disengages a friction lock, as is known in the art. The shaft 5145 is located outside the shaft 5120 and within the collar 5150. The shaft 5145 is turned by the lever 912a includes a recess 5155 to receive an o-ring positioned between the shaft 5145 and the collar 5150 to seal the threaded region and the friction lock.

Figure 72A:
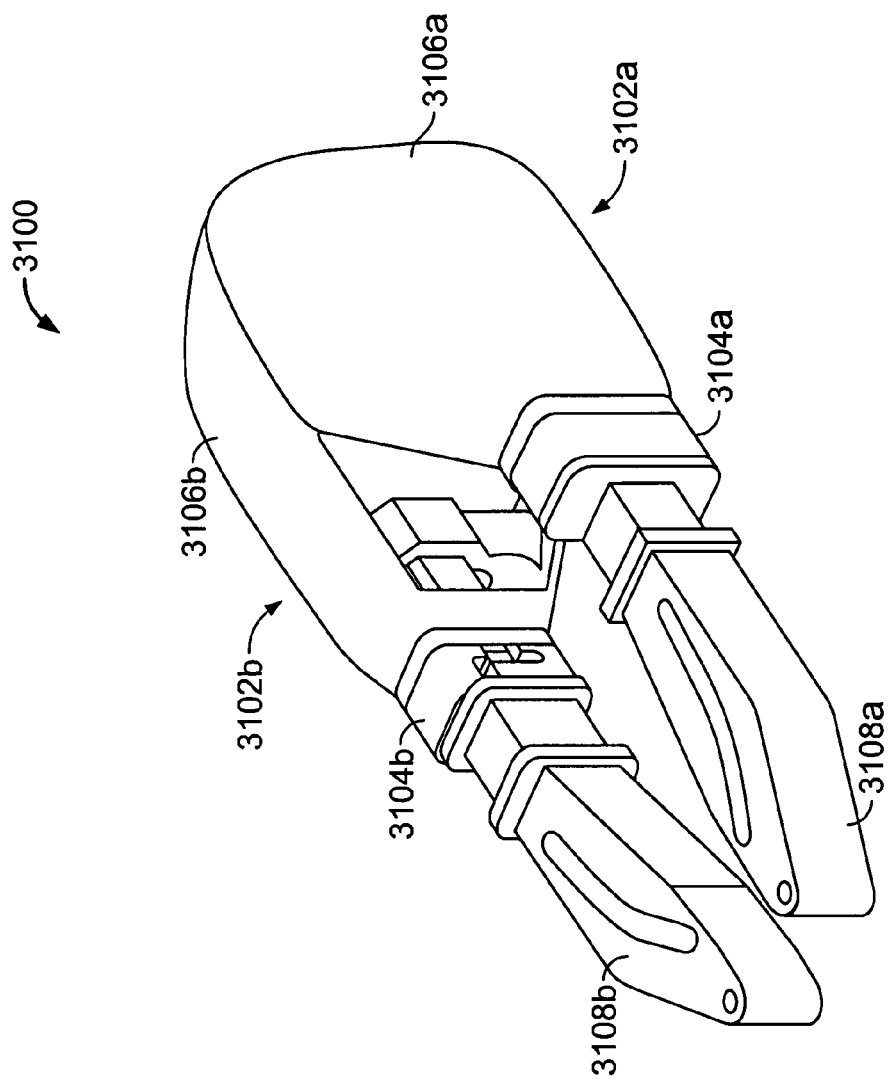
FIG. 72A is an illustration of an alternative embodiment of an end effector.
Figure 72B:
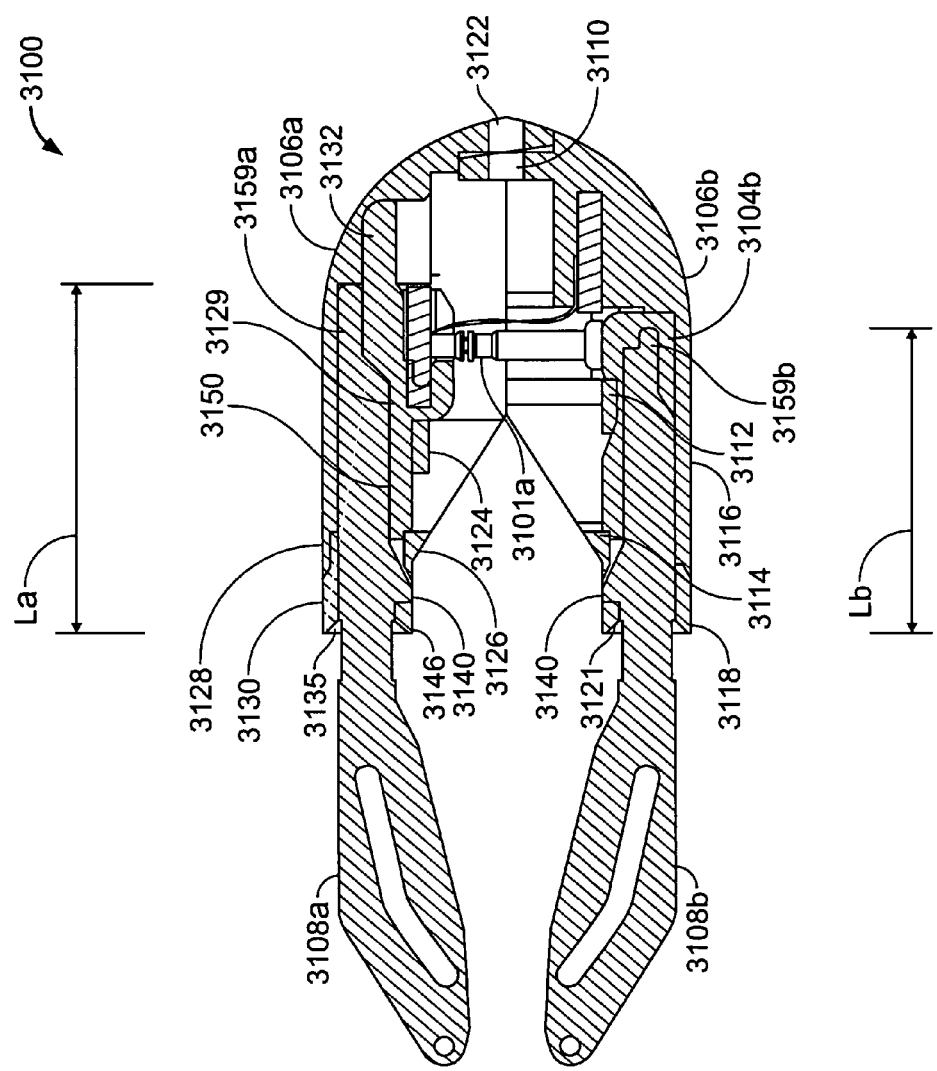
FIG. 72B is a cross-sectional view of the end effector of FIG. 72A.

Referring to FIGS. 72A and 72B, an end effector 3100 includes jaw members 3102a, 3102b, each of which includes a tissue manipulating cartridge 3104a, 3104b covered by a rubber shell 3106a, 3106b, respectively. Each jaw member 3102a, 3102b is releasably mounted to a respective actuating arm 3108a, 3108b. The cartridge 3104a, 3104b is configured to receive needles 3101a that include tissue penetrating elements 3101b having tissue penetrating tips 3101c. The portion of the actuating arm 3108a, 3108b received within the respective jaw member 3102a, 3102b is referred to as the coupler of the actuating arm.

Figure 73:
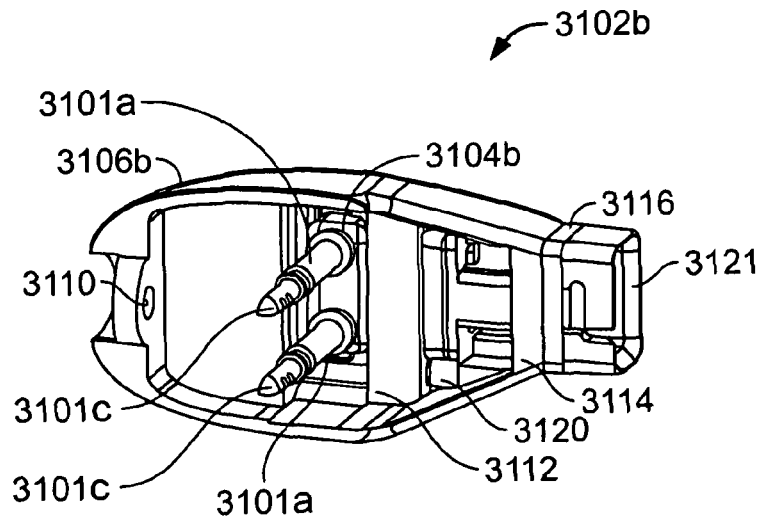
FIG. 73 is a perspective view of a jaw member of the end effector of FIG. 72.
Figure 74:
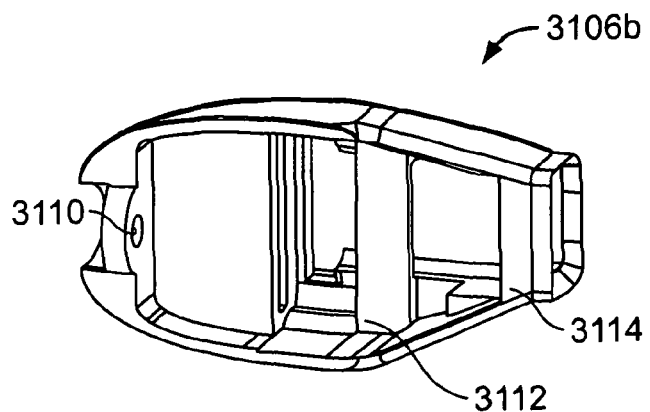
FIG. 74 is a perspective view of a shell of the jaw member of FIG. 73.
Figure 75:
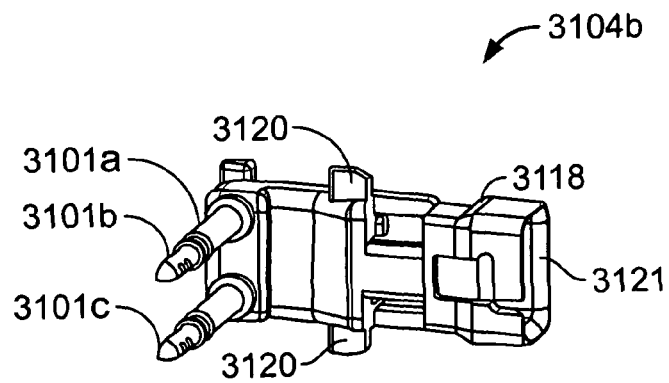
FIG. 75 is a perspective view of a cartridge of the jaw member of FIG. 73.

Referring to FIGS. 73-75, rubber shell 3106b defines a guide wire receiving hole 3110 and two webs of material 3112, 3114 that span over cartridge 3104b. Webs 3112, 3114 hold the shell 3106b onto the cartridge 3104b but allow the tissue to push the shell back when squeezing the tissue between the jaw members. Rubber shell 3106b has a rectangular-shaped end 3116 that meets up uniformly about a mating region 3118 of cartridge 3104b. Cartridge 3104b includes sideways extending posts 3120 that limit any tendency of the rubber shell to fold over the cartridge needles 3101a and potentially get pierced by the needles. When cartridge 3104b is loaded onto its respective actuating arm 3108b, as described above, the metal actuating arm extends into the plastic cartridge and terminates in a region behind the needles 3101a to support the needles. Cartridge 3104b has a chamfered inlet region 3121 that receives actuating arm 3108b.

Figure 76:
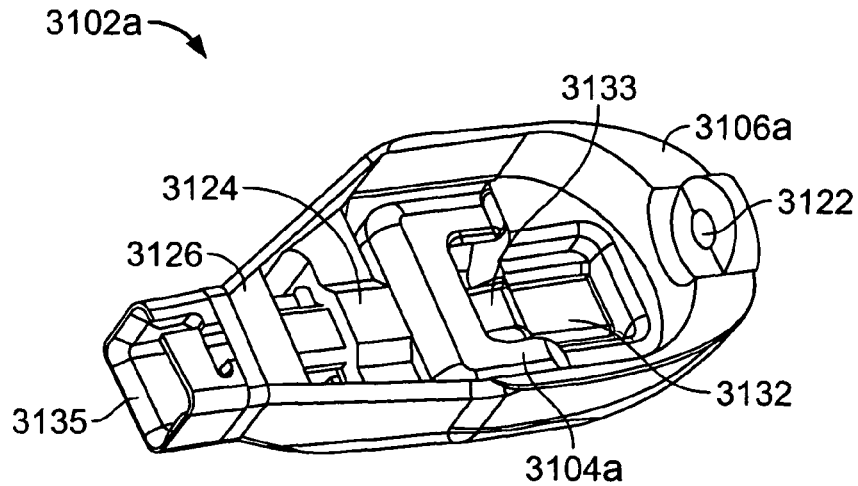
FIG. 76 is a perspective view of a second jaw member of the end effector of FIG. 72.
Figure 77:
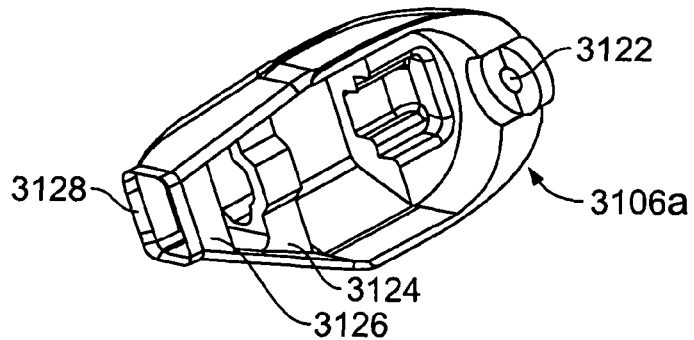
FIG. 77 is a perspective view of a shell of the jaw member of FIG. 76.
Figure 78:
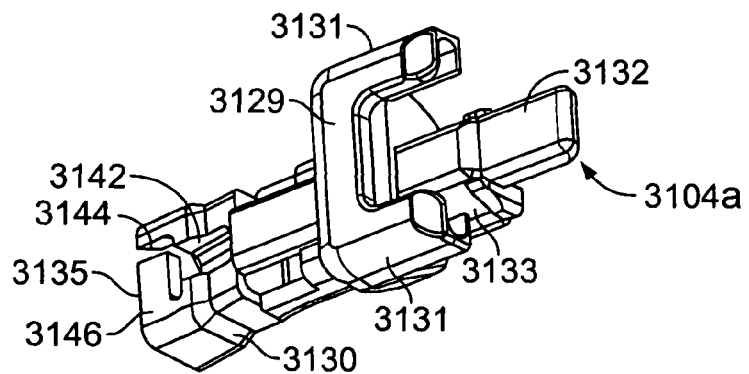
FIG. 78 is a perspective view of a cartridge of the jaw member of FIG. 76.

Referring to FIGS. 76-78, rubber shell 3106a defines a guide wire receiving hole 3122 and two webs of material 3124, 3126 that span over cartridge 3104a. Rubber shell 3106a has a rectangular-shaped end 3128 that meets up uniformly about a mating region 3130 of cartridge 3104a. Cartridge 3104a includes a distally extending post 3132 that limits any tendency of the rubber shell to fold over the cartridge needles 3101b and potentially get pierced by the needles when the actuating arms 3108a, 3108b are closed. The extending post 3132 extends from a metal clip 3133 that protrudes from a center U-shaped region 3129 of the cartridge 3104a. The U-shaped region 3129 defines a slot between legs 3131 positioned on opposite sides of clips 3133. Cartridge 3104a has a chamfered inlet region 3135 that receives actuating arm 3108a.

Referring also to FIG. 79, the elements 3101b are pushed through the slot between the legs 3131 (not shown in FIG. 79) as the actuating arms are closed to their deployed position. The elements 3101b are pushed against angled or ramped surfaces 3134 of the clip 3133 such that the elements 3101b break off and out to the sides and the breaking forces oppose each other. The clip 3133 is formed as a metal protrusion extending from the cartridge 3104a. In particular, while an inner side of the element 3101b contacts the angled surface 3134, an outer side of the base of the needle 3101a contacts the surface of the leg 3131, thus providing support for the needle 3101a as the element 3101b is pushed against the angled surface 3134. The opposed breaking forces help keep cartridge 3104a in alignment with cartridge 3104b, and ensures that both needles are subjected to a force that reliably deploys the implant. Metal clip 3133 keeps the elements 3101b from digging into the otherwise plastic body of cartridge 3104a and controls the break load by reducing friction and by setting the angle of the surface 3134. The load needed to break off the element 3101b ranges from 2.5 to 5.0 pounds and the angle at which the element 3101b breaks off from the cartridge 3104b ranges from 10° to 14°.

Referring also to FIG. 80, in another implementation, the legs 3131 of the cartridge 3104a define conical shaped sections 3158 that help center the needles 3101a of the cartridge 3104b relative to the metal clip 3133 of cartridge 3104a as the elements 3101b are pushed through the slot between the legs 3131 and while contacting the angled surfaces 3134 of the metal clip 3133.

When jaw members 3102a, 3102b are in position for passing the distal end of the instrument though the esophagus, guide wire receiving holes 3110 and 3122 are in alignment such that a guide wire can be passed through holes 3110 and 3122 to aid passage of the instrument and to assure the actuating arms 3108a, 3108b remain closed during insertion.

Figure 81:
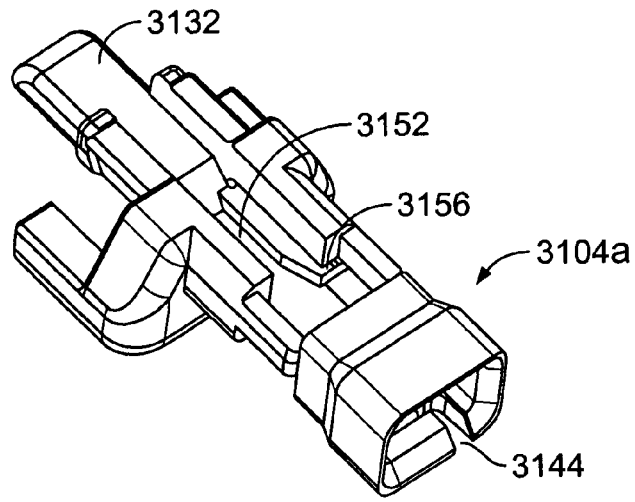
FIG. 81 is an additional illustration of the cartridge of FIGS. 78 and 80.
Figure 82:
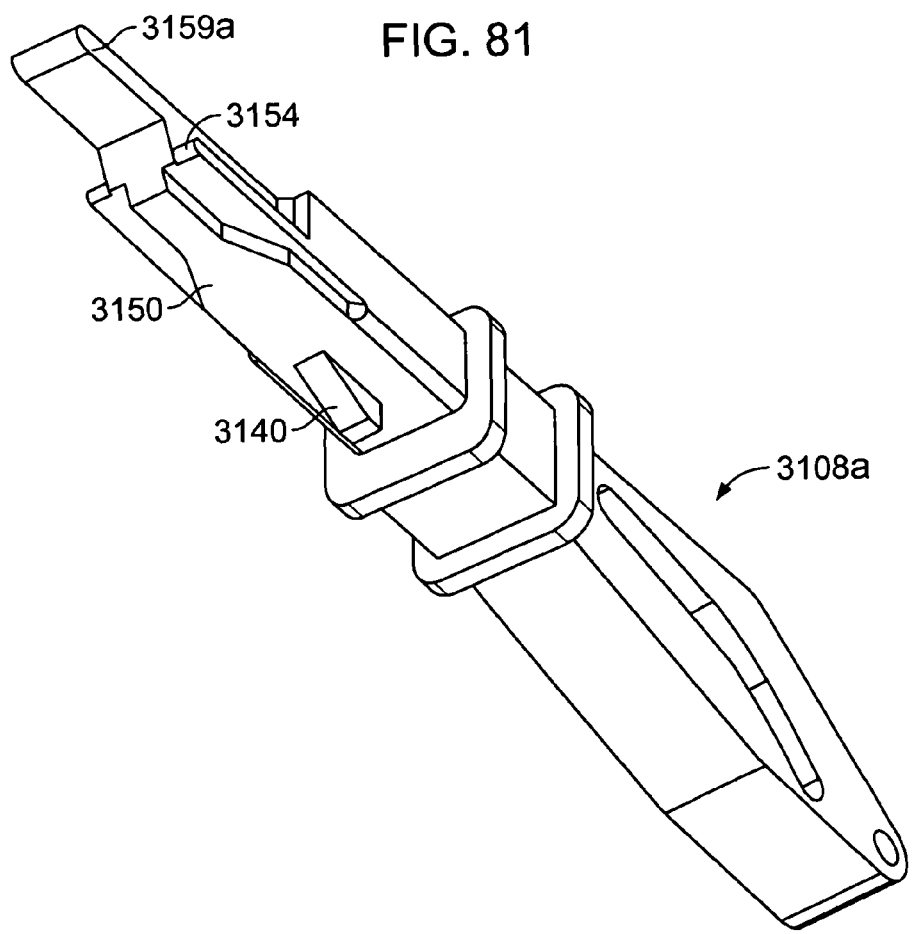
FIG. 82 is an illustration of the actuating arm of FIG. 80.

Referring to FIGS. 80-82, actuating arm 3108a is preferably formed of steel and includes a raised ramp 3140 that is received within an opening 3142 in cartridge 3104a. Opening 3142 has a proximally extending slot 3144 that extends to the end of cartridge 3104a. Cartridge 3104a has a section of material 3146 forming a retainer that holds the cartridge to the actuating arm and acts as a bailout mechanism, that is, when a given load (that is, an overload) is applied to actuating arm 3108a, section 3146 bends or breaks off allowing the instrument to be removed from the patient. This is a safety feature that is incorporated into both cartridges and accounts for any possibility of the cartridges being stuck to the implant after delivery of the implant in the tissue or the arms being jammed in the closed position with tissue between the arms. In these situations the instrument arms can be removed from the cartridge by applying load on the instrument. Thus the instrument can be removed from the patient in the situations when the cartridges are not disengaged from the implant after deploying, or when the arms will not open. The given load is selected to be less than the load that would pull the implant through the muscle tissue, which is about 27 pounds. The portions of cartridges 3104a, 3104b that are exposed proximal of rubber shells 3106a, 3106b (see in particular FIG. 72) allow the operator to unlock the cartridges from the actuating arms if necessary by accessing and manipulating section 3146.

Actuating arm 3108a includes a shaped region 3150 that keys into a corresponding shaped region 3152 of cartridge 3104a, a lip 3154 that is received within a slot 3156 in cartridge 3104a, and a metal end 3159a (FIGS. 72B and 82) that rests against post 3132 to keep the cartridge 3104a from bending. The length $L_a$ of the cavity within the cartridge 3104a that receives the coupler of the actuating arm 3108a is approximately 0.7 inches. Actuating arm 3108b includes a metal end 3159b (FIG. 72B) that fits within a cavity of cartridge 3104b and extends to the base of the needles 3101a. The length $L_b$ of the cavity within the cartridge 3104b that receives the coupler of the actuating arm 3108b is approximately 0.6 inches.

Figure 83:
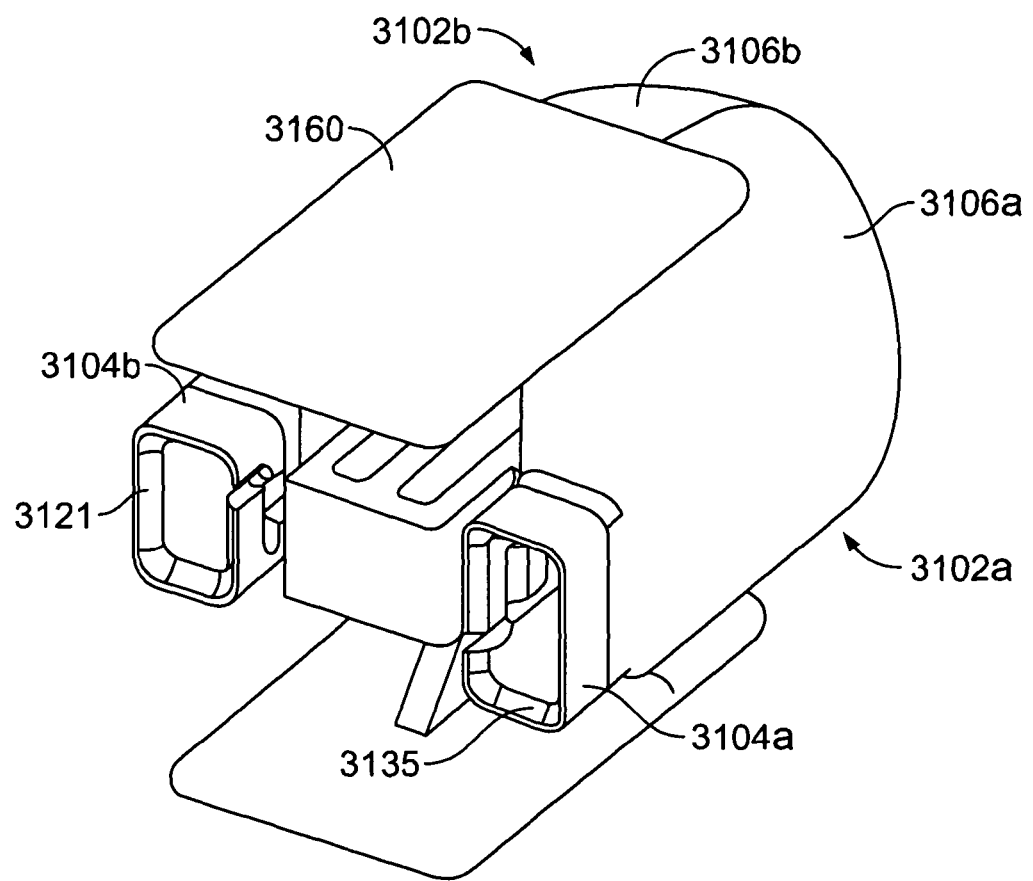
FIG. 83 shows the cartridges and shells attached to a holder.
Figure 84:
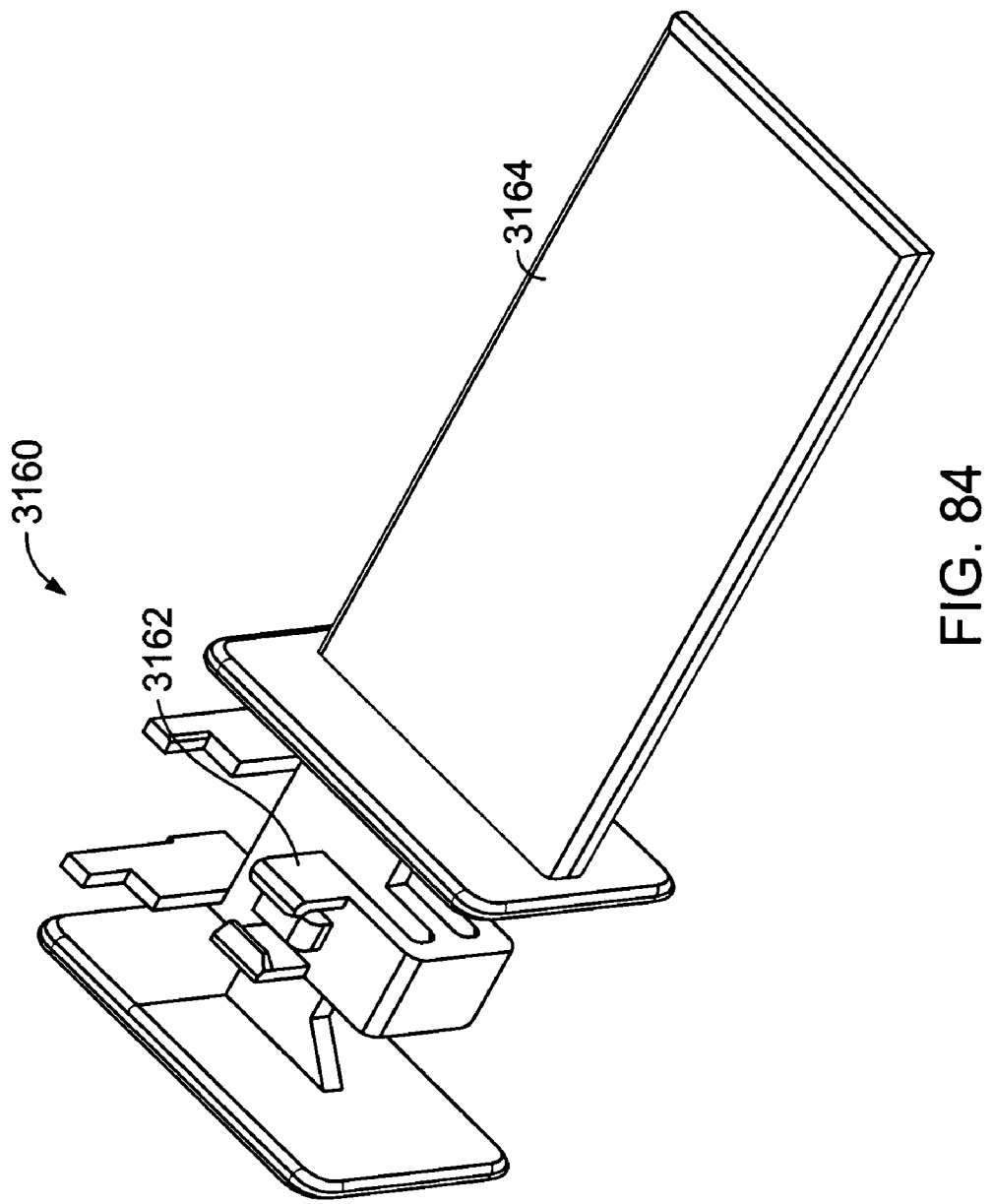
FIG. 84 is an illustration of the holder for the cartridges and shells.

As described above with reference to FIGS. 46A and 46B, the cartridges are supplied to the medical personnel in a holder. Referring to FIGS. 83 and 84, jaw members 3102a, 3102b are mounted to a holder 3160 in a manner generally as described above. The portions 3162 (only one of which can be seen in the view of FIG. 84) of holder 3160 that attach the cartridges to the holder are flexible to allow for automatic alignment when loading the cartridges onto the actuating arms. Holder 3160 can include a tab 3164 with a notation, such as "remove before use," to remind the operator to remove the holder from the cartridges before use. The tab can be sized such that it would be obvious to the user to not insert the cartridge into the patient with the holder in place.

Figure 85:
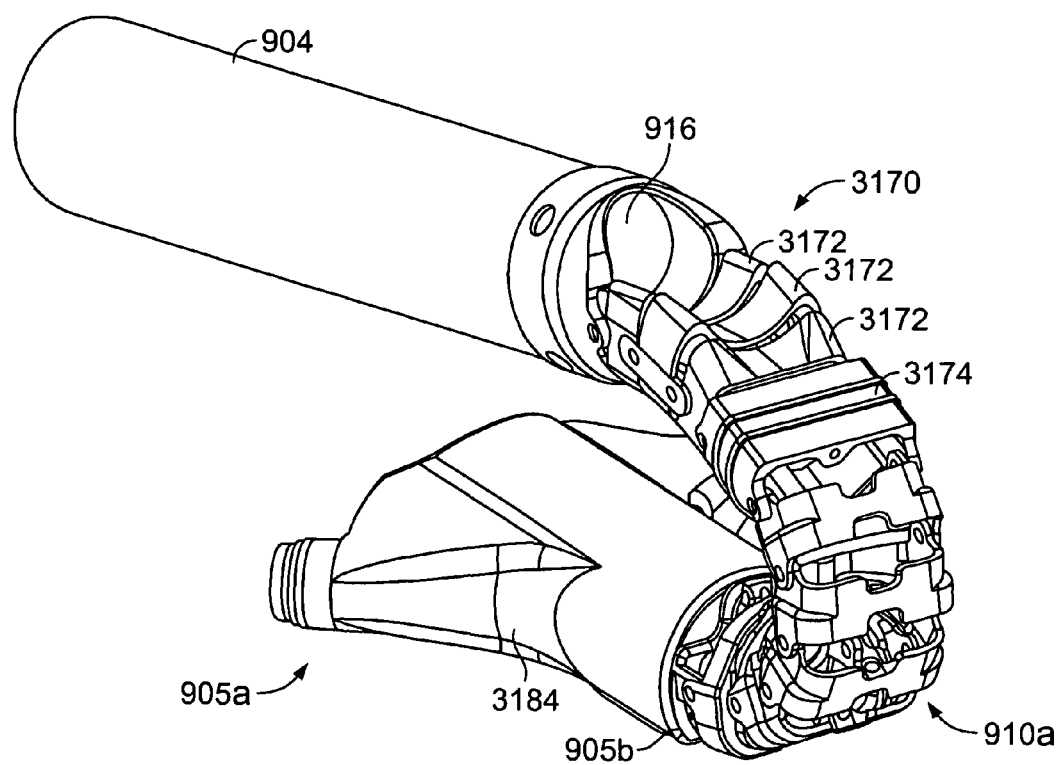
FIGS. 85 and 86 are illustrations of an alternative embodiment of a retroflex portion of the instrument.
Figure 86:
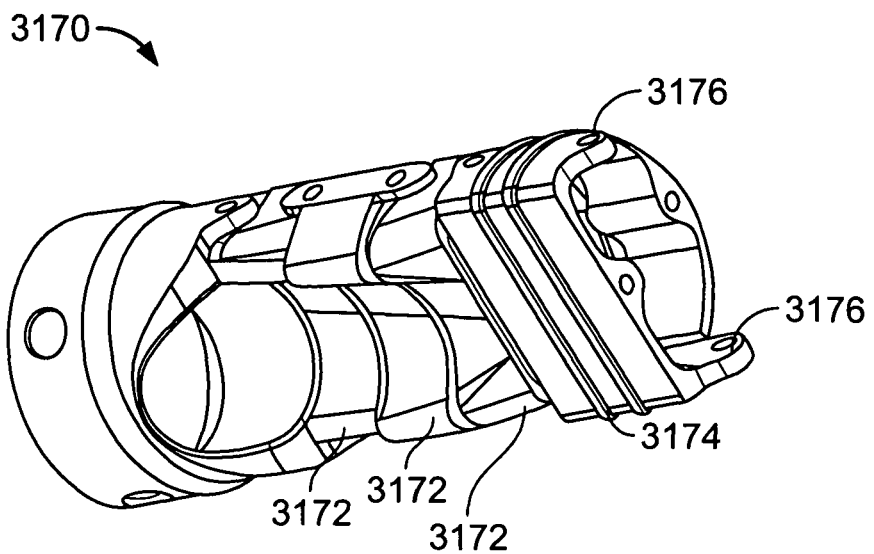

FIGS. 24A-24D show a retroflex portion 910 that includes a series of links. Referring to FIG. 85, a retroflex portion 910a includes a proximal mount section 3170 that is also formed from a series of links 3172 to provide additional flexibility to the retroflex portion to ease insertion. Referring also to FIG. 86, section 3170 includes a coupling portion 3174 with prongs 3176 for attaching section 3170 to the remainder of retroflex portion 910a.

Figure 87A:
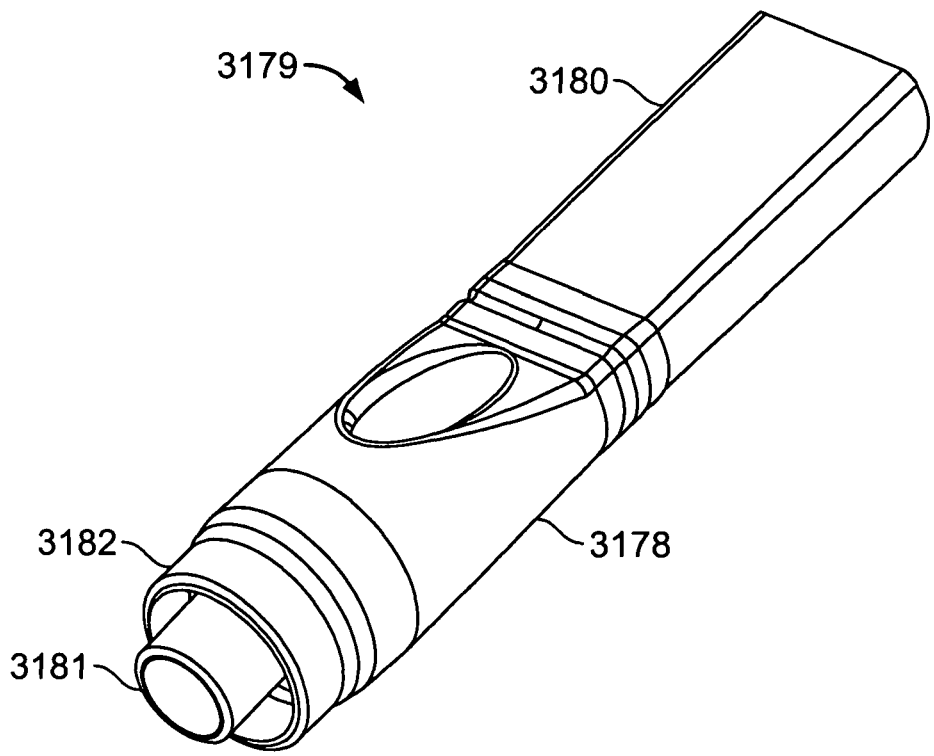
FIGS. 87a-87c are illustrations of a boot for sealing off portions of the retroflex portion of FIGS. 85 and 86.
Figure 87B:
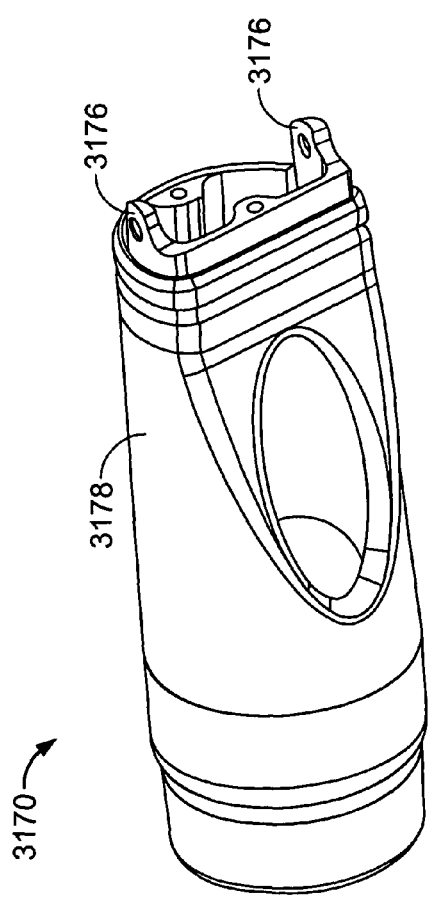
Figure 87C:
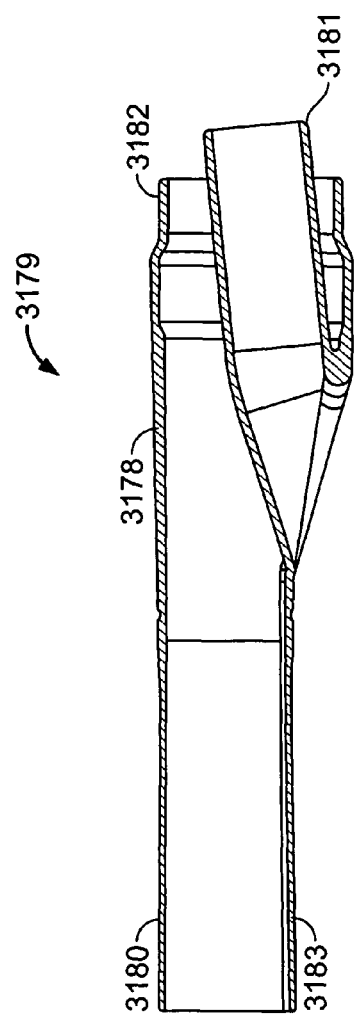

Referring also to FIG. 87A, a flexible boot 3179 having a portion 3178 and a portion 3180 covers the retroflex portion 910a. In particular, as shown in FIGS. 87B and 87C, portion 3178 covers links 3172 of proximal mount section 3170 and coupling portion 3174, except for prongs 3176, and portion 3180 covers the remaining links of the retroflex portion 910a. Portion 3178 includes an inner tube end 3181 that seals to lumen 916 and an outer tube end 3182 that seals to shaft 904. Portion 3180 includes a tube end 3183 that seals to the distal end 905a at end region 905b (FIG. 85) of the retroflex portion 910a.

Figure 88A:
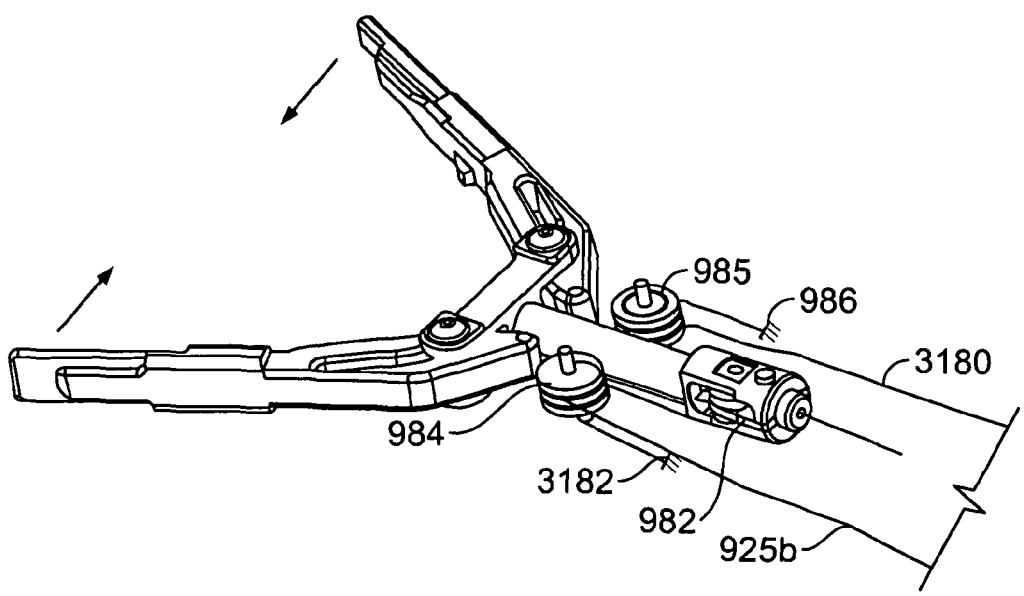
FIG. 88a is an illustration of an alternative embodiment of a distal actuating mechanism of the instrument.
Figure 88B:
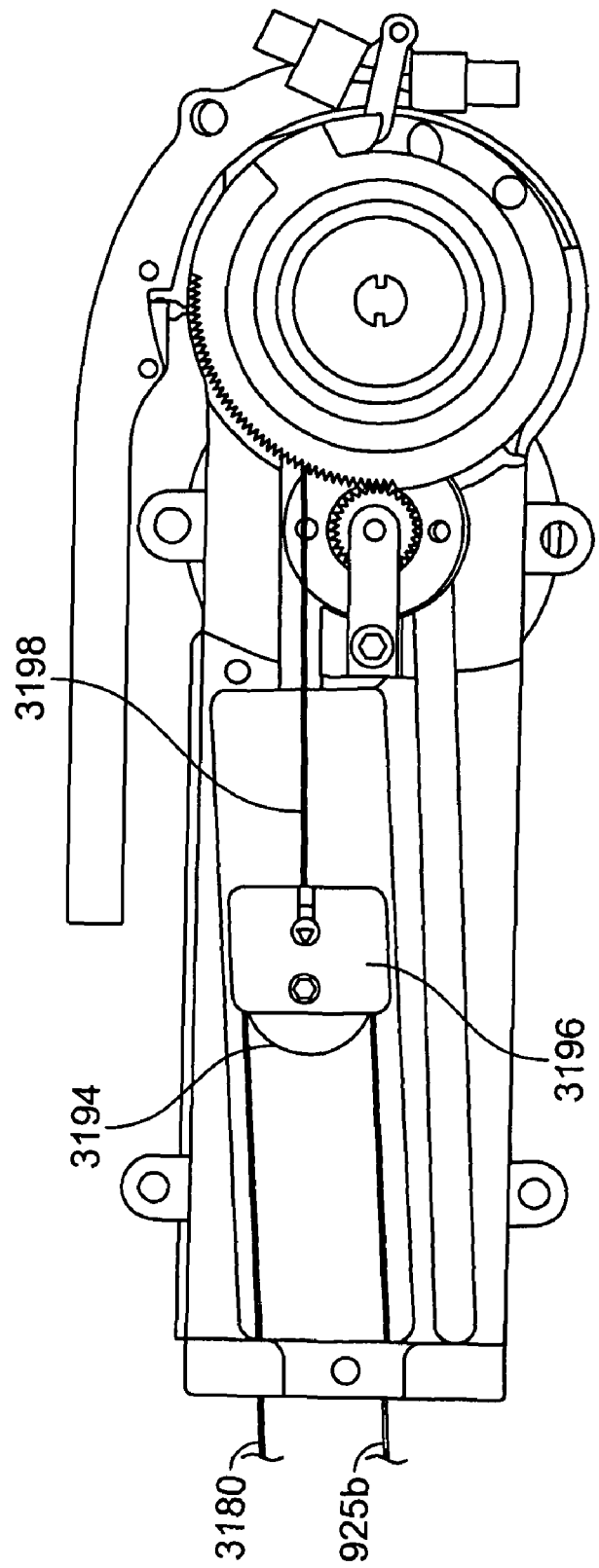

FIGS. 23A-23D show a jaw closing cable 925b wound around pulleys 984, 982 and 985, and terminating at a fixed point 986. Referring to FIG. 88a, to reduce the load on cable 925b needed to deploy the implant, a second jaw closing cable 3180 is wound around pulleys 984, 982 and 985 and terminates at a fixed point 3182. The double pulley system achieves a closing force at the tip of the arms of approximately 35 pounds with less than about 15 pounds being applied to each of cables 925b and 3180. Referring to FIG. 88b, cables 925b, 3180 both terminate at a balancing pulley 3194 of the handle mechanism. Balancing pulley 3194 is connected to a yoke 3196 that is connected to the closing pulley, described above, by a short cable 3198. The pulley 3194 and yoke 3196 move back and forth as the arms are opened and closed. Balancing pulley 3194 ensures that both cables 925b and 3180 are pulled with the same force.

Figure 89:
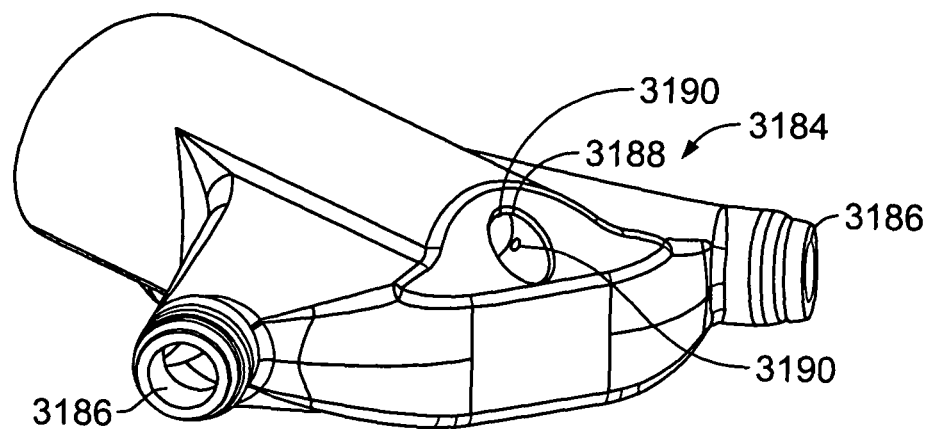
FIGS. 89 and 90 show a boot for sealing off portions of the distal end of the instrument.
Figure 90:
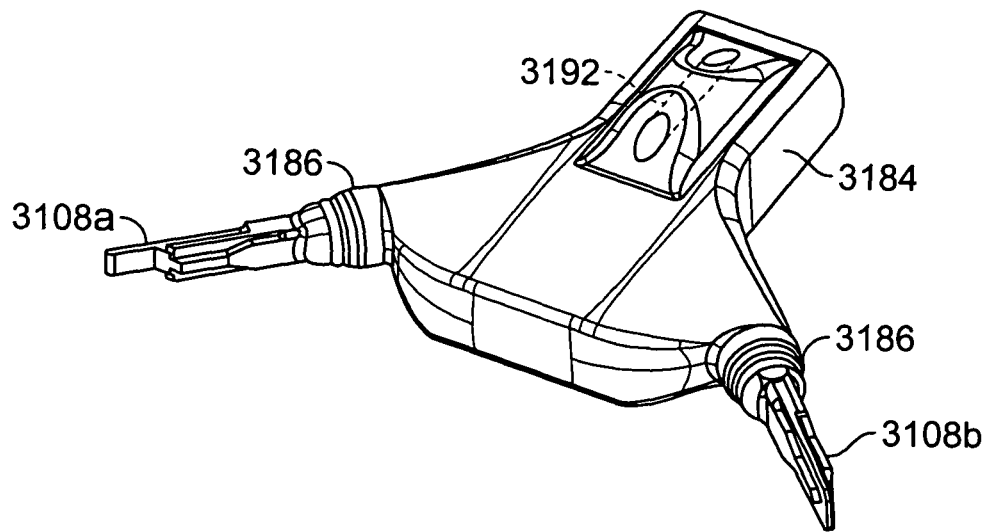

Referring to FIGS. 89 and 90, a boot 3184 covers the distal end 905a of the retroflex portion 910a except for the part of the actuating arms 3108a, 3108b that engage the cartridges. The boot 3184 is flexible to allow for opening and closing of the actuating arms 3108a, 3108b. The boot includes seals 3186 for sealing off the actuating arms and a seal 3188 for sealing off a port for the retractor (such as retractor 740 or 2020 above). The seals 3186 and 3188 are formed by first wrapping and tying string around the part of the boot 3184 adjacent the actuating arms 3108a, 3108b and then applying glue over the string. Seal 3188 includes interference bumps 3190 that act to hold the distal end of the retractor within the boot 3184 during insertion. Boot 3184 defines a hole 3192 for receiving the guide wire. The boot prevents body fluids from contacting the cables and pulleys during the procedure, and prevents cleaning solutions from contacting the cables and pulleys during cleaning, providing for reuse of the instrument.

Figure 91:
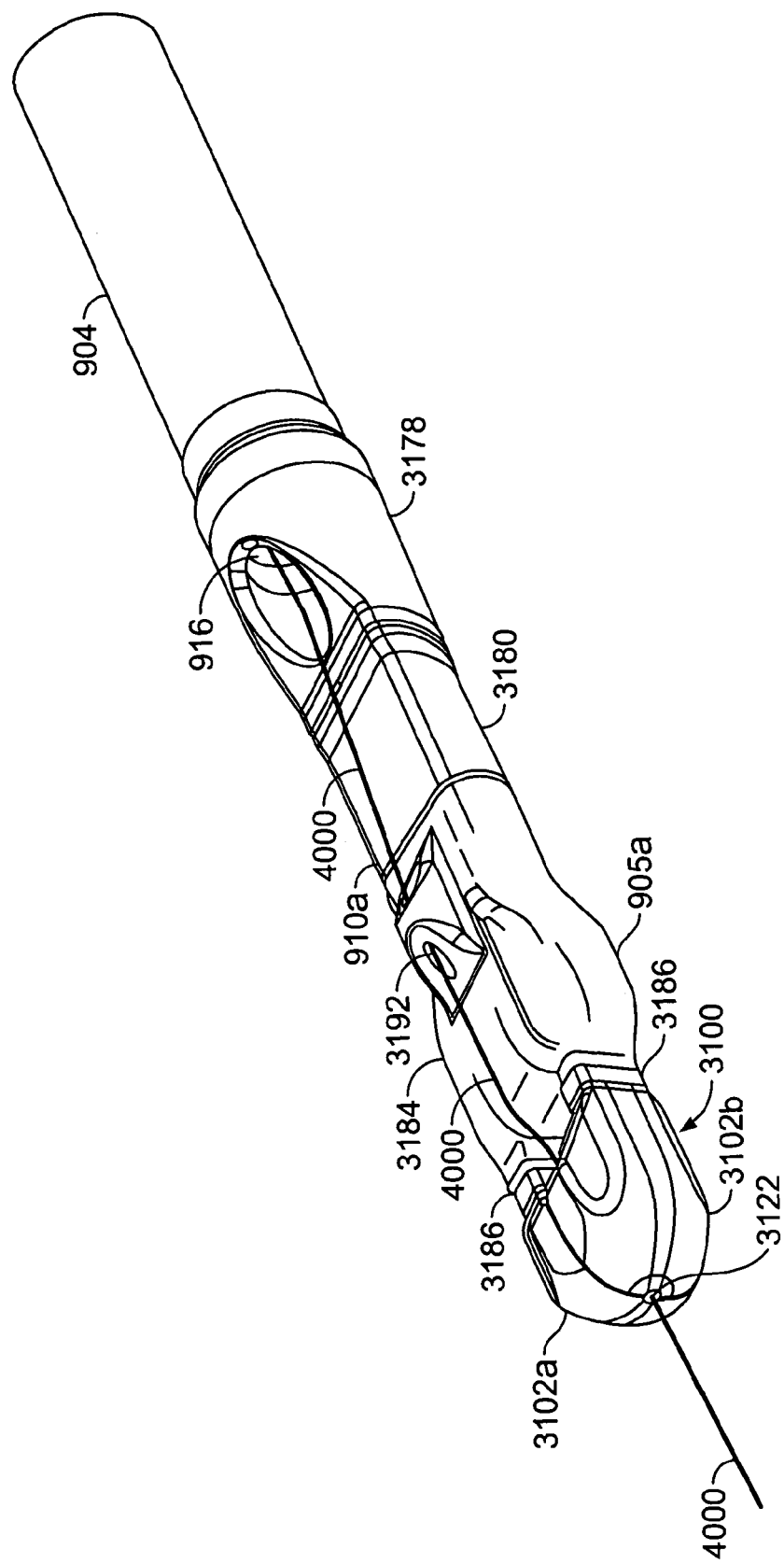
FIG. 91 is an illustration of a distal portion of the instrument.

Referring to FIG. 91, end effector 3100 is coupled to the retroflex portion 910a, which is coupled to the shaft 904. As shown, the boot 3184 covering the distal end 905a seals off the actuating arms 3108a, 3108b (FIG. 72A) of the jaw members 3102a, 3102b. As discussed above, the instrument 900 can be introduced transorally over guide wire 4000 by threading the guide wire 4000 through the shaft 904, through the lumen 916, through the hole 3192 of the boot 3184, and through the guide wire receiving holes 3110 and 3122, which are in alignment.

Other implementations are within the scope of the following claims. Though the clutch spring 4002 is shown with three legs (FIGS. 92 and 93) and with four legs (FIGS. 94 and 95), the clutch spring 4002 can be configured with any number of legs 4010. For example, the clutch spring 4002 may have one leg, two legs or 10 legs. The seals 3186 and 3188 can be formed using other methods, such as, for example, with an interference fit between the actuating arms and the part of the boot 3184 adjacent the actuating arms.

The clip 3133 can be integral with the cartridge 3104a and the cartridge 3104a (and the clip 3133) can be formed from metal. The clip 3133 can be molded to the end of the cartridge 3104a, which can be formed from plastic.

What is claimed is:

1. A medical instrument, comprising:
   a tissue manipulator configured for introduction into a patient and including first and second jaws,
   a sealing member configured to substantially seal a section of the tissue manipulator from contact with bodily fluids, the first and second jaws being movable within the sealing member and having a portion extending out of the sealing member, the first and second jaws being configured to move in a first plane such that the first and second jaws can move toward and away from one another, and the first and second jaws being configured to move in a second plane generally perpendicular to the first plane such that the first and second jaws can move out of axial alignment with the sealing member, and
   a tissue engaging member configured to contact and stabilize tissue, the tissue engaging member being axially movable within the sealing member and having a portion extending out of the sealing member, the tissue engaging member being configured to articulate with the first and second jaws when moving out of axial alignment with the sealing member.

2. The medical instrument of claim 1 wherein the tissue manipulator includes pivots about which the first and second jaws rotate in opposite directions.

3. The medical instrument of claim 1 wherein the sealing member defines a hole for receiving a guide wire to permit advancement of the tissue manipulator into the patient over the guide wire.

4. The medical instrument of claim 1 wherein the sealing member comprises a flexible member.

5. The medical instrument of claim 1 further comprising:
a flexible linkage coupled to the tissue manipulator, and
a sealing portion covering the linkage.

6. The medical instrument of claim 5 wherein the sealing portion abuts the sealing member.

7. The medical instrument of claim 1, wherein the tissue engaging member is axially movable within the sealing member between the first and second jaws.

8. The medical instrument of claim 1, wherein the tissue engaging member is configured to be axially aligned with the first and second jaws and to articulate with the first and second jaws when moving out of axial alignment with the sealing member while remaining axially aligned with the first and second jaws.

9. The medical instrument of claim 1, further comprising an actuating member extending through the sealing member and configured to be actuated to simultaneously articulate the tissue engaging member and the first and second jaws.

10. The medical instrument of claim 1, further comprising a central mount, wherein proximal ends of the first and second jaws are mounted to the central mount, and a proximal end of the tissue engaging member is mounted to the central mount.

* * * * *